US012805885B1

(12) United States Patent
Shifflette

(10) Patent No.: US 12,805,885 B1
(45) Date of Patent: Nov. 24, 2026

(54) VISCO-VOLUMETRIC ASPIRATION SYSTEM AND METHODS

(71) Applicant: J Michael Shifflette, Alachua, FL (US)

(72) Inventor: J Michael Shifflette, Alachua, FL (US)

( * ) Notice: Subject to any disclaimer, the term of this patent is extended or adjusted under 35 U.S.C. 154(b) by 4 days.

(21) Appl. No.: 19/192,224

(22) Filed: Apr. 28, 2025

Related U.S. Application Data

(60) Provisional application No. 63/795,616, filed on Apr. 27, 2025, provisional application No. 63/640,180, filed on Apr. 29, 2024.

(51) Int. Cl.
*A61B 17/22* (2006.01)

(52) U.S. Cl.
CPC .... *A61B 17/22* (2013.01); *A61B 2017/22079* (2013.01)

(58) Field of Classification Search
CPC .............. A61B 17/22; A61B 2217/005; A61B 2090/064; A61B 17/32037; A61B 2017/00154; A61B 2017/22079; A61B 2217/007; A61B 17/00; A61B 17/3498; A61B 18/245; A61B 2017/00172; A61B 2017/00199; A61B 2017/00561; A61B 90/06; A61M 1/74; A61M 1/75; A61M 1/77; A61M 1/774; A61M 1/76; A61M 2205/3334; A61M 2205/3344; A61M 2205/7545; A61M 39/105; A61M 5/14212; A61M 5/16804
See application file for complete search history.

(56) References Cited

U.S. PATENT DOCUMENTS

| | | | | |
|---|---|---|---|---|
| 2021/0353323 A1* | 11/2021 | Teigen | .................. | A61B 17/22 |
| 2022/0168000 A1* | 6/2022 | Naglreiter | .............. | A61B 17/22 |
| 2023/0277199 A1* | 9/2023 | Duffy | ..................... | A61B 17/22 604/30 |

* cited by examiner

*Primary Examiner* — Mohamed G Gabr
(74) *Attorney, Agent, or Firm* — Kaplan Breyer Schwarz, LLP

(57) ABSTRACT

An aspiration thrombectomy system comprising components such as a vacuum source, catheter, connecting tubing, pressure transducer, controllable valves, a non-isovolumetric component, and a system controller is disclosed. The system controller is configured to operate the valves, analyze pressure data, and determine a key parameter: time. Using this time parameter, the controller computes and stores derived variables—such as viscosity, flow rate, volume, and spatial location within the catheter—in a time-resolved data array. This time history may be displayed as a dynamic visualization of the aspiration process and may also be extrapolated or modeled to predict future values of the derived variables. The system controller may further actuate components, including the valves and the non-isovolumetric component, to influence future outcomes based on the evolving dataset.

10 Claims, 39 Drawing Sheets

Bulb Pressure 310 ≈ $P_{atm}$
Bulb Volume 320 ≈ $V_0$
310
320
301

Bulb Pressure 310 ≈ $P_{atm}$
Bulb Volume 320 ≈ 10% $V_0$
320
370
370
310

Bulb Pressure 310 ≈ $P_{atm}$
Bulb Volume 320 ≈ $V_0$
320
310
380
330
water Bulb Pressure 310 ≈ 60%$P_{atm}$
Bulb Volume 320 ≈ 60%$V_0$
320
310
340
cream Bulb Pressure 310 ≈ 40%$P_{atm}$
Bulb Volume 320 ≈ 40%$V_0$
320
310
350
tomato juice Bulb Pressure 310 ≈ 15%$P_{atm}$
Bulb Volume 320 ≈ 15%$V_0$
320
310
360
syrup
Prior Art FIG. 6A
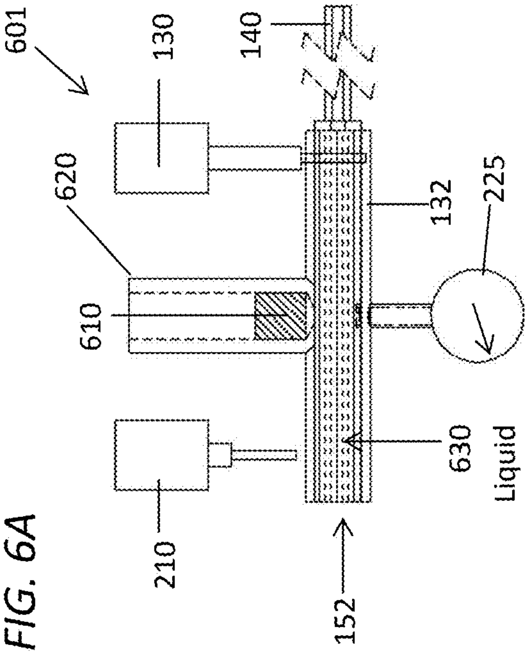
FIG. 6B
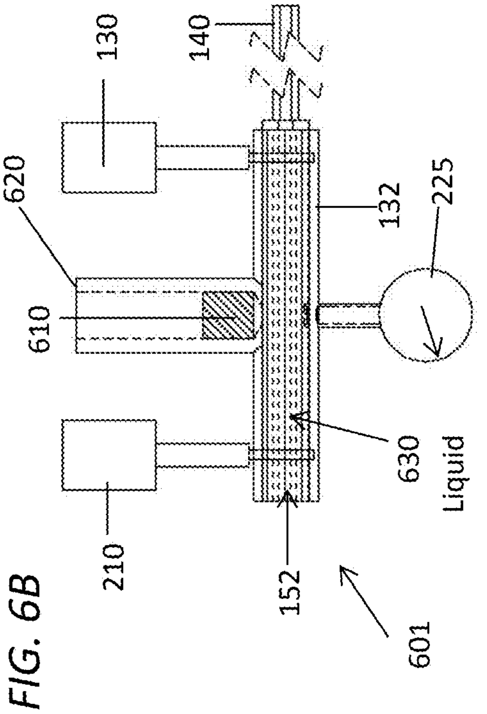
FIG. 6C $t \approx t_0$
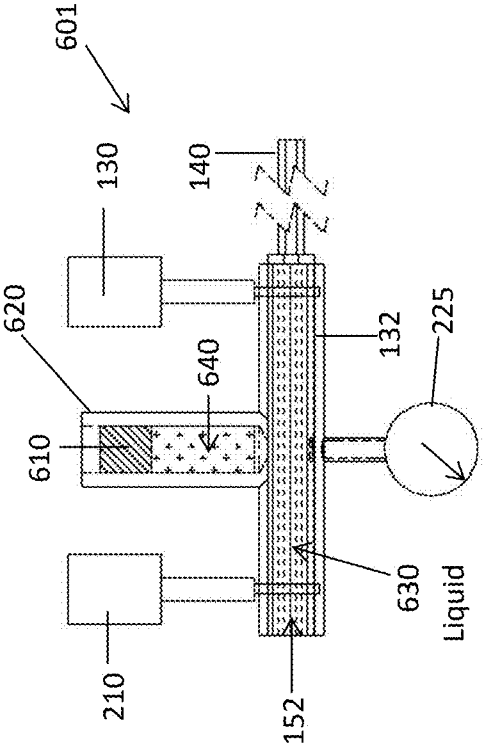
FIG. 6D $t > t_0$
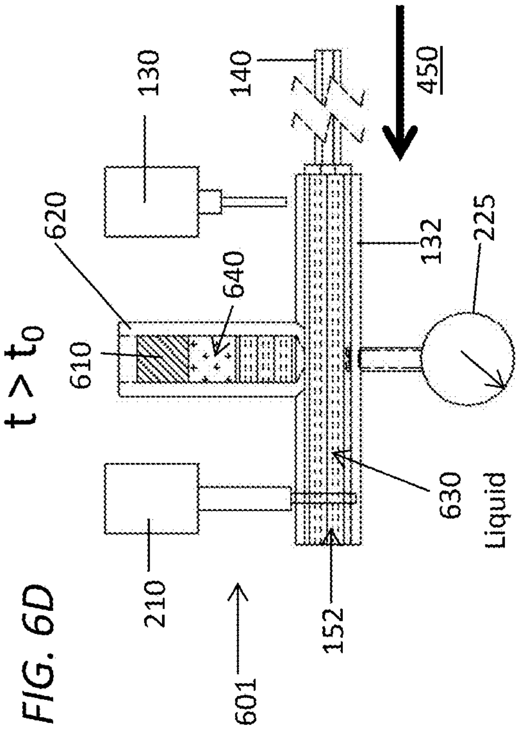

*FIG. 7C* Pressure – Volume Lookup Table – Includes Bulk Modulus (K)

| Normalized Pressure | Linear (K=10) Volume | Variable Volume | Variable K | Isothermal Volume | Isothermal K |
|---|---|---|---|---|---|
| 0.05 | 0.5 | 0.40 | 19.50 | 20.00 | 266.67 |
| 0.075 | 0.75 | 0.89 | 19.00 | 13.33 | 133.33 |
| 0.1 | 1 | 1.36 | 18.50 | 10.00 | 80.00 |
| 0.125 | 1.25 | 1.83 | 18.00 | 8.00 | 53.33 |
| 0.15 | 1.5 | 2.28 | 17.50 | 6.67 | 38.10 |
| 0.175 | 1.75 | 2.71 | 17.00 | 5.71 | 28.57 |
| 0.2 | 2 | 3.14 | 16.50 | 5.00 | 22.22 |
| 0.225 | 2.25 | 3.55 | 16.00 | 4.44 | 17.78 |
| 0.25 | 2.5 | 3.95 | 15.50 | 4.00 | 14.55 |
| 0.275 | 2.75 | 4.34 | 15.00 | 3.64 | 12.12 |
| 0.3 | 3 | 4.71 | 14.50 | 3.33 | 10.26 |
| 0.325 | 3.25 | 5.08 | 14.00 | 3.08 | 8.79 |
| 0.35 | 3.5 | 5.43 | 13.50 | 2.86 | 7.62 |
| 0.375 | 3.75 | 5.76 | 13.00 | 2.67 | 6.67 |
| 0.4 | 4 | 6.09 | 12.50 | 2.50 | 5.88 |
| 0.425 | 4.25 | 6.40 | 12.00 | 2.35 | 5.23 |
| 0.45 | 4.5 | 6.70 | 11.50 | 2.22 | 4.68 |
| 0.475 | 4.75 | 6.99 | 11.00 | 2.11 | 4.21 |
| 0.5 | 5 | 7.26 | 10.50 | 2.00 | 3.81 |
| 0.525 | 5.25 | 7.53 | 10.00 | 1.90 | 3.46 |
| 0.55 | 5.5 | 7.78 | 9.50 | 1.82 | 3.16 |
| 0.575 | 5.75 | 8.01 | 9.00 | 1.74 | 2.90 |
| 0.6 | 6 | 8.24 | 8.50 | 1.67 | 2.67 |
| 0.625 | 6.25 | 8.45 | 8.00 | 1.60 | 2.46 |
| 0.65 | 6.5 | 8.65 | 7.50 | 1.54 | 2.28 |
| 0.675 | 6.75 | 8.84 | 7.00 | 1.48 | 2.12 |
| 0.7 | 7 | 9.01 | 6.50 | 1.43 | 1.97 |
| 0.725 | 7.25 | 9.18 | 6.00 | 1.38 | 1.84 |
| 0.75 | 7.5 | 9.33 | 5.50 | 1.33 | 1.72 |
| 0.775 | 7.75 | 9.46 | 5.00 | 1.29 | 1.61 |
| 0.8 | 8 | 9.59 | 4.50 | 1.25 | 1.52 |
| 0.825 | 8.25 | 9.70 | 4.00 | 1.21 | 1.43 |
| 0.85 | 8.5 | 9.80 | 3.50 | 1.18 | 1.34 |
| 0.875 | 8.75 | 9.89 | 3.00 | 1.14 | 1.27 |
| 0.9 | 9 | 9.96 | 2.50 | 1.11 | 1.20 |
| 0.925 | 9.25 | 10.03 | 2.00 | 1.08 | 1.14 |
| 0.95 | 9.5 | 10.08 | 1.50 | 1.05 | 1.08 |
| 0.975 | 9.75 | 10.11 | 1.00 | 1.03 | 1.03 |
| 1 | 10 | 10.14 | 1.00 | 1.00 | 1.00 |

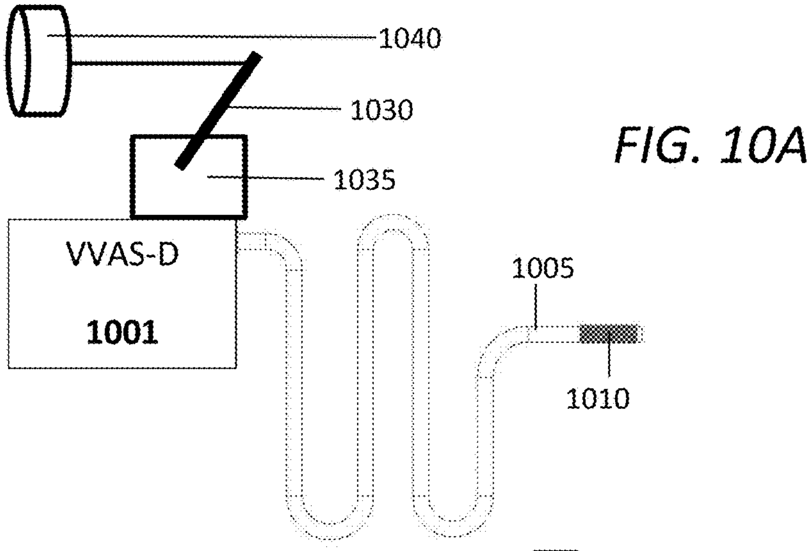
FIG. 10A
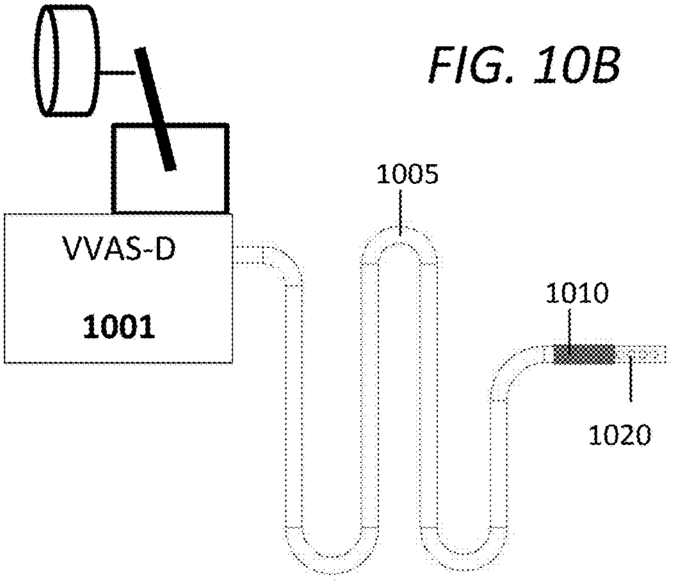
FIG. 10B
FIG. 10C
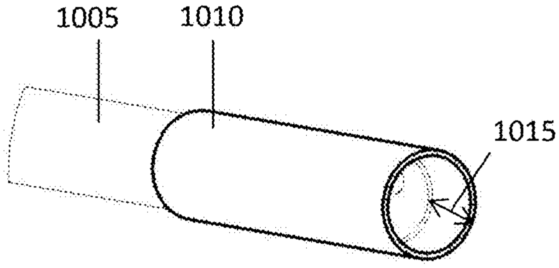
FIG. 10D
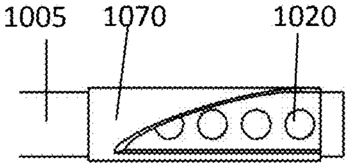
FIG. 10E
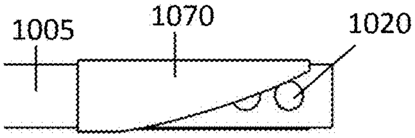

*FIG. 13A*
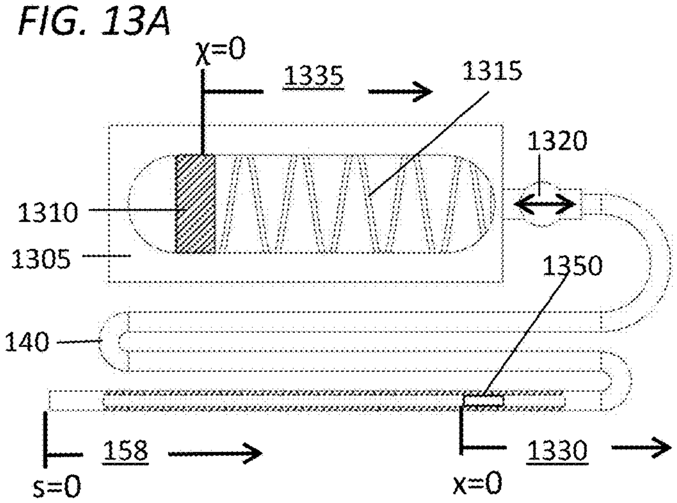
*FIG. 13B*
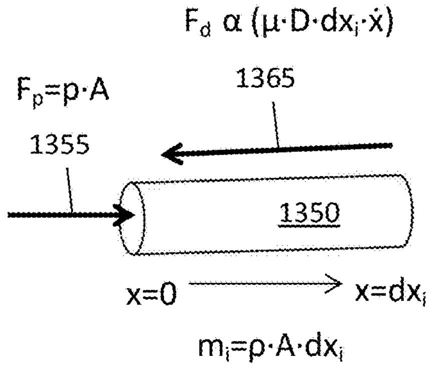
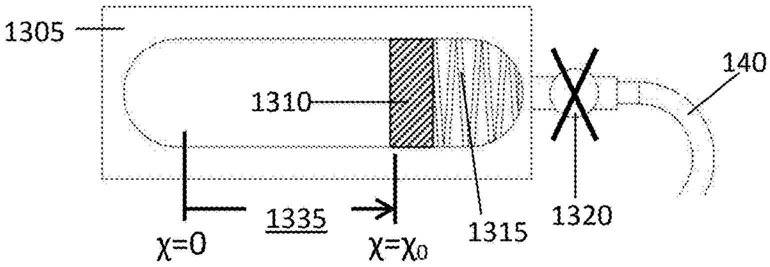
*FIG. 13C*
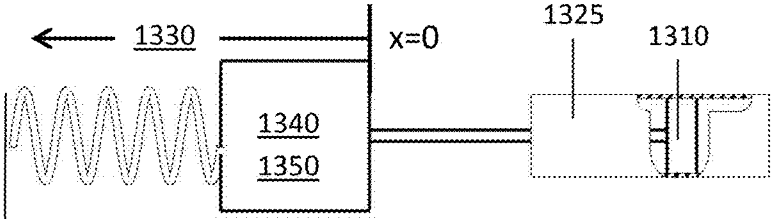
*FIG. 13D*
Prior Art
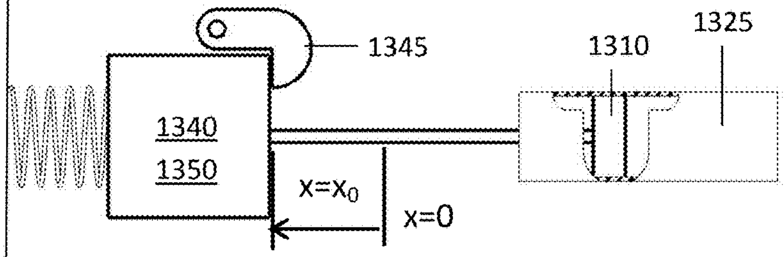
*FIG. 13E*
Prior Art
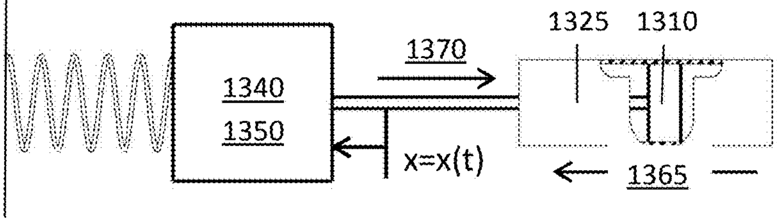
*FIG. 13F*
Prior Art

1901

| % PD | µ x l | length | µ | Bolus# |
|---|---|---|---|---|
| 0.50% | 0.4 | 0.1 | 4 | B1 |
| 3.26% | 2.6 | 0.5 | 5.2 | B2 |
| 1.51% | 1.2 | 0.25 | 4.8 | B3 |
| 1.76% | 1.4 | 0.25 | 5.6 | B4 |
| 9.97% | 7.95 | 0.75 | 10.6 | B5 |
| 9.53% | 7.6 | 0.5 | 15.2 | B6 |
| 6.02% | 4.8 | 0.75 | 6.4 | B7 |
| 1.98% | 1.575 | 0.25 | 6.3 | B8 |
| 3.89% | 3.1 | 0.5 | 6.2 | B9 |
| 0.87% | 0.69 | 0.1 | 6.9 | B10 |
| 0.74% | 0.59 | 0.1 | 5.9 | B11 |
| 4.06% | 3.24 | 0.4 | 8.1 | B12 |
| 1.74% | 1.39 | 0.1 | 13.9 | B13 |
| 3.84% | 3.06 | 0.2 | 15.3 | B14 |
| 5.52% | 4.4 | 0.25 | 17.6 | Bi-2 |
| 11.20% | 8.925 | 0.75 | 11.9 | Bi-1 |
| 6.33% | 5.05 | 0.5 | 10.1 | Bi |
| 10.44% | 8.325 | 0.75 | 11.1 | Bi+1 |
| 4.89% | 3.9 | 0.25 | 15.6 | Bi+2 |
| 3.95% | 3.15 | 0.25 | 12.6 | Bi+3 |
| ..... | ..... | ..... | ..... | ..... |
| 1.32% | 1.05 | 0.25 | 4.2 | Bn-2 |
| 4.05% | 3.225 | 0.75 | 4.3 | Bn-1 |
| 2.63% | 2.1 | 0.5 | 4.2 | Bn |

*FIG. 25*

2501

Thrombus Model Matrix by Clinical Variables and VVA Process Variables

| IS | Morph | Physical Properties | Volume (cc) | Modes / Simulations | a | b | c | d | e | f | g | h |
|---|---|---|---|---|---|---|---|---|---|---|---|---|
| **MCA*** | fresh | cohesive, elastic | <5 to 20+ | a, b, c, d, f, g | 22% | 17% | 18% | 15% | | 10% | 18% | |
| ICA | fresh | cohesive, elastic | <10to 30+ | a, b, c, d, f, g | 15% | 21% | 12% | 13% | | 26% | 13% | |
| PE | | | | | | | | | | | | |
| Moderate | fresh | elastic, cohesive | <30 to 100+ | a,b,c,d,e,f,g,h | 21% | 17% | 6% | 18% | 8% | 2% | 18% | 10% |
| Sub-Massive | fresh | elastic, cohesive | <80 to 150+ | a,b,c,d,e,f,g,h | 17% | 17% | 8% | 18% | 6% | 4% | 20% | 10% |
| Massive | organized | elastic to firm | <100 to 300+ | a,b,c,d,e,f,g,h | 16% | 7% | 6% | 18% | 17% | 8% | 18% | 10% |
| DVT | | | | | | | | | | | | |
| Popliteal | fresh | elastic, adhesive | <20 to 40+ | a, b, c, d, e, g | 27% | 13% | 20% | 5% | 5% | | 30% | |
| Femoral | fresh to org. | firm | <40 to 60+ | a, b, c, d, e, g | 22% | 18% | 18% | 10% | 5% | | 27% | |
| Iliac | organized | firm to brittle | <60 to 100+ | a, b, c, d, e, g | 28% | 20% | 15% | 7% | 16% | | 14% | |
| CTO | | | | | | | | | | | | |
| Popliteal | org, fibrotic | firm, cohesive | <30 to 50+ | a,b,c,d,e,f,g,h | 31% | 18% | 8% | 10% | 13% | 8% | 4% | 8% |
| Femoral | org, fibrotic | cohesive, brittle | <50 to 150+ | a,b,c,d,e,f,g,h | 31% | 13% | 5% | 10% | 19% | 8% | 4% | 10% |
| Coronary | org, calcified | cohesive, brittle | <5 to 20+ | a,b,c,d,e,f,g,h | 35% | 3% | 15% | 18% | 5% | 12% | 5% | 7% |

← Clinical Variables 2510 | VVA System Variables 2520 →

AMC Modes / Simulations Legend a: system vacuum b: reduced vacuum c: pressure pulse d: pulse train
e: dilution f: saline flush g: make/break contact h: full aspiration

Fig. 26A

2601

Page 1 of x

| Time | AMC Mode | Time Const | P initial | P final | Valve Duration | Bolus Volume | Bolus Visc. | Cath Visc. | Damp | Bulk Mod | Outome Score |
|---|---|---|---|---|---|---|---|---|---|---|---|
| 15:45:00.000 | Seek | 0.1 | 25 | 20 | 0.25 | 0.5 | 4 | 4 | 0 | 10 | 5 |
| 15:45:00.275 | Seek | 0.7 | 25 | 20 | 2 | 0.5 | 4 | 4 | 3 | 10 | 5 |
| 15:45:02.475 | Seek | 0.7 | 25 | 20 | 2 | 0.5 | 4 | 4 | 3 | 10 | 5 |
| 15:45:04.675 | Seek | 0.7 | 25 | 20 | 2 | 0.5 | 4 | 4 | 3 | 10 | 5 |
| 15:45:06.875 | Seek | 0.7 | 25 | 20 | 2 | 0.5 | 4 | 4 | 3 | 10 | 5 |
| 15:45:09.075 | Seek | 0.7 | 25 | 20 | 2 | 0.5 | 4 | 4 | 3 | 10 | 5 |
| 15:45:11.275 | Seek | 0.7 | 25 | 20 | 2 | 0.5 | 4 | 4 | 3 | 10 | 5 |
| 15:45:17.795 | Seek | 0.75 | 25 | 20 | 2.5 | 0.5 | 25 | 5 | 3 | 10 | 10 |

Duration: 00:17.795 Average Bolus Viscosity: 6.63 Avg Cath Viscosity: 4.13
Avg Outcome Score: 5.63 Average Bolus Volume: 0.50 Volume: 4

| Time | AMC Mode | Time Const | P initial | P final | Valve Duration | Bolus Volume | Bolus Visc. | Cath Visc. | Damp | Bulk Mod | Outome Score |
|---|---|---|---|---|---|---|---|---|---|---|---|
| 15:45:20.545 | Norm | 0.4 | 27 | 10 | 1.75 | 1 | 40 | 5.25 | 0 | 10 | 15 |
| 15:45:22.470 | Norm | 0.5 | 27 | 15 | 2 | 1 | 60 | 6 | 0 | 10 | 30 |
| 15:45:24.670 | Norm | 0.55 | 27 | 18 | 2.5 | 1 | 40 | 7.5 | 0 | 10 | 25 |
| 15:45:27.420 | Norm | 0.54 | 27 | 15 | 2.7 | 1 | 40 | 8.1 | 0 | 10 | 25 |
| 15:45:30.390 | Norm | 0.54 | 27 | 15 | 2.6 | 1 | 30 | 7.8 | 0 | 10 | 23 |
| 15:45:33.250 | Norm | 0.45 | 27 | 15 | 2.25 | 1 | 20 | 6.75 | 0 | 10 | 20 |
| 15:45:35.725 | Norm | 0.4 | 27 | 15 | 2 | 1 | 20 | 6 | 0 | 10 | 20 |
| 15:45:37.925 | Norm | 0.4 | 27 | 20 | 1.75 | 1 | 6 | 5.25 | 0 | 10 | 10 |
| 15:45:39.850 | Norm | 0.4 | 27 | 20 | 1.5 | 1 | 4 | 4.5 | 0 | 10 | 10 |
| 15:45:41.500 | Norm | 0.4 | 27 | 20 | 1.5 | 1 | 4 | 4.5 | 0 | 10 | 10 |
| 15:45:43.150 | Seek | 0.76 | 25 | 20 | 2.5 | 0.5 | 4 | 4.3 | 3 | 10 | 5 |

Duration: 00:22.605 Average Bolus Viscosity: 24.36 Avg Cath Viscosity: 6.00
Avg Outcome Score: 17.55 Average Bolus Volume: 0.95 Volume: 10.5

2651

*Fig. 26B*

Page 2 of x

| Time | AMC Mode | Time Const | P initial | P final | Valve Duration | Bolus Volume | Bolus Visc. | Cath Visc. | Damp | Bulk Mod | Outome Score |
|---|---|---|---|---|---|---|---|---|---|---|---|
| 15:47:09.550 | a | 0.4 | 28.5 | 8 | 1.8 | 2.41 | 60 | 6.2 | 0 | 10 | 40 |
| 15:47:11.530 | a | 0.48 | 29 | 14 | 2 | 1.76 | 80 | 7.5 | 0 | 10 | 52 |
| 15:47:13.730 | c | 0.53 | 27 | 12 | 2.5 | 1.76 | 85 | 8.3 | 0 | 10 | 65 |
| 15:47:16.480 | c | 0.59 | 27 | 12 | 2.6 | 1.76 | 92 | 9.5 | 0 | 10 | 73 |
| 15:47:19.340 | d | 0.64 | 27 | 16 | 2.3 | 1.29 | 59 | 9.9 | 0 | 10 | 45 |
| 15:47:21.870 | g | 0.69 | 27 | 14 | 2.5 | 1.53 | 40 | 10 | 0 | 10 | 55 |
| 15:47:24.620 | a | 0.72 | 28.7 | 18 | 2.3 | 1.26 | 105 | 11.7 | 0 | 10 | 70 |
| 15:47:27.150 | g | 0.75 | 27 | 14 | 2.8 | 1.53 | 48 | 11.8 | 0 | 10 | 40 |
| 15:47:30.230 | d | 0.8 | 27 | 19 | 2.6 | 0.94 | 70 | 12 | 0 | 10 | 55 |
| 15:47:33.090 | c | 0.83 | 27 | 14 | 2.9 | 1.53 | 60 | 12.6 | 0 | 10 | 58 |
| 15:47:36.280 | c | 0.85 | 27 | 14 | 3 | 1.53 | 45 | 13.1 | 0 | 10 | 47 |
| 15:47:39.580 | c | 0.86 | 27 | 12 | 3.1 | 1.76 | 31 | 13.3 | 0 | 10 | 45 |
| 15:47:42.990 | c | 0.87 | 27 | 12 | 3.2 | 1.76 | 16 | 13.5 | 0 | 10 | 40 |
| 15:47:46.510 | a | 0.87 | 28.4 | 11 | 3.3 | 2.05 | 4 | 13.5 | 0 | 10 | 10 |

Duration: 00:36.960 Average Bolus Viscosity: 56.79 Avg Cath Viscosity: 10.92

Avg Outcome Score: 49.64 Average Bolus Volume: 1.64 Volume: 22.89

*Fig. 26C*

| Time | AMC Mode | Time Const | P initial | P final | Valve Duration | Bolus Volume | Bolus Visc. | Cath Visc. | Damp | Bulk Mod | Outome Score |
|---|---|---|---|---|---|---|---|---|---|---|---|
| 15:54:58.510 | c | 0.4 | 27 | 8 | 1.8 | 2.24 | 14 | 6.2 | 0 | 10 | 40 |
| 15:55:00.490 | d | 0.42 | 27 | 14 | 1.5 | 1.53 | 28 | 7.5 | 0 | 10 | 52 |
| 15:55:02.140 | c | 0.48 | 27 | 12 | 1.6 | 1.76 | 49 | 8.3 | 0 | 10 | 65 |
| 15:55:03.900 | d | 0.53 | 27 | 12 | 1.6 | 1.76 | 72 | 9.5 | 0 | 10 | 73 |
| 15:55:05.660 | g | 0.57 | 27 | 16 | 1 | 1.29 | 60 | 9.9 | 0 | 10 | 45 |
| 15:55:06.760 | g | 0.6 | 27 | 14 | 1.5 | 1.53 | 50 | 10 | 0 | 10 | 55 |
| 15:55:08.410 | d | 0.63 | 27 | 18 | 1.25 | 1.06 | 105 | 11.7 | 0 | 10 | 70 |
| 15:55:09.785 | a | 0.4 | 28.5 | 14 | 1.6 | 1.71 | 120 | 11.8 | 0 | 10 | 40 |
| 15:55:11.545 | a | 0.8 | 28.5 | 19 | 1.2 | 1.12 | 120 | 12 | 0 | 10 | 55 |
| 15:55:12.865 | c | 0.8 | 27 | 14 | 1.5 | 1.53 | 60 | 12.6 | 0 | 10 | 58 |
| 15:55:14.515 | d | 0.85 | 27 | 14 | 1.5 | 1.53 | 45 | 13.1 | 0 | 10 | 47 |
| 15:55:16.165 | c | 0.86 | 27 | 12 | 1.5 | 1.76 | 31 | 13.3 | 0 | 10 | 45 |
| 15:55:17.815 | d | 0.87 | 27 | 12 | 1.5 | 1.76 | 12 | 13.5 | 0 | 10 | 40 |
| 15:55:19.465 | a | 0.87 | 28.5 | 11 | 2 | 2.06 | 6 | 13.5 | 0 | 10 | 10 |

Duration: 00:20.955 Average Bolus Viscosity: 55.14 Avg Cath Viscosity: 10.92
Avg Outcome Score: 49.64 Average Bolus Volume: 1.62 Volume: 22.65

Procedure Totals

Duration: 10:19.46 Average Bolus Viscosity: 59.57 Avg Cath Viscosity: 15.70
Avg Outcome Score: 47.67 Average Bolus Volume: 1.36 Volume: 158.70

Date: 1/1/2025 Clinic: *North Regional* Procudure: *Pulm. Emb.* Cath: *XY-123*
Patient: *Doe, John* Phys: *H. Wilkins, MD* Notes: *Routine* Case ID: *X123-VVAS-PE*

VISCO-VOLUMETRIC ASPIRATION SYSTEM AND METHODS

STATEMENT OF RELATED CASES

This case relates to U.S. patent application Ser. No. 17/409,635 filed Aug. 23, 2021, U.S. patent application Ser. No. 18/128,224 filed Mar. 30, 2023, U.S. patent application Ser. No. 18/380,784 filed Oct. 17, 2023, U.S. Pat. App. 63/640,180 filed Apr. 29, 2024, U.S. Pat. App. 63/702,051, filed Oct. 1, 2024, and U.S. Pat. App. 63/795,616, filed Apr. 27, 2025, all of which are incorporated by reference herein.

FIELD OF THE INVENTION

The present invention relates to thrombectomy, aspiration, viscometry, control systems, process optimization, flow visualization, measurement and control.

BACKGROUND INFORMATION

Many aspiration thrombectomy systems feature clear tubing, syringes and vacuum reservoirs so that the clinician may visually observe thrombus during and after aspiration. During the procedure, the clinician is provided a view of the size, composition, position, and speed of thrombus and/or blood as it passes through the clear tubing. Many systems feature a porous tray in the vacuum reservoir to separate aspirated thrombus from blood. Post-procedurally, the thrombus may be laid out on graph paper for photography and size estimation.

Some existing aspiration thrombectomy systems, particularly the evacuated-reservoir type, employ one or more pressure transducers and an on/off "vacuum" valve. An objective of existing control systems is to minimize blood loss by cycling the vacuum valve. Existing methods of determining when to open and close the vacuum valve include terms such as "system states," "flow states," "characteristic of flow," in terms of words, e.g., "free flow," "open flow," "occluded flow," "clot," "clog," etc. Exemplary of such evacuated-reservoir systems are those disclosed in U.S. Pat. Nos. 11,730,499; 11,227,712, 10,390,962, 12,156,667, and published U.S. Pat. App. 2024/0164800. A commercial example of an evacuated-reservoir type aspiration thrombectomy system is the Penumbra System® brand fully integrated mechanical thrombectomy system, available from Penumbra Inc, of Alameda, CA.

Certain prior-art aspiration thrombectomy systems utilize Artificial Intelligence/Machine Learning (AI/ML) algorithms to analyze pressure waveform data; the result of these analyses is a determination of one or more system state scores. Therein, pressure waveform data are typically parameterized, utilizing a number of feature extraction tools that break down a complex pressure waveform into a number of identifiable patterns. Example parameterization methods, referenced above, include both detecting and computing a significant number of identified, parameterized variables such as: mean absolute deviation, median pressure, start/ending distal pressure, median ending distal pressure, maximum absolute rebound pressure, etc.

Certain prior-art aspiration thrombectomy systems utilize a "system score" method comprising combinations of: (1) open scores, (2) occlusion scores, (3) escalate counts, (4) threshold scores, (5) flow states, (e.g. " . . . open flow state, an occluded flow state, and/or a partially occluded flow state."), and/or (6) geometric characteristics of the catheter (e.g., " . . . one or more of the system state scores are further based on one or more geometric characteristics of the aspiration catheter . . . "). As disclosed in the '800 reference: " . . . system score determination may be based on automatically identifying specific features from the detected pressure profiles, extracting pressure parameters . . . and calculating one or more system scores based on the pressure parameters of those features."

Thus, certain disclosed prior-art methods comprise:

(1) Identifying, detecting, parameterizing and machine-computing values for as many as 15 features (e.g., mean absolute deviation, median pressure, start/ending distal pressure, median ending distal pressure, maximum absolute rebound pressure, peak pressure levels, variance in pressure levels, maximum and minimum pressure differential windows, distal median at middle, pressure deviation, confidence intervals/multipliers, etc.).

1a) These methods comprise performing multiple computations upon pressure waveform data, identifying and extracting as many as approximately 15 machine-computed, numerical values, expressed as variable data (i.e., real or floating point numbers), (2) subjecting these machine-computed values to rule-based algorithms that increment, decrement and/or leave unchanged as many as 5 system state scores (e.g., open score, occlusion score, escalate count, etc.).

2a) these methods comprise transforming approximately 15 (floating point) numbers into a decision to increment and/or decrement as many as approximately 5 (integer) system state scores.

(3) " . . . operating, based on the determined system states, one or more of the valves . . . " These methods thereby determine the operation (e.g., opening and closing) of one or more valves by evaluating one or more system state scores.

Some existing (e.g., syringe-based) aspiration thrombectomy systems utilize flow-control mechanisms such as: (1) manually operated tubing clamps that "squeeze down" tubing to restrict flow rate, and/or (2) manually selectable stroke-limited syringe to control the volume of fluid aspirated. The clinician is charged with deciding when to squeeze down the tubing clamp and/or when to select full- or limited-stroke syringe cycles.

The aforementioned aspiration thrombectomy systems take very different approaches to solve at least one common problem: limit blood loss. Blood loss typically occurs when the distal end of a catheter is not within necessary proximity to a thrombus, and suction is applied to the proximal end of that same catheter. Blood loss is not the only serious complication of thrombectomy procedures; clogging or corking of a catheter (with excessive thrombus) is also a problem. A clogged catheter may require additional steps, such as removing and replacing the catheter or attempting to clear the obstruction. This can extend the overall duration of the medical procedure.

Two major problems with aspiration thrombectomy procedures are related to the flow within the catheter. When a catheter contains, and is ingesting, only pure blood, then the "flow state" may be inferred to be among a group of: "open flow," "free flow," etc. When a catheter is clogged (or nearly clogged), the "flow state" may be inferred to be among the group of: "clog," "clot," "occluded," etc.

SUMMARY OF THE INVENTION

Embodiments of the present invention address shortcomings of the prior art, including those disclosed above, and represent further developments to the inventor's aspiration thrombectomy systems. Co-pending U.S. patent application Ser. No. 17/409,635, Multi-Mode Viscometric Thrombectomy System, discloses viscometric measurements in aspiration thrombectomy systems utilizing a running peristaltic pump. Co-pending U.S. patent application Ser. No. 18/128,224, Time-Domain Viscometry, discloses improvements to viscometric measurements in thrombectomy systems utilizing a motion-controlled peristaltic pump and more advanced, linear mathematical models. Co-pending U.S. patent application Ser. No. 18/380,784, Knowledge-Based Thrombectomy System, discloses the integration of viscometric measurements into aspiration thrombectomy systems to utilize techniques including closed-loop feedback, multi-factor step response testing, Design of Experiments, etc., to systematically aspirate thrombus. Procedure log files were disclosed in the '784 application; novel improvements to procedure log files are disclosed herein. The present disclosure includes improvements to aspiration systems by incorporating volumetric measurements as well as expanding Time-Domain Viscometry to a more generalized form.

The present invention provides systems and methods for visco-volumetric aspiration ("VVA"), which solves many of the problems and shortcomings of the prior-art, as disclosed herein. Briefly, the descriptor "visco-volumetric aspiration" means withdrawing a finite volume of bodily tissue, herein a "bolus," from patient vasculature into the distal end a catheter, and determining any or all of the following properties of the bolus: (1) volume, (2) viscosity, (3) spatial location within the catheter. From a succession of these data, a catheter may be mathematically modelled as a linear array of discrete boluses of aspirate, each of measured volume and viscosity.

VVA paradigms are different from those of prior-art. Prior-art paradigms are evident both in disclosures and commercially-available products. In certain prior-art embodiments, a substantial number of pressure parameterizations (floating-point numbers) are analyzed to determine system state scores (integers). The system state score is correlated to a static database of responsive actions. These prior-art responsive actions are substantially variations of certain "operational states," i.e., proprietary sequences of changing valve states.

A contrasting example VVA paradigm is: an aspiration thrombectomy catheter contains a mixture of fluids and solids in a proportion at any instant in time. In cases where the proportion of fluids is increased, the flow rate through the catheter will be consequently increased. A logical conclusion is that if the measured flow rate increases, then the proportion of fluids increased. Conversely, in cases where the proportion of solids is increased, the flow rate through the catheter will be consequently decreased. Changes in the proportion result from a combination of the effects of clinical variables (e.g., procedure, thrombus type, morphology, etc.) and VVA system variables (e.g., vacuum level, valve timing, catheter position, etc.). Certain VVA embodiments quantitatively determine the proportion of fluids and solids within the catheter at certain time intervals; the proportion is typically changing with time. Thereby, certain VVA embodiments determine not only the current proportion within the catheter (i.e., catheter state), but the time history of catheter states leading up to the current catheter state.

Variable data instead of attribute data. A significant shortcoming of certain prior art thrombectomy systems is the use of attribute data (e.g., clogged or not clogged, occluded or not occluded, etc.), the determination of system scores (e.g., occlusion score=3, open score=1, escalate count=3, etc.) and the use of flow states (e.g., occluded flow, free flow, partially-occluded flow, etc.). By contrast, certain VVA embodiments utilize variable data, e.g., pressure, volume, time, length, etc.

Dimensional analysis and similarity. Certain principles of dimensional analysis and/or similarity are utilized in many VVA embodiments. In certain instances, VVA embodiments infer that, as an example, flow of a first fluid through a 3 Fr (1 mm diameter)×1 meter long catheter is similar to flow of second fluid through a 20 Fr (6.7 mm diameter)×0.45 meter long catheter. Certain VVA embodiments are thereby insensitive to scale or "geometric characteristics of the aspiration catheter."

The problem of blood loss in aspiration thrombectomy procedures is exacerbated by "geometric characteristics" and dimensional scaling effects associated with large-bore catheters (e.g., greater than approximately 8 Fr). For example, doubling the diameter of a catheter typically causes the flow rate to increase by approximately 16-fold. Flow rate does not scale linearly with catheter diameter; this lack of linear scalability is a problem for many prior-art embodiments. A consequence is that prior-art systems may require new training data sets for AI/ML algorithms that are specific to the "geometric characteristics" of each new catheter under development. Furthermore, the "geometric characteristics" of any catheter that is fluidically coupled to certain prior-art embodiments must substantially "match the geometric characteristics" of the parameterization model of the control algorithm that is selected in order to ensure valid performance. In contrast, certain VVA embodiments are typically any combination of scale-invariant, dimensionally robust, normalized and/or self-similar.

Certain prior art methods analyze raw pressure waveform by computing as many as 15 parameters. In contrast, certain VVA embodiments parameterize raw pressure waveform data with a key parameter: time. The inventor observed many prior-art attempts to characterize the contents of a catheter based upon a combination of words (e.g., "free flow," "restricted flow," "escalate count," etc.), as examples of attribute data. The inventor subsequently developed and disclosed methods to quantify the contents of a catheter in variable data terms which may be expressed in engineering units (e.g., viscosity in cP, flow rate in cc/second, etc.). A characteristic of these engineering units is that the fundamental physical quantities: mass [M], length [L] and time [T], are intermixed and raised to powers. For instance, volumetric flow rate (e.g., cc/second, liters per minute, etc.) has dimensions of $[L^3\ T^{-1}]$, pressure (e.g., Pa, psi, etc.) has dimensions of $[MLT^{-2}]$, and dynamic viscosity (e.g., cP, slug/(foot second), etc.) has dimensions of $[M\ L^{-1}\ T^{-1}]$. The inventor identified a key parameter that quantitatively characterizes certain properties of the fluid contents of a catheter: time; more specifically a time constant (t) as disclosed herein and in the references.

Certain VVA embodiments transform pressure data $[MLT^{-2}]$ into time data [T] as a parameter and/or variable, thereby eliminating the dimensions mass [M] and length [L] from the formulation. Aspiration catheters are commercially available in a broad range of diameters and lengths; a time-parameterized formulation eliminates the length [L] dimension. With length eliminated from the parameterization, certain aspects of VVA embodiments are substantially independent of either the length or the diameter of a catheter. Such aspects include, without limitation: control algorithms, historical data, mathematical models, calibrations, simulations, operational modes, etc. Certain VVA embodiments utilize mathematical models that are self-similar in time-domain response.

An intuitive perspective of a time constant (τ) is, for instance, the amount of time it takes for a finite volume (herein, a "bolus") of thrombus to traverse an arbitrary distance along a catheter. It doesn't matter if the catheter is large-bore or small-bore, long or short; under certain circumstances, if two time constants, for two VVA apparatuses are substantially equal, then the flows may be considered similar. Another intuitive perspective of a time constant (τ) is the length of time required to aspirate a certain volume of fluid. For instance, in order to aspirate 1 cc of fluid, it may take 1 second or it may take 4 seconds; again, measurement of this time is independent of catheter dimensions. As an example, under certain circumstances, if 1 second is required for 1 cc of water (at 1 cP viscosity) to flow through a catheter (of arbitrary dimensions); a valid inference is that, under the same conditions, then it "is expected to" require approximately 4 seconds for 1 cc of blood (at 4 cP viscosity) to be aspirated. Certain VVA embodiments measure system variables typically including pressure and time, and transform these data into measurements of volume and viscosity by way of a key parameter: a "time constant." It should be understood that the example definitions of a time constant are used herein in an illustrative, not restrictive, sense; alternative definitions of time constants may be applicable in other embodiments.

Measurement and/or determination of a time constant effectively "unlocks" many derived variables including catheter viscosity, bolus viscosity, flow rate, etc. Herein, emphasis is placed upon measurement of a time constant, because many derived variables may be computed from this key parameter (τ). Derived variables may be expressed in engineering units, or any other metric(s) or descriptor(s). In certain VVA embodiments, principles including dimensional analysis are used to eliminate length dimensions, time is selected as the system parameter, and similarity is utilized further reduce the size of the data set. Thereby, many VVA embodiments feature less complex experimentation with universality of results.

Consequently, certain VVA control algorithms are typically scale-agnostic, dimensionally normalized, and parameterized based upon similarity criteria. Furthermore, certain VVA algorithms incorporate certain governing equations of fluid mechanics, constitutive equations of solid mechanics, state and/or rate equations of many branches of physics, etc., acting as mathematical models of physical systems. In certain VVA embodiments, measurement data and mathematical models are formally coupled. In this context, formally coupled means that two or more pressure measurements, obtained at two or more times, are fitted to a mathematical model that characterizes time-dependent response of the apparatus. This formal coupling enables reliable inference of system variables from sparse data; as a result, one or more key parameters (e.g., a time constant) may be extracted efficiently using minimal input data.

Prior-art methods disclose one or more system scores utilized to determine a system state; one of these system states may be a flow state (e.g., free-flow, occluded-flow, partially-occluded flow, etc.). In a VVA paradigm, any flow rate or flow state is highly dependent upon variables including differential pressure, catheter diameter, fluid viscosity, hydraulic transients, etc. As an example, consider a 3 Fr (i.e., 1 mm diameter)×2 m length catheter containing blood at approximately 4 cP; the flow rate is highly dependent upon the differential pressure at opposite ends of a catheter. For instance, if the differential pressure is 28 inHg, the corresponding flow rate is calculated to be approximately 0.291 cc/second; at 25 inHg the corresponding flow rate is approximately 0.260 cc/second; at 20 inHg the corresponding flow rate is approximately 0.208 cc/second, and at 5 inHg the corresponding flow rate is approximately 0.062 cc/second. Same catheter, same fluid, yet the example calculations provide four solutions for flow rate, based upon four values of differential pressure. In contrast to prior-art, certain VVAS embodiments directly measure a pressure state and utilize certain governing, rate and/or state equations to quantify the flow rate.

Fluid-based paradigms and/or mathematical formulations. In certain VVA embodiments, certain physical properties of the fluid within the catheter are determined. This highlights a significant distinction and improvement over prior-art that determines system states and/or flow states; in these prior-art systems, the state of the apparatus is determined. Certain VVA embodiments determine certain physical properties, and/or corresponding spatial locations, of the fluid(s) within the catheter, and a corresponding real-time mathematical model may be updated with as-measured data. In part because the flow rate of the fluid within the catheter may be controlled (e.g., by changing the differential pressure, catheter diameter, etc.), the VVA paradigm focuses upon the fluid, rather than the flow, as in typical of prior-art paradigms. The prior-art determines a system state of an apparatus. In contrast, certain VVA embodiments determine multiple derived variables that, collectively and/or individually, mathematically model and/or "map" the fluid within an aspiration catheter in real time.

Aspiration Measurement Cycles (AMC or AMCs). Certain VVA embodiments use Aspiration Measurement Cycles that typically comprise:

(1) Initiating and stopping flow within a catheter, e.g., opening and closing a vacuum valve; a finite volume (i.e., a bolus) of aspirate is drawn into the catheter, through the tip.

(2) Measuring, calculating or otherwise determining variables such as: bolus volume, catheter viscosity, bolus viscosity, time constant, etc.

In certain VVA embodiments, these variables may be determined by: (1) the initial pressure, (2) the final pressure, and (3) the time required for the initial pressure to "decay" to the final pressure. Certain VVA embodiments select, prescribe, or otherwise predetermine the initial and final pressures of certain AMCs; measuring the amount of time required for pressure decay is a method of determining a time constant for that AMC. In certain AMC modes, the initial and final pressures are prescribed or predetermined; regardless of the time required, a finite volume of fluid is concurrently aspirated. A relevant definition of flow rate may be obtained by dividing the finite volume of fluid aspirated by the period of time required.

A catheter model/data array. In certain VVA embodiments, data from successive AMCs are written to a catheter model/data array that corresponds to a catheter model (i.e., the physical contents of a catheter). In this context, "corresponds" means that, for instance, the first data element(s) of catheter model/data array correspond to the first bolus (i.e. entering bolus) of fluid in the catheter (see FIG. 19). In certain cases, the first bolus, or entering bolus, is the distal-most bolus within the catheter. Thereby, certain VVA embodiments not only determine the volume and viscosity of each entering bolus, but also infer that the position of each entering bolus is at the distal end of the catheter.

The inventor observed that: "all clogs start at the catheter tip" or more precisely, flow variabilities within the catheter typically originate upon entry of thrombus into the catheter through the tip. If no thrombus enters the catheter at any time during a thrombectomy procedure, then no flow variabilities are likely to arise. Such flow variabilities include: reduced flow rate, clogging, corking, "occlusion score≠0," reduced vacuum levels at distal portions of the catheter, etc. This highlights a significance of the catheter model/data array, because if "all clogs start at the catheter tip" then the catheter model/data array enables certain VVA embodiments to "immediately" detect potential clogs as thrombotic masses enter the catheter through the tip. In other words, each bolus of aspirate is evaluated for a propensity to clog a catheter as it enters the catheter; and each bolus is "tracked" in real time from the distal to proximal ends of the catheter.

In some VVA embodiments, the catheter model/data array is utilized to generate real-time, dynamic visualization of the contents of the catheter. In some VVA embodiments, dynamic visualization comprises displaying the viscosity or "thrombus load" vs. position along the catheter in real-time (see FIG. 21). In some VVA embodiments, dynamic visualization comprises displaying the vacuum level vs. position along the catheter in real-time (see FIGS. 11A, 11B).

Computational Fluid Dynamics. Aspects of the present invention comprise a non-iterative, one-dimensional Computational Fluid Dynamics (CFD) algorithm that solves for derived variables including, but not limited to: volume, viscosity, flow rate, pressure/viscosity distribution within a catheter, etc. Functional VVA algorithms may be implemented in as few as 50 lines of source code. As an example, certain VVA embodiments comprise an Arduino® single board computer, an evacuated reservoir, a pressure transducer, a length of elastic tubing and two electromagnetic valves. Catheters of substantially any dimension (diameter range of approximately 0.5 mm to 20 mm, and length range of approximately 10 cm to 500 cm) may be connected to typical VVA systems without substantial revision of typical VVA control algorithms. Fluids of substantially any viscosity (range of less than 1 cP to in excess of 10,000 cP) may be aspirated and measured without substantial revision of typical VVA control algorithms. Many control algorithms utilized in typical VVA embodiments and/or methods are compact, robust, accurate, precise, efficient, and scalable.

Simulations. In certain instances of a catheter model/data array, as-measured data are written to the array; this is called a current instance of catheter model/data array. Alternatively, simulation or synthetic data may be written to simulation instances of a catheter model/data array. Thereby, certain VVA embodiments compute one or more simulations that "project into the future," "expect," "anticipate" and/or "predict" the results of upcoming AMCs. In certain instances, these simulations are extrapolations (e.g., linear- or curvilinear-regression, trend-line analysis, etc.). VVA simulations comprising extrapolation methods may be utilized in certain VVA embodiments to anticipate and avert adverse events such as clogging or corking a catheter, excessive blood loss, etc.

An example method of generating synthetic data for simulations is linear extrapolation of the current catheter viscosity ($\mu_{current}$ or $\mu_0$), from the previous four measurements (e.g., $\mu_{-3}=10$, $\mu_{-2}=20$, $\mu_{-1}=30$, $\mu_0=40$), to calculate "expectation values" of the next four measurements (e.g., $<\mu_{+1}>=50$, $<\mu_{+2}>=60$, $<\mu_{+3}>=70$, $<\mu_{+4}>=80$, etc.); where values in <angle brackets> are expectation values. Certain VVA embodiments compare one or more expectation values against threshold values for variables such as: catheter viscosity, entering bolus viscosity, blood loss, etc. Certain VVA embodiments are thereby enabled to "detect," "predict," "anticipate," "expect," and/or "avert" potential clogs before the clogging material enters the catheter. From the example above, a VVA embodiment may impose a threshold value for catheter viscosity of 75 cP (i.e., $<\mu_{current}>>75$ cP); this threshold is "expected" to be reached in the fourth iteration of the simulation (e.g., $<\mu_{+4}>=80$). Certain VVA embodiments consequently invoke certain responsive actions including, but not limited to: dilution, pressure pulse, pulse trains, repositioning and/or reconfiguring catheter, make/break contact methods, etc. to avert the potential clog.

Thrombus model matrix. Certain VVA embodiments and/or methods utilize mathematical modelling methods to generate synthetic data, and further compute one or more simulation instances of catheter model/data array. Among the mathematical models utilized to generate synthetic data for simulation is a thrombus model matrix (see FIG. 25). A typical VVA thrombus model matrix categorizes thrombus (a clinical variable) by characteristics including, but not limited to: (1) procedure type, (2) thrombus morphology, (3) thrombus physical properties, and (4) anticipated thrombus volume. As an example, an aspiration thrombectomy procedure may be a Deep Vein Thrombosis (DVT) of the popliteal vein. From an example VVA thrombus model matrix, the thrombus morphology is "expected to be fresh"; the physical properties of the thrombus "are expected to be elastic and adhesive;" the anticipated thrombus volume "is expected to range between 20 cc and 40 cc." These clinical data (to the left) are correlated to VVA system variable data (to the right) in certain instances of a thrombus model matrix. Among other functions, a thrombus model matrix may be utilized to supply input data to VVA algorithms and/or simulations. In this function, thrombus model matrix comprises data utilized for operations and/or functions including, but not limited to: selecting AMC modes, vacuum levels, anticipating procedure endpoints, changing or adapting threshold values, etc.

Prescribed AMC modes, expectation values and outcome scores. Certain VVA embodiments prescribe one or more upcoming AMC modes. In some cases, prescribing an AMC mode means selecting a machine state, initial and final pressures, initial and final volumes, and in certain instances, calculating an expectation value of the amount of time required. But the expectation value for time is dependent upon an expectation value for the viscosity of the entering bolus. In cases wherein the measured viscosity of an entering bolus exceeds the expectation value for viscosity, then the time required typically exceeds the expectation value for time. Certain prescribed AMC modes "anticipate," "predict" or otherwise determine an expectation value for viscosity of an entering bolus. Certain VVA embodiments compute one or more simulations that provide machine-computed expectation values for one or more upcoming AMCs.

Certain VVA embodiments define one or more outcome scores for AMCs. Presented as an example and not limitation, an outcome score may be based upon thrombus harvested in an AMC. In this example, aspirating substantially pure blood may be scored a 5 or 10 out of 100, for reasons including that the catheter did not clog. A corresponding example outcome score for an AMC aspirating a 1 cc bolus of 80 cP viscosity may be scored a 75 or 80, for reasons including that viscous thrombus was aspirated.

In certain instances, prescribed AMC modes are based upon expectation values for volume, viscosity and time for an "anticipated" entering bolus. Upon execution of that prescribed AMC mode, measurement data may be quantitatively assessed against the expectation values. Alternative definitions of outcome scores are based upon the accuracy or fidelity of measurement data to expectation values. As an example, a prescribed AMC mode may be to aspirate 1 cc of substantially pure blood, for instance to dilute the contents of the catheter, increase the flow rate and decrease the clog risk. In this example case, successful aspiration of 1 cc of substantially pure blood may be assigned an outcome score of 100, because the as-measured data substantially match the prescribed, anticipated and/or desired result.

Physically-meaningful and/or intuitive variables/success metrics and corresponding threshold values. Many VVA embodiments parameterize raw pressure waveform data and determine a time constant. This enables computation of derived variables including, but not limited to: catheter viscosity, bolus viscosity, pressure distribution, flow rate, etc. Physically-meaningful threshold values (e.g., 30 cP, 0.1 cc/sec, 50%, etc.) may be determined for physically-meaningful variables (e.g., catheter viscosity, bolus viscosity, flow rate, clog risk, etc.) by any combination of logic- or data-driven factors.

Instances of catheter model/data array enable certain VVA embodiments and/or methods to additively determine cumulative effects of all boluses, and the collective risk of clogging a catheter. For instance, certain VVA embodiments define and calculate an intuitive success metric "clog risk." For instance, a numerical value for clog risk may be obtained by computed by adding, summing and/or integrating the viscous contribution of each bolus "currently" in the catheter. It should be understood that the example definitions and methods of determining success metrics including, but not limited to clog risk, are used herein in an illustrative, not restrictive, sense. Alternative definitions of success metrics may be utilized in other VVA embodiments. Certain VVA embodiments compare success metrics against one or more threshold values to trigger responsive actions; threshold values may be any combination of fixed, user-adjustable, dynamically updated, or adapted based on patient-specific data, clinical context, or risk evaluation. In cases wherein one or more threshold values is/are exceeded, certain VVA embodiments enact responsive actions comprising any of multiple counter-measures including, but not limited to: repositioning and/or reconfiguring a catheter, dilution, pressure pulses, pulse trains, make/break contact, etc.

Threshold values for derived variables and/or success metrics, e.g., catheter viscosity, bolus viscosity, clog risk, etc., may be procedure and/or patient specific. As an example, threshold values for clog risk may be reduced for less-healthy patients that may not tolerate or survive extended procedures and additional blood loss. As another example, a threshold clog risk value may be adjusted throughout a lengthy procedure such as a massive pulmonary embolism. From a VVA thrombus model matrix 2501 (see FIG. 25), a range of approximately <100 cc to 300+cc of "organized," "elastic to firm" thrombus "is expected to be aspirated." Certain VVA embodiments prioritize a clog at 50 cc of aspirate harvested to be a more adverse outcome than a clog at 290+cc of aspirate harvested. This is an example of terminal state optimization and/or risk-benefit logic; the acceptable risk thresholds shift as the procedure endpoint nears. Certain VVA embodiments adapt and/or change threshold values for derived variables and/or success metrics that are specific for procedure variables and/or parameters including, but not limited to: patient, procedure, progress to endpoint, blood loss, etc.

Variable and maximum-attainable vacuum levels. Many prior-art aspiration systems have the inherent limitation that the vacuum level (e.g., within a vacuum reservoir) remains at a substantially constant value (e.g., 27.5 inHg, 26.9 inHg, etc.) while in operation. Each instance of opening a vacuum valve fluidically couples a proximal end of a connecting tube to a characteristic vacuum level (e.g., 27.5 inHg). That characteristic vacuum level is substantially constant during operation of the apparatus. Each instance of closing the vacuum valve causes the flow of aspirate to stop; the pressure within the connecting tube typically tends toward a reference pressure (e.g., intravascular pressure, atmospheric pressure, etc.).

Certain VVA embodiments feature AMC modes wherein initial and final pressures are prescribed or predetermined. This is significant, not only because vacuum levels are utilized as a VVA system variable, but also because the certain VVA embodiments are enabled to generate "maximum-attainable" vacuum levels. In this context, maximum-attainable vacuum levels are equilibrium pressures referenced to a vapor pressure of one or more working fluids (e.g., saline, blood, plasma, oils, alcohols, etc.). Certain VVA embodiments and/or methods may generate vacuum levels sufficient to "boil" one or more working fluids, and in doing so generate vacuum levels herein termed maximum-attainable. In many instances, the presence of water vapor evolving from evaporation of blood components is indicative of a maximum-attainable vacuum level (see FIGS. 6B and 6C).

Herein, the vapor pressure of water at 37° C. is a reference pressure taken to be approximately 6,280 Pa≈1.85 inHg in absolute pressure units. Adopting the standard atmospheric reference pressure of 29.92 inHg, an example definition of maximum-attainable vacuum level under equilibrium conditions is (29.92 inHg−1.85 inHg=28.07 inHg). It should be understood that the example definition of "maximum-attainable vacuum" is used to describe an equilibrium pressure state herein in an illustrative, not restrictive, sense; alternative definitions may be applicable in other embodiments and/or methods. It is important to note that maximum-attainable vacuum levels are AMC mode-specific, and that maximum fluid acceleration and differential pressures are typically "instantaneously" generated upon opening the vacuum valve. Only certain AMC modes are prescribed with maximum-attainable vacuum levels; in other AMC modes, lesser vacuum levels (e.g., 26 inHg, 23 inHg, 17 inHg, etc.) are prescribed, and/or preferred as initial pressures.

In the VVA paradigm, wherein time is a key parameter, the rate at which certain events occur—including flow rate—is of particular significance. An example is averting excessive blood loss; in cases where the contents of a catheter contains substantially pure blood, certain AMC modes act to reduce the aspiration rate for reasons including blood conservation, thrombus-seeking AMC modes, etc. Examples of AMC modes that reduce the aspiration rate include reduced initial pressure, damping, rapid timing of a vacuum valve, pulse trains, etc. In certain other situations, certain VVA flow events occur "too slowly." Examples include a catheter in a "partially-occluded state," an impending clog, a thrombus-laden catheter, clog-risk values exceeding thresholds, etc. In such cases, certain AMC modes effectively increase the aspiration rate for reasons including clog-aversion, aspiration of certain thrombus types and morphologies, etc. Example VVA AMC responsive actions for low catheter flow rates include: dilution, pressure pulse, pulse train, maximum-attainable vacuum, repositioning/reconfiguring catheter, make/break contact methods, etc.

Valve "noise" and "clean" data. A problem with many prior-art aspiration thrombectomy is "noise" generated by electromagnetic valves. In this context, valve noise refers to the repeatable pressure disturbances that occur with each opening and closing of a typical valve, consisting of phenomena such as hydraulic transients, acoustic wave propagation, water hammer, pressure dips, and/or oscillatory ringing. In many cases, meaningful data analysis cannot occur until transient effects have subsided. This highlights a benefit of certain VVA embodiments: by operating at reduced vacuum levels, flow rates are correspondingly reduced, and valves may remain open for longer durations. By reducing the frequency of valve actuation, certain VVA embodiments increase the proportion of high-integrity pressure data, and decrease the proportion and impact of transient disturbances associated with each change of valve state.

Closing a vacuum valve typically induces a static equilibrium state (i.e., flow stops, pressures equilibrate, etc.); a pressure discontinuity or "jump" may exist "across" the valve (see FIG. 1C). This is an example of a boundary condition of fluid mechanics. At times when the valve is in the closed state, there is no flow across the boundary, and a pressure discontinuity may exist. At times when the valve is in the open state, there may be flow across the boundary, and a pressure discontinuity typically does not exist (i.e., there is substantially zero differential pressure across an "ideal" valve). When the valve state is changed (i.e., from open to closed, and closed to open), transient disturbances in pressure waveform data are a consequence of phenomena including rapid fluid acceleration/deceleration, pressure equilibration across the boundary, etc. Certain VVA embodiments control the flow of aspirate by means other than changing the state of the vacuum valve alone. This typically generates cleaner pressure waveform data, in part because the boundary condition at the vacuum valve is not changed as data are collected. Pressure(s) within certain VVA embodiments is (are) changed to thereby control flow of fluid through the catheter. For reasons including improved data quality, certain VVA embodiments include AMC modes that, among other functions (1) operate at reduced vacuum levels and corresponding flow rates, (2) reduce the frequency of valve actuation, and/or (3) control the flow rate by means other than a actuating a vacuum valve alone.

In the VVA paradigm, changing a vacuum valve state generates noise in the pressure waveform. This is in stark contrast to certain prior-art (e.g., published U.S. Pat. App. 2024/0164800). Therein a prior-art apparatus is disclosed to ". . . operate . . . valves . . . to generate . . . changes in . . . pressure levels . . . " and subsequently ". . . changes in the detected pressure levels are correlated with the . . . generated changes in pressure levels." The apparatus (1) operates valves to generate changes in the pressure levels, (2) detects the changes in the pressure levels, and (3) correlates the changes in the pressure levels with operation of the valves; the same valve operation that generated the changes in the pressure levels in step (1). From this prior-art disclosure, it is evident that if the valves are not operated, then detected changes in pressure levels of the fluid are not correlated to anything.

In these prior art systems and methods, changing the state of the valve generates changes in pressure levels; and thereby generates data for analysis. Further disclosed in the '800 application are pulse sequences (e.g., valve operational states), wherein the vacuum valve is cycled in a characteristic pattern. Pulse sequences generate the necessary changes in pressure levels for correlation in these embodiments. These prior-art systems essentially "send a physical signal to the fluid" by operating valves, "receive a pressure signal from the fluid" and correlate the physical signal sent to the pressure signal received. Thereafter, a correlation between a valve actuation and a pressure disturbance is utilized to determine a system state score by an opaque algorithm.

In certain VVA embodiments, changing the valve state generates noise; data for analysis are collected substantially after and/or between changes of valve state. In certain prior-art systems, when the vacuum valve is in the open state, the system tends toward a dynamic equilibrium state at uncontrolled, i.e., maximum, flow rate. In certain VVA embodiments, when the vacuum valve is in the open state, the system tends toward a static equilibrium state at a characteristic rate. Measurement of the characteristic rate occurs substantially after changing the vacuum valve to the open state and valve noise has subsided. In certain VVA embodiments, derived variables, e.g., flow rate, catheter viscosity, bolus viscosity, etc., are computed utilizing algebraic expressions in closed form (e.g., Eq. 8, Eq. 9, etc.).

Non-contact thrombus detection. Certain VVA embodiments feature non-contact thrombus detection. As the tip of a catheter approaches a thrombotic mass, flow variabilities may be detected as aspirate inflow is disturbed, restricted, occluded or otherwise affected (see FIGS. 16A-16E). The range of non-contact thrombus detection is between approximately 0 and 3 catheter diameters away from a thrombotic mass. In addition to detecting and averting clogs before they happen, certain VVA embodiments are enabled to detect and/or measure the proximity to a thrombotic mass before physical contact with the catheter tip is established.

Bolus patterns and thrombus type identification. Certain VVA embodiments feature dynamic visualization of fluid properties within a catheter (see FIG. 21). Several representative Bolus Patterns are depicted in FIG. 22. Many bolus patterns comprise one or more identifiable features (e.g., peaks, valleys, rise-times, slopes, inflection points, plateaus, etc.); each identifiable feature serves as a functional signature or "fingerprint" of each thrombotic mass that is aspirated.

It should be noted that certain VVA embodiments parameterize derived variables (e.g., catheter viscosity, bolus viscosity, bolus volume, bolus position, flow rate, etc.); this is entirely distinct from prior-art embodiments that parameterize raw pressure waveform data. Certain VVA embodiments first calculate certain derived variables, and then parameterize those derived variables with respect to time and/or spatial location.

In certain VVA embodiments, bolus patterns are parameterized and analyzed for identifiable features including, but not limited to: "shapes", slopes, peaks, valleys, rise times, amplitudes, plateaus, etc., thus characterizing the thrombus within the catheter. Example shapes include statistical distributions such as Gaussian, Student's T, chi-squared, bimodal, polynomial, Weibull, exponential, log-normal, etc. In certain VVA embodiments, parameterized (i.e. mathematically expressed or modeled) bolus patterns are compiled and correlated to clinical variables including, but not limited to procedure type, thrombus morphology, physical properties, volume, etc. This is in contrast to certain prior art, wherein parameterized raw pressure waveform data are compiled to generate a database of mathematical models of pressure waveforms. These prior-art mathematical models of pressure waveforms are correlated to system state scores, e.g., open score, occlusion score, escalate count, etc., expressed in integer-valued terms, i.e., 0, 1, 2, . . . 7, i.e., attribute data.

Certain thrombus types and/or morphologies (e.g., fresh, soft, elastic, cohesive, etc.) may tend to conform to a catheter tip, forming something akin to a seal. Certain VVA embodiments may detect and identify this sealing thrombus type, for instance because fresh thrombus "immediately" conforms to the catheter tip and forms a seal. In certain instances, fresh, elastic thrombus may be identified by rapid increase in viscosity; this may be for reasons including that the thrombus is: (1) soft and conforming, and/or (2) cohesive and does not readily separate from itself. Certain VVA embodiments subsequently infer that bolus patterns exhibiting a rapid increase (i.e., greater values of slope) in viscosity is characteristic of a soft, conforming, cohesive, "sealing" thrombus.

Other thrombus types and/or morphologies (e.g., organized, fibrotic, firm, brittle, etc.) may tend to agglomerate at or near the catheter tip, forming something akin to a filter. This agglomeration of thrombus may be comprised of blood components including macromolecules such as: fibrin, fibrinogen, hemoglobin, albumin, white-blood cells, etc. This in-situ agglomeration may impede passage of other macromolecules, while admitting passage of smaller molecules and/or aqueous solutions. In certain VVA embodiments, thrombus types such as organized, fibrotic, calcified, etc. may be identified by bolus patterns exhibiting a gradual increase in viscosity, for instance because lower-molecular weight molecules pass through an agglomerated thrombus of growing size and diminishing flow. Certain VVA embodiments may detect and identify this filtering thrombus type, for instance because fibrotic thrombus "builds up" a porous barrier that is increasingly restrictive over time. Certain VVA embodiments subsequently infer that a gradual increase (i.e., lesser values of slope) in viscosity is characteristic of organized, fibrotic, "filtering" thrombus.

Dilution. Certain VVA embodiments comprise any one or more of: (1) determining a current viscosity of the catheter, (2) determining a viscosity of a current entering bolus, (3) determining an expectation value for the viscosity of a next entering bolus, (4) determining a likelihood that the next entering bolus will result in a threshold value being exceeded, and (5) enacting one or more responsive actions (e.g., reposition and/or reconfigure catheter, make/break contact, etc.) to aspirate substantially pure blood. Certain VVA embodiments comprise dilution of the fluid contents of the catheter, for instance to increase flow rate and/or to reduce the likelihood of clogging. In certain instances, the diluent is substantially pure blood; in certain instances, the diluent is saline, i.e., saline flush.

It is acknowledged that "dilution" of a catheter with substantially pure blood (during certain portions of an aspiration thrombectomy procedure) may seem counter-intuitive in a paradigm wherein blood loss is typically undesirable. But that intuition does not consider that, in certain cases, the viscosities of fluids within the catheter affect the pressure distribution within the catheter. Intuition and prior-art methods may consequently focus upon increasing the vacuum level (e.g., 27.5 inHg, 28.0 inHg, etc.) at the vacuum reservoir for maximum thrombus aspiration efficacy. Certain VVA embodiments and methods act to increase the vacuum level (e.g., 5 inHg, 7.5 inHg, etc.) at or near the distal end of the catheter for maximum thrombus aspiration efficacy. It is important to note that certain VVA embodiments that utilize dilution typically evaluate current data against one or more threshold criteria (e.g., clog risk, catheter viscosity, bolus viscosity, etc.) as a condition for certain dilution AMC modes to be prescribed and/or executed.

Make/Break contact methods and/or techniques. One method of invoking dilution (e.g., aspirating substantially pure blood) is to manually withdraw or retract the catheter tip such as by manipulating the proximal end of the catheter. Of course, manipulating and withdrawing a catheter is a routine procedural technique. However, certain VVA embodiments determine appropriate times to withdraw the catheter and dilute with blood, and appropriate times to advance the catheter and aspirate thrombus.

Certain VVA embodiments include any one or more of the following features: dilution, thrombus characterization, clog risk assessment, etc., and methods. Thereby, certain VVA embodiments are enabled to intermittently invoke dilution interspersed with intermittently contacting and aspirating thrombus. Objectives of these methods and/or techniques include: (1) Limiting the viscosity of the catheter, which typically decreases the clog risk and increases the flow rate. (2) Sequential disintegration of larger thrombi into smaller thrombotic masses; these smaller thrombotic masses are segregated from one another to minimize agglomeration within the catheter (see FIG. 9F). (3) Minimizing the risk of a "sudden" or "immediate" clogging or corking of the catheter; certain VVA embodiments detect "abnormally large" "abnormally high?" viscosity of entering bolus (e.g., exceeding 1,000 cP, $\mu_0/\mu_{-1} \geq$ user-defined parameter, etc.). In certain instances, VVA embodiments implement and/or execute make/break methods to avoid clogging the catheter. Subsequent AMC modes may be prescribed to perform functions, operations including, but not limited to: disintegration, aspiration, and/or characterization of the thrombus that did not clog the catheter.

Procedure log files (previously disclosed in the inventor's co-pending '784 application). Certain VVA procedure log files include formal parameterization of the spatial geometry of the catheter and other improvements. In many instances, procedure log files comprise data including, but not limited to: viscosity, volume, pressure, time, AMC mode, outcome score, etc. Certain instances of VVA procedure log files are significant because sufficient data are stored to analyze and/or recreate any or all of the following: dynamic visualizations, thrombus type characterization, AMC mode efficacy, assessing AMC mode selection, changing/adapting threshold values, assessing computed simulations, etc. Certain embodiments of VVA procedure log files are significant because any dynamic visualizations that were available in real-time during the procedure, are typically preserved and will be available to be recreated in the future. Many VVA embodiments comprise compiling multiple procedure log files, from multiple VVA apparatuses, such as in a database/compiler/server. These compiled data may be collectively analyzed; the data may be segmented into subgroups (i.e., procedure type, thrombus morphology, thrombus physical properties, device and/or apparatus type, etc.). Compiled data from VVA procedure log files may be analyzed for VVA control algorithm development; this may result in changes or modifications to system parameters including, but not limited to: threshold values, outcome score determination, arbitrary and/or user-defined constants, VVA control algorithms, historical data base(s), etc.

Further distinctions. Typical prior-art aspiration thrombectomy systems are substantially isovolumetric in operation; the volume of fluid (e.g., blood, saline, thrombus, etc.) contained within the apparatus is substantially constant in time. In contrast, typical VVA embodiments comprise one or more non-isovolumetric components and/or elements. In certain embodiments, the internal volume of a VVA apparatus changes with time. In many cases, flow of aspirate (e.g., blood, saline, thrombus, etc.) into and through a catheter is dynamically coupled to the time rate of change of the volume of the VVA apparatus. The rate of change of the volume of a VVA apparatus is, in certain cases, substantially equal to the volumetric flow rate of aspirate through the catheter.

States: machine, equilibrium and thermodynamic. The VVA paradigm defines "states" (e.g., valve state, machine state, equilibrium state, volumetric state, pressure state, apparatus state, etc.) that may be readily distinguished from the prior art definitions of "states" (e.g., system state, operational state, flow state, occlusion state, free-flow state, etc.). Herein, a valve state may be either "open" or "closed." An actuator (e.g., displacement mechanism of FIGS. 2A-2C, damping mechanism of FIGS. 15A-15D, etc.) state defines the position of a movable component along a bounded range, including a first limit state (e.g., open, up, etc.), a second limit state (e.g., closed, down, etc.) and, in certain cases, any intermediate value in therebetween. Volumetric states and pressure states are thermodynamic states that characterize the condition of a system by defining its volume-related and pressure-related properties, respectively. It is important to note that the pressure state and the volumetric state of a system may, in certain cases, be inter-related by an "equation of state" or a "state equation." Certain VVA embodiments measure a pressure state and, using an equation of state, calculate a corresponding volumetric state, thereby determining two thermodynamic states from a single measurement.

An equilibrium state is a condition in which system variables remain substantially constant over time in the absence of external disturbance, including: (i) a static equilibrium state, in which there is no net motion or flow within the system; and (ii) a dynamic equilibrium state, in which opposing flows or forces are balanced such that overall system variables remain steady despite ongoing internal movement. A machine state is defined as a combination of valve states and actuator states, wherein each of a plurality of valves and/or actuators is independently settable to a discrete state. A catheter state is defined as one or more quantitative determinations of one or more physical properties of the fluid within a catheter; examples include: viscosity, volume, pressure, spatial location, etc. An apparatus state is defined as comprising any or all of: machine state, volumetric state, pressure state, equilibrium state, catheter state.

Typical prior-art aspiration thrombectomy systems are operable in two machine states: a first state when the vacuum valve is closed (closed state) and a second state when the vacuum valve is open (open state). When the vacuum valve is in the closed state, fluid within the apparatus rapidly attains a state of static equilibrium (range of approximately Oms to 100 ms). When the vacuum valve is changed to the open state, fluid within the apparatus accelerates toward a characteristic terminal or maximum velocity. While the vacuum valve is in the open state, the prior-art apparatus typically tends toward a state of dynamic equilibrium, tending toward a substantially maximum fluid flow rate.

Many prior art aspiration thrombectomy embodiments comprise steps such as: (1) attaining an "alpha" static equilibrium state (i.e., substantially zero flow rate) while the vacuum valve is closed, (2) tending toward a dynamic equilibrium state (i.e., substantially maximum flow rate) while the vacuum valve is open, and (3) attaining an "omega" static equilibrium state upon closing the vacuum valve. Subsequently, the omega static equilibrium state becomes the alpha static equilibrium state of the successive valve cycle; the alpha and omega static equilibrium states of prior art are typically indistinguishable. A static equilibrium state, of prior-art aspiration thrombectomy systems, typically exists in any combination of two distinct cases (1) when the apparatus is clogged, and (2) when the vacuum valve is in the closed state.

In contrast, typical VVA embodiments comprise steps such as: (1) attaining a first static equilibrium state while the vacuum valve is closed, (2*) tending toward a second static equilibrium state at a characteristic rate while the vacuum valve is open, and (3) attaining a third static equilibrium state upon closing the vacuum valve. In this context, "tending toward an equilibrium state" means that fluid within the apparatus is accelerating/decelerating toward a characteristic velocity (e.g., zero, "terminal," "maximum," "mathematically modeled," etc.). Step (2*) is significant because certain VVA embodiments tend toward a static equilibrium state; this is distinct from step (2) of prior art, wherein an apparatus tends toward a dynamic equilibrium state. In certain instances, the first static equilibrium state, the second static equilibrium state, and/or the third static equilibrium states may be indistinguishable (i.e., substantially equal pressure and volumetric states).

Step (2*) of the above VVA sequence, tending toward a second static equilibrium state, is significant for reasons including: first, the second static equilibrium state is typically attained upon transfer of a corresponding, finite volume of fluid into the VVA apparatus through the catheter; this fluid transfer occurs at a characteristic rate. And second, determining a characteristic rate at which a VVA apparatus tends toward a static equilibrium state is a means of determining derived variables including, but not limited to: catheter viscosity, bolus viscosity, flow rate, etc. The characteristic rate at which certain VVA embodiments tend toward a static equilibrium state may be quantified by the time constant, t. There is no implication or requirement that any equilibrium state is attained; certain valuable data lie in the characteristic rate at which an apparatus tends toward an equilibrium state. Once this characteristic rate is determined, the timing for vacuum valve closure may either remain fixed or dynamically updated with, for instance, as-measured data.

Adopt first principles, first. Certain VVA embodiments utilize first principles of physics (state equations, constitutive equations, governing equations, rate equations, conservation laws, etc.) in apparatus design specifications as well as control algorithms. In many VVA embodiments, pressure waveform data are mathematically transformed, before performing parameterization and analysis. Certain VVA embodiments determine system behavior from invariant physical laws rather than from empirical data subject to substantial fluctuation, thereby avoiding the need for numerous calculations to parameterize those fluctuations. Certain VVA embodiments utilize conservation laws (e.g., mass, momentum, energy, etc.) in the mathematical formulations.

Conservation of energy and the First Law of Thermodynamics are significant in certain VVA embodiments because an apparatus may be in a stored energy state, e.g., a pressure state substantially different from the surroundings. It is important to note that certain VVA embodiments, at certain times, store a finite quantity of potential energy in a state of static equilibrium based upon the machine state, pressure state, etc. That finite quantity of potential energy may be released, for instance by changing a valve state. The First Law of Thermodynamics states that energy is conserved; a portion of that stored energy performs measurable work while the remainder is transformed into heat. It is generally impractical measure the rate at which heat is generated. Certain VVA embodiments measure the rate at which work is performed, and utilize a rate equation to calculate the frictional losses. The frictional losses in a conduit are governed by the viscosity of the fluid, a measurable property with units of Pa·s (or centipoise). Certain VVA embodiments thereby measure the flow rate of a fluid and utilize a rate equation to calculate the viscosity of that fluid.

It is important to note that first principles of physics are applied first in the design and construction of typical VVA system embodiments. Certain VVA system designs comprise: a vacuum source, non-isovolumetric components, a valve network, and a control algorithm that, at times, "isolates" a region within the apparatus, thereby creating a closed system. The closed system, within the VVA apparatus, typically stores or contains a finite amount of potential energy, arising from distortion of non-isovolumetric components. Release of that finite amount of potential energy results in two measurable quantities: (1) the finite volume of fluid that was aspirated by utilizing an equation of state and (2) the viscosity of the fluid that was aspirated by utilizing a rate equation. By contrast, vacuum aspiration systems of prior art store a substantially unlimited quantity of energy in the vacuum reservoir, and this energy level is continuously replenished by the vacuum pump. Prior-art aspiration thrombectomy systems do not create a closed system when the vacuum valve is closed. With the vacuum valve closed, the distal end of the catheter is open to the patient vasculature; intravascular pressure typically is deterministic of the pressure level within the catheter. With the vacuum valve closed, the air pump is continuously evacuating the reservoir of air and vapor; pump performance, air leaks and thermodynamic considerations are typically deterministic of the vacuum level within the reservoir. Opening the vacuum valve of a prior-art aspiration thrombectomy system releases substantially unlimited quantities of energy, and subsequently aspirates substantially unlimited volumes of fluid until the vacuum valve is closed. The rate at which this happens, i.e., the flow rate, is substantially dependent upon the viscosity of the fluid within the catheter.

Theoretical Basis. A set of governing equations for fluid flow are provided by the Navier-Stokes equations, notably the continuity and momentum equations. These are differential equations; therefore boundary and initial conditions must be applied in a well-posed problem. The axial symmetry and boundary conditions of a catheter enable utilization of the Hagen-Poiseuille equation (a special case of the Navier-Stokes equations), which relates viscosity to flow rate in a cylindrical conduit, such as a pipe or catheter. Certain VVA embodiments exert control over boundary, initial and final conditions; this enables measurement of system parameters and/or, including a time constant and subsequent calculation of relevant derived variables (e.g., flow rate, catheter viscosity, etc.). Several useful forms of the Hagen-Poiseuille equation are presented as Eq. 1.

$$\Delta p = \frac{8\mu LQ}{\pi R^4};\ Q = \frac{\pi R^4 \Delta p}{8\mu L};\ \mu = \frac{\pi R^4 \Delta p}{8QL};\quad \mu Q = \frac{\pi R^4}{8L}\Delta p;\ \mu Q = \Gamma \Delta p;\ Q = \Gamma \Delta p/\mu \qquad \text{Eq. 1}$$

Where Δp is the differential pressure between opposite ends of the conduit, u is the viscosity of the fluid, Q is the volumetric flow rate, and R and L are the radius and length of the conduit. In the rightmost arrangement of Eq. 1, a proportionality constant ($\Gamma = \pi R^4/8L$) is introduced for compactness, and is specific for the characteristic dimensions, R and L of the conduit. Γ may, in some cases, be assumed to be constant, because a catheter typically does not significantly change in either length or radius in operation of the apparatus. Eq. 1 asserts that, for any differential pressure (Δp), any increase in viscosity results in a decrease in flow rate, and any decrease in viscosity results in an increase in flow rate. The rightmost form of Eq. 1 ($Q = \Gamma\Delta p/\mu$) further asserts that, for a given differential pressure and viscosity, the flow rate is directly proportional to Γ. The dimensional proportionality constant, Γ may be referred to herein as the "flowability" of a catheter.

Herein, Eq. 1 may be applied across the total length of a catheter, meaning that Δp is substantially the pressure difference between the proximal and distal ends of the catheter. Alternatively, the catheter may be discretized along its length into substantially contiguous boluses of uniform, characteristic and/or variable length (and/or volume), see FIG. 9F. Eq. 1 may also be applied along and between these boluses; for instance, a bolus of length 1 cm may be analyzed (for pressure drop and viscosity) by Eq. 1 setting length L≈1 cm. Each bolus of aspirate thereby contributes a portion to the overall pressure drop observed between ends of the catheter.

The Hagen-Poiseuille equation (Eq. 1) is a, somewhat rare, exact analytical (closed-form) solution of the Navier-Stokes equations for the special case of a cylindrical conduit. While Eq. 1 is utilized in many VVA embodiments, certain VVA embodiments utilize alternative governing equations and formulations (e.g., Moody Chart, Darcy Friction Factor, etc.). The inventor recognized that significant algorithm elegance, robustness and compactness can be realized by utilizing Eq. 1 as a mathematical model or governing equation. In contrast to computing solutions of prior art, certain VVA embodiments continuously and/or intermittently measure variables (e.g., flow rate, catheter viscosity, entering bolus viscosity, clog risk, etc.) with minimal computational requirements. Eq. 1 is utilized by certain VVA embodiments to relate the fluid flow rate to the viscosity. Thereby, a measurement of a time constant enables determination of derived variables including, but not limited to: flow rate, bolus viscosity, catheter viscosity, etc. However, Eq. 1 may be "best" utilized for fully-developed laminar flow, in order to accurately inter-relate Δp, μ and Q.

For Eq. 1 to be valid, the fluid ideally has achieved or tends toward to a "steady-state" or "quasi-equilibrium" flow rate for meaningful inferences to be drawn. Prior-art aspiration thrombectomy systems rapidly cycle the vacuum valve such that fluid (within the catheter) repetitiously accelerates and decelerates. At times, the fluid attains significant velocity, only to be abruptly stopped when the vacuum valve is closed. The inventor observed the phenomenon of "ringing" or oscillations in the pressure waveform, particularly upon closing of the vacuum valve and stopping flow. Application of Eq. 1 to oscillating pressure-waveform data is non-trivial and not addressed herein. The inventor further recognized that oscillatory flow (particularly upon deceleration) is characteristic of high-speed flow, and may be characteristic of a low-viscosity aspirate, such as when only blood is in the catheter. Furthermore, waiting for oscillatory flow to subside toward a steady or equilibrium state requires time. In some operational modes, certain VVA embodiments actively limit the flow rate such that fluid velocity does not typically exceed predetermined thresholds (e.g., 10 cm/sec, any characteristic "ringing" threshold, etc.). This effectively "slows down" certain portions of an aspiration thrombectomy procedure that would otherwise occur "too fast," as evidenced by blood loss.

In the context of aspiration thrombectomy systems, oscillatory flow is not anticipated by Eq. 1, and additional considerations are required to understand and control the phenomenon. Each time a vacuum valve is opened, a finite mass of aspirate typically accelerates to some unknown velocity, whereupon that mass abruptly decelerates to approximately zero velocity. This finite mass (i.e., the contents of a catheter) may range from less than approximately 50 mg to in excess of approximately 200 g, depending substantially upon catheter dimensions. Because the system response may be oscillatory, the equations of motion of a mass-spring-damper may be applied (in certain VVA embodiments) as an additional and/or alternate mathematical model, or governing equation. In a VVA apparatus, the inventor recognized a pressure force as analogous to a spring force and a fluid viscosity as analogous to a damper. The equations of motion for a mass-spring-damper provide solutions for underdamped, overdamped and critically damped systems; this provided insight and motivation to develop novel VVA embodiments and methods to damp systems that would otherwise tend toward oscillatory behavior.

Certain VVA embodiments utilize solutions to the equations of motion for a mass/spring/damper or Damped Harmonic Oscillator (DHO) as a mathematical model. Some VVA embodiments utilize a plurality of mathematical models and/or governing equations (e.g., Hagen-Poiseuille equation, DHO, Moody Chart, Darcy Friction Factor, etc.). Among other VVA improvements, the benefits of utilizing one or more mathematical models and/or governing equations include: elegance and efficiency of programming and computation, robustness and insensitivity to length/scale consideration, reduced development and implementation costs, etc. In other words, applying mathematical models and/or governing equations provides a more direct means to more fully utilize the abundance of relevant data contained within the pressure waveform data of VVA embodiments. This is in contrast to prior art, wherein the pressure waveform data are relegated to computationally intensive, multi-parameter, pattern-matching algorithms.

BRIEF DESCRIPTION OF THE DRAWINGS

FIG. 6A depicts a VVA system in accordance with an illustrative embodiment of the present invention, wherein the system includes a connecting tube, a vapor tube and a moveable piston, and wherein the aspiration system is in a first volumetric state.

FIG. 6B depicts the VVA system of FIG. 6A, wherein the vacuum valve is in the closed state, the isolation valve is in the closed state, and the piston is in a down state.

FIG. 6C depicts the VVA system of FIG. 6A, wherein the vacuum valve and the isolation valve are each in the closed state, and the piston is in an up state; the system in in a second volumetric state, at least a portion of that volume is comprised of vapor.

FIG. 6D depicts the VVA system of FIG. 6A, wherein the vacuum valve is in the open state, the isolation valve is in the closed state, and the system is in substantially the second volumetric state, the portion of vapor is reduced from FIG. 6C.

FIG. 7C depicts an illustrative lookup table generated in accordance with certain embodiments of the present invention, wherein certain pressure-volume characteristics and bulk modulus (K) of non-isovolumetric VVA components and/or elements are depicted in tabular form.

FIG. 10A depicts a VVA system in accordance with an illustrative embodiment of the present invention, wherein the system includes a catheter with a moveable distal sleeve.

FIG. 10B depicts the VVA system of FIG. 10A, wherein the sleeve is translated proximally.

FIG. 10C depicts a detail view of the VVA system of FIG. 10A, wherein the sleeve is extended past the distal end of the catheter.

FIG. 10D depicts a detail view of the VVA system of FIG. 10A, wherein a twist sleeve is in partially-open state, exposing certain instances of dilution orifices.

FIG. 10E depicts a detail view of the VVA system of FIG. 10A, wherein a twist sleeve is in partially-closed state, occluding certain instances of dilution orifices.

FIG. 13A diagrammatically depicts a mass/spring/damper conceptual representation of a VVA embodiment in static equilibrium.

FIG. 13B depicts a representative $i^{th}$ bolus of aspirate subjected to pressure and viscous forces.

FIG. 13C diagrammatically depicts the mass/spring/damper conceptual representation of FIG. 13A, wherein the spring is compressed and the valve is in the closed state.

FIG. 13D diagrammatically depicts a prior-art mass/spring/damper conceptual representation of an $i^{th}$ bolus of aspirate in static equilibrium.

FIG. 13E diagrammatically depicts the mass/spring/damper conceptual representation of FIG. 13D, wherein spring is compressed and held in place by hook.

FIG. 13F diagrammatically depicts the mass/spring/damper conceptual representation of FIG. 13A, wherein the system is tending toward the static equilibrium state of FIG. 13A.

FIG. 25 depicts an illustrative data array in accordance with embodiments of the present invention, comprising a thrombus model matrix in tabular form.

FIG. 26A depicts an illustrative data array in accordance with embodiments of the present invention, illustrating a first page of procedure log file in tabular form.

FIG. 26B depicts a second page of procedure log file.

FIG. 26C depicts a last page of procedure log file.

DETAILED DESCRIPTION OF THE DRAWINGS

Figure 1A:
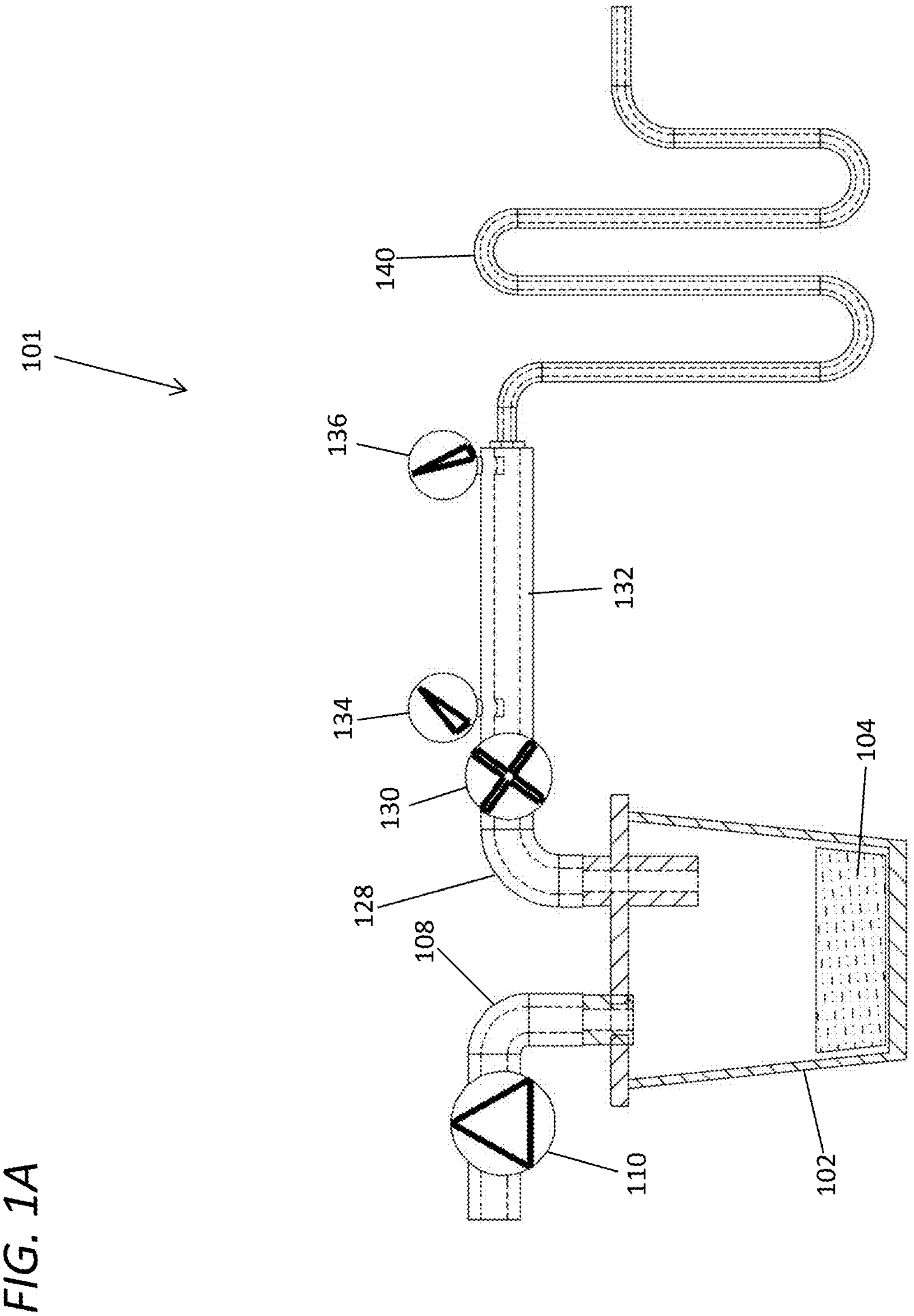
Prior Art FIG. 1A
FIG. 1A depicts a representative prior-art evacuated reservoir aspiration system with a vacuum valve in the closed state.
Figure 1B:
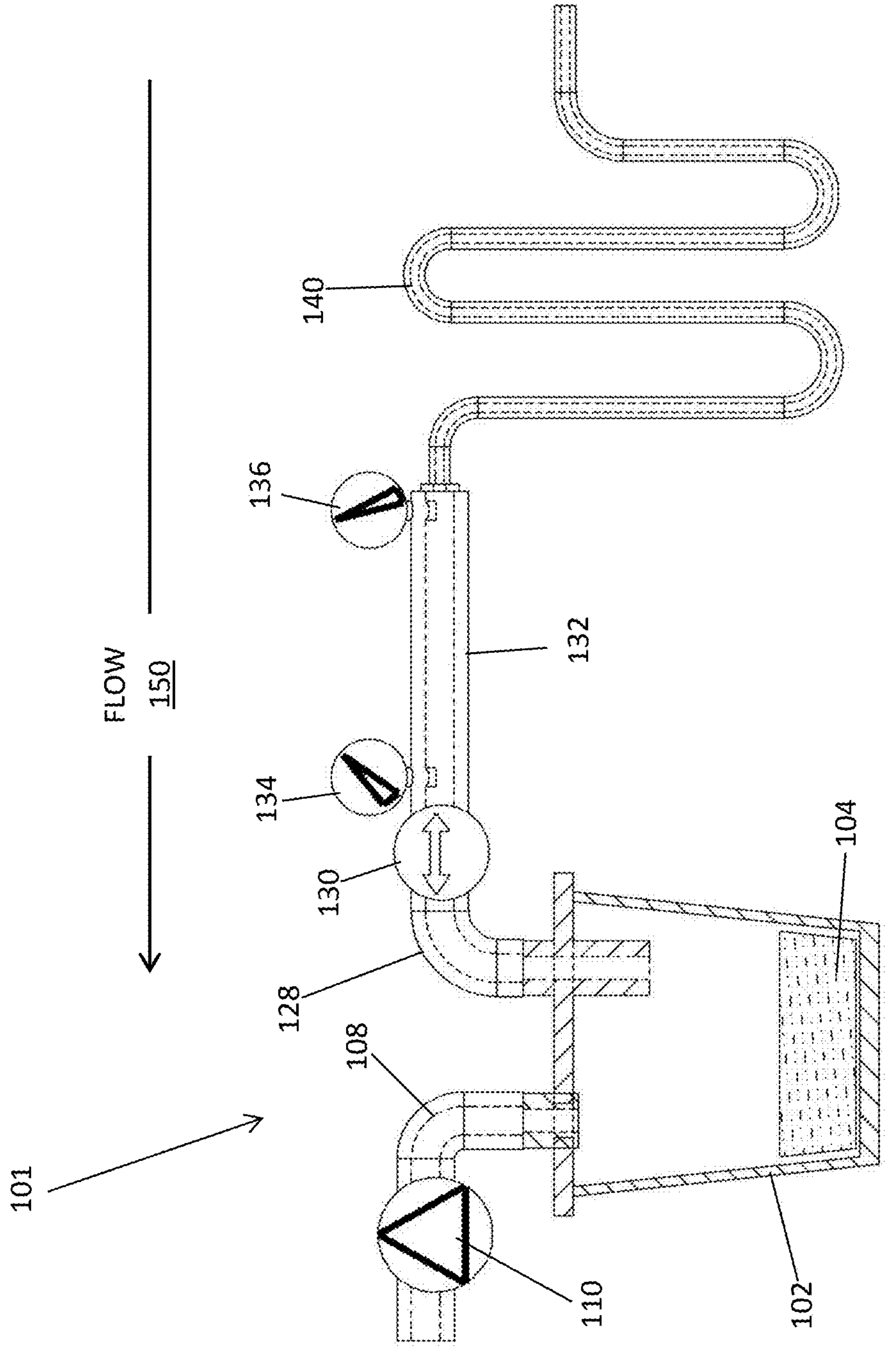
FIG. 1B depicts the prior-art evacuated reservoir aspiration system of FIG. 1A with the vacuum valve in the open state.

FIG. 1A and FIG. 1B depict a representative evacuated reservoir aspiration system 101 of prior art. Air pump 110 evacuates air from reservoir 102 through air conduit 108; blood/thrombus 104 are collected in reservoir 102. Flow 150 of fluid is typically from right to left (FIG. 1B), such that aspirated fluids enter and traverse catheter 140, past distal pressure gage 136, through connecting tube 132, past proximal gage 134, through vacuum valve 130, through vacuum conduit 128 and into reservoir 102; aspirated fluid is shown as blood/thrombus 104. Pressure is measured at two locations within connecting tube 132: proximal pressure gage 134 and distal pressure gage 136.

In use, a more distal portion of catheter 140 is deployed in a patient vascular system (not shown) and a more proximal portion of catheter 140 is fluidically coupled to connecting tube 132, which is typically of larger diameter than catheter 140. Distal pressure gage 136 and/or proximal pressure gage 134 may comprise a gage, a pressure transducer, strain gage or any other suitable means to measure pressure. Connecting tube 132 provides a flexible connection between reservoir 102 and catheter 140 such that a clinician may manipulate the proximal end of catheter 140. Catheter 140 is typically of rigid construction in the axial and radial directions such that catheter 140 exhibits "pushability" and resistance to crushing or kinking. Vacuum valve 130 is fluidically coupled to vacuum conduit 128 on the downstream (i.e., left) end, and is fluidically coupled to connecting tube 132 on the upstream (i.e., right) end. Vacuum valve 130 may comprise a pinch valve, angle valve, ball valve or any suitable means to block or otherwise restrict fluid flow through connecting tube 132. FIG. 1A depicts an evacuated reservoir aspiration system 101 with vacuum valve 130 in the closed state, and FIG. 1B is depicted with vacuum valve 130 in the open state, enabling aspirate flow 150.

Certain prior-art discloses "automatically" determining a number of pressure parameters (e.g., starting pressure level, ending pressure level, differential in starting/ending pressure levels, peak pressure levels, "variance," etc.). Determination of "system scores" based upon these parameters involves opaque algorithms, and "weighting" and "correction" factors. Pressure waveform data are "turned over" to opaque algorithms to determine attribute data including flow state, system states, and system scores. System scores may even be represented by integers resulting from counting occurrences of identified patterns. Flow state, system state and system scores are determined by cycling vacuum valve 130 and counting repetitions of discernable patterns in measurements from either/or proximal pressure gage 134 and distal pressure gage 136.

Figure 1C:
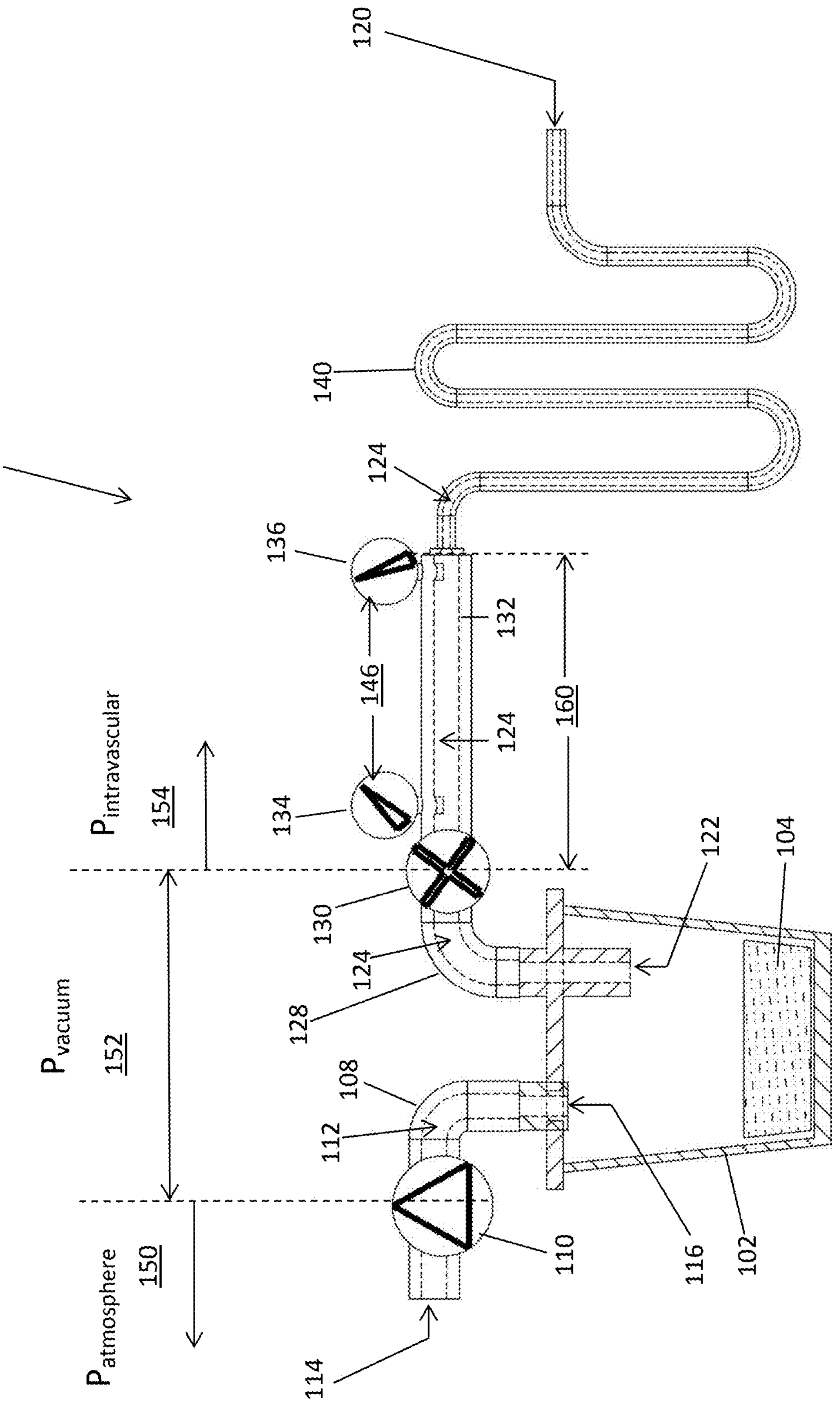
FIG. 1C identifies pressure zones, control surfaces and control volumes in FIG. 1A.
Figure 1D:
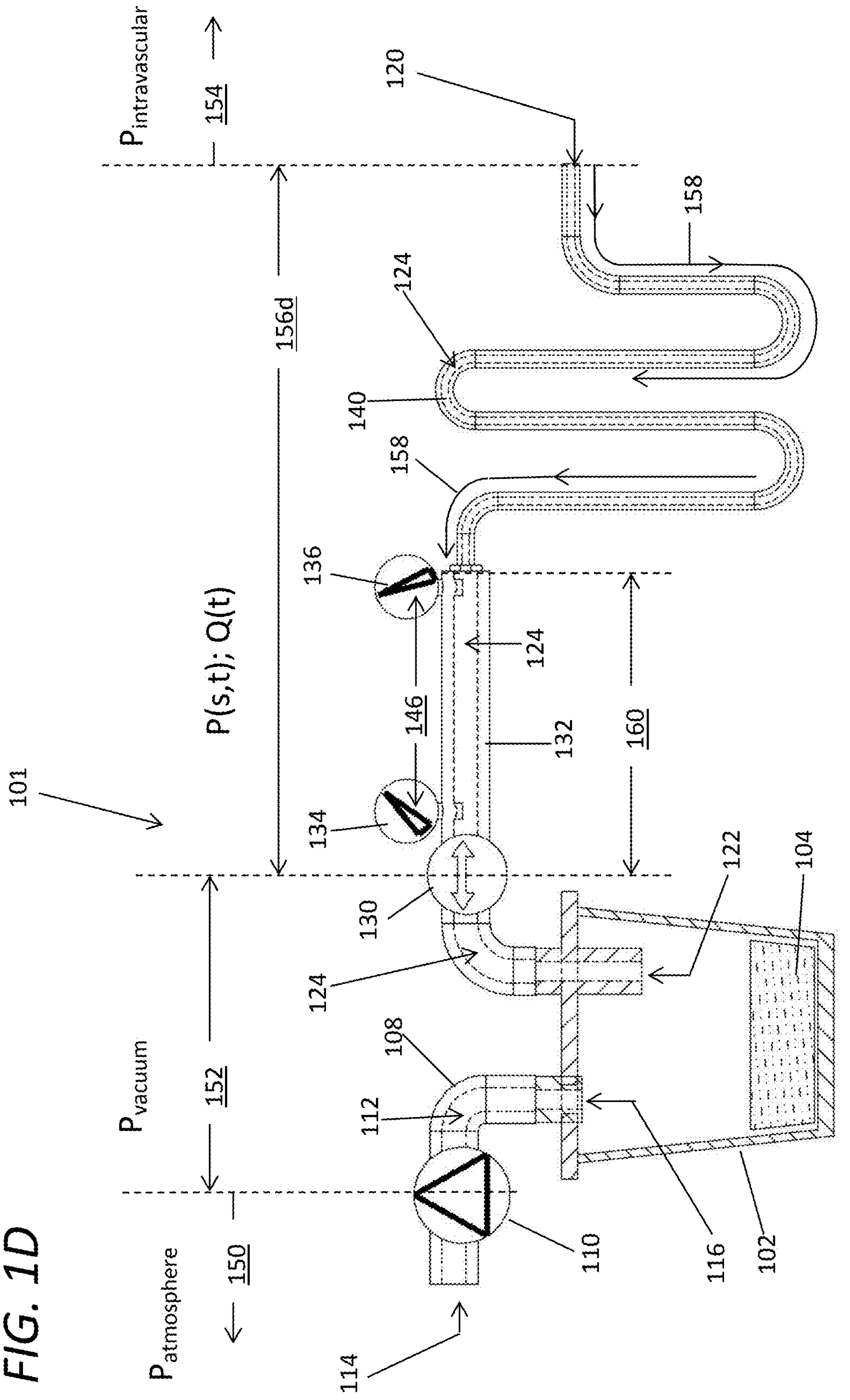
FIG. 1D identifies pressure as a function of time and the s-coordinate in the evacuated reservoir aspiration system of FIG. 1A.

FIG. 1*c* is similar to FIG. 1A, where vacuum valve 130 is in the closed state; FIG. 1D is similar to FIG. 1B, where vacuum valve 130 is in the open state. However, FIGS. 1C-1D introduce novel, formal parameterization of the spatial geometry, such as an s-coordinate to represent curvilinear coordinates, definitions of control volumes, control surfaces, pressure regions, distances and lengths.

Control surfaces. Four control surfaces are identified. Control surface$_{liquid\ in}$ 120, is located at the distal (i.e., right) end of catheter 140; aspirated fluids enter the aspiration system through control surface$_{liquid\ in}$ 120. Control surface$_{liquid\ out}$ 122, is depicted as internal to reservoir 102; aspirated fluids, such as blood/thrombus 104, pass through control surface$_{liquid\ out}$ 122, and are collected in waste reservoir 102. Reservoir 102 is operable at substantially below atmospheric pressure, because air is removed therefrom by air pump 110. Air in reservoir 102 passes through control surface$_{air\ in}$ 116 and exits the aspiration system through control surface$_{air\ out}$ 114.

Control volumes. Catheter 140 is depicted with a solid outer boundary and a dashed inner boundary (annotated in FIG. 1C as "control volume$_{liquid}$ 124"). Control volume$_{liquid}$ 124 may typically be defined as: the volume contained within the inner wall(s), or lumen(s), of components such as catheter 140, connecting tube 132, vacuum valve 130, and vacuum conduit 128, etc. Control volumes may be referenced by the surfaces that bound the control volume; alternatively, the volume bounded by (i.e. contained within) these surfaces may be referenced. Control surfaces in aspiration systems certainly exist, although they are unrecognized as a tool or criterion for system analysis in prior art. They are identified herein to facilitate subsequent analyses. Fluids, solids and/or gasses or vapors contained within system components such as catheter 140, connecting tube 132, vacuum conduit 128, etc. may be considered to be inside of control volume$_{liquid}$ 124. The contents of reservoir 102 are typically comprised of combinations of air (in the "headspace" of reservoir 102) and blood/thrombus 104 in varying proportions throughout a procedure. Air and blood/thrombus 104, contained within reservoir 102, are not part of either control volume$_{liquid}$ 124 or control volume$_{air}$ 112. Aspiration system 101 is isovolumetric because neither control $volume_{liquid}$ 124 nor control $volume_{air}$ 112, operationally change volume. That is, in operation apparatus 101, the internal volume remains substantially constant.

Pressure regions. Certain pressure regions are identified herein. These regions include: (1) Region 150, which is to the left of air pump 110, (2) region 152, located between air pump 110 and vacuum valve 130, and (3) region 154, located to the right of vacuum valve 130. The pressure in region 150 is atmospheric pressure, designated "$P_{atmosphere}$". The pressure in region 152 is less than atmospheric pressure, designated "$P_{vacuum}$". And the pressure in region 154, designated "$P_{intravascular}$" is substantially equal to the intravascular pressure. For convenience, the identified regions (as characterized by the pressure therein) may be referred to as $P_{atm}$ 150, $P_{vacuum}$ 152, and $P_{IV}$ 154 to provide context.

The S-coordinate. FIG. 1D introduces a coordinate system; in particular, s-coordinate 158, along the length of catheter 140, regardless of any bending or curvature of these components. S-coordinate 158 uniquely defines a position in space that is typically: (1) within control $volume_{liquid}$ 124, and (2) between control $surface_{liquid\ in}$ 120 and control $surface_{liquid\ out}$ 122. In certain VVA embodiments, s-coordinate 158 terminates at or near the interface of catheter 140 and connecting tube 132; in other embodiments, s-coordinate 158 extends through other components (e.g., connecting tube 130, vacuum valve 130, vacuum conduit 128, etc.).

Distances/Lengths. FIG. 1D introduces connecting tube length 160 and pressure tap distance 146. Connecting tube length 160 is the distance between vacuum valve 130 and the proximal end of catheter 140. Pressure tap distance 146 is the distance between proximal pressure gage 134 and distal pressure gage 136.

Pressure as a function of position and time, P(s,t). With continuing reference to FIG. 1D, utilizing s-coordinate system 158; the pressure at any point and at any time, may be calculated or inferred in certain VVA embodiments. Vacuum valve 130 is typically cycled repetitiously; this causes the pressure, and volumetric flow rate, to continuously change with time. Pressure vs. time "pressure waveform" data may be acquired at locations including proximal pressure gage 134 and distal pressure gage 136. These data may be subtracted from one another to calculate a differential pressure (i.e., pressure drop) across pressure tap length 146. Such data may be of some quantitative value in a steady-state flowing condition, but the "noise" of vacuum valve 130 degrades the signal of proximal pressure gage 134.

From the continuity equation of fluid mechanics, the volumetric flow rate at any time, denoted Q(t), through aspiration system 101 is substantially equal at all locations along s-coordinate 158. At any time, the volumetric flow rate, Q(t), through control $surface_{liquid\ in}$ 120 is substantially equal to the volumetric flow rate through control $surface_{liquid\ out}$ 122. Certain prior-art aspiration thrombectomy system embodiments feature a "tee-junction" or "y-connector" within connecting tube 132, for purposes including infusion of non-biological (i.e., exogeneous) fluids (e.g., saline, air, etc.). In such cases, additional control surfaces (e.g., control $surface_{saline\ in}$, etc.) may be required for mass balance within control $volume_{liquid}$ 124.

FIG. 1C depicts evacuated reservoir aspiration system 101 in a static equilibrium state wherein closed vacuum valve 130 prevents flow between catheter 140, connecting tube 132 and reservoir 102. This establishes a pressure discontinuity (i.e. a step change) between connecting tube 132 and reservoir 102. In the static equilibrium state depicted in FIG. 1C, the pressure in control $volume_{liquid}$ 124 is discontinuous, jumping from $P_{vacuum}$ in region 152 to intravascular pressure $P_{intravascular}$ in region 154, at the dotted interface line. As previously noted, the pressure in region 154 is substantially equal to $P_{intravascular}$. This is because there is substantially zero viscous dissipation (loss) resulting from flow, and, therefore, pressure tends toward equilibrium; substantially that of the intravascular pressure $P_{intravascular}$ 154. An underlying assumption is that a catheter is not clogged or otherwise occluded, and that flow exists until a static equilibrium state (e.g., FIGS. 1A, 1C) may be established. In cases where catheter 140 is clogged or occluded (i.e., flow does not exist), this does not affect static equilibrium conditions (approximately zero fluid velocity, pressures and forces are balanced) from arising, however $P_{intravascular}$, in region 154, may be shifted rightward, e.g., to in the vicinity of a clog.

The distance between proximal pressure gage 134 and distal pressure gage 136 is annotated as pressure tap distance 146. This distance defines the measurement zone wherein a difference in pressure (i.e., differential pressure) provides information about fluid flowing between the two gauges. In this context, if the fluid in connecting tube 132 is more viscous, then the differential pressure "signal" will typically be greater. If the fluid flow rate is larger, the differential pressure "signal" will typically be greater. This highlights a problem of prior art: when the differential pressure signal increases, is this because the flow rate is greater, or because the fluid in the connecting tube is more viscous? This also illustrates that any measurement of viscosity is taken upon fluid in connecting tube 132 and not in catheter 140. Furthermore, if pressure tap distance 146 is increased, or if connecting tube 132 diameter is decreased, then the differential pressure signal strength will typically be greater. This may necessitate that pressure tap distance 146 and connecting tube 132 diameter are standardized; if these dimensions are changed, then the pressure waveforms, patterns and pressure waveform parameterization will likely change. The distance between vacuum valve 130 and the proximal end of catheter 140 is referenced as connecting tube length 160. Clinically, connecting tube length 160 is typically approximately 1 m to 1.5 m in length, 3 mm to 10 mm in diameter, and has an internal volume ranging from approximately 5 cc to in excess of 100 cc.

Distal pressure gage 136 is located to measure pressure substantially near a proximal end of catheter 140. Because connecting tube 132 is typically of substantially greater diameter than catheter 140, distal pressure gage 136 need not be located in immediate proximity to catheter 140 for accurate pressure measurement. In some prior-art embodiments, such as depicted in FIG. 1C, distal pressure gage 136 is located some distance away from vacuum valve 130. This may be deemed advantageous because the shock and rapidly changing boundary conditions (at vacuum valve 130) tend to generate noise in proximal pressure gage 134; by virtue of its distance from vacuum valve 130, distal pressure gage 136 tends to exhibit a "less noisy" pressure waveform data stream. Some prior art embodiments incorporate a user-selectable, electric on/off switch at or about the location of distal pressure gage 136. This switch disables actuation of vacuum valve 130 to prevent flow of aspirate, such as while catheter 140 is being positioned or manipulated.

FIG. 1D illustrates a prior-art definition of differential pressure in the context of such an evacuated reservoir aspiration system: pressure tap distance 146. Also introduced in FIG. 1D is a newly conceptualized VVA definition of differential pressure across region 156*d*: the difference in pressure between $P_{Intravascular}$, in region 154, and vacuum, in region 152. Note that this "VVA" differential pressure, P(s,t), includes catheter 140, whereas the prior-art differential pressure (i.e., distance 146) is significantly shorter, excluding at least the length of catheter 140. FIG. 1D illustrates that pressure is a function of both position (s-coordinate 158) and time (t) and is referenced as P(s,t); Q(t) is the flow rate at any time.

FIG. 1D depicts evacuated reservoir aspiration system 101 with vacuum valve 130 in the open state. A differential pressure exists across region 156*d*, between control $surface_{liquid\ out}$ 122 and control $surface_{liquid\ in}$ 120. This differential pressure (between the distal tip of catheter 140 and reservoir 102) provides force to cause fluid to flow through control $volume_{liquid}$ 124. The term "liquid" and/or "fluid" may be used herein to represent any fluid, which clinically may contain arbitrary amounts of thrombus, proteins, clots, collagen, fats, blood, saline, liquids, solids, slurries, etc. Experimentally, liquids and fluids are virtually unlimited in composition; relevant examples include: water, oils, viscosity standards, glycerine/water mixtures, mock thrombus and/or clot, ketchup, mustard, scrambled egg, etc. Herein, liquids may contain gasses (and/or vapors) that may be naturally present, dissolved, evaporated or evolved by degassing; gasses (e.g., air, nitrogen, oxygen, etc.) may leak into or otherwise be infused in certain VVA embodiments.

FIG. 1D identifies pressure P(s,t) in region 156*d*; certain prior-art efforts to experimentally measure pressure using various instrumentation within catheter 140 are known to exist. Among other functionalities, and in distinction to the prior art, some VVA embodiments calculate and/or infer (rather than measure) intra-catheter pressure at locations (e.g., s-coordinate, 1 cm from the tip, etc.) within catheter 140. This obviates the need for such prior-art instrumentation. Pressure P(s,t) is the pressure at any point along s-coordinate 158, at any time, t. For instance, pressure P(s,t) may be calculated to be approximately 1 inHg vacuum at s≈1 cm at time to. Because pressure is a function of time and space, this enables analysis of spatial pressure gradients, or "how does the pressure change with respect to position (i.e., along the s-coordinate)?"

Typical prior art embodiments of aspiration system 101, an example of which is depicted in FIGS. 1A-1D, are substantially isovolumetric, meaning that they do not operationally deform due to pressure or operationally-applied surface forces. Prior-art aspiration systems typically utilize electrically actuated valves (e.g., pinch valve, angle valve, ball valve, needle valve, globe valve, etc.). Upon actuation, certain of these valves displace a small amount of process fluid. Any change in aspiration system control volume (e.g., control $volume_{liquid}$ 124, control $volume_{air}$ 112, etc.) due to valve actuation is deferred to experimental results sections herein. Any dimensional change in components (e.g., catheter 140, connecting tube 132, vacuum conduit 128, etc.) of FIG. 1A through FIG. 1D due to pressure or surface forces may be considered negligible. Because control $volume_{liquid}$ 124 is given to be isovolumetric, the flow rate into control $surface_{liquid\ in}$ 120 is substantially equal to the flow rate out of control $surface_{liquid\ out}$ 122 at all times (any deviation from theoretical/approximate may be about 0% to 5% deviation and is considered negligible herein). In other words, the aspiration system 101 volume (i.e., control $volume_{liquid}$ 124) does not "grow" or "shrink" to the extent that the volume is substantially changed during operation of the apparatus. FIG. 1C and FIG. 1D also illustrate that the mass flux into and out of the evacuated reservoir aspiration system 101 is effected through two control surfaces: (1) control $surface_{liquid\ in}$ 120 and (2) control $surface_{air\ out}$ 114, i.e., from the tip of catheter 140 to the discharge of air to atmosphere through control $surface_{air\ out}$ 114. FIG. 1A and FIG. 1C depict prior-art aspiration system 101 in static equilibrium states; FIG. 1B and FIG. 1D depict aspiration system 101 tending toward dynamic equilibrium states, wherein fluid "tends toward" some maximum velocity to waste.

Figure 2A:
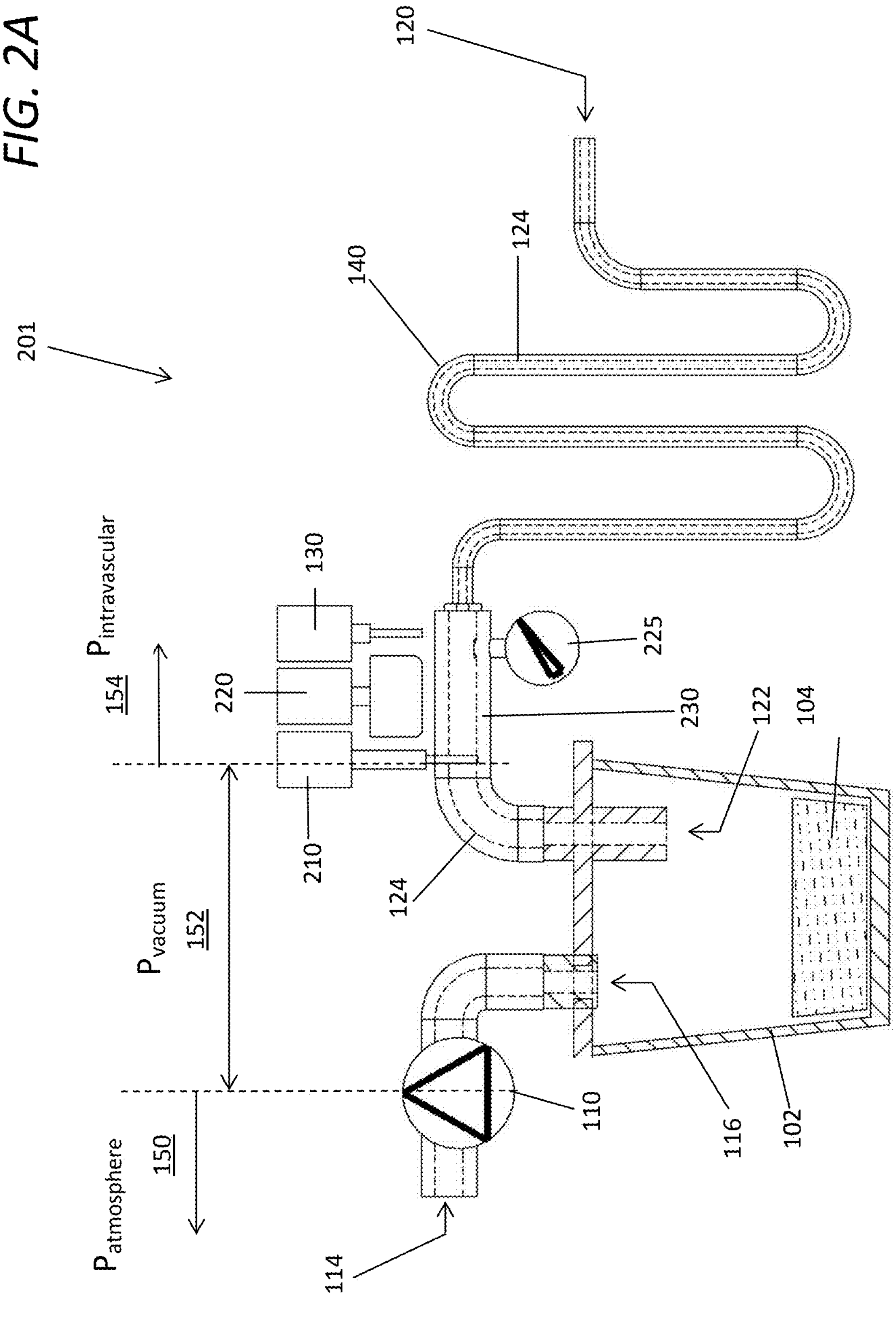
FIG. 2A depicts a VVA system in accordance with an illustrative embodiment of the present invention, wherein an isolation valve is in the closed state, a vacuum valve is in the open state, and a displacement mechanism is in the open state.
Figure 2B:
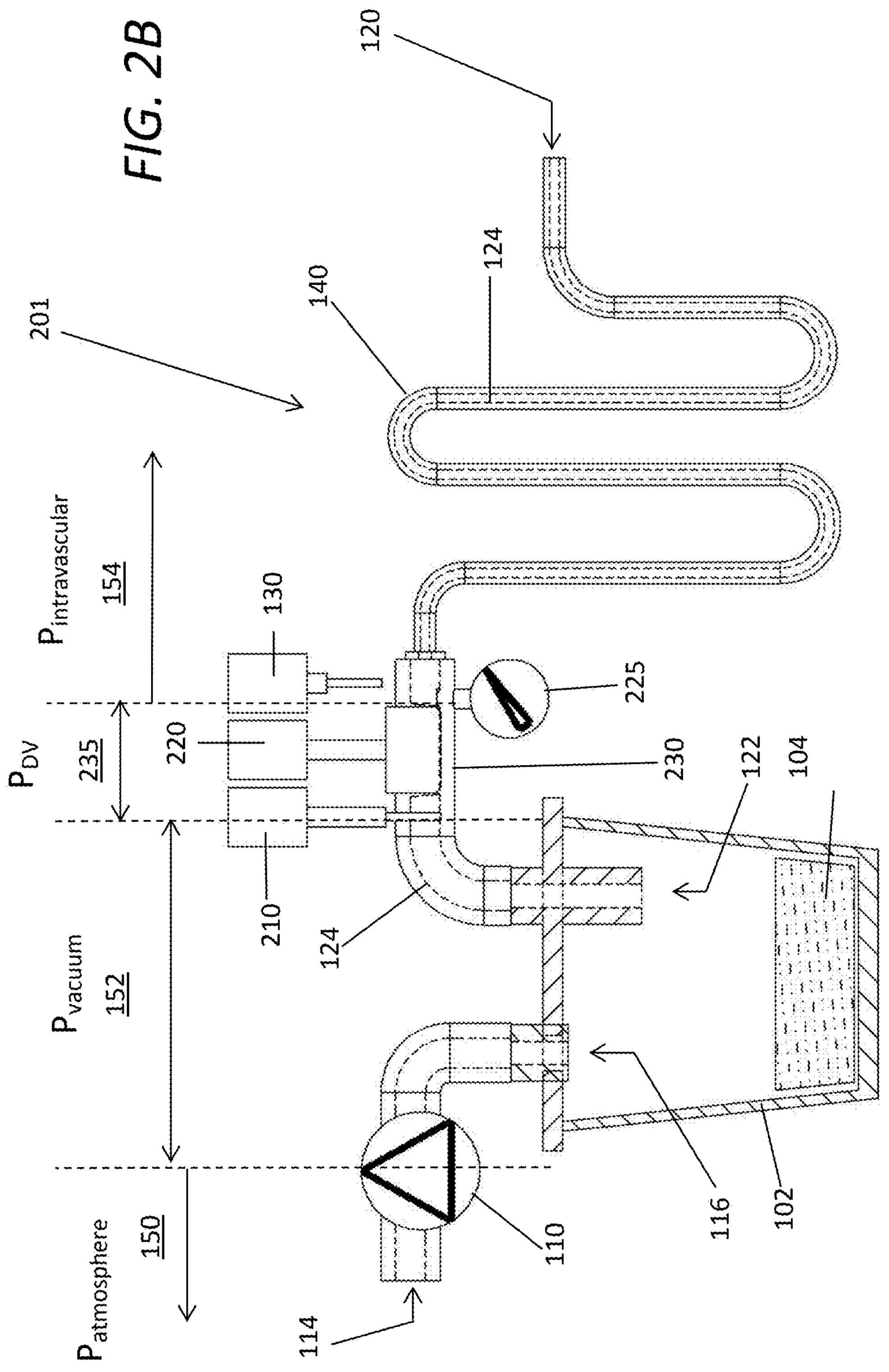
FIG. 2B depicts the VVA system of FIG. 2A, wherein the isolation valve is in the closed state, the vacuum valve is in the open state, and the displacement mechanism is shown in the closed state.

FIG. 2A depicts VVA (Visco-Volumetric Aspiration) system 201 in accordance with an illustrative embodiment of the present invention. FIG. 2A depicts VVA system 201 in a first machine state and a first volumetric state. FIG. 2B depicts system 201 in a second machine state and a second volumetric state. The substantially different volumetric states of system 201, depicted in FIG. 2A and FIG. 2B, illustrate that the internal volume of system 201 is variable with time during operation of the apparatus.

VVA system 201 is depicted in FIG. 2A in a machine state wherein isolation valve 210 is in the closed state and each of displacement mechanism 220 and vacuum valve 130 is in the open state. VVA system 201 differs from the prior art in many significant ways, including:

(1) A single pressure gage 225, located proximally (i.e., to the left) of vacuum valve 130, (2) A displacement mechanism 220, located proximally (i.e., to the left) of vacuum valve 130, (3) An isolation valve 210, located proximally (i.e., to the left) of displacement mechanism 220, and (4) Elastic tubing 230 replaces connecting tube 132 (of prior art).

VVA system 201 changes the machine state (e.g., valve states, actuator states, etc.) and consequently changes the volumetric state of control $volume_{liquid}$ 124 by mechanically deforming elastic tubing 230.

FIG. 2A depicts VVA system 201 in a similar static equilibrium state as the prior-art aspiration system 101 depicted in FIG. 1C. In both FIG. 1C and FIG. 2A, fluid flow between reservoir 102 and catheter 140 is blocked by physical means (e.g., isolation valve 210, vacuum valve 130, etc.) whereby the flow rate is reduced to substantially zero. Three pressure zones are identified in FIG. 2A; region 150, region 152, and region 154. The pressure in region 150 is substantially at atmospheric pressure, identified as "$P_{atmosphere}$", the pressure in region 152 is substantially less than atmospheric pressure, identified as "$P_{vacuum}$", and the pressure in region 154 is approximately equal to the intravascular pressure, identified as "$P_{intravascular}$".

FIG. 2B depicts VVA system 201 of FIG. 2A wherein the machine state is: each of isolation valve 210 and displacement mechanism 220 is in the closed states and vacuum valve 130 is in the open state; flow is substantially zero. Elastic tubing 230 is shown to be mechanically deformed by surface contact force of displacement mechanism 220 in the closed state. Pressure gage 225 is fluidically coupled to a proximal portion of catheter 140. In the static equilibrium state depicted in FIG. 2B, the pressure measured at pressure gage 225 may be substantially equal to the intravascular pressure, $P_{intravascular}$.

FIG. 2B introduces region 235, which is an intermediate zone between isolation valve 210 and vacuum valve 130. Region 235, having pressure $P_{DV}$, is an intermediate pressure zone, located between region 152 having pressure $P_{vacuum}$ and region 154 having pressure $P_{intravascular}$. Region 235 is of significance because VVA system 201 utilizes this region of the apparatus to generate, store, and release a finite quantity of potential energy. Releasing that finite quantity of stored energy typically causes a finite volume of aspirate to flow through catheter 140. This is one example of a VVA system storing a finite quantity of potential energy in a static equilibrium state.

Figure 2C:
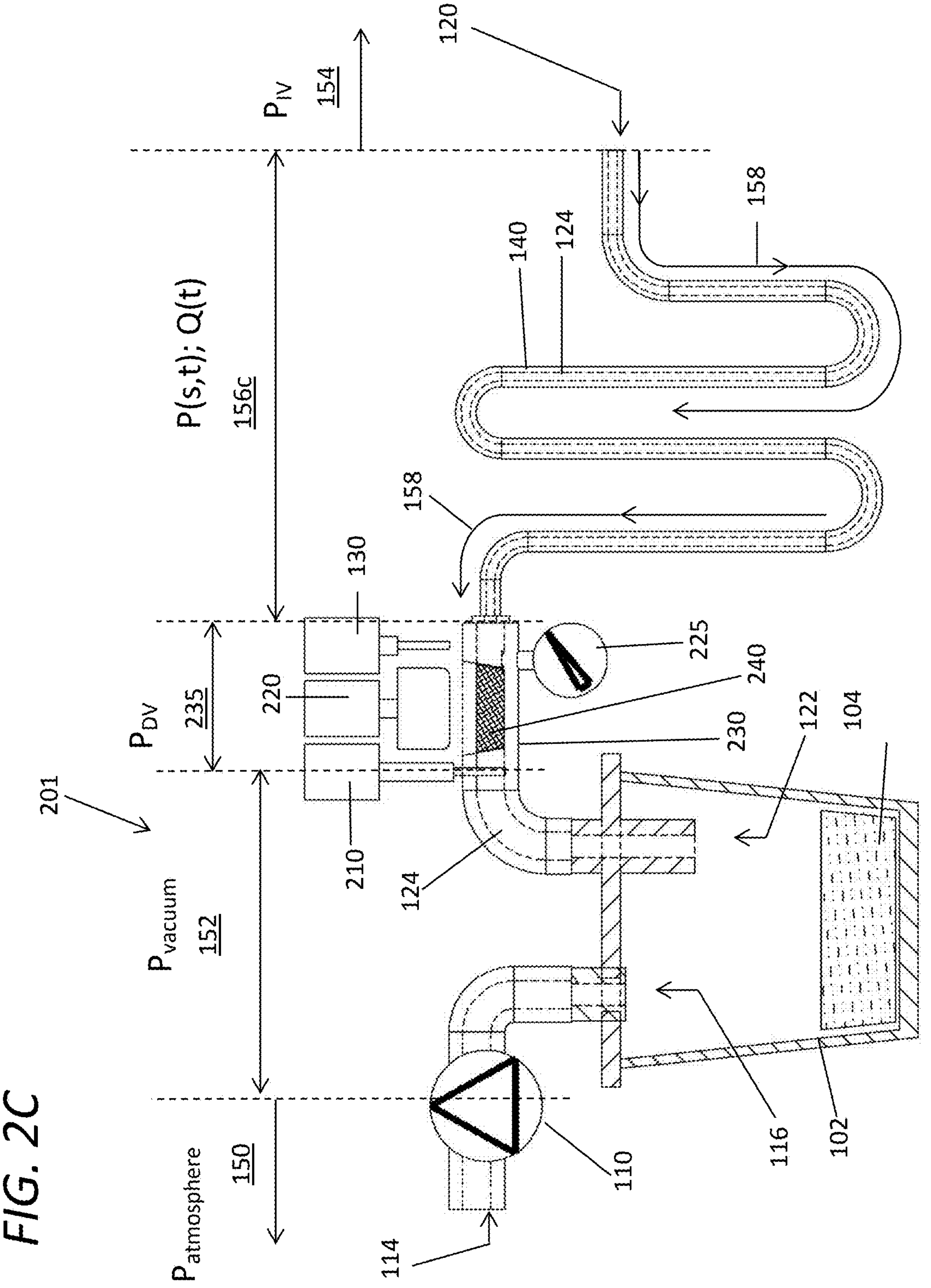
FIG. 2C depicts the VVA system of FIG. 2A, wherein the vacuum valve is in the open state, the isolation valve is in the closed state, and the displacement mechanism is shown in the open state.

FIG. 2C depicts VVA system 201 of FIG. 2B in a machine state wherein isolation valve 210 is in the closed state, and each of displacement mechanism 220 and vacuum valve 130 is in the open state. FIG. 2C depicts VVA system 201 at an instant after displacement mechanism 220 is changed to the open state. FIG. 2C introduces displaced volume 240, depicted as a cross-hatched "void" in elastic tubing 230.

Figure 2D:
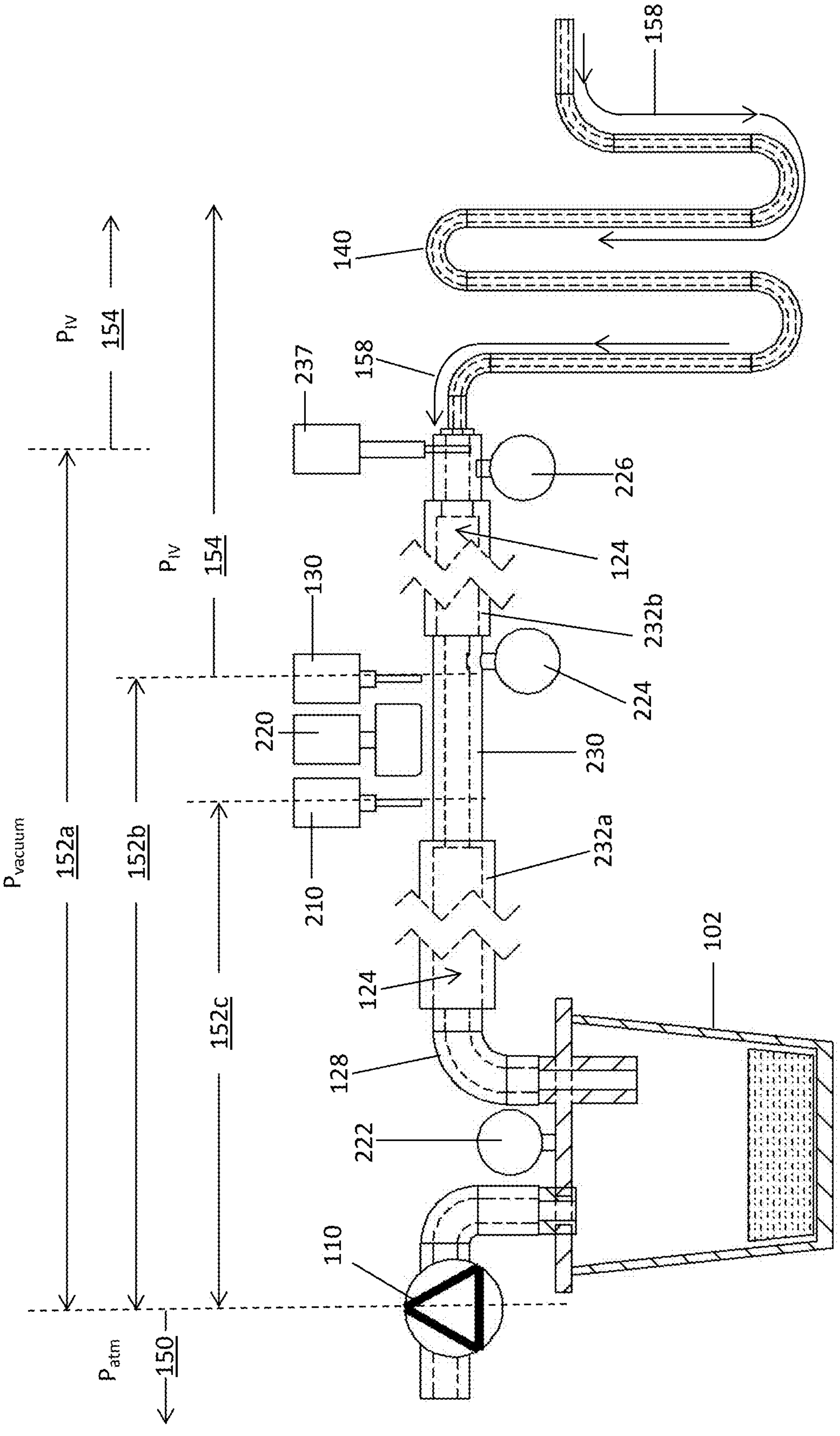
FIG. 2D depicts a modification of the VVA system of FIG. 2A, wherein components including connecting tubes are added.

A convention used herein is that displaced volume 240 is depicted as substantially maximum in FIG. 2B and FIG. 2C; displaced volume 240 is depicted as substantially zero in FIG. 2A and FIG. 2D. Accordingly, control $volume_{liquid}$ 124 is at substantially maximum volume in FIGS. 2A and 2D, and at substantially minimum volume in FIGS. 2B-2C. The machine state and volumetric states depicted in FIG. 2C are significant because displaced volume 240 is decreasing with time, tending toward zero at a characteristic rate. Measuring this characteristic rate is a means of measuring a time constant. FIG. 2C depicts VVA system 201 in an instantaneous, non-equilibrium volumetric state that is tending toward the static equilibrium state depicted in FIG. 2A at a characteristic rate. This transition from the volumetric state of FIG. 2C to the volumetric state of FIG. 2A typically occurs: (1) in a characteristic period of time and (2) concurrently with transferring a characteristic volume of aspirate (e.g., bolus volume).

FIG. 2C depicts VVA system 201 "tending toward the static equilibrium state," depicted in FIG. 2A. The static equilibrium state may be achieved if displaced volume 240 is reduced to substantially zero, as in FIG. 2A. As displaced volume 240 tends toward zero (the static equilibrium state), pressure $P_{DV}$, in region 235, tends toward intravascular pressure $P_{IV}$ in region 154. The rate at which pressure $P_{DV}$ (e.g. as measured by pressure gage 225) increases toward intravascular pressure $P_{IV}$ may be directly correlated to the rate at which displaced volume 240 tends toward zero. The rate of increase in pressure $P_{DV}$ may thereby be directly correlated to the rate of fluid flow through catheter 140.

In the machine and volumetric states depicted in FIG. 2C, flow of aspirate through catheter 140 typically exists as elastic tubing 230 "returns" or "recovers" toward its equilibrium volumetric state. During this recovery period of time, the volumetric state of control $volume_{liquid}$ 124 increases toward a maximum and the volumetric state of displaced volume 240 decreases toward zero. Displaced volume 240, by convention, tends toward zero irrespective of the volumetric state of control $volume_{liquid}$ 124, which may be some 100 cc, 250 cc or any arbitrary volume at any time. While the total volume of control $volume_{liquid}$ 124 control $volume_{liquid}$ 124 typically tends toward some arbitrary maximum value, displaced volume 240 tends toward the fixed constant 0. Defining displaced volume 240 in this manner enables certain VVA control algorithms to consistently parameterize the volumetric state as tending toward zero, instead of an arbitrary system maximum volume.

FIG. 2C illustrates a significant distinction of VVA embodiments over the prior art. Namely, at certain times, the flow rate (of aspirate) into control $surface_{liquid\ in}$ 120 is substantially unequal to the flow rate out through control $surface_{liquid\ out}$ 122. This occurs because the volumetric state of control $volume_{liquid}$ 124 is increasing with time as aspirate fills the "void" of displaced volume 240. As this happens, the volumetric state of displaced volume 240 is decreasing toward zero, thereby drawing aspirate into catheter 140 through the distal end, or tip.

FIG. 2D depicts VVA system 201 comprising additional components including connecting tubes 232*a*, 232*b*, distal vacuum valve 237, distal pressure gage 226, and reservoir pressure gage 222. VVA system 201, as depicted in FIG. 2D, is in a static equilibrium state with machine state configured such that distal vacuum valve 237 is in the closed state, and each of vacuum valve 130, displacement mechanism 220 and isolation valve 210 is in the open state.

Design locations of certain components of VVA system 201 (e.g., vacuum valve 130, displacement mechanism 220, isolation valve 210, etc.), with respect to a proximal portion of catheter 140, affect fluid flow through the aspiration system. Because aspirate flow is "differential pressure driven" throughout the apparatus, relocating certain components, e.g., vacuum valve 130, consequently moves certain pressure regions within the apparatus. In the machine state configuration depicted in FIG. 2D, region $P_{vacuum}$ 152*a* extends through connecting tube 232*b*, thereby extending the pressure boundary condition to a first distance from a proximal portion of catheter 140. However, other machine state configurations may generate different pressure states such as illustrated by pressure regions 152*b*, and 152*c*.

It is important to note that the pressure discontinuity, between $P_{vacuum}$ 152*a* and $P_{IV}$ 154, at distal vacuum valve 237, is also a "stored energy discontinuity" across a boundary. Changing distal valve 237 to the open state releases the stored energy into the adjacent surroundings. VVA system 201 is depicted in FIG. 2D with a proximal portion of catheter 140 in proximity to the adjacent surroundings of distal valve 237, this may increase the magnitude of any local effects of a machine-state change upon a proximal end of catheter 140. In certain VVA embodiments, connecting tube 232*b* may be of substantial length, perhaps exceeding one meter. Locating distal vacuum valve 237 as depicted in FIG. 2D "relocates" the stored energy boundary substantially nearer a proximal end of catheter 140. This substantial distance imposes (1) a time delay (2) viscous losses, and (3) decreased kinetic energy release to a proximal portion of catheter 140. This is one illustration of how certain VVA embodiments generate optimized pressure states in optimized locations and times; thereby generating improved pressure distributions and, consequently, improved flow regimes within the apparatus.

In certain VVA system 201 embodiments, connecting tubes 232*a* and/or 232*b* is/are non-isovolumetric component(s); in the machine state depicted in FIG. 2D, energy may be stored in any of all of: connecting tubes 232*a*, 232*b*, elastic tubing 230, and vacuum conduit 128). The stored energy of VVA system 201, as depicted in FIG. 2D, typically comprises elastic potential energy of collapsing or contracting any or all of those components under differential pressure forces.

FIGS. 2A-2C depict catheter 140 directly connected to elastic tubing 230; this is done to clearly identify the pressure regions or zones. Clinically, reservoir 102 assembly is typically positioned on a tabletop, with flexible components (e.g., connecting tube 132, 232*a*, 232*b*, etc.) being utilized to make a flexible fluid connection between the fixed reservoir 102 assembly and moveable catheter 140. FIG. 2D illustrates VVA system 201 featuring one or more connecting tube(s) 232*a*, 232*b* for reasons including facilitating manipulation of catheter 140 by a clinician. This manual manipulation may be performed upon a housing or "handpiece," as in prior-art embodiments. In certain VVA embodiments, components such as vacuum valve 130, distal vacuum valve 237, displacement mechanism 220, isolation valve 210, etc. may be contained within a "remote unit," housing or handpiece.

S-coordinate 158 may terminate at the proximal end of catheter 140 in some embodiments. In some embodiments, s-coordinate 158 may extend through components such as connecting tube 232*b*, elastic tubing 230, and connecting tube 232*a*. Certain VVA embodiments calculate the pressure drop along the s-coordinate 158 within catheter 140. Pressure drop through connecting tube(s) 232*a*, 232*b* and through elastic tubing 230 may be calculated, or assumed to be (1) zero, (2) constant or (3) negligible. These assumptions may be based upon the larger diameter of these components when compared to the smaller diameter of catheter 140; refer to the Hagen-Poiseuille equation (Eq. 1). Connecting tube 232*a*, 232*b*, 132, etc. may range from approximately 2 mm to 30 mm in diameter and from approximately 1 cm to in excess of 2 meters in length.

FIG. 2D depicts VVA system 201 featuring a plurality of pressure gages 224, 226 and a plurality of vacuum valves 130, 237. Certain VVA system 201 embodiments cycle proximal vacuum valve 130 and measure pressure at distal pressure gage 226; this may reduce noise in pressure waveform data by increasing the spatial separation between an actuator (e.g., vacuum valve 130, 237, etc.) and a sensor (e.g., distal pressure gage 226, proximal pressure gage 224, etc.). Likewise, certain VVA system 201 embodiments cycle distal vacuum valve 237 and measure pressure at proximal pressure gage 224. In some VVA system 201 embodiments, only distal vacuum valve 237 and distal pressure gage 226 are present; these components may be contained within a "remote unit," housing or handpiece located intermediate between reservoir 102 assembly and a proximal end of catheter 140. In some VVA system 201 embodiments, only proximal vacuum valve 130 and proximal pressure gage 224 are present; these components may be any combination of (1) affixed to reservoir 102 assembly, (2) fluidically coupled to reservoir 102 assembly by connecting tube 232*a* or (3) contained within a housing or handpiece. Certain VVA system 201 embodiments may have any combination of one or more vacuum valves 130, 237, one or more pressure gages 222, 224, 226, and one or more connecting tubes 232*a*, 232*b*, etc. In certain VVA system 201 embodiments, connecting tube(s) 232*a*, 232*b*, etc. are isovolumetric components, meaning that internal volume of these components remains substantially constant during operation of the apparatus. In certain VVA system 201 embodiments, connecting tube(s) 232*a*, 232*b*, etc. are non-isovolumetric components, meaning that internal volume of these components changes substantially (i.e., in excess of approximately 5%) during operation of the apparatus. It is important to note that certain additional VVA components, e.g., distal vacuum valve 237, connecting tube 232*a*, 232*b*, etc. are depicted as integrated to VVA system 201. These additional VVA components may be equally-well integrated to various VVA system embodiments, e.g., VVA systems 401, 501, 601, etc.; these additional VVA components are omitted subsequently, for clarity and compactness.

Among other salient points, FIG. 2D illustrates that a significant distance (range of approximately 1 m to 4 m) typically exists between evacuated reservoir 102 and a proximal end of catheter 140 in many vacuum aspiration systems. The flowing pressure drop along this significant distance is typically not of significant concern, typically being in the range of approximately 0.2% to 5% of the total pressure drop from the distal tip of catheter 140 to evacuated reservoir 102. However, in the VVA system 201 static equilibrium state depicted in FIG. 2D, potential energy is stored in portions or regions of the apparatus that are in a pressure state of substantially $P_{vacuum}$, which may extent to locations annotated as 152*a*, 152*b*, 152*c*, or any other location within the apparatus.

For clarity, the remaining figures of this disclosure exclude certain components that are common to many embodiments, such as vacuum reservoir 102, connecting tubes 232*a*, 232*b*, vacuum conduit 128, etc. In successive figures herein, it is to be assumed that an omitted source of vacuum is present "to the left" of the figures, and that a patient vascular system is present at the distal end, i.e., "right end," of catheter 140. The pressure state "to the left" of the figures is given to be substantially $P_{vacuum}$ 152, and that the pressure state at the distal end of catheter 140 is given to be substantially $P_{IV}$ 154.

FIGS. 3A-3F are presented as prior art examples that illustrate a real-world example of how visco-volumetric aspiration works, utilizing familiar items: turkey baster 310 and household liquids. This example illustrates that the viscosity of a fluid affects the transferred volume of that fluid, in an amount of time. This example introduces normalized volumes, such as $V_0$; this non-dimensionalizes volume to a reference volume (e.g., $V_0$, $V_{maximum}$, $V_{minimum}$, 3 cc, 0.05 cc, etc.). Also introduced is a reference pressure $P_{atm}$; pressures are normalized to this reference pressure and are expressed as a percentage. For illustrative and numerical purposes, it is stated that the normalize volume of turkey baster 301 undergoes change ranging from 100% to 10%; the normalized pressure undergoes change ranging from 10% to 100%. This volumetric normalization method eliminates the length dimension; thereby a "small" turkey baster and a "large" turkey baster are "similar." Similarly, this pressure normalization method eliminates the magnitude of atmospheric pressure; thereby operation at sea level is similar to operation at elevations exceeding 10,000 ft.

Figures 3A, 3B, 3C, 3D, 3E, 3F:
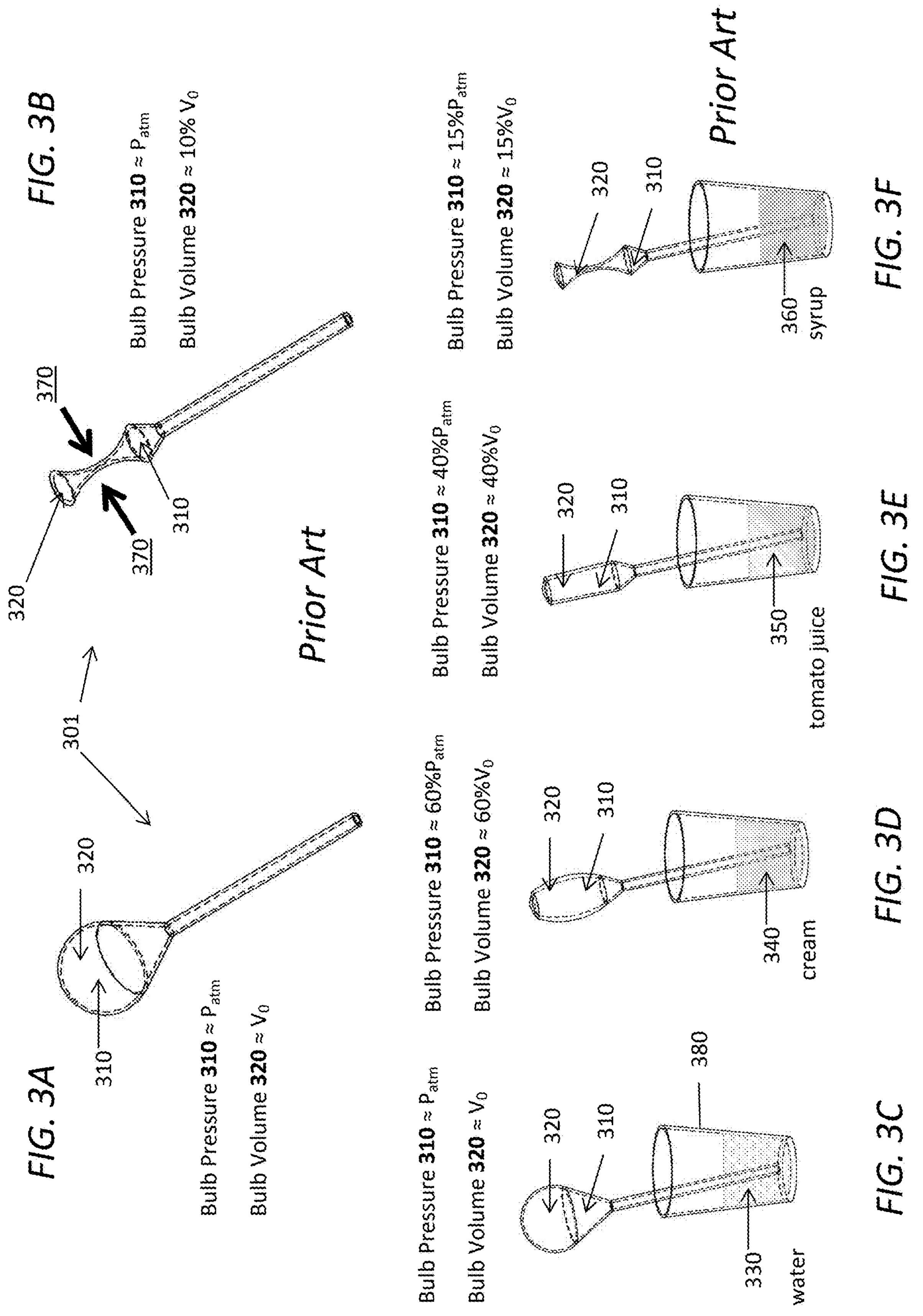
Prior Art FIG. 3C
FIG. 3A depicts an undeformed prior-art turkey baster in air.
FIG. 3B depicts the turkey baster of FIG. 3A after deformation.
FIG. 3C depicts the turkey baster of FIG. 3A undeformed in a tumbler of water.
FIG. 3D depicts the turkey baster of FIG. 3A partially deformed in a tumbler of cream.
FIG. 3E depicts the turkey baster of FIG. 3A partially deformed in a tumbler of tomato juice.
FIG. 3F depicts the turkey baster of FIG. 3A substantially deformed in a tumbler of syrup.

FIG. 3A depicts a turkey baster 301 in equilibrium with air. Bulb pressure 310 is $P_{atm}$, substantially 100% of atmospheric pressure. Normalized bulb volume 320 is substantially at a reference or nominal volume, annotated as $V_0$. FIG. 3B depicts turkey baster 301 shown compressed by external force 370 such as may be applied by fingers or a hand. Normalized bulb pressure 310 is substantially atmospheric and normalized bulb volume 320 is stated to be approximately 10% of $V_0$. Turkey baster 301 (in the configuration of FIG. 3B) is then immersed in tumbler 380 containing liquid and external force 370 is released. Liquids flow into turkey baster 301 at characteristic rates that are predominantly governed by the viscosity of each liquid. More viscous liquids require a longer time for turkey baster 301 to recover to substantially nominal volume ($V_0$), or, analogously, for the displaced volume 240 of FIG. 2C to approach zero. Because many biological liquids (e.g., blood, plasma, serum, lymph, CSF, etc.) have substantially the same specific gravity (i.e., density), mass and density considerations of fluids are overlooked herein; thereby, any differences in gravitational effects between the representative liquids are also considered negligible and overlooked.

FIG. 3C depicts turkey baster 301 immersed in tumbler 380 containing water 330 at some time (t*, range of approximately 0.5 to 5 seconds) after external force 370 is released. At time t*, bulb volume 320 of turkey baster 301 has recovered to approximately nominal volume (i.e., normalized volume≈100% $V_0$). Bulb pressure 310 is substantially atmospheric, this may be expressed as a normalized pressure of 1 (i.e., normalized pressure≈100% $P_{atm}$).

FIG. 3D depicts turkey baster 301 immersed in tumbler 380 containing cream 340 at time t* (after external force 370 is released). At time t*, the bulb volume 320 of turkey baster 301 has recovered to approximately 60% of nominal volume (60% $V_0$), and bulb pressure 310 is approximately 60% of atmospheric (60% $P_0$). Cream 340 is more viscous than water 330, and the flow rate is correspondingly lower; this reduced flow rate results in bulb volume 320 and bulb pressure 310 not having enough time (by time t*) to recover to nominal size of approximately $V_0$ at substantially atmospheric pressure. As time is extended beyond t*, bulb pressure 310 and bulb volume 320 may recover to substantially nominal size and pressure. The viscosity of the fluid (e.g., water, cream, blood, oil, etc.) is typically deterministic of the length of time required to recover to substantially nominal size and pressure.

FIG. 3E depicts turkey baster 301 immersed in tumbler 380 containing tomato juice 350 at time t* (after external force 370 is released). At time t*, the bulb volume 320 of turkey baster 301 has recovered to approximately 40% of nominal volume (40% $V_0$) and bulb pressure 310 is approximately 40% of atmospheric (40% $P_{atm}$). FIG. 3F depicts turkey baster 301 immersed in tumbler 380 containing syrup 360 at time t* (after external force 370 is released). At time t*, bulb volume 320 of turkey baster 301 has recovered to approximately 15% of nominal volume (15% $V_0$) and bulb pressure 310 to approximately 15% of atmospheric (15% $P_{atm}$). In theory, and given enough time, the configurations of FIG. 3D, FIG. 3E and FIG. 3F will recover to substantially nominal or equilibrium dimensions at bulb pressure $310 \approx P_{atm}$ and bulb volume $320 \approx V_0$. FIG. 3A, FIG. 3B and FIG. 3C depict turkey baster 301 in a static equilibrium state; FIG. 3D, FIG. 3E and FIG. 3F depict turkey baster 301 tending toward a static equilibrium state at a characteristic rate. That characteristic rate is, in some cases, inversely proportional to the viscosity of the liquid. Tomato juice 350 is a heterogeneous mixture of suspension containing solids of varying size; this makes tomato juice a reasonable experimental analogue for thrombus-laden blood.

Figures 4A, 4B, 4C, 4D:
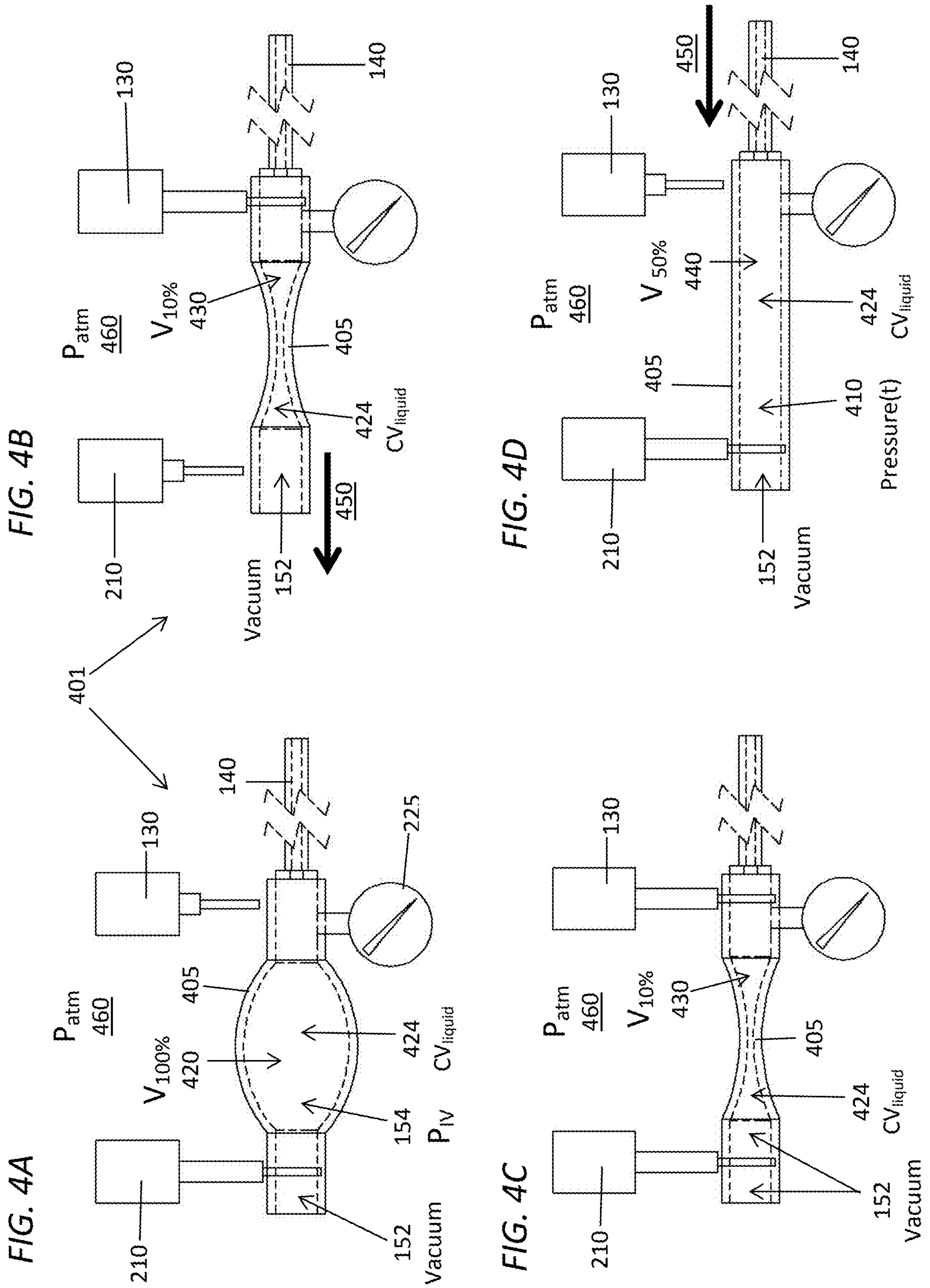
FIG. 4A depicts a VVA system in accordance with an illustrative embodiment of the present invention, wherein the system includes a bulb, and wherein the bulb is in a first volumetric state, a vacuum valve is in open state, and an isolation valve is in the closed state.
FIG. 4B depicts the VVA system of FIG. 4A, wherein the bulb is in a second volumetric state, the vacuum valve is in the closed state, and the isolation valve is in the open state.
FIG. 4C depicts the VVA system of FIG. 4A, wherein the bulb is substantially in the second volumetric state, the vacuum valve is in the closed state, and the isolation valve is in the closed state.
FIG. 4D depicts the VVA aspiration system of FIG. 4A, wherein the bulb is in a third volumetric state, the vacuum valve is in the open state, and the isolation valve is in the closed state.

FIG. 4A depicts VVA (Visco-Volumetric Aspiration) system 401 in accordance with an illustrative embodiment of the present invention. FIG. 4A depicts VVA system 401 in a first static equilibrium state, a first machine state and a first volumetric state. The volumetric state is normalized to 1.0 or 100%, and the pressure state (e.g., $P_{IV}$ 154, $P_{atm}$, any reference pressure, etc.) is normalized to 1.0 or 100%. FIG. 4C depicts system 401 in: a second static equilibrium state, a second machine state and a second volumetric state. The volumetric state is normalized to 0.1 or 10%, and the pressure state is normalized to 0.1 or 10%. The substantially different volumetric states of system 401 depicted in FIG. 4A and FIG. 4C illustrate that the internal volume of system 401 is variable with time during operation of the apparatus. Bulb 405 is a non-isovolumetric system component assuming variable volumetric states in operation. The apparatus state of FIG. 4A is: vacuum valve 130 in the open state, isolation valve 210 in the closed state, the pressure state is substantially equal to $P_{IV}$ 154 and the normalized volumetric state is 1 ($V_{100\%}$ 420).

FIG. 4B depicts VVA system 401 of FIG. 4A wherein the apparatus state is: vacuum valve 130 in the closed state, isolation 210 valve in the open state, the pressure state is tending toward Vacuum 152 and the normalized volumetric state is 0.1 ($V_{10\%}$ 430). Aspirate flow 450 from bulb 405 to waste is shown in this non-equilibrium state.

FIG. 4C depicts VVA system 401 of FIG. 4B wherein the apparatus state is: vacuum valve 130 in the closed state, isolation 210 valve in the closed state, the pressure state is substantially that of Vacuum 152 and the normalized volumetric state is 0.1 ($V_{10\%}$ 430). FIG. 4C depicts VVA system 401 in a static equilibrium state, with a finite amount of stored energy available to aspirate a finite volume of fluid.

FIG. 4D depicts VVA system 401 of FIG. 4C wherein the apparatus state is: vacuum valve 130 in the open state, isolation 210 valve in the closed state, the pressure state is the instantaneous value of Pressure(t) 410 and the instantaneous normalized volumetric state is 0.5 ($V_{50\%}$ 440). FIG. 4D depicts VVA system 401 tending toward the static equilibrium state depicted in FIG. 4A. Aspirate flow 450 through catheter 140 is shown.

VVA system 401 utilizes differential pressure (between the inside and outside of bulb 405) to change the pressure state and volumetric state of bulb 405; this consequently changes the volumetric state of control $volume_{liquid}$ 124. This is in contrast to turkey baster 310 and VVA system 201 (of FIGS. 2A-2D), which utilize external contact forces (e.g., displacement mechanism 220, hand squeeze, etc.) to change the volumetric state of the apparatus.

For analysis herein, it is convenient to approximately quantify the value of "full vacuum" to be approximately 30 inHg. Consequently, a vacuum level of 27 inHg is a convenient example operating vacuum level, because 27 inHg vacuum is approximately 10% of one atmosphere (in absolute pressure units). A convention used herein (for example purposes) is to normalize 30 inHg vacuum to a pressure state of 0.0 (≈0.0% of atmospheric pressure), 27 inHg vacuum is normalized to a pressure state of 0.1 (≈10% of atmospheric pressure), and zero vacuum is normalized to a pressure state of 1.0 (≈100% of atmospheric pressure $P_{atm}$ 460, intravascular pressure $P_{IV}$ 154, or any other reference pressure). This convention facilitates an "expansion ratio" of approximately 1:10 which serves as basis for examples. There is no implication or requirement that either normalized volumetric states or normalized pressure states remain within the example limits of 0.1 and 1.0. For instance, a normalized volumetric state of 0.05, or a normalized pressure state of 1.15, etc. are anticipated in ordinary operation of the apparatus.

In FIG. 4A, the interior of bulb 405 is at substantially intravascular pressure ($P_{IV}$ 154) in a static equilibrium state; the exterior of bulb 405 is at substantially atmospheric pressure ($P_{atm}$ 460). Control $volume_{liquid}$ CV 424 is at substantially maximum volume, because non-isovolumetric component bulb 405 is at maximum normalized volumetric state (annotated $V_{100\%}$ 420). In FIG. 4B, control $volume_{liquid}$ CV 424 is at substantially minimum volume because non-isovolumetric component bulb 405 is at substantially minimum normalized volumetric state (annotated $V_{10\%}$ 430).

As a numerical example, the volume of $V_{10\%}$ 430 (FIG. 4C) is stated be 1 cc and the volume of $V_{100\%}$ 420 (FIG. 4A) is stated to be 10 cc. In this example, the stated 1:10 volumetric "expansion ratio" of non-isovolumetric components (e.g., bulb 405) is convenient for use in examples. Of course any arbitrary expansion ratios may be selected (e.g., 2 cc to 8 cc for a 1:4 expansion ratio, 0.1 cc to 5 cc for a 1:50 expansion ratio, etc.) and normalized similarly. It is important to note that the expansion ratio of any AMC is independent of all other AMCs; in other words a first AMC may have a 1:10 expansion ratio, a second AMC may have a 1:4.5 expansion ratio, a third AMC may have a 1:15 expansion ratio, etc. Furthermore, the minimum and maximum pressure states of each AMC are independent of all other AMCs.

At or near the static equilibrium condition depicted in FIG. 4A, intravascular pressure ($P_{IV}$ 154) is an approximate measurement of the "local" blood pressure; local meaning at or near a distal end of catheter 140. While intravascular pressure ($P_{IV}$ 154) may fluctuate (as does blood pressure during systole and diastole), methods such as time-averaging, superpositioning and/or predictive methods are utilized in certain VVA embodiments. In certain VVA embodiments, time derivatives of pressure are utilized; thereby focusing on the rate of change, rather than absolute pressure magnitudes. This approach inherently minimizes certain biases or offsets caused by intravascular pressure fluctuations, such as those between systolic and diastolic extremes (e.g., 120/80 mmHg), focusing upon the slope of the pressure waveform that is under analysis.

In some cases, from the apparatus state of VVA system 401 depicted in FIG. 4D, vacuum valve 130 remains in an open state for sufficient time to substantially attain the apparatus state depicted in FIG. 4A. However in other cases, vacuum valve 130 is changed to the closed state at intermediate pressure states and/or intermediate volumetric states (e.g., pressure≈20 inHg, bulb volume≈40%, etc.). In certain embodiments, the state of vacuum valve 130 is changed a plurality of times at a plurality of intermediate pressure states. Typically, subsequent to execution of any AMC, VVA system 401 may be returned to the machine and pressure states of FIG. 4B wherein bulb 405 is evacuated; this may be done to increase the vacuum level and/or flow rate of successive AMCs.

Some embodiments continuously and/or intermittently measure pressure and quantitatively compute VVA derived variables such as viscosity, flow rate, etc. These measurements may occur during flowing (i.e., vacuum valve 130 in the open state) or non-flowing (i.e., vacuum valve 130 in the closed state) conditions. Under certain circumstances, some VVA embodiments place both vacuum valve 130 and isolation valve 210 in the open state to enable unrestricted flow, thus attaining the prior-art aspiration system 101 flow regimes depicted in FIG. 1B and FIG. 1D.

The instantaneous volumetric state depicted in FIG. 4D may exhibit rapid or slow expansion toward the static equilibrium volumetric state depicted in FIG. 4A (range of approximately 0.020 seconds to in excess of 1 hour, in cases such as a clogged catheter). From the apparatus state depiction of FIG. 4D, aspirate flow 450 may be blocked by changing vacuum valve 130 to the closed state; this is to reassume the configuration of FIG. 4C, albeit at different pressure and volume levels (i.e., $P \neq P_{vacuum}$, $V \neq V_{10}$%). From the apparatus state depiction of FIG. 4D, vacuum valve 130 may be set to the closed state and isolation valve 210 may be set to the open state to reassume the machine state of FIG. 4B, thereby evacuating bulb 405 to a different vacuum level, e.g., substantially vacuum 152.

Operationally, certain VVA embodiments collect data in machine state configurations such as depicted in FIG. 4D, where one or more non-isovolumetric components (e.g., bulb 405, connecting tubes, etc.) is/are expanding toward equilibrium with some reference pressure. If the machine state configuration of FIG. 4D is left undisturbed for a sufficient time period, it will typically tend toward reassuming the static equilibrium volumetric state depicted in FIG. 4A. During any or all of this sufficient time period, the state of vacuum valve 130 may be cycled a plurality of times (range of 1 to greater than approximately 200); any or all of these valve state cycles may provide data that enable calculation of relevant variables including, but not limited to, flow rates, volumetric data, viscometric data, etc. of the contents of catheter 140 and/or any incoming aspirate.

FIGS. 4A-4D depict bulb 405 experiencing a differential pressure across its solid boundary (i.e., the enclosing wall), such that the internal pressure state is, at many times, substantially unequal to the external pressure state. The external pressure state is depicted to be $P_{atm}$ 460 at all times.

FIG. 4A depicts VVA system 401 in a machine state configuration (i.e., vacuum valve 130 in the open state, isolation valve 210 in the closed state), pressure state (i.e., $P_{IV}$ 154) and volumetric state (i.e., $V_{100\%}$ 420=10 cc). From this state, an increase in the external pressure state (i.e., $P > P_{atm}$ 460), while the internal pressure state remains fixed, typically results in a decrease in the internal volumetric state (e.g., $V < V_{100\%}$ 154, etc.). A first implication of this is that the local atmospheric pressure, $P_{atm}$ 460, as well as $P_{IV}$ 154, have significant influence upon the volumetric state depicted in FIG. 4A ($V_{100\%}$ 420). Consider an example wherein the volumetric state depicted in FIG. 4A is given to be 10 cc. From this state, if the external pressure (i.e., $P_{atm}$ 460) is significantly increased, and/or if the internal pressure (i.e., $P_{IV}$ 154) is significantly decreased, the equilibrium volumetric state will typically be decreased to significantly less than 10 cc, for instance 7.2 cc, as an arbitrary example. In such a case, $V_{100\%}$ 420 may be normalized to 7.2 cc. This highlights a characteristic of certain VVA embodiments: neither the magnitude of the internal pressure state (e.g., $P_{IV}$ 154) nor the magnitude of the external pressure state (e.g., $P_{atm}$ 460) affects certain normalization methods utilized in certain VVA control algorithms. This illustrates an example method, utilized in certain VVA embodiments, to dynamically normalize pressure states and volumetric states to different clinical variables including atmospheric pressure and patient blood pressure.

Certain VVA embodiments re-normalize to different volumetric states and/or pressure states dynamically during operation of the apparatus. Thereby, certain VVA embodiments thereby "shift" or "transition" between pressure and volume scales with continuous fidelity and without need for "re-zeroing" or "recalibrating" to differing pressure state conditions (e.g., $P_{atm}$ 460, $P_{IV}$ 154, any reference pressure, etc.). It is important to note that $P_{IV}$ 154 varies both in time and patient-to-patient, and that local atmospheric pressure ($P_{atm}$ 460) remains substantially constant throughout a typical thrombectomy procedure; certain VVA embodiments automatically re-normalize to those specific environmental and/or clinical pressure states. However, certain VVA system 401 embodiments are not constrained by the local atmospheric pressure, rather the pressure state external to bulb 405 is utilized as a VVA system variable.

Figure 4E:
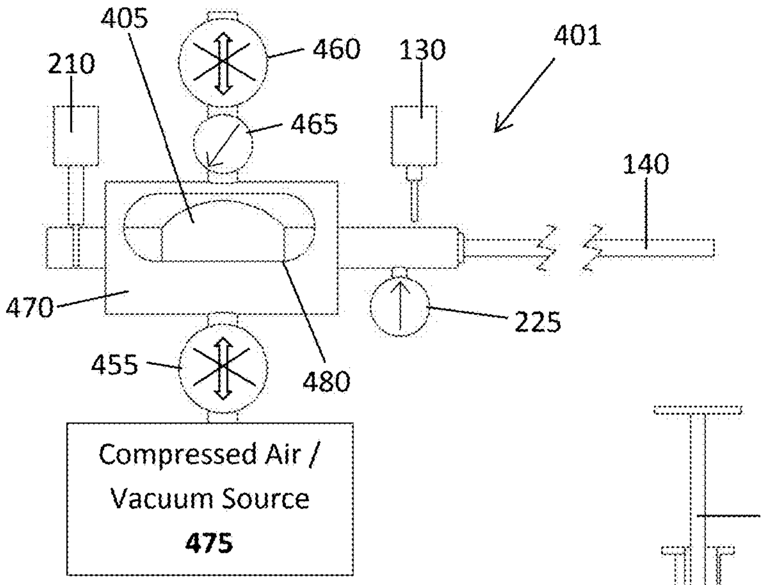
FIG. 4E depicts a modification of the VVA aspiration system of FIG. 4A, wherein the bulb is in a first volumetric state and is enclosed within a pressure/vacuum chamber.
Figure 4F:
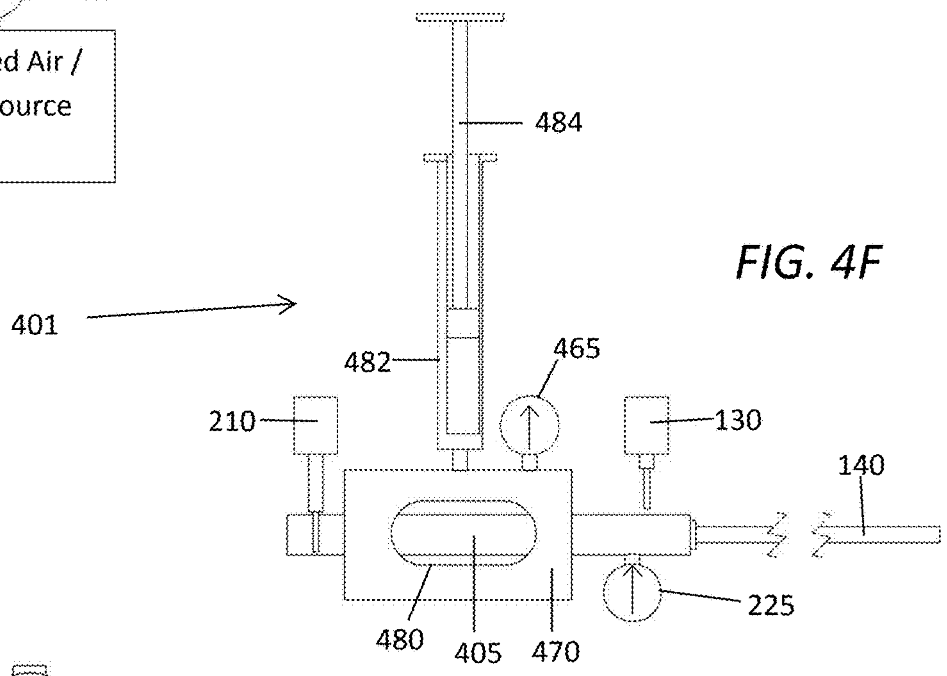
FIG. 4F depicts the VVA aspiration system of FIG. 4E, wherein the bulb is in a second volumetric state, liquid is transferred to the pressure/vacuum chamber by utilizing a syringe.
Figure 4G:
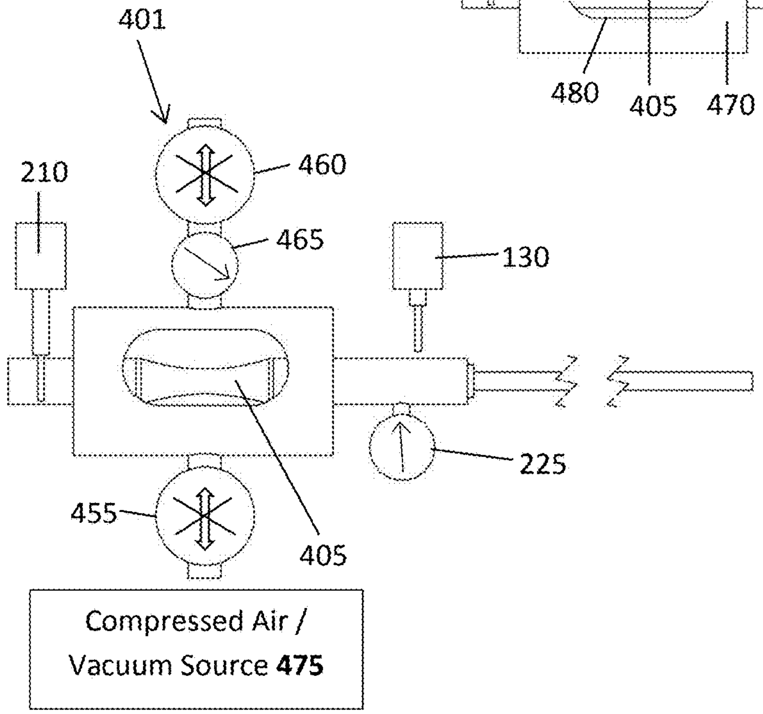
FIG. 4G depicts the VVA aspiration system of FIG. 4E, wherein the bulb is in a third volumetric state.

FIG. 4E depicts VVA system 401, wherein pressure/vacuum chamber 470 "encapsulates," and creates an adjustable pressure state surrounding bulb 405. FIGS. 4E-4G depict VVAS system 401 in indistinguishable internal pressure states and static equilibrium states, however the volumetric states and external pressure states are visibly different. The machine state depicted in FIG. 4E is: vacuum valve 130 is in the open state, each of isolation valve 210, source valve 455 and vent valve 460 is in the closed state. Compressed air/vacuum source 475 may be configured to supply pressure substantially pressure either greater than or less than atmospheric.

As depicted in FIG. 4E, Compressed air/vacuum source 475 has been configured to supply vacuum, i.e., pressure less than atmospheric. The external pressure state of bulb 405 has been reduced by previously changing source valve 455 to the open state, thereby "evacuating" pressure/vacuum chamber 470 of air. FIG. 4E depicts chamber pressure gage 465 indicating a reading in the "vacuum" region of the scale. Pressure gage 225 measures substantially the pressure inside of bulb 405, indicating a pressure in the "nominal" or central region of the scale. Clinically, the indicated "nominal pressure" is typically substantially intravascular pressure. VVA system 401, as depicted in FIG. 4E, is in a static equilibrium pressure state with substantially intravascular pressure on the inside of bulb 405, and substantially lower pressure on the outside of bulb 405. Therefore, bulb 405 is depicted in a distended volumetric state, as may be observed through optional chamber viewport 480. In the machine configuration depicted in FIG. 4E, the pressure state within pressure/vacuum chamber 470 is changed by changing the states of either source valve 455 or vent valve 460, thereby either adding or removing a finite volume of a compressible fluid, typically air.

FIG. 4F depicts a variation of VVA system 401 of FIG. 4E in a static equilibrium state with substantially intravascular pressure on both the inside and outside of bulb 405. This is illustrated by both of chamber pressure gage 465 and pressure gage 225 indicating in the "nominal" zone. Bulb 405 is in a nominal volumetric state, because internal and pressures are substantially equalized across the wall.

In embodiment and apparatus configuration of FIG. 4F, the volumetric state within pressure/vacuum chamber may be changed by adding or removing a finite volume of an incompressible fluid, typically water, though saline or oil are utilized in certain embodiments. The volumetric state of pressure/vacuum chamber 470 may be changed by changing the position of plunger 484 with respect to barrel 482, as with an ordinary syringe. Certain VVA system 401 embodiments utilize one more actuators, or linear motors, to change the position of plunger 484, thereby changing the volumetric state within pressure/vacuum chamber 470. In certain embodiments, the position of plunger 484 is controlled by VVA system controller. In certain embodiments, a commercially available syringe pump, such as Fisherbrand® Single Syringe Pump or equivalent, is utilized. In certain embodiments, oil (e.g., silicone oil, SAE 10 oil, etc.) is utilized as the incompressible fluid within pressure/vacuum chamber 470. This is done because the vapor pressure of oil is substantially less that of water. This may further reduce the pressure state within pressure/vacuum chamber 470 and bulb 405 to vacuum levels substantially lower than may be attained with typical prior-art aspiration systems.

VVA system 401, as depicted in FIG. 4F, may additionally be utilized to generate maximum-attainable vacuum levels within pressure/vacuum chamber 470. In certain cases, this may consequently generate maximum-attainable vacuum levels within bulb 405; this may improve aspiration efficacy in certain AMC modes. In many instances, plunger 484 may be forced upward more rapidly than fluid may be aspirated through catheter 140. This typically results in boiling of liquid within pressure/vacuum chamber 470 and/or barrel 482, thereby generating a vapor space at or below the vapor pressure of the liquid inside. From the machine state, volumetric state and pressure state depicted in FIG. 4F, certain embodiments: (1) change vacuum valve 130 to the closed state, and (2) force plunger 484 upward, generating a vapor space within barrel 482. Vapor may form inside of bulb 405 as aqueous blood components boil in the reduced pressure state. In the resulting static equilibrium state, a substantial, finite quantity of potential energy is stored; changing vacuum valve to the open state releases this finite quantity of energy. VVA embodiments that utilize vapor and/or gas headspaces within the apparatus are discussed in further detail in conjunction with FIG. 5A.

FIG. 4G depicts VVA system 401 of FIG. 4E in a machine state that is indistinguishable from that of FIG. 4E. Both FIGS. 4E and 4G depict static equilibrium states; however the volumetric state and external pressure state are different in the two figures. FIG. 4G depicts a high-pressure state within pressure/vacuum chamber 470; bulb 405 is collapsed to a reduced volumetric state.

As depicted in FIG. 4G, Compressed air/vacuum source 475 has been configured to supply compressed air, or pressure greater than atmospheric. The external pressure state of bulb 405 has been increased by previously changing source valve 455 to the open state, thereby "pressurizing" pressure/vacuum chamber 470. FIG. 4E depicts chamber pressure gage 465 indicating a reading in the "pressure" region of the scale; pressure gage 225 indicates (internal) pressure in the "nominal" or central region of the scale.

From the machine state, pressure state and volumetric state depicted in FIG. 4G, certain VVA system 401 embodiments change vent valve 460 to the open state, thereby decreasing the pressure within pressure/vacuum chamber 470. Consequently the pressure state within bulb 405 is decreased; this creates a differential pressure between opposite ends of catheter 140, typically causing a flow of fluid therein. It is instructive to note that the pressure state and volumetric state depicted in FIG. 4E may evolve from those depicted in FIG. 4F by forcing plunger 484 upward. Similarly, the pressure state and volumetric state depicted in FIG. 4G may evolve from those depicted in FIG. 4F by forcing plunger 484 downward.

FIG. 4E, FIG. 4F and FIG. 4G depict variations of VVA system 401 wherein the external pressure acting upon certain non-isovolumetric components (e.g., bulb 405, elastic tubing 230, etc.) is controlled. This control may be any combination of manual and/or automated (e.g., VVA system controller, keyboard/keypad/touchscreen/mouse, WiFi, cellular phone, knobs, etc.) setpoint control over certain VVA components (e.g., valve states, pressure regulators, actuators, pumps, syringe positioning, etc.). In certain VVA embodiments, non-isovolumetric components exposed to differing external vacuum and/or pressure levels dynamically during a procedure.

The VVA 401 embodiments depicted in FIGS. 4E-4G are significant for at least 4 reasons:

1. The VVA static equilibrium state (i.e., volumetric state and/or pressure state) may be changed by means other than changing the state of vacuum valve 130. Flow of aspirate may be initiated, measured and stopped without inducing valve noise into the pressure waveform data.
2. The external pressure acting upon bulb 405 may be reduced to, or substantially below, the vapor pressure of water (approximately 50 mmHg, ≈1 psia, ≈6.6 kPa at 37° C.). The internal pressure state bulb of bulb 405 may thereby be reduced to a "maximum-attainable vacuum" level. The maximum-attainable vacuum level may be substantially less that the vacuum level attained in prior-art vacuum aspiration systems.
3. The range of displaced volumes may be extended such that example bulb 405 may be "expanded" to volumes greater than 10 cc by reducing the external pressure (acting upon bulb 405). Likewise, the minimum volume of any non-isovolumetric component may be further reduced by the application of increased external pressure. Incompressible fluids may be utilized in certain VVA system 401 embodiments to apply very high and very low external pressures (range of approximately 0.1 Pa ($8\times10^{-3}$ mmHg) absolute to greater than 35 bar, ≈500 psig). This is in contrast to certain other VVA embodiments, typically having atmospheric pressure acting upon non-isovolumetric components at all times during an aspiration procedure.

4. Certain VVA 401 embodiments, such as depicted in FIGS. 4E-4G, may utilize sources of fluid motive power other than an evacuated reservoir 102 to create low pressure regions that cause aspirate flow. As an example, from the machine state, volumetric state and equilibrium state depicted in FIG. 4E, certain embodiments:
(a) change vacuum valve 130 to the closed state and isolation valve 210 to the open state,
(b) configure compressed air/vacuum source 475 to supply compressed air,
(c) change chamber valve 455 to the open state; this increases the pressure state within pressure/vacuum chamber 470 and decreases the volumetric state of bulb 405, and after sufficient time,
(d) change isolation valve 210 to the closed state and vacuum valve 130 to the open state.

The above-listed sequence typically causes VVA apparatus 401 to attain the equilibrium state, pressure state and volumetric state depicted in FIG. 4G, wherein the volumetric state of bulb 405 is at substantially minimum.

From the apparatus state depicted in FIG. 4G, vent valve 460 may be opened to reduce the pressure state within pressure/vacuum chamber 470, and consequently reduce the pressure state within bulb 405, as it tends toward substantially the volumetric state depicted in FIG. 4F. The pressure state within pressure/vacuum chamber 470 and bulb 405 may be further reduced by configuring compressed air/vacuum source 475 to supply vacuum, thereby further increasing the volumetric state of bulb 405, as it tends toward the volumetric state depicted in FIG. 4E. In certain cases, a state configuration indistinguishable from that depicted in FIG. 4E may develop. This illustrates that certain VVA system embodiments utilize sources of fluid motive power (i.e., differential pressure) other than an air-evacuated reservoir which operates at substantially below atmospheric pressure.

Figure 5B:
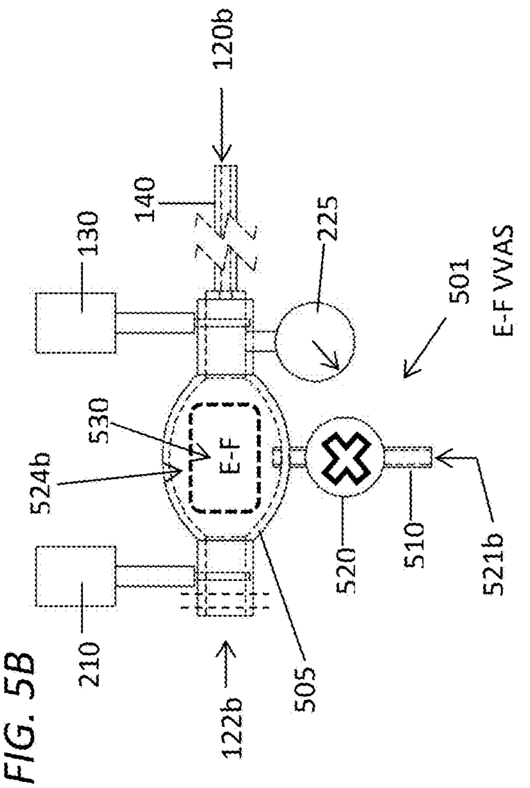
FIG. 5B depicts the VVA aspiration system of FIG. 5A, wherein the vacuum valve is in the closed state, the isolation valve is in the closed state, the E-F valve is in the closed state and the compressible exogenous fluid is in a first volumetric state.
Figure 5D:
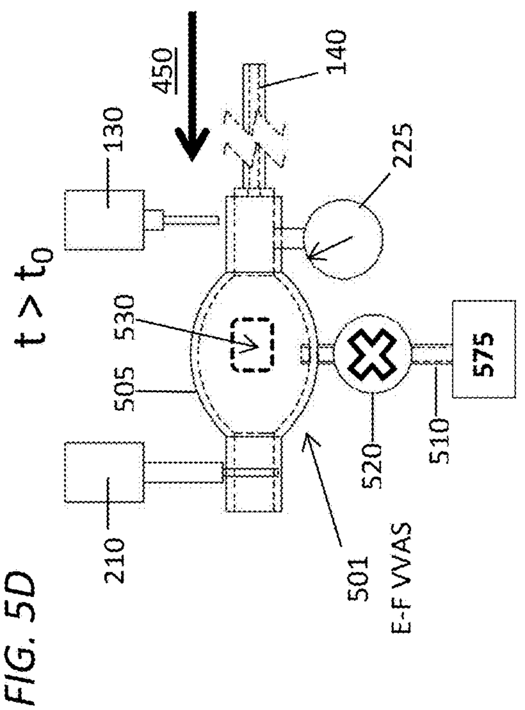
FIG. 5D depicts the VVA aspiration system of FIG. 5A, wherein the vacuum valve is in the open state, the isolation valve is in the closed state, the E-F valve is in the closed state and the compressible exogenous fluid is in a second volumetric state.
Figure 5A:
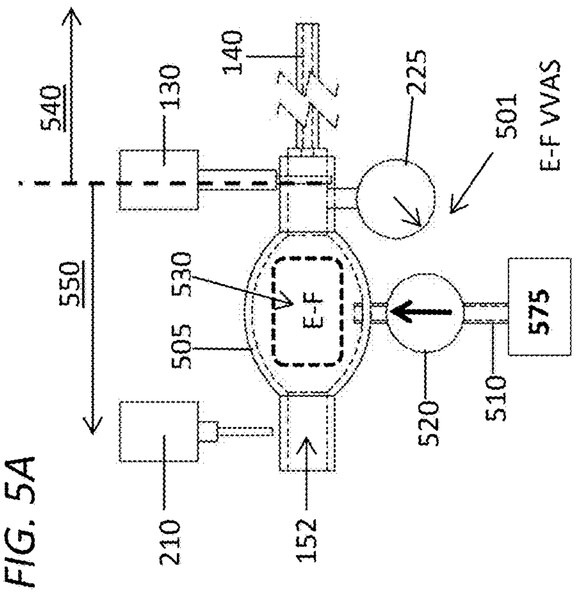
FIG. 5A depicts a VVA aspiration system in accordance with an illustrative embodiment of the present invention, wherein the system includes Exogenous-Fluid ("E-F") housing, and the aspiration system is configured for a compressible exogenous fluid. A vacuum valve is in the closed state, an isolation valve is in the open state, and an E-F valve is in the open state.

FIG. 5A depicts VVA (Visco-Volumetric Aspiration) system 501 in accordance with an illustrative embodiment of the present invention. VVA system 501 injects, infuses or otherwise admits one or more compressible and/or incompressible exogenous fluids into E-F housing 505 through E-F valve 520, shown in the open state. In FIGS. 5A-5D, VVA system 501 is configured to inject or infuse a compressible exogenous fluid (e.g., air, helium, nitrogen, water vapor, etc.) into E-F housing 505. In FIGS. 5E-5G, VVA system 501 is configured to inject or infuse an incompressible exogenous fluid (e.g., saline, water, silicone oil, etc.). Two regions are identified in FIG. 5A, region 540 (to the right of the dotted line) comprising incompressible biological fluids (e.g. blood, thrombus, plasma, etc.), and region 550 (to the left) comprising a mixture of compressible exogenous fluid 530 and incompressible biological fluids.

As depicted in FIG. 5A, the machine state of VVA system 501 is: each of isolation valve 210 and E-F valve 520 is in the open state and vacuum valve 130 is in the closed state. The pressure state depicted in FIG. 5A is substantially that of system vacuum 152. A first finite volume (V1) of compressible exogenous fluid 530 is depicted in the interior space of E-F housing 505, thereby displacing a substantially equal volume of biological liquid therein. In certain VVA system 501 embodiments, E-F housing 530 is substantially flexible and therefore a substantially non-isovolumetric system component. In certain VVA system 501 embodiments, E-F housing 530 is substantially rigid and therefore a substantially isovolumetric system component. As depicted in FIGS. 5A-5D, VVA system 501 components are configured to be isovolumetric; compressible exogenous fluid 530 is utilized as a non-isovolumetric element or non-isovolumetric fluid.

VVA system 501, as depicted in FIG. 5A-5H, comprises E-F fluid source 575, which may be configured to supply either compressible or incompressible fluids. Pressure gage 225 measures the pressure state within E-F housing 505. E-F inlet tube 510 and E-F valve 520 supply and control the flow of exogenous fluid into E-F housing 505. Referencing FIGS. 5A and 5B, the pressure state at control surface$_{liquid\ out}$ **122*b* is that of vacuum 152; the pressure state at control surface$_{liquid\ in}$ 120*b* is that of intravascular pressure. The pressure state at control surface$_{E\text{-}F}$ 521*b* is dependent upon the configuration of E-F source 575**, typical pressures range between approximately 0.1 psia to in excess of 500 psia.

FIG. 5B depicts VVA system 501 of FIG. 5A in a machine state wherein each of isolation valve 210, E-F valve 520 and vacuum valve 130 is in the closed state. The pressure state within E-F housing 505 is substantially that of vacuum 152. Compressible exogenous fluid 530 is isolated at a first volume (V1). is It is important to note that, as depicted in FIG. 5B, E-F housing 505 is isolated (1) in a static equilibrium state and (2) in a pressure state significantly below that of intravascular pressure, which is present at control surface$_{liquid\ in}$ **120*b*. A finite quantity of stored potential energy is present in the apparatus state depicted in FIG. 5**B.

VVA system 501, as depicted in FIG. 5B, is noteworthy because a third control surface, control surface$_{E\text{-}F}$ **521*b*, is present at an end of E-F inlet tube 510. Control volume$_{liquid}$ 524*b* and three control surfaces, control surface$_{E\text{-}F}$ 521*b*, control surface$_{liquid\ in}$ 120*b* and control surface$_{liquid\ out}$ 122*b* are depicted in FIG. 5B. A third control surface enables certain VVA system 501 embodiments to change the pressure state of the apparatus to a third pressure, this pressure is dependent upon the configuration of E-F fluid source 575. In FIG. 5B, VVA system 501 is in a closed state (no fluid flow into or out of) because each of vacuum valve 130, isolation valve 210, and E-F valve 520 is in the closed state. In many instances, a finite quantity of potential energy is stored in this machine state, and the finite quantity of potential energy is substantially dependent upon the pressure state and/or volumetric state of the apparatus. Admitting or removing fluid from the VVA system through control surface$_{E\text{-}F}$ 521*b*** enables certain VVA embodiments to change any or all of the: pressure state, volumetric state and stored energy state.

Figure 5C:
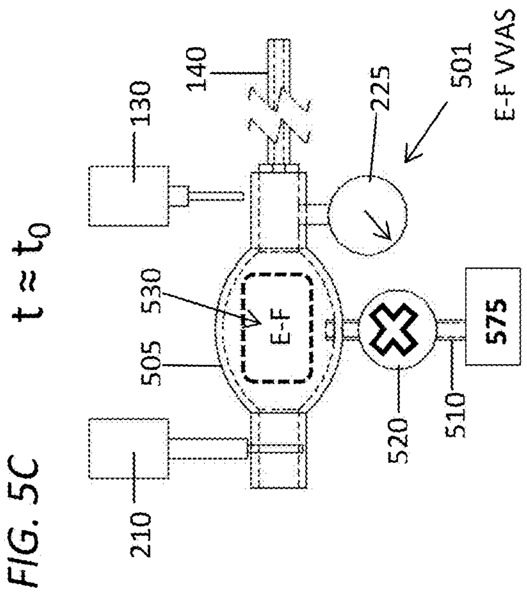
FIG. 5C depicts the VVA aspiration system of FIG. 5A, wherein the vacuum valve is in the open state, the isolation valve is in the closed state, the E-F valve is in the closed state and the compressible exogenous fluid is in substantially the first volumetric state.
Figure 5E:
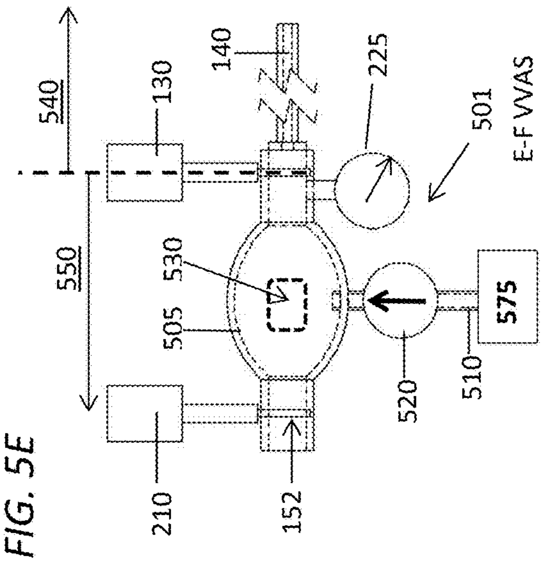
FIG. 5E depicts the VVA aspiration system of FIG. 5A, wherein the apparatus is configured for incompressible exogenous fluids. Each of the isolation valve and the vacuum valve is in the closed state and the E-F valve is in the open state.
Figure 5F:
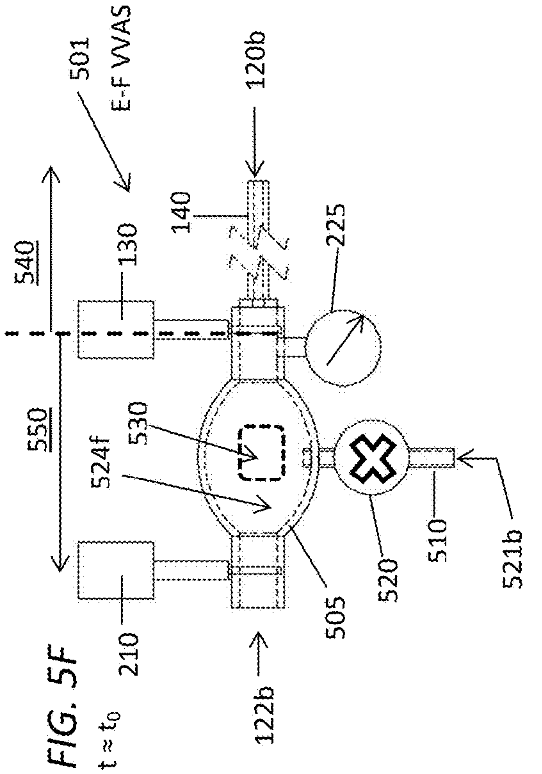
FIG. 5F depicts the VVA aspiration system of FIG. 5E wherein the E-F valve is in the closed state; an incompressible fluid is isolated under pressure, storing energy.
Figure 5G:
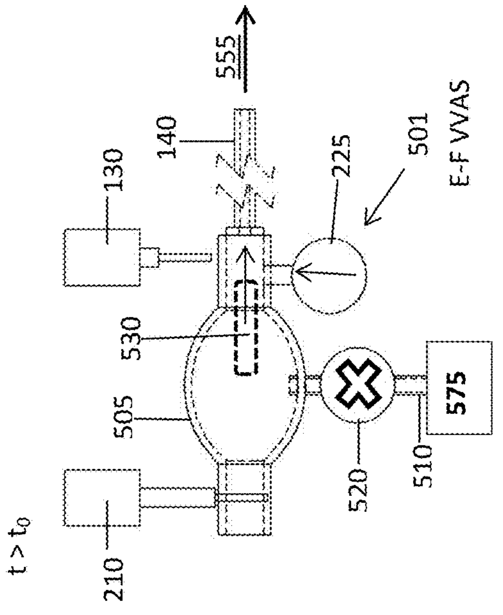
FIG. 5G depicts the VVA aspiration system of FIG. 5E releasing stored energy by changing the vacuum valve to the open state.

FIG. 5C depicts VVA system 501 of FIG. 5B at time $t=t_0$, whereupon vacuum valve 130 is changed to the open state, releasing the stored energy in the apparatus state depicted in FIG. 5B. The pressure state is "instantaneously" depicted to be substantially equal to that depicted in FIG. 5B. Compressible exogenous fluid 530 is "instantaneously" depicted to be substantially at the first volume (V1).

FIG. 5D depicts VVA system 501 of FIG. 5C at time $t>t_0$, wherein the pressure state within E-F housing 505 is substantially greater than at time $t=t_0$, and the volume of exogenous fluid 530 is a second volume (V2) that is substantially less than the first volume (V1). Aspirate flow 450 of aspirate is shown. Consequently, a finite volume of biological fluid, substantially equal to (V1−V2), has passed through control surface$_{liquid\ in}$ **120*b* and into control volume$_{liquid}$ 524*b*; see FIG. 5**B.

FIG. 5E depicts VVA system 501 of FIG. 5A that is configured to infuse or inject incompressible exogenous fluids (e.g., saline, water, etc.) into E-F housing 505. The machine state is: each of vacuum valve 130 and isolation valve 210 is in the closed state, and E-F valve 520 is in the open state. A finite volume of incompressible exogenous fluid 530 is present within E-F housing 505. The pressure state within E-F housing 505 is substantially that of E-F source 575, as may be observed and/or measured at pressure gage 225.

FIG. 5F depicts VVA system 501 of FIG. 5E wherein each of E-F valve 520, isolation valve 210 and vacuum valve 130 is in the closed state, thereby isolating E-F housing 505. The pressure state within E-F housing 505 is substantially that of E-F source 575. A finite volume of exogenous fluid 530, along with a finite volume of biological fluid, are isolated, under pressure, within E-F housing 505. A finite quantity of stored energy exists in the apparatus state depicted in FIG. 5F.

It is important to note that the stored energy state of VVA system 501 as configured and depicted FIG. 5F is stored "pressure" energy, that pressure being substantially greater than intravascular pressure, present at control surface$_{liquid\ in}$ 120*b*. From this apparatus state, opening vacuum valve 130 typically causes outward flow 555 of fluid through catheter 140. This is in contrast to the configuration and apparatus state of VVA system 501 as configured and depicted in FIG. 5B wherein "vacuum" energy is stored. From the apparatus state of FIG. 5B, opening vacuum valve 130 typically causes aspirate flow 450, in this case.

FIG. 5G depicts VVA system 501 of FIG. 5A wherein vacuum valve 130 is changed to the open state, releasing the stored "pressure" energy. A finite volume of outward flow 555 through catheter 140 is shown, as incompressible exogenous fluid 530, deforms and translates distally (i.e., to the right). It is important to note that the finite volume of exogenous fluid 530 injected into E-F housing 505, as depicted in FIG. 5E, is substantially equal to the finite volume of aspirate that subsequently flows outward through catheter 140. The significance of this is that, in certain cases, the finite volume of exogenous fluid 530 injected into E-F housing 505 may be very small (range of approximately 1 μl to in excess of 2 cc), however the pressure may be very high (ranging to in excess of 500 psi).

The sequence of apparatus states, as configured and depicted in FIGS. 5E-5G, is significant because certain VVA system 501 embodiments are thereby enabled to:

(1) Generate significant pressure pulses that may clear clogs within a catheter and/or disrupt thrombus in proximity to the catheter tip, and (2) Quantitatively limit the volume of blood, thrombus-laden aspirate, clots and/or clogging material that may be forcibly infused to the patient bloodstream at high velocity by the pressure pulse.

The importance of limiting the outflow volume is to avoid "blowing the cork" of a clogged or corked catheter. This may expel uncontrolled quantities of biological debris into the patient vasculature at high velocity. Certain VVA systems and embodiments thereby contrast with prior art, wherein pressure pulses do not effectively limit the volume of aspirate that flows outward from the tip of the catheter. Certain VVA embodiments exert volumetric control over aspirate fluids in both the aspirate flow 450 and outward flow 555 directions.

Figure 5H:
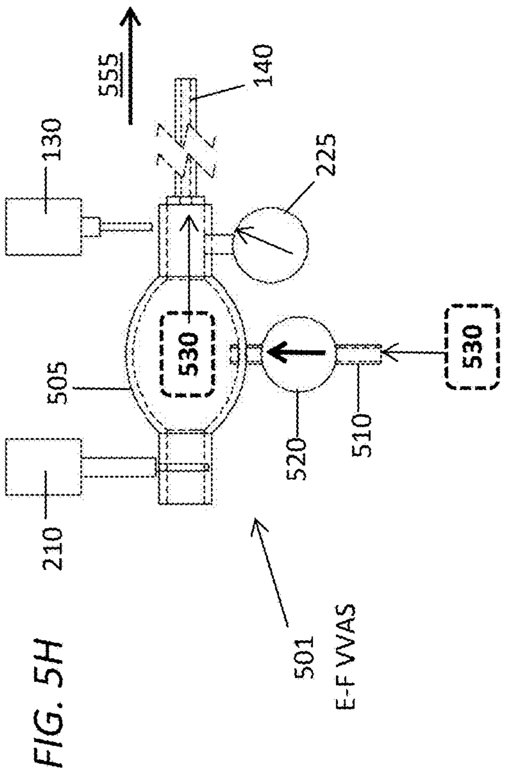
FIG. 5H depicts the VVA aspiration system of FIG. 5A configured to infuse an exogenous fluid (e.g., saline) continuously or intermittently into the catheter.

FIG. 5H depicts VVA system 501 of FIG. 5E that is configured to infuse an exogenous fluid (e.g., saline, heparinized saline, thrombolytic agents, etc.) to the patient vasculature. The machine state is: isolation valve 130 is in the closed state and each of E-F valve 520 and vacuum valve 130 is in the open state. Exogenous fluid 530 is supplied through E-F tube 510 and E-F valve 520, flows through E-F housing 505 and into catheter 140; outward flow 555 of fluid is shown.

FIG. 5H depicts VVA system 501 in a configuration and apparatus state that may be utilized to perform a saline flush of the catheter. In certain embodiments, exogenous fluid 530 is supplied to E-F inlet tube 510 by means of a pump, such that the pressure state at control surface$_{E\text{-}F}$ 521*b* is at least greater than intravascular pressure. The pressure state of E-F housing 505 may be observed and/or measured at pressure gage 225. A metering pump is utilized in certain embodiments to measure and control the volume of exogenous fluid 530 that is infused into E-F housing 505, and subsequently into catheter 140.

Certain VVA operating modes include a saline flush of catheter 140, in some cases this is done to reduce the viscosity of the fluid therewithin. The saline flush process involves "pushing" existing aspirate through catheter 140 and replacing it with saline. In certain instances, a moving interface between existing aspirate (e.g., blood) and infused aspirate (e.g., saline) exists. Certain VVA embodiments utilize volumetric measurements of infused exogenous fluid 530 to calculate or infer the position of that blood/saline interface within catheter 140. Certain VVA embodiments infuse volumes of exogenous fluid that significantly exceed the volume of catheter 140, thereby diluting the blood surrounding a stationary thrombus. Certain VVA embodiments infuse a volume of exogenous fluid that fills catheter 140 without substantial excess or under-filling. Because certain VVA embodiments may utilize saline flush operational modes a plurality of times during a procedure, effectively filling catheter 140 with saline without substantial excess reduces both the procedure time and saline required. In a VVA paradigm, saline acts a diluent, and may be utilized to reduce the viscosity within catheter 140.

Returning to VVA system 501 apparatus state depicted in FIG. 5B, E-F housing 505 is isolated at a certain pressure (i.e., vacuum level) measured at pressure gage 225. In certain cases, the vacuum level within E-F housing 505 may be greater than prescribed for an upcoming AMC mode (e.g., 22 inHg, 17 inHg, etc.). To reduce the vacuum level in such cases, certain VVA system 501 embodiments change exogenous fluid valve 520 to the open state, as depicted in FIG. 5A. This typically admits a finite quantity of exogenous fluid into E-F housing 505, thereby increasing the pressure state within E-F housing 505. Exogenous fluid valve 520 may be changed to the closed state when the vacuum level, within E-F housing 505, reaches a predetermined vacuum level that was prescribed for an upcoming AMC mode. Under many circumstances wherein the vacuum level within E-F housing 505 is greater than a prescribed vacuum level, the vacuum level may be decreased by opening exogenous fluid valve 520. Conversely, in cases where the vacuum level within E-F housing 505 is less than a prescribed vacuum level, the vacuum level may be increased by opening isolation valve 210 to vacuum 152. Introduction of exogenous fluid into certain VVA embodiments is significant because the vacuum level for an upcoming AMC may be adjusted. This enables certain VVA embodiments to tailor vacuum level and flow rate to the immediate clinical conditions.

FIG. 6A depicts VVA system 601 in accordance with an illustrative embodiment of the present invention. VVA system 601 is depicted in a machine state wherein vacuum valve 130 is in the closed state, isolation valve 210 is in the open state and moveable piston 610 is in a down state. The pressure state is substantially that of system vacuum 152, as may be observed and/or measured by pressure gage 225. The equilibrium state is "tending toward static equilibrium" at substantially vacuum 152. Because moveable piston 610 is in a down state, the volumetric state is at a substantially minimum ($V_{min}$); liquid 630 comprises substantially all of the system fluid volume depicted. The significantly different volumetric states of VVA system 601 depicted in FIG. 6A and FIG. 6C illustrate that the internal volume of VVA system 601 is variable with time during operation of the apparatus. Collectively, moveable piston 610 sliding in vapor tube 620 comprise a non-isovolumetric system component; the apparatus thereby assumes variable volumetric states while in operation.

FIG. 6B depicts the VVA system 601 of FIG. 6A wherein isolation valve 210 is changed to the closed state. System 601 is depicted in a static equilibrium state with pressure state at substantially that of vacuum 152. Connecting tube 132 is isolated at this "vacuum" pressure state, and may store a finite amount of energy in deforming the fluid and components; for instance, connecting tube 132 may be non-isovolumetric. Any stored energy in this apparatus states depicted in FIGS. 6A and 6B is overlooked for this discussion.

Because liquid 630 comprises substantially all of the fluid volume depicted in FIG. 6B, it may be inferred that the pressure state within connecting tube 132 is not less than the vapor pressure of blood. Among other functionalities, VVA system 601, in certain embodiments and cases, acts to reduce the pressure state to substantially less than or equal to the vapor pressure of blood. This causes certain blood components to boil, generating vapor 640, thereby attaining a pressure state that is at substantially "maximum-attainable vacuum level" available for aspiration.

FIG. 6C depicts the VVA system 601 of FIG. 6B at time ($t \approx t_0$) wherein each of isolation valve 210 and vacuum valve 130 is in the closed state; the position of moveable piston 610 has been changed to an up state. The volumetric state of VVA system 601 is at a substantially maximum volume ($V_{max}$), although the volume of liquid 630 remains substantially constant. Vapor 640 typically forms within vapor tube 620, therefore the pressure state is at or below the vapor pressure of liquid 630. The VVA system 601 apparatus state depicted in FIG. 6C is a stored energy state. Releasing that energy causes a "substantially larger" ($V_{max}$) finite volume of vapor 640 to literally condense into a "substantially smaller" ($V_{min}$) finite volume of liquid 630. The volumetric ratio of $V_{max}$:$V_{min}$ is approximately 150:1 for water at operational temperatures.

FIG. 6D depicts the VVA system 601 of FIG. 6C at time ($t > t_0$) after vacuum valve 130 was changed to the open state. Aspirate flow 450 is shown, thereby increasing the volume of liquid 630 within vapor tube 620 and/or connecting tube 132, and decreasing the volume of vapor 640. Any or all portions of vapor 640 may condense to liquid 630. In cases wherein all portions of vapor 640 condense to liquid 630, then the volume of aspirate transferred is substantially equal to ($V_{max}-V_{min}$).

In certain VVA 601 embodiments, the position of piston 610 is controlled by an actuator having one or more discrete actuator states, for instance 10%, 20%, . . . 100% of the range of travel of moveable piston 610. Thereby, each specific actuator state of moveable piston 610 corresponds to a specific volumetric state of the apparatus. This is an example of how certain VVA embodiments control the volumetric state of non-isovolumetric components and/or elements. In certain embodiments, a linear actuator is utilized to control the position of piston 610 and thereby the volumetric state of VVA system 601. In certain VVA system 601 embodiments, VVA system controller provides position control of moveable piston 610 thereby controlling the volumetric state. This is similar to other VVA system embodiments that control the volumetric state of the apparatus though alternate means.

Figure 7A:
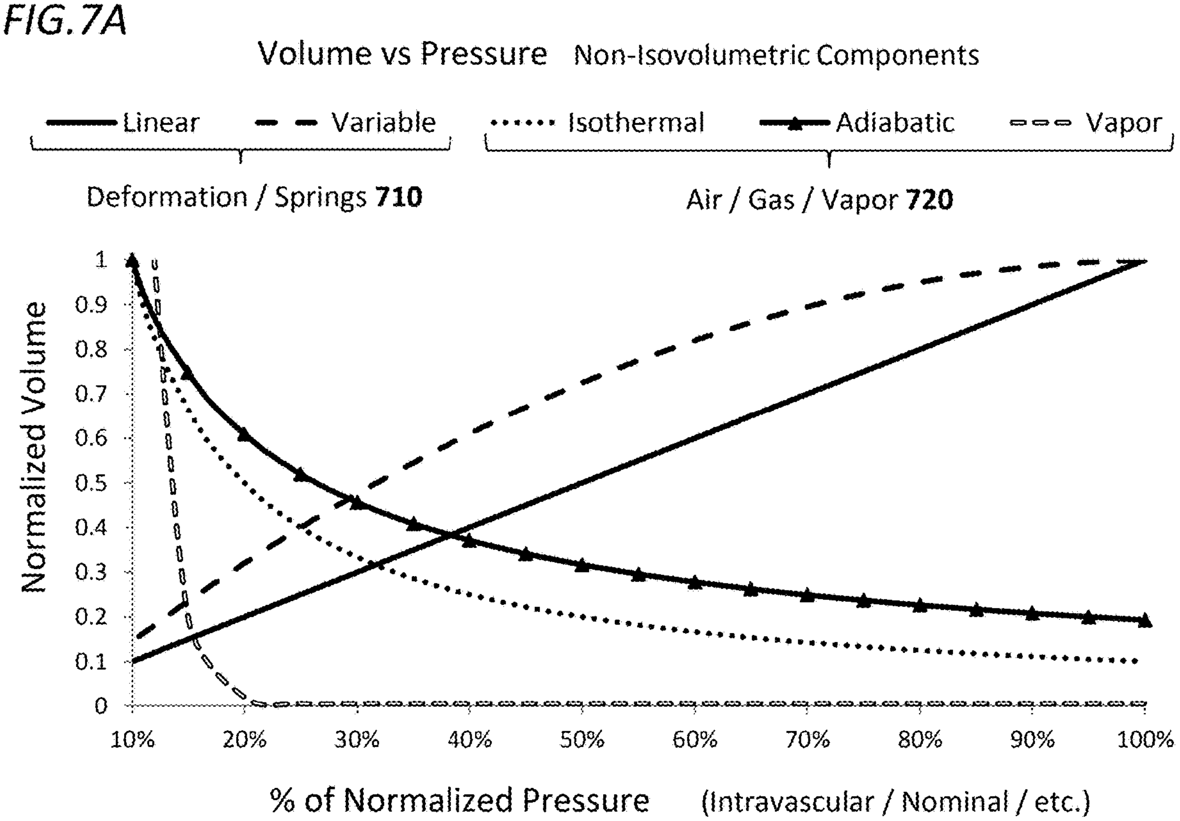
FIG. 7A depicts an illustrative graph generated in accordance with certain embodiments of the present invention, wherein pressure-volume characteristics of certain non-isovolumetric VVA components and/or elements are depicted in graphical form.

FIG. 7A graphically depicts 5 mathematical models utilized in certain VVA system embodiments to transform measurements of pressure into measurements of volume. Certain VVA embodiments comprise one or more non-isovolumetric system components/elements including, but not limited to, elastic tubing 230, bulb 405, connecting tube 130, 232*a*, 232*b*, bellows, syringes, diaphragms, air, vapor, gasses, water vapor, etc. Each non-isovolumetric system component/element typically exhibits a characteristic volume vs pressure relationship. FIG. 7A depicts 5 representative volume vs. pressure "mapping functions" for certain example non-isovolumetric VVA system components/elements. The mapping functions of FIG. 7A are divided into two classifications: deformation/springs 710, and air/gas/vapor 720. Pressure-volume maps of deformation/springs 710 components exhibit generally positive slope because the volume increases as the pressure increases. Pressure-volume maps of air/gas/vapor 720 elements exhibit generally negative slope because the volume decreases as the pressure increases. In many VVA system embodiments, pressure is measured and correlated to volume at one or more times during an AMC. For instance, certain AMCs (1) measure an initial pressure, $P_0$, (2) cycle vacuum valve 130 between the open and closed states, (3) measure a final pressure, $P_f$, and (4) transform ($P_0-P_f$) to ($V_0-V_f$), where $V_0$ and $V_f$ are the initial and final volumes of aspirate fluid contained within the apparatus.

Examples of deformation/springs 710 include representative VVA system 201 depicted in FIG. 2A through FIG. 2D, where a non-isovolumetric component, (e.g., elastic tubing 230) is deformed by means of a surface contact force. Representative VVA system 401, depicted in FIG. 4A through FIG. 4D, physically deforms a non-isovolumetric component (e.g., bulb 405) by means of differential pressure. The two depicted VVA system embodiments (VVA system 201 of FIGS. 2A-2D and VVA system 401 of FIGS. 4A-4G) utilize one or more deformable components (e.g., elastic tubing 230, bulb 405, connecting tube 232*a*, 232*b*, etc.) as non-isovolumetric components. The volumetric state of control $volume_{liquid}$ 124 is thereby changing during operation of the VVA apparatus. Deformable components (e.g., elastic tubing 230, bulb 405, connecting tube 232*a*, 232*b*, etc.) act as springs, which may exhibit linear, progressive, variable, "hard" or "soft" spring characteristics. Progressively wound springs, variable-rate springs or coupled springs are examples of common non-linear springs.

Examples of air/gas/vapor non-isovolumetric elements includes representative exogenous-fluid VVA system 501 that is configured to utilize compressible fluids (e.g., air/gas/vapor 710) as non-isovolumetric elements, as depicted in FIG. 5A through FIG. 5D. In such embodiments, the physical dimensions of structural VVA components may or may not be substantially isovolumetric; regardless of this, a compressible fluid acts as a non-isovolumetric element of, and within such VVA system embodiments. Representative VVA system 601, as depicted in FIG. 6A through FIG. 6D, changes the physical dimensions of control $volume_{liquid}$ 124*c* by utilizing a syringe analogue. Conversely, representative VVA system 501, may, in certain instances, be substantially isovolumetric whereas compressible exogenous fluid 530 (e.g., air, nitrogen, etc.) acts as a non-isovolumetric component.

Air and gasses (e.g., nitrogen, helium, argon, etc.) are modeled herein as ideal gasses undergoing a compression-expansion cycle; this cycle may be modeled as isothermal (i.e., constant temperature) or adiabatic (i.e., perfectly insulated). At pressures below a characteristic vapor pressure, evaporative liquids (e.g., water, saline, blood, isopropanol, ethanol, etc.) boil; this typically creates a vapor 640 space within control $\text{volume}_{liquid}$ 124*c*. As the pressure increases (e.g., to above a characteristic vapor pressure), the volume of vapor 640 tends toward zero as vapor 630 condenses to the liquid 630 phase. Aspirate flow 450 "fills the void" of the condensing vapor 630.

The remainder of this disclosure is primarily focused upon VVA embodiments utilizing non-isovolumetric components (i.e. not gas or vapor system elements), and will focus upon deformation/springs 710 mapping functions. FIG. 7A is normalized to an arbitrary reference pressure (e.g., intravascular/nominal/etc.), and is normalized to any arbitrary characteristic volume (e.g., 10 cc, 1 cc, 3.74 cc, etc.); graph axes are expressed as percentages. In FIG. 7A lines deformation/spring 710 graphically depicts both linear and variable (non-linear) "spring rate" embodiments. The lines of deformation/spring 710 (of FIG. 7A) reflect a normalization convention used herein where approximately 27 inHg vacuum is assigned a corresponding normalized volume of approximately 0.1 (10%). At zero vacuum, or at substantially atmospheric/intravascular/any reference pressure, the corresponding normalized volume is assigned to be approximately 1.0 (100%). In certain VVA embodiments (e.g., VVA 201, etc.), control $\text{volume}_{liquid}$ 124 typically is at substantially minimum volume when at substantially maximum vacuum. In certain VVA embodiments, control $\text{volume}_{liquid}$ 124 typically is at substantially maximum volume when at substantially atmospheric/intravascular/any reference pressure.

By convention herein, displaced volume 240 (see FIG. 2C) is a positive value that tends toward substantially zero concurrently as control $\text{volume}_{liquid}$ 124 tends toward a substantially maximum volume. The numerical example referencing bulb VVA 401 (FIGS. 4A-4D) stated a displaced volume 240 of 9 cc. The volume of VVA system non-isovolumetric component(s) being approximately 1 cc at 27 inHg (max vacuum) and approximately 10 cc at 0 inHg (substantially atmospheric/nominal/intravascular pressure). It is important to note that chosen arbitrary normalization parameters: 10 cc (maximum volume), 1:10 volumetric expansion ratio, 27 inHg (maximum vacuum) and a reference pressure (e.g., intravascular/nominal/etc.) are, in a sense, scaling factors. Normalized volume vs. pressure relationships, as graphically depicted in FIG. 7A, may be utilized regardless of the "scale" of the apparatus or the "range" of the pressure (e.g., ranging between 0 inHg to 27 inHg vacuum).

From the graph line (_Linear) of deformation/springs 710 of FIG. 7A, it may be observed that as the normalized pressure increases from say, 50% to 60%, the normalized volume correspondingly increases from 50% to 60%. The change in physical volume (in cc) of a VVA apparatus may be determined by multiplying the change in normalized volume (e.g., 50% to 60%) by the normalization "scaling factor" of 10 cc (because 10 cc is defined to be 100%). In this case, an increase in normalized pressure from 50% to 60% corresponds to an increase of normalized volume from 5 cc to 6 cc. Thereby, control $\text{volume}_{liquid}$ 424 volumetrically increases by approximately 1 cc as approximately 1 cc of fluid enters the apparatus through catheter 140 concurrently with a normalized pressure increase from 50% to 60%. It is important to note that the graphically depicted pressure-volume relationships of FIG. 7A may be experimentally generated for any non-isovolumetric component and/or element regardless of shape, materials of construction, etc. FIG. 7A depicts equations of state (and/or constitutive equations); certain VVA embodiments utilize one or more equations of state to transform measurements of pressure states into measurements of volumetric states.

FIG. 7A graphically illustrates that volume (e.g., displaced volume 240, control $\text{volume}_{liquid}$ 124, etc.) may be expressed as a function of pressure, as in Eq. 2.

$$V = f(P);\ \Delta V = f(P_{final}) - f(P_{initial}); \qquad \text{Eq. 2}$$

$$\Delta V_{linear} = K(P_{final} - P_{initial});\ \Delta V = K\Delta P$$

Eq. 2 includes both general (left forms) and specific (right forms) expressions for volume as a function of pressure. The right-most forms of Eq. 2 represent a special case for a linear spring (_Linear) of deformation/springs 710; this represents one method (of many) to transform a measurement of pressure into a measurement of volume. Eq. 2 provides an example of algebraic expressions for transforming pressure measurements into volume measurements that are suitable for machine computation.

The functional relationships of Eq. 2, V=f(P), are graphically depicted in FIG. 7A, and were generated from mathematical models including: linear and non-linear springs, gasses under adiabatic and isothermal compression and evaporation/condensation phenomena. It is important to note that algebraic functional relationships of Eq. 2 may be experimentally determined for virtually any non-isovolumetric VVA component (e.g., bellows, diaphragm, compliance chamber, etc.). The numerically-convenient examples and normalization techniques of this disclosure (e.g., 1:10 expansion ratio, 10 cc "maximum" volume, 27 inHg=max vacuum of substantially 10% of atmospheric pressure, linear spring line, constant K, etc.) are selected for brevity and clarity.

Previously disclosed herein are embodiments and/or methods that, among other functionalities, transform measurements of pressure into measurements of volume. We now turn attention to viscosity, which significantly affects the rate at which the volume changes with time, i.e., the flow rate. Eq. 3A expresses the instantaneous flow rate in terms of total derivatives:

$$Q(t) = dV/dt = (dP/dt)\cdot(dV/dP) \qquad \text{Eq. 3A}$$

$$K \equiv dP/dV;\ Q(t) = (dP/dt) \div K \qquad \text{Eq. 3B}$$

where V is volume (e.g., displaced volume 240, control $\text{volume}_{liquid}$ 124, etc.), P is pressure and t is time. dV/dt is the volumetric flow rate, Q(t). dP/dt is the time rate-of-change of pressure. Certain VVA embodiments compute dP/dt from the pressure waveform data by utilizing numerical or computational methods. Taking a time derivative of pressure is an example of parameterizing the pressure waveform data in time. Eq. 3B introduces the convenient variable, K=dP/dV, herein referred to as bulk modulus. In certain VVA embodiments, bulk modulus (K) is a system variable that changes with pressure; in other embodiments, K remains substantially constant throughout a pressure range. In cases wherein bulk modulus, K, is variable and/or unknown, volume vs. pressure experimental data may be collected upon substantially any reference fluid to experimentally determine values of K.

The slope of each line (at any point) of FIG. 7A is dV/dP; this value has physical significance as the inverse of the bulk modulus, K (herein bulk modulus, K=dP/dV or ΔP/AV). Many sources define K≡−V dP/dV; herein the negative sign is omitted by convention for graphical and discussion reasons. The unit volume V is omitted in the definition because herein volumes are typically normalized to 1, and we are primarily concerned with the slope dP/dV.

Figure 7B:
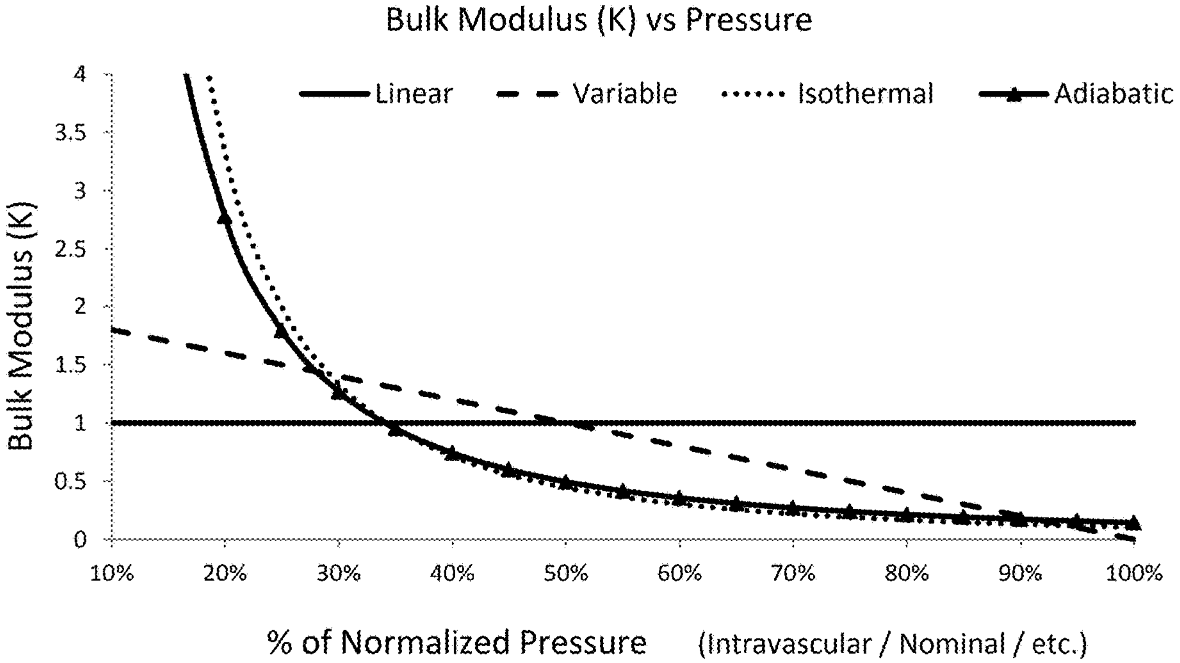
FIG. 7B depicts an illustrative graph generated in accordance with certain embodiments of the present invention, wherein the VVA bulk modulus (K) of certain non-isovolumetric VVA components and/or elements are depicted in graphical form.

FIG. 7B graphically depicts values of bulk modulus (K) for linear and variable "springs," as well as for ideal gasses under adiabatic and isothermal expansion cycles. Water vapor is not considered herein to possess a bulk modulus (K) due to evaporation/condensation phenomena. Because the bulk modulus (K) is the slope of the lines of FIG. 7A, FIG. 7B is the first derivative (dV/dP), or slope of, FIG. 7A. Experimentally, values for VVA bulk modulus (K) may be determined from experimental data by utilizing numerical or computational methods such as numerical differentiation, finite difference approximations, etc. Certain VVA embodiments and/or methods utilize experimentally determined values for K, for instance by numerically differentiating experimental data.

FIG. 7B graphically depicts values of bulk modulus (K) vs pressure. Linear spring exhibits constant value of K=10 and a slope of zero. Variable spring exhibits values of K ranging from approximately 20 to 2 and a constant slope of approximately negative 2. Adiabatic and Isothermal lines exhibit negative slopes and values of K exceeding 200 (off scale of FIG. 7B) to a value normalized to 1 at approximately 100% of nominal/intravascular pressure.

FIG. 7C depicts a pressure-volume relationship in tabular form, also known as a lookup table. The left-most dataset shows volume as a function of normalized pressure for the linear (K=10) case. The center dataset of FIG. 7C shows volume as a function of normalized pressure for the variable K "progressive rate" spring VVA embodiments. The value of K ranges from approximately K=20.5 @ P=0.1 to K=2 @ P=1.0. The right-most dataset of FIG. 7C shows the volume as a function of normalized pressure for isothermal compression of an ideal gas. Adiabatic compression is similar to isothermal compression and is omitted for brevity. Ideal gasses are shown to exhibit VVA bulk modulus (K) values ranging from in excess of 250 to approximately 1 throughout the pressure range. FIG. 7C is included because (1) experimental data may be readily collected and arranged in tabular form, and (2) certain VVA embodiments exploit the computational efficiency of a lookup table.

The example non-isovolumetric VVA components/elements of FIG. 7A and FIG. 7B graphically depict mathematical models of certain pressure-volume relationships. Some VVA embodiments utilize mathematical models of pressure-volume relationships to calculate derived variables by algebraic means (i.e., evaluate a mathematical expression). Some VVA embodiments utilize lookup tables to determine relevant derived variables (e.g., volume, flow rate, viscosity, etc.). Some VVA embodiments utilize numerical or computational methods (e.g., finite difference approximations, numerical integration & differentiation, algebraic expressions, etc.) to determine relevant derived variables (e.g., volume, flow rate, viscosity, etc.). The mathematical models (depicted graphically in FIG. 7A and FIG. 7B, and in tabular form in FIG. 7C) are more accurately termed mapping functions, which maps a pressure measurement to a volume measurement. A general term for the process is coordinate transformation; in this case, numerical data are transformed from pressure-time space to volume-time space. Note that this transformation is from an intensive physical property (pressure) to an extensive system property (volume).

Eq. 1 and Eq. 3B each provide expressions for flow rate, Q; Eq. 1 and Eq. 3B are combined to form Eq. 4.

$$Q = \Gamma\Delta p/\mu = (dP/dt) \div K \qquad \text{Eq. 4}$$

Δp and P may be substantially the same differential pressure between ends of a catheter, Γ is the (dimensional) proportionality constant (of Eq. 1), u is the viscosity of the fluid (in the catheter) and K is the bulk modulus. It is important to note that the bulk modulus, K=dP/dV, is taken to be constant (i.e. the slope is constant) for linear spring line (_Linear) of deformation/springs 710 of FIG. 7A. Other example non-isovolumetric components exhibit various non-linearities; mathematical models for these VVA embodiments may be similarly solved. Certain non-linear VVA non-isovolumetric components may utilize table lookup data, such as disclosed in FIG. 7C, to determine the value of the bulk modulus (K, as a function of pressure).

Eq. 4 may be rearranged to the familiar form of Eq. 5; an example definition of a time constant (τ≡μ/KΓ) is substituted, and a solution is presented in Eq. 6. The numerical example initial value of $P_0$=27 inHg is inserted in the right form of Eq. 6; of course, any value of $P_0$ may be utilized in Eq. 6, 27 inHg is a convenient numerical example. Eq. 7 expresses volume as a function of time, V(t); example numerical values of $V_0$=1 cc and $V_f$=10 cc are inserted in the right form of Eq. 7.

$$P'/P = -K\Gamma/\mu;\ \tau \equiv \mu/K\Gamma;\ P'/P = -1/\tau \qquad \text{Eq. 5}$$

$$P(t) = P_0 e^{-t/\tau};\ P(t) = 27e^{-K\Gamma t/\mu} \qquad \text{Eq. 6}$$

$$V(t) = V_f - (V_f - V_0)e^{-t/\tau};\ V(t) = 10 - 9e^{-K\Gamma t/\mu} \qquad \text{Eq. 7}$$

Methods to transform (i.e., map) pressure measurements into volume measurements have been disclosed previously herein by methods such as e.g., Eq. 2, FIGS. 7A-7C, etc. Eq. 5 is a differential equation (P'/P=−KΓ/μ) derived to mathematically model a characteristic rate of pressure decay in certain VVA embodiments. Solving Eq. 5 (P'/P=−1/τ) yields Eq. 6 ($P(t)=P_0e^{-t/\tau}$). Eq. 6 expresses, characterizes, and/or mathematically models the time rate of change of pressure as certain VVA embodiments tend toward a static equilibrium volumetric state. Eq. 6 and Eq. 2 are combined to form Eq. 7, a corresponding model for the time rate of change of volume, or flow rate, Q(t).

A first example method of utilizing these derivations in certain VVA embodiments and control algorithms comprises:

(1) measuring an initial pressure, $P_0$, (2) cycling vacuum valve 130 state from open to closed for an arbitrary period of time, (3) measuring a final pressure, $P_f$, (4) inserting $P_f$, $P_0$, the initial and final times into Eq. 6, (5) solving Eq. 6 for the time constant, τ, and (6) calculating the viscosity $\mu=K\Gamma\tau$, from the example definition of a time constant: $\tau=\mu/K\Gamma$.

In another example method, the time constant may be calculated under flowing conditions (e.g., while vacuum valve 130 is in the open state). The pressure data stream may be computationally or numerically differentiated to find instantaneous values of P' and P; these data may be inserted into Eq. 5 ($P'/P=-1/\tau$) to solve for the time constant, $\tau$, and viscosity, $\mu$. Determining P'/P at a point in time (e.g., to calculate t by Eq. 5) is an example of measuring "instantaneous" derived variables such as dP/dt (time rate of change of pressure), dV/dt (time rate of change of volume), Q, (volumetric flow rate), etc.

Certain AMCs continuously and/or intermittently compute certain derived variables, such as flow rate, Q. Any decrease in flow rate typically correlates to the presence or aspiration of thrombus within or near a distal portion of catheter 140. As a clog develops, the flow rate typically approaches zero at a characteristic rate. Regardless of that characteristic rate (of decreasing flow, Q) toward an impending clog, early detection is advantageous. Certain VVA embodiments "immediately abort" or "terminate" an AMC (e.g., by closing vacuum valve 130, etc.) based upon a measured flow rate that falls outside of predetermined ranges. Closing vacuum valve 130 "immediately" upon detection of a flow rate below predetermined thresholds enables certain VVA embodiments to avert clogs before they develop. Subsequent to detection of an impending clog, certain VVA embodiments enact responsive actions such as selecting AMC modes including, but not limited to: pressure pulses, pulse trains, making/breaking contact, dilution, repositioning and/or reconfiguration of catheter 140, etc.

The right hand form of Eq. 7 incorporates the initial value of 1 volumetric unit (e.g., 1 cc, 500 μl, etc.) at 10% of atmospheric pressure (≈27 inHg vacuum). The final volume is 10 volumetric units (e.g., 10 cc, 5 cc, etc.) after vacuum decay to substantially atmospheric/nominal/intravascular/any reference pressure (i.e., approximately zero differential pressure). Various numerical or computational methods may be employed to measure a time constant (e.g., from a pressure data stream) by techniques including, but not limited to: conversion, transformation, normalization, differentiation, integration, root finding, etc. It is important to note that, while Eq. 5 provides "a definition" of a time constant, many other forms or "definitions" may be utilized by various VVA embodiments. For instance, VVA time constants may be arbitrarily defined such as: the length of time for 20%, 50%, 75%, 90%, etc. of the total volumetric flow to equilibrium. The term "time constant" is used herein as an intuitive phrase that is representative of a more descriptive term: "equilibrium rate characteristic."

Measurement of a time constant ($\tau$) enables calculation of derived variables including, but not limited to: viscosity, relative flow rate, flow rate, etc. Further details are provided in references including U.S. patent application Ser. Nos. 18/128,224 and 18/380,784.

Figure 8A:
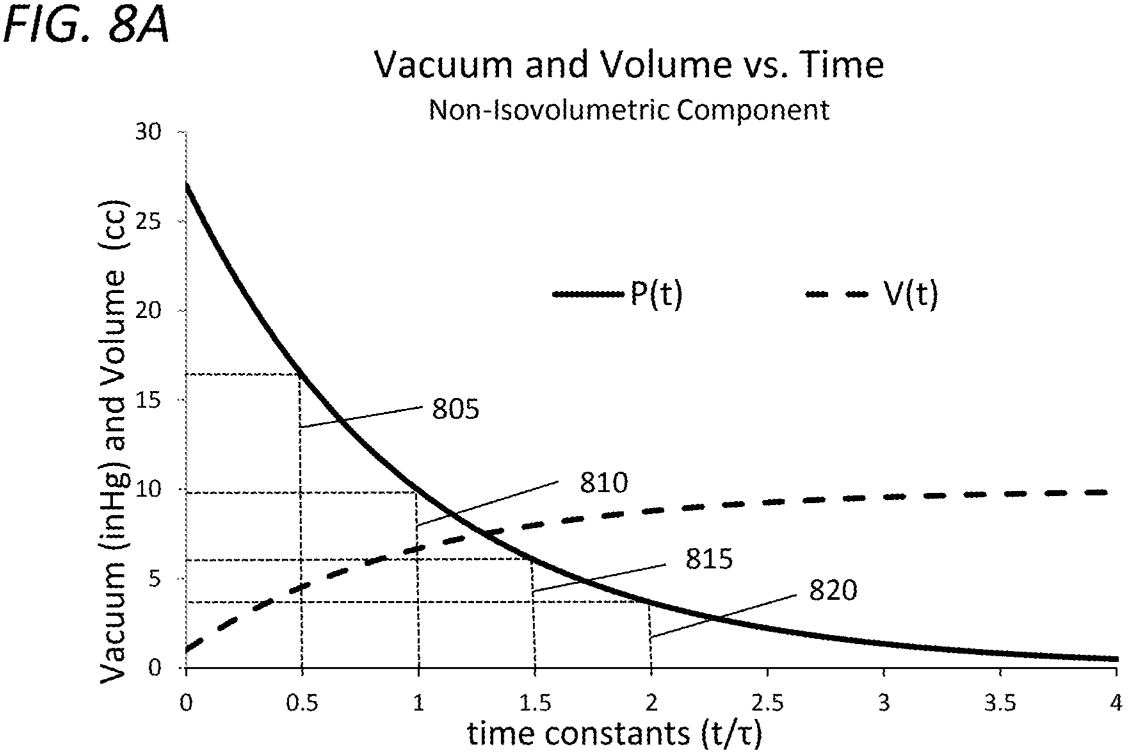
FIGS. 8A-8C depict illustrative graphs generated in accordance with certain embodiments of the present invention, wherein vacuum decay and aspirated volume vs time are graphically depicted.
Figure 8B:
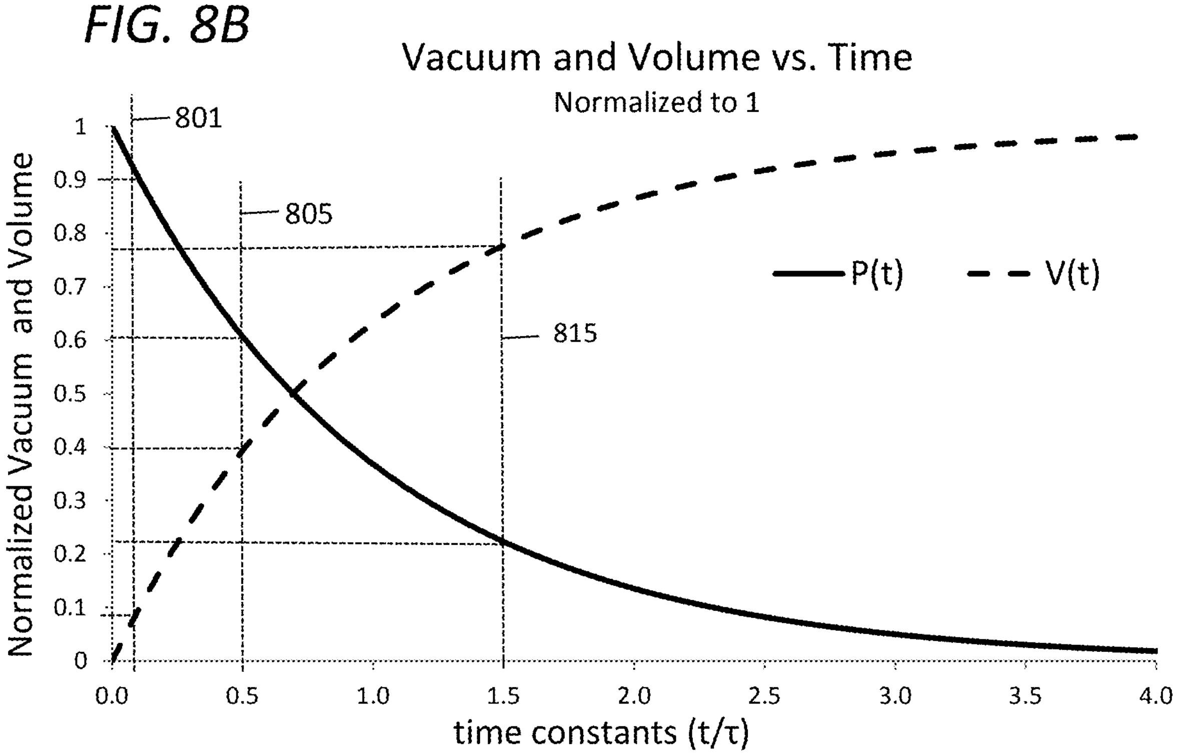
Figure 8C:
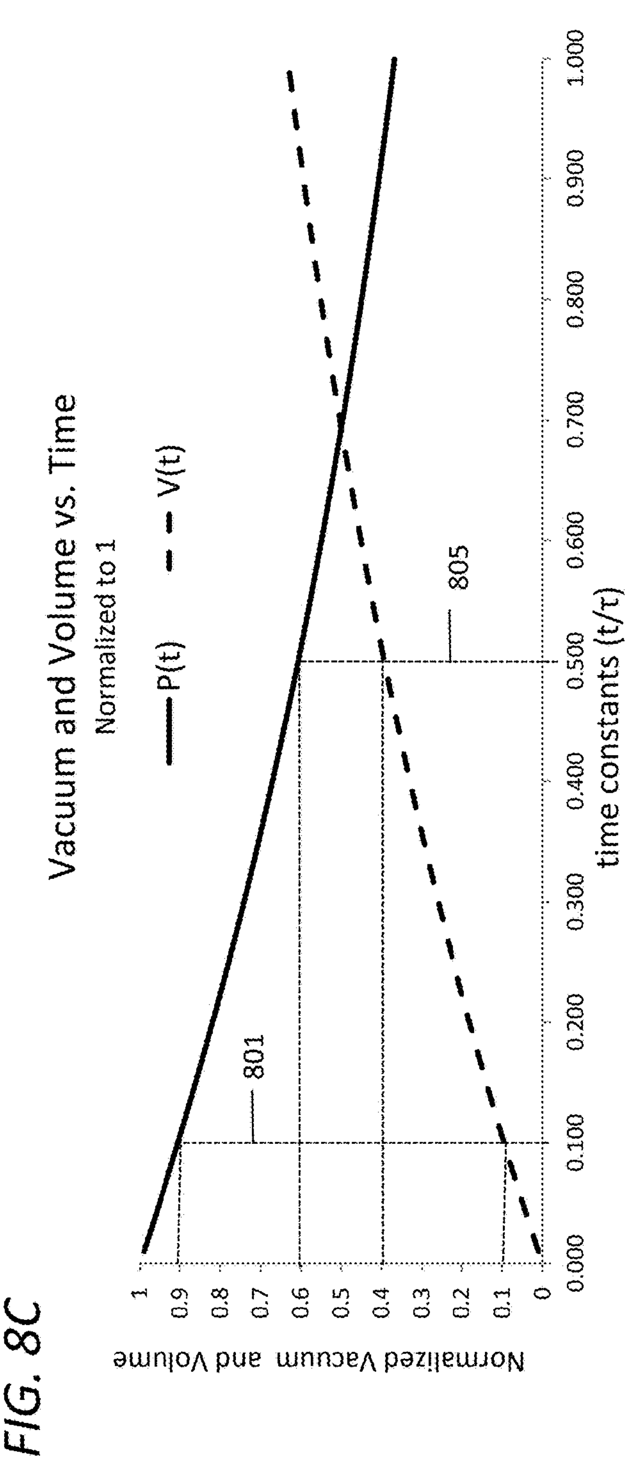

FIG. 8A graphs Eq. 6 (pressure) and Eq. 7 (volume) as functions of time, herein called a pressure decay model or vacuum decay model. At time 0, the apparatus is at maximum vacuum of approximately 27 inHg and minimum volume of approximately 1 cc. After approximately 4 time constants, vacuum has decayed to substantially zero, and volume has increased to substantially 10 cc. FIG. 8B normalizes the ordinates to dimensionless values ranging from 0 to 1. FIG. 8C depicts normalized volume and pressure curves during the first time constant, or $1.0\tau$. The curves of FIGS. 8A-8C are generated from numerical solution of Eq. 6 and Eq. 7; certain VVA embodiments numerically solve Eq. 6 and Eq. 7. Certain VVA embodiments and/or methods utilize a "lookup table" of numerical solutions of Eq. 6 and Eq. 7 for reasons including computational efficiency.

FIG. 8A depicts four vertical lines at four values of time, referenced as 805 (at $0.5\tau$), 810 (at $1.0\tau$), 815 (at $1.5\tau$), and 820 (at $2.0\tau$). Corresponding horizontal lines indicate the vacuum level (in units of inHg). After $0.5\tau$, vacuum has decayed to approximately 17 inHg, corresponding to vertical line 805. After $1.0\tau$, vacuum has decayed to approximately 10 inHg, corresponding to vertical line 810. After $1.5\tau$, vacuum has decayed to approximately 7 inHg, corresponding to vertical line 815. After $2.0\tau$, vacuum has decayed to approximately 3 inHg, corresponding to vertical line 820. FIGS. 8A-8C graphically depicts curves calculated from Eqs. 5, 6 and 7; certain VVA embodiments transform between time, volume and vacuum by computational means such as utilizing Eqs. 2, 5, 6 and 7. Alternatively, lookup tables such as depicted in FIG. 7C, may be utilized to relate pressure to volume.

FIGS. 8A-8C illustrate the "predictive" nature of utilizing mathematical models (e.g., Hagen-Poiseuille Equation, Hooke's Law, Newton's Law of Viscosity, etc.) in certain VVA algorithms and embodiments. As an example, if the current catheter contents is identified as pure blood ($\mu_{current}\approx 4$ cP), and the time constant is 1 second then, after 1 second of aspiration, an expected value for pressure is approximately 10 inHg; this corresponds to a normalized aspirate volumetric transfer of approximately 63%. A logical inference utilized in certain VVA embodiments is: if, after a single time constant has elapsed, and the vacuum level is greater than 10 inHg, then the viscosity ($\mu_{current}$) of the fluid in catheter 140 has increased. In selecting an upcoming AMC mode, a straightforward algorithm utilized in certain VVA embodiments is to assume that $\tau$ and, consequently $\mu_{current}$, remain constant during the next AMC. This "predicts" what period of vacuum valve 130 is to be in the open state for the desired vacuum decay and aspirate volume transfer. For instance, if an AMC normalized target volume is approximately 78% (e.g., 7.8 cc, 0.78 cc, etc.), then the "predicted" time required is approximately $1.5\tau$ (e.g., 1.5 s, 3 s, 0.094 s, etc.), depending upon the numerical value of $\tau$. In this manner, certain VVA embodiments prescribe AMC modes with specified initial and final pressures ($P_0$ and $P_f$), specified initial and final volumes ($V_0$ and $V_f$) and a prediction of length of time required. Alternatively, certain VVA embodiments prescribe AMC modes with known or specified initial pressure ($P_0$), initial volume ($V_0$) and a specified duration for vacuum valve 130 to remain in the open state; these parameters enable a prediction of the final pressure ($P_f$) and final volume ($V_f$). While vacuum valve 130 is in the open state (i.e., under flowing conditions), numerical differentiation of pressure data enables concurrent calculation of an instantaneous time constant. Any change in aspirate viscosity may be detected by certain VVA embodiments during portions of an AMC under flowing conditions; this enables VVA apparatuses to respond quickly to a rapidly-changing aspirate compositions.

In many VVA embodiments (e.g., VVA system 201 of FIG. 2C), the time constant is deterministic of the time required for the vacuum (e.g., 27 inHg, etc.) to decay toward substantially zero, and displaced volume 240 to decrease toward substantially zero. For example, if the time constant is one second, FIG. 8A illustrates that, after approximately 4 seconds (4 time constants), the vacuum level decays to less than 1 inHg and the volume increases to approximately 10 cc. Time constants for many VVA embodiments may range from approximately 20 ms to in excess of hours or days; but this is typically a function of the viscosity of the fluid within a conduit or catheter. A plugged or corked catheter may exhibit vacuum decay rate approaching zero (i.e., static equilibrium). Calculating a time constant for a VVA apparatus at or very near static equilibrium typically results in measured time constant of minutes, hours, days, etc., because of division by values approaching zero. Many VVA embodiments typically are operable with time constants ranging from approximately 50 ms to in excess of 20 s for blood (viscosity, $\mu\approx4$ cP).

Displaced volume 240 (e.g., as depicted in FIG. 2C) is used herein as an amount of volumetric change from equilibrium volumetric capacity; this volumetric change may be used as a basis to normalize volumes. In many VVA embodiments, a change in displaced volume 240 is typically also a change in the size of control $\text{volume}_{liquid}$ 124 as depicted in FIG. 2C. However, control $\text{volume}_{liquid}$ 124 is an arbitrary volume (e.g., 100 cc, 175 cc, 243.3 cc, etc.) because it typically comprises components including catheter 140, elastic tubing 230, bulb 405, connecting tube(s) 132, 232*a*, 232*b*, etc. Typically, displaced volume 240 is a specific volume (e.g., 1 cc, 5 cc, 12.7 cc, etc.) that is an initial condition for an AMC. As an example, a first AMC has an initial displaced volume 240 of 6.7 cc at a corresponding first vacuum level, and a second AMC has an initial displaced volume 240 of 4.3 cc at a corresponding second vacuum level. In certain VVA system embodiments, the first AMC is normalized to 1 by dividing all values by 6.7 cc, and the second AMC is normalized to 1 by dividing all values by 4.3 cc. Pressures may be normalized similarly. This demonstrates how normalization removes dependence on the initial values of both volume and pressure, allowing direct comparison of characteristic rate behavior regardless of initial conditions. This substantially eliminates dependence upon the magnitude of control $\text{volume}_{liquid}$ 124 (i.e., lengths and diameters of catheters, connecting tubes, conduits, etc.) from computations; this further contributes to the inherent scalability of typical VVA embodiments.

Calibration of typical VVA embodiments is straightforward, and integrates many of the features and benefits disclosed herein. Referring to FIG. 8A, consider catheter 140, containing and aspirating water at approximately 1 cP viscosity. Upon startup and initialization of certain VVA embodiments, the time constant for the apparatus is considered unknown because parameters including catheter dimensional/flowability constant (I) and bulk modulus (K) may be considered unknown. An example method to a calibrate VVA apparatus comprises (1) opening vacuum valve 130 at 27 inHg, (2) closing vacuum valve 130 when the vacuum has decayed to approximately 10 inHg, and (3) measuring the time constant. Of course, vacuum valve 130 may be closed at substantially any pressure, 10 inHg is a convenient numerical value. In cases where the elapsed time for vacuum to decay (from approximately 27 inHg to approximately 10 inHg), in this water-filled catheter, is measured to be approximately 1 second, then the time constant for water is measured to be approximately 1 second. Measuring a time constant upon a liquid of known viscosity (e.g., saline, water, blood, etc.) effectively calibrates a VVA apparatus to any arbitrarily selected complement of system variables including, but not limited to: catheter length and diameter, connecting tube(s), displaced volume, etc.

After calibration, and upon aspirating a fluid of unknown viscosity, if the measured elapsed time for vacuum decay (from approximately 27 inHg to approximately 10 inHg) is measured to be approximately 6.5 seconds, then the viscosity of the fluid in the catheter may be calculated to be approximately 6.5 cP. This is because the unknown fluid requires 6.5 seconds (i.e., 6.5 time constants, $6.5\tau$) for a specific vacuum decay, whereas water requires 1 second (i.e., 1 time constant, $1.0\tau$). In this example, one time constant is the period of time required for vacuum decay from approximately 27 inHg to approximately 10 inHg. The starting and ending pressures are typically immaterial, convenient numerical examples are selected. Subsequent to calibration, should the time constant of the example VVA apparatus be measured to be approximately 4 seconds, certain VVA embodiments calculate that the "average" viscosity of fluid in the catheter is approximately 4 cP, and infer that the fluid in the catheter may be identified as blood.

The example, pressure decay from 27 inHg to 10 inHg is substantially an exponential decay after 1 time constant for certain VVA embodiments. Substituting the value of t=1 s into Eq. 6 yields the value of $P/P_0=e^{-1}\approx0.3679\approx10/27$. It is important to note that the value of the maximum system vacuum ($P_0$, taken to be 27 inHg) does not affect these calculations; the initial vacuum may be any value (e.g., 27.8 inHg, 25 inHg, 20 inHg, etc.). Consequentially, VVA embodiments are typically insensitive to changes in the system vacuum level, this includes variabilities including, but not limited to: apparatus-to-apparatus, day-to-day, local atmospheric pressure, patient blood pressure, etc.

The convention of FIGS. 8A-8C employs vacuum and volume on the ordinate (y-) axis (in engineering and normalized/non-dimensionalized units), where a greater value indicates a greater differential pressure and typically, a greater flow rate. Representative VVA embodiments (system 201, system 401, etc.) utilize pressure gage 225 which may, in certain VVA embodiments, comprise an absolute pressure transducer. Some embodiments employ a transducer to measure pressure in digitized absolute pressure units (e.g., atm≈370, 15 inHg=250, 27 inHg≈130). The transducer output may be converted from absolute pressure to vacuum or other units such as mmHg, inHg, psia, etc.

In FIGS. 8A-8C, curve differential pressure, P(t) is a decaying function of time; this is the differential pressure that drives aspirate flow 450 through catheter 140. In these figures, the term "vacuum" may be taken to mean a differential pressure between a measured pressure and another reference pressure such as atmospheric pressure 150, intravascular pressure 154, etc. Herein, the term "vacuum decay" typically means an increase in pressure toward any reference pressure such as atmospheric 150, nominal, intravascular pressure 154, etc. The rate of vacuum decay may be quantitatively associated to the rate of aspirate flow 405 of fluid into catheter 140. If the vacuum decay is "slower" it may be inferred that the time constant ($\tau$) and the fluid viscosity ($\mu$) are correspondingly "larger." Changes in fluid viscosity ($\mu$) do not substantially affect the volume of fluid aspirated as control $\text{volume}_{liquid}$ 124 increases with time; it is substantially the length of time (i.e., period) required for the volumetric fluid transfer to occur that is germane. In instances where the vacuum decay is measured to be outside of expected values, some embodiments interrupt vacuum decay (e.g., by closing vacuum valve 130, etc.) to invoke responsive actions such as repositioning or reconfiguring catheter 140, pressure pulses, allowing full, unrestricted flow such as by simultaneously opening isolation valve 210 and vacuum valve 130, etc.

Figure 9A:
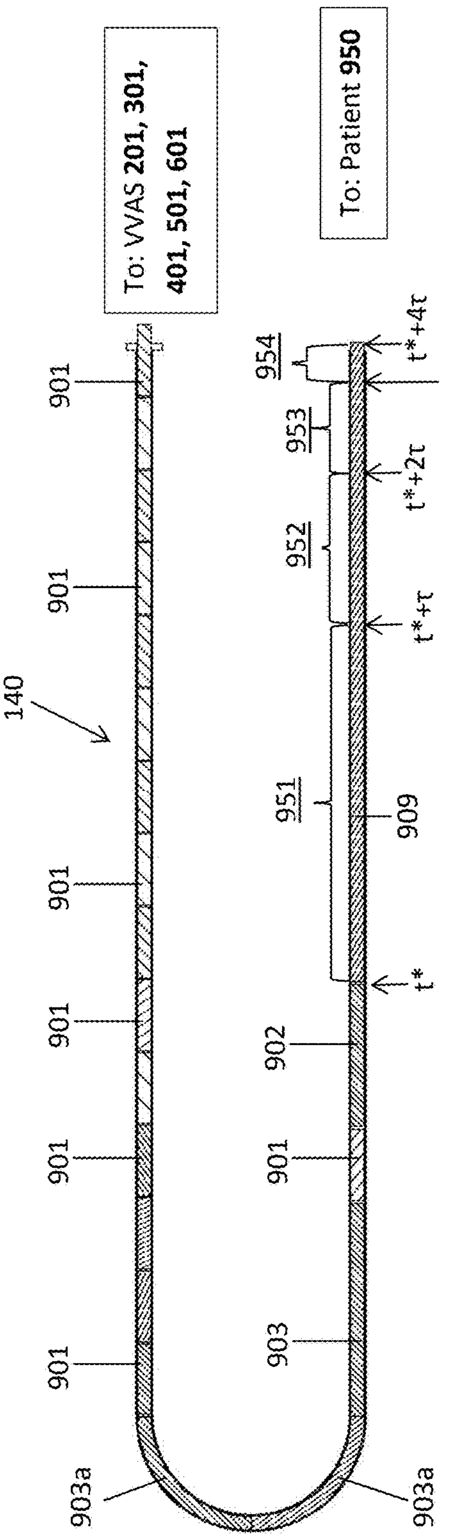
FIG. 9A depicts a catheter, the contents comprising a plurality of discrete boluses of aspirate.

FIG. 9A depicts an example catheter 140 of stated dimensions 15 Fr×45 cm (5 mm diameter×45 cm length); the volume of this example catheter 140 is approximately 36 cc. The proximal end of catheter 140 is shown in fluid communication with representative VVA system 401 (such as depicted in FIGS. 4A-4D), and the distal end of catheter 140 is deployed within patient 950. The representative VVA system 401 has stated displaced volume 240 (e.g., of bulb 405) of approximately 9 cc. The volume of bulb 405 ranges from 1 cc (at substantially "maximum" vacuum) to 10 cc (at substantially "zero" vacuum); where maximum and zero are typically normalized. For numerical simplicity, the example VVA apparatus is stated to have a time constant (τ) of 1 second for blood at approximately 4 cP viscosity.

FIG. 9A depicts a catheter state wherein catheter 140 is filled with a number of discrete boluses of aspirate (e.g., 1 cc bolus 901, 2 cc bolus 902, 3 cc bolus 903, 9 cc bolus 909, etc.). The discrete boluses of aspirate depicted are shown with different cross-hatching to illustrate that each bolus of aspirate was drawn into catheter 140 as a discrete volume element. FIG. 9A illustrates that the aspirate contained within catheter 140 may be discretized into a linear array of aspirate boluses of known/measured volume and viscosity. The fluid contents depicted in FIG. 9A may be homogeneous (e.g., pure saline, pure blood, pure SAE 30 oil, etc.); in this case, each bolus of aspirate (in a linear array) may be considered identical in composition and viscosity. FIG. 9A also illustrates that, in other cases, the contents of catheter may be may be inhomogeneous (e.g., a saline bolus adjacent to a blood bolus, adjacent to a bolus of 10% thrombus+blood, adjacent to a bolus of 25 cP viscosity, etc.).

As an example referencing FIG. 9A, wherein the content of catheter 140 is stated to be homogeneous pure blood, and the time constant is stated to be approximately 1 second for blood. Consider that the distal tip of catheter 140 is located within a patient vascular system where no thrombus is present, i.e., only pure blood is subsequently aspirated. In one operational embodiment, at time t*, vacuum valve 130 is changed to the open state for a duration exceeding approximately 4 seconds (4 time constants). During this time period, the volume of bulb 405 increases by approximately 9 cc as the vacuum decays from approximately 27 inHg to substantially zero. During these four seconds, the vacuum may steadily decay (as depicted in FIG. 8A) as approximately 9 cc of aspirate is concurrently drawn into catheter 140. A representative 9 cc bolus of aspirate is depicted in FIG. 9A and annotated 9 cc bolus 909.

9 cc bolus 909 is shown subdivided into 4 regions, each of 1 time constant duration 951, 952, 953 and 954. In this example, the volume of aspirate contained within $1^{st}$ time constant 951 comprises approximately 64% of displaced volume 240, or approximately 5.75 cc of the example 9 cc displaced volume 240. The approximate time interval (between to and $t_1$ of FIG. 9B) required for the ingestion of 1 cc bolus 901 may be calculated (e.g., Eq. 6, Eq. 7, etc.) or interpolated from graphs such as FIG. 8A and FIG. 8B to be approximately 0.120τ, or 0.120 seconds, using the example time constant (τ) to be 1 second. Thus, closing vacuum valve 130 after approximately 0.120 seconds may result in ingesting entering bolus 911 of approximately 1 cc; of course this may require modification for factors including response time of valves, fluid acceleration, etc.

The catheter state depicted in FIG. 9A comprises boluses of variable volume, e.g., 2 cc bolus 902, 1 cc bolus 901, 3 cc bolus 903, and 3 cc arc-bolus 903*a*, etc. Under certain conditions, 1 cc bolus 901 may be aspirated by closing vacuum valve 130 at approximately 120 ms (0.120 s, 0.120° C.). 2 cc bolus 902 may be aspirated by closing vacuum valve 130 at approximately 240 ms (0.240 s, 0.240τ). 3 cc bolus 903 may be aspirated by closing vacuum valve 130 at approximately 360 ms (0.360 s, 0.360τ). But this is very dependent upon the viscosity of the aspirate; clinical variations in aspirate viscosity result in corresponding variations in the time constants (τ). The approximate times listed above neglect additional time required for vacuum valve 130 to change state; other neglected factors include fluid acceleration and flow through partially-open valves, etc. More accurate values of the length of time required for a bolus of any arbitrary size may be readily determined through experimentation.

From the glossary, Eq. 0 provides both integral and summation-notation expressions for the measured, average or effective viscosity (μ) of the contents of a catheter.

$$\mu \approx \frac{1}{L}\int_0^L \hat{\mu}\,dx \approx \frac{1}{v}\sum_1^N \hat{v}_i\hat{\mu}_i \qquad \text{Eq. 0}$$

Where L is the length of the catheter, $\hat{\mu}$ is the viscosity of a differential length element (of fluid), i is a summation index, N is the number of boluses, v is the volume of the catheter, $\hat{v}_i$ is the volume of the $i^{th}$ bolus and $\hat{\mu}_i$ is the viscosity of the $i^{th}$ bolus. Eq. 0 also illustrates equivalence between certain VVA embodiments utilizing bolus volumes for computations, and those VVA embodiments utilizing bolus lengths for computations. Herein, any examples utilizing either bolus lengths or bolus volumes are intended for clarity. Conversion between bolus volume and bolus length may be calculated by multiplying/dividing by the cross-sectional area of the catheter.

In the catheter state depicted in FIG. 9A, N=21, 0; is from the set of {1, 2, 3 and 9 cc boluses}; $\hat{\mu}_i$≈4 cP (pure blood) and v≈36 cc. The summation-notation convention of Eq. 0 illustrates that the measured, average or effective viscosity (μ) is similar to a weighted arithmetic mean. Some VVA embodiments utilize algorithms treating the measured, average or effective viscosity as a weighted arithmetic mean. Some VVA embodiments utilize algorithms that store some or all values of $\hat{v}_i$ and $\hat{\mu}_i$ in memory and compute a summation over the terms, as in Eq. 0. Certain VVA embodiments generate a mathematical model/data array of aspirate boluses e.g., resulting from successive AMCs, viscosity measurements, time constant measurements, etc. This catheter model/data array is typically comprised of variable data including, but not limited to: aspirate boluses of varying lengths/volumes, measured viscosities, spatial location, etc.). A weighted arithmetic mean, such as disclosed in Eq. 0, is well suited because boluses of larger volumes are "weighted" more heavily than boluses of smaller volumes. Similarly, aspirate boluses of high viscosity contribute more to the viscous losses than do aspirate boluses of low viscosity; aspirate boluses of greater viscosity are "weighted" more heavily than aspirate boluses of lesser viscosity.

A convention used herein is to typically use lower case v and $\hat{v}_i$, for the volume of a catheter and bolus of aspirate; upper case V is typically used in reference to non-isovolumetric system components including control volume, bulb volume, displaced volume, etc. FIG. 9A further illustrates that any catheter containing any homogeneous fluid (e.g., pure saline, pure blood, pure SAE 30 motor oil, glycerine/water mixtures, etc.) may be discretized into any arbitrary number of boluses of arbitrary length/volume. In this manner, certain VVA embodiments "initialize" catheter states and/or catheter models by subdividing the catheter into discrete length/volume array elements, each array element being initialized to a viscosity of a homogeneous fluid. A catheter model/data array may be initialized into any number of bolus typically ranging from 2 to in excess of 10,000. Note that for a catheter containing a homogeneous fluid, a single-element array exists (i.e. there is only 1 bolus); any subdivisions increase the bolus count, starting at number of boluses=2. Many VVA embodiments initialize a catheter with approximately N=1,000 regularly-spaced boluses (range of less than 30 to in excess of 10,000) of equal viscosity.

Figure 9C:
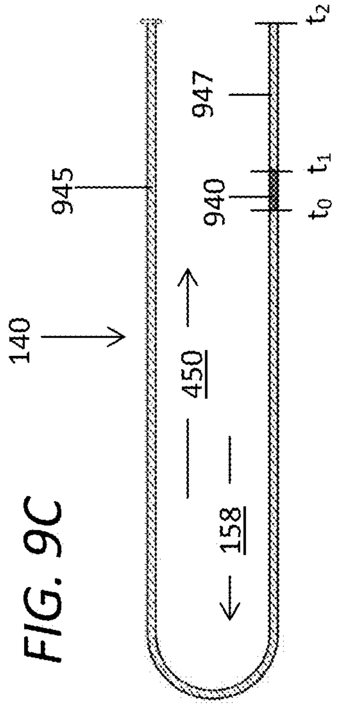
FIG. 9C depicts the catheter of FIG. 9A, wherein the bolus is translated proximally.
Figure 9E:
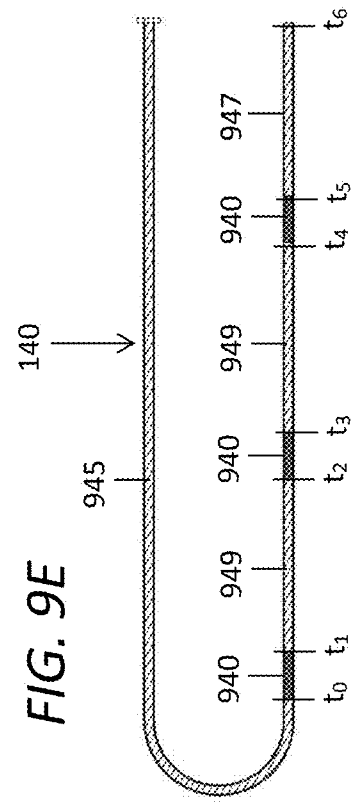
FIG. 9E depicts the catheter of FIG. 9A, wherein 3 boluses are translated proximally.
Figure 9G:
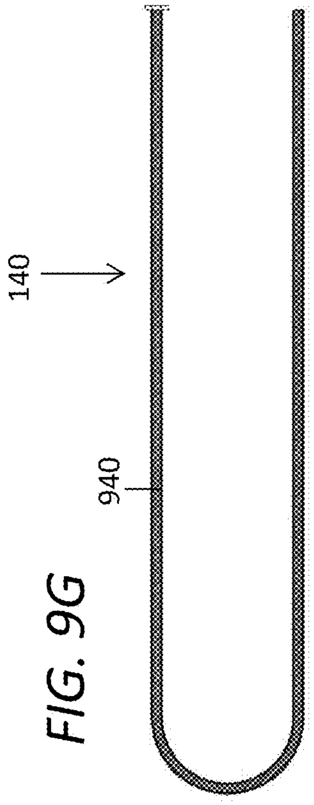
FIG. 9G depicts the catheter of FIG. 9A, wherein a single bolus is present, or a catheter containing a homogeneous fluid.
Figure 9B:
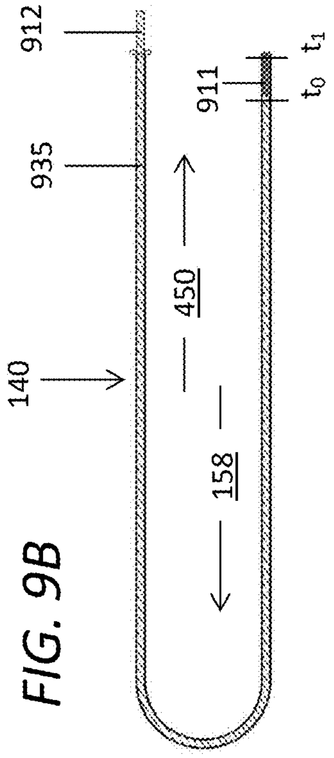
FIG. 9B depicts the catheter of FIG. 9A, wherein an entering bolus is aspirated.

FIG. 9B depicts catheter 140 approximately ($t_1$–$t_0$) after the catheter state depiction of FIG. 9A; the contents of catheter 140 are now comprised of a 35 cc bolus of pure blood (annotated 35 cc blood bolus 935) and entering bolus 911 of unknown viscosity. For numerical simplicity, approximately 20 blood boluses, of FIG. 9A, are merged to a single blood bolus, referenced as 35 cc blood bolus 935. In the time period of approximately ($t_1$–$t_0$), entering bolus 911 is drawn into the distal end of catheter 140; aspirate flow 450 direction is shown. In certain VVA embodiments, the time constant may be measured before time $t_1$, i.e., under flowing conditions. In FIG. 9B, the numerical example measured time constant ($\tau_{current}$) is stated to be 1.25 seconds.

In the example referencing FIG. 9B, the time constant for blood is stated to be 1 second ($\tau_{blood}$=1 s). Upon ingestion of entering bolus 911 (of unknown viscosity) the measured time constant is stated to be 1.25 ($\tau_{current}$=1.25 s). From this increase in time constant (e.g., from $\tau_{current}$=1.0 to $\tau_{current}$=1.25, etc.), certain VVA embodiments infer that entering bolus 911 is thrombus-laden, i.e., the viscosity is substantially greater than 4 cP. Certain VVA embodiments are enabled to quantify the viscosity of entering bolus 911.

Eq. 8 is adapted from the summation-convention form of Eq. 0, to the entering bolus 911 convention depicted in FIG. 9B. The volume of entering bolus 911 ($V_0$) is typically determined substantially at time $t_1$; as a numerical example, volume of entering bolus 911 ($V_0$) is stated to be 1 cc. The time constant ($\tau_{current}$) is typically determined at or before time $t_1$; as a numerical example, the time constant is stated to be 1.25 seconds. Eq. 8 may be utilized to relate the measured time constant ($\tau_{current}$) to the viscosity of the catheter ($\mu_{current}$). The example numerical values are inserted into Eq. 8A. In this example, N=2, catheter 140 contains: 35 cc blood bolus 935 at approximately 4 cP, and 1 cc entering bolus 911 of unknown viscosity ($\hat{\mu}_0$).

$$\mu_{current} \approx \left(\frac{\tau_{current}}{\tau_{blood}}\right)\mu_{blood} \approx \frac{\hat{v}_0\hat{\mu}_0 + \sum_1^N \hat{v}_i\hat{\mu}_i}{v} \quad \text{Eq. 8}$$

$$\mu_{current} \approx \left(\frac{1.25s}{1.0s}\right)4cP \approx \quad \text{Eq. 8A}$$

$$\frac{(v-\hat{v}_0)\mu_{prev} + \hat{v}_0\hat{\mu}_0}{v} \approx \frac{(36-1)4 + 1(\hat{\mu}_0)}{36} \approx 5cP$$

$$\hat{\mu}_0 \approx \frac{(\mu_{current}v) - (v-\hat{v}_0)\sum_1^N \hat{v}_i\hat{\mu}_i}{\hat{v}_0} \quad \text{Eq. 9}$$

$$\hat{\mu}_0 \approx \frac{(\mu_{current}v) - (v-\hat{v}_0)\mu_{prev}}{\hat{v}_0} \approx \frac{(5)36 - 35(4)}{1} \to \to 40cP \quad \text{Eq. 9A}$$

Where $\tau_{current}$ is the currently measured time constant, $\tau_{blood}$ and $\mu_{blood}$ are the time constant and viscosity for blood, $\mu_{current}$ is the viscosity of the catheter, $\mu_{prev}$ is the previously measured (catheter) viscosity, v is the catheter volume, $\hat{v}_0$ and $\hat{\mu}_0$ are the volume and viscosity of the $0^{th}$ bolus, or entering bolus 911. N is the current number of boluses of aspirate within the catheter.

The volume of entering bolus 911 ($V_0$) may be calculated by mapping the difference in pressure (e.g., $\Delta P=P_0-P_{final}$) to the difference in volume (e.g., $V_0=V_{final}-V_0$). Examples of this mapping operation are outlined in the descriptions of FIG. 7A, FIG. 7B and FIG. 7C. FIG. 7C provides a representative lookup table that enables calculation of $\hat{V}_0$, given $P_0$ and $P_{final}$. Eq. 9 is a rearrangement of Eq. 8 to solve for $\hat{\mu}_0$, the viscosity of entering bolus 911 ($\hat{\mu}_0$). Example numerical values are inserted into Eq. 9A to solve for the viscosity of entering bolus 911 $\hat{\mu}_0$≈40 cP.

In certain VVA embodiments, entering bolus 911 is typically assigned as the $0^{th}$ array element of the catheter model/data array. Subsequently, as the catheter model/data array is updated, the array indices are shifted such that the $0^{th}$ array element(s) become(s) the $1^{st}$ array element(s), the previous $1^{st}$ array element(s) become(s) the $2^{nd}$ array element(s), and so forth until the $N^{th}$ array element(s). At the proximal end of catheter 140, exiting bolus 912 is the $N+1^{th}$, or a discarded, array element(s), FIG. 9B.

FIG. 9C depicts catheter 140 at time $t_2$, wherein the catheter state of catheter 140 comprises leading blood bolus 945, 40 cP bolus 940 and trailing bolus 947. Trailing bolus 947 is shown aspirated into catheter 140 in the time interval of approximately $t_2$–$t_1$. The volume of trailing bolus 947 ($\hat{v}_0$) is stated to be 3 cc and the time constant is stated to be 1.23 seconds ($\tau_{current}$=1.23 s). Substituting these values into Eq. 8 and Eq. 9 yields numerical solutions of Eq. 10 and Eq. 11:

$$\mu_{current} \approx \frac{(v-\hat{v}_0)\mu_{prev} + \hat{v}_0\hat{\mu}_0}{v} \approx \frac{(36-3)5 + 3(\hat{\mu}_0)}{36} \approx 4.92cP; \quad \text{Eq. 10}$$

$$\tau \approx (4.92/4) \approx 1.23s$$

$$\hat{\mu}_0 \approx \frac{\mu_{current}v - (v-\hat{v}_0)\mu_{prev}}{(\hat{v}_0)} \approx \frac{(4.92)36 - 33(5)}{3} \approx 4cP \quad \text{Eq. 11}$$

Eq. 10 calculates the average or effective viscosity ($\mu_{current}$), at time $t=t_2$, to be approximately 4.92 cP; substituting this value of $\mu_{current}$ into Eq. 9 yields a calculated viscosity of trailing bolus 947 to be approximately 4 cP. Trailing bolus 947 has measured viscosity of approximately 4 cP and is inferred to be blood in certain VVA embodiments.

Eq. 8 and Eq. 9 were utilized a first time to determine the viscosity of entering bolus 911 to be 40 cP. Eq. 8 and 9 were utilized a second time (numerical values were inserted to form Eq. 10 and Eq. 11) to determine the viscosity of trailing bolus 947 to be approximately 4 cP. Thus, Eq. 8 and Eq. 9 are "iterative" equations, suitable for machine computation.

Figure 9D:
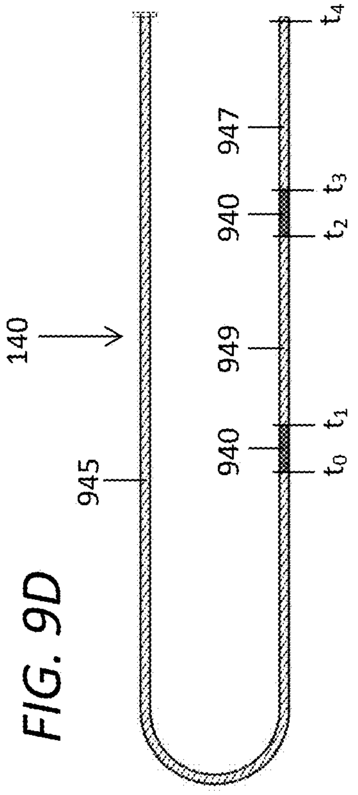
FIG. 9D depicts the catheter of FIG. 9A, wherein 2 boluses are translated proximally.

For numerical simplicity, the catheter state depicted in FIGS. 9D-9G are comprised of boluses of either: blood (at 4 cP) or thrombus-laden blood (at 40 cP). FIG. 9D depicts catheter 140 at a time (≈$t_4$) wherein the catheter state of catheter 140 is comprised of leading blood bolus 945, 40 cP bolus 940, intermediate blood bolus 949, 40 cP bolus 940, and trailing blood bolus 947. In the interim period between the depictions of FIG. 9C and FIG. 9D (i.e. $t_4$–$t_2$), a second 40 cP bolus 940 and trailing bolus 947 have been aspirated into catheter 140. The measured, average or effective viscosity (u or $\mu_{current}$) of FIG. 9D may be calculated to be approximately 5.9 cP.

Figure 9F:
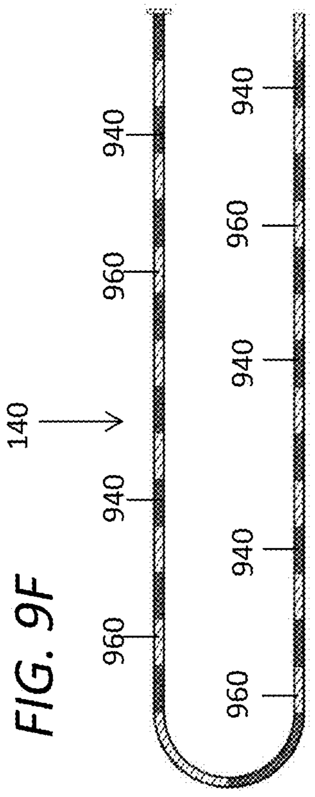
FIG. 9F depicts the catheter of FIG. 9A, wherein a plurality of regularly-spaced boluses is present.

FIG. 9E depicts catheter 140 at a time (≈$t_6$) wherein the catheter state of catheter 140 is comprised of leading blood bolus 945, 40 cP bolus 940, intermediate blood bolus 949, 40 cP bolus 940, intermediate blood bolus 949, 40 cP bolus 940 and trailing blood bolus 947. The measured, average or effective viscosity may be calculated to be approximately 6.84 cP FIG. 9F depicts catheter 140, the catheter state comprising interspersed blood bolus 960 and 40 cP bolus 940; the volumes of the boluses are approximately equal. The measured, average or effective viscosity (μ) of FIG. 9F is approximately 22 cP (the arithmetic mean of 4 cP and 40 cP). An arithmetic mean formulation is substantially accurate when applied to configuration of FIG. 9F, because the respective volumes of blood and thrombus are depicted and stated to be approximately equal (i.e., a weighted arithmetic mean with equal weights).

FIG. 9G depicts catheter 140, the catheter state comprising fluid of approximately 40 cP and is annotated as 40 cP bolus 940. The measured, average or effective viscosity of the contents of catheter 140 is approximately 40 cP and the time constant is approximately 10 seconds. This is because the viscosity of the contents of catheter 140 is approximately 10 times greater than the viscosity of blood. From Eq. 5, the time constant is approximately 10 times greater in FIG. 9G than in FIG. 9A, wherein the stated contents of catheter 140 is approximately 4 cP (pure blood).

The sequence of catheter state depictions of FIG. 9A through FIG. 9G typically exhibits an increase in the measured time constant, and a corresponding increase in the measured viscosity, as more viscous aspirate displaces blood within catheter 140. The time constant for FIG. 9A is stated to be approximately 1 second for blood. The time constant for FIG. 9B and FIG. 9C (each with one 1 cc, 40 cP bolus 940 may be calculated (from Eq. 5) to be approximately 1.25 seconds. The time constant for FIG. 9D (with two 1 cc, 40 cP bolus 940) may be calculated to be approximately 1.5 seconds. The time constant for FIG. 9E (with three 1 cc, 40 cP bolus 940) may be calculated to be approximately 1.8 seconds. The time constant for FIG. 9F (with equal boluses of blood at 4 cP and 40 cP) may be calculated to be approximately 5.5 seconds.

The sequence of catheter states depicted in FIG. 9A-9G, and corresponding calculations, may be experimentally conducted using a clear length of tubing and immiscible fluids such as water and one or more appropriate oils (e.g. SAE 10, 30, 50, 80, 120, etc.). This experimental setup enables engineers to observe, measure and confirm the position of an oil/water interface against machine computed determinations. Many VVA embodiments are typically independent of scale; therefore experimentation conducted upon catheters of substantially any dimension, and fluids of substantially any viscosity, is typically valid throughout a substantial range of experimental and clinical conditions.

The act of aspirating a mixture of blood and thrombus may lead to a separation of the components based upon characteristics including; viscosity, molecular weight, solubility, particle size, etc. More specifically, certain macromolecules (e.g., hemoglobin, albumin, lipoproteins, fibrin, fibrinogen, etc.) may agglomerate at/near the catheter tip, wall or otherwise within the catheter. This agglomeration may act as a "filter" such that only smaller, more perfusive, components (e.g., saline, plasma, serum, etc.) are "preferentially" aspirated. Thus, aspiration of certain "filtering" types of thrombus may exhibit a gradual an increase in time constant as successive AMCs and aspirate flow "build up" more and more occlusive solids, for instance at or near a catheter tip. Certain thrombotic material types do form a not seal the with a catheter, but rather act as "filters" allowing certain aspirate components, e.g., lower-molecular weight, soluble, inviscid, etc. components to be preferentially aspirated.

Alternatively, the act of aspirating a thrombus may cause an effective seal between the thrombus and catheter tip to develop. In cases wherein the distal end of catheter 140 forms a "seal" with a thrombus-laden bolus of aspirate, pure blood is typically unable to breach the seal and the thrombus-laden bolus may either be aspirated or the catheter may clog. In the case of a "sealing" thrombus at or near the tip of catheter 140, the time constant may be observed to increase rapidly, perhaps over only 1 or 2 AMCs. Thus, the rate at which the VVA time constant increases provides insight to whether or not the catheter tip is "filtering" or "sealing."

FIG. 10A depicts VVA (Visco-Volumetric Aspiration) system 1001 and dilution catheter 1005 in accordance with an illustrative embodiment of the present invention in a first machine state. Among other functionalities, VVA system 1001 and dilution catheter 1005 may be utilized to generate "interspersed" catheter states, as depicted in FIGS. 9C-9F, wherein blood boluses are interspersed with thrombotic masses within catheter 140 or dilution catheter 1005.

VVA system 1001 comprises dilution mechanism 1035, dilution handle 1030 and dilution actuator 1040; these components are utilized to change the configuration of dilution catheter 1005. FIG. 10A depicts VVA system 1001 in a machine state wherein dilution handle 1030 is in the closed state. Dilution handle 1030 is mechanically coupled to sleeve 1010 of dilution catheter 1005 by means including sliding sheaths, cables, etc. The position of dilution handle 1030 may be under manual control of a clinician and/or automatic control of VVA system controller in various embodiments. In certain VVA embodiments, the actuator state of dilution actuator 1040 is controlled by VVA system controller.

FIG. 10B depicts the VVA system 1001 and dilution catheter 1005 of FIG. 10A in a second machine state wherein the position of dilution handle 1030 is changed to the open state. Sleeve 1010 is correspondingly translated proximally (i.e., leftward) with respect to dilution catheter 1005. This exposes one or more instances of dilution orifice 1020. Dilution orifice 1020 is significant because fluid may enter dilution catheter 1005 through openings or orifices that are separate and distinct from the primary orifice at the distal tip thereof. IG. 10C depicts a machine state of VVA system 1001 and dilution catheter 1005 of FIG. 10A wherein sleeve 1010 is extended past the distal tip of dilution catheter 1005 by a distance annotated extension distance 1015. In certain embodiments, moveable sleeve 1005 effectively changes the working length of dilution catheter 1005. In some cases sleeve 1010, in the extended configuration depicted in FIG. 10C, contacts a thrombotic mass; in certain cases, a seal is formed between sleeve 1010 and a thrombotic mass. Certain embodiments of dilution catheter 1005 may be reconfigured to adjustable working lengths. Certain embodiments of dilution catheter 1005 may be reconfigured to admit fluid through openings or orifices separate and distinct from the primary opening at the distal end. Some embodiments have a range of travel of sleeve 1010 from approximately 0.1 cm to in excess of 10 cm. Some embodiments may have a range of extension distance 1015 of approximately 0.1 cm to in excess of 2 cm.

In certain VVA system 1001 embodiments, reconfiguring dilution catheter 1010 to different working lengths is utilized, for instance in make/break contact operational modes. In cases wherein a VVA system controller detects a thrombotic mass or impending clog, sleeve 1010 may be repositioned to perform a variety of functions including, but not limited to:

(1) retracting and disengaging from thrombus, and aspirating blood, (2) advancing and/or retracting to physically macerate, cleave or otherwise disintegrate a thrombotic mass, and aspirating mechanically disrupted thrombus, (3) retracting to expose instances of dilution orifice 1020, and aspirating blood.

FIG. 10D depicts a twist sleeve 1070 embodiment of dilution catheter 1005 in a substantially open state, exposing instances of dilution orifice 1020. FIG. 10E depicts the twist sleeve 1070 embodiment of FIG. 10D configured to an intermediate state. Twist sleeve 1070 may be selected for use in conjunction with certain dilution catheter 1005 and dilution mechanism 1035 that utilize rotary, rather than linear, dilution actuator 1040.

Typical acts of repositioning a catheter involve pushing, pulling and twisting the proximal end of that catheter in order to change the distance between the catheter tip and thrombus. The accuracy and precision that a catheter tip may be repositioned (by the hub end) may be termed "gross" or "coarse" adjustments. Extending sleeve 1010 past the distal end of a catheter enables certain VVA embodiments to enact "fine" adjustments to the distance between the catheter tip and a thrombus. As a first benefit, advancing a catheter tip toward a thrombus is illustrated in FIGS. 16A-16D; the resulting flow anomalies may be measured and correlated to distance. This is beneficial in "sampling" a thrombotic mass for characteristics, rather than ingesting a large, thrombotic, entering bolus 911 suddenly, which may cause a clog. A second benefit of variable catheter length to enact make/break methods wherein physical contact between a catheter tip and a thrombus is established intermittently. One objective of make/break contact methods is to aspirate a thrombotic mass in discrete portions, in some cases the discrete portions being interspersed with blood as illustrated in the catheter states depicted in FIGS. 9C-9F.

Figure 11A:
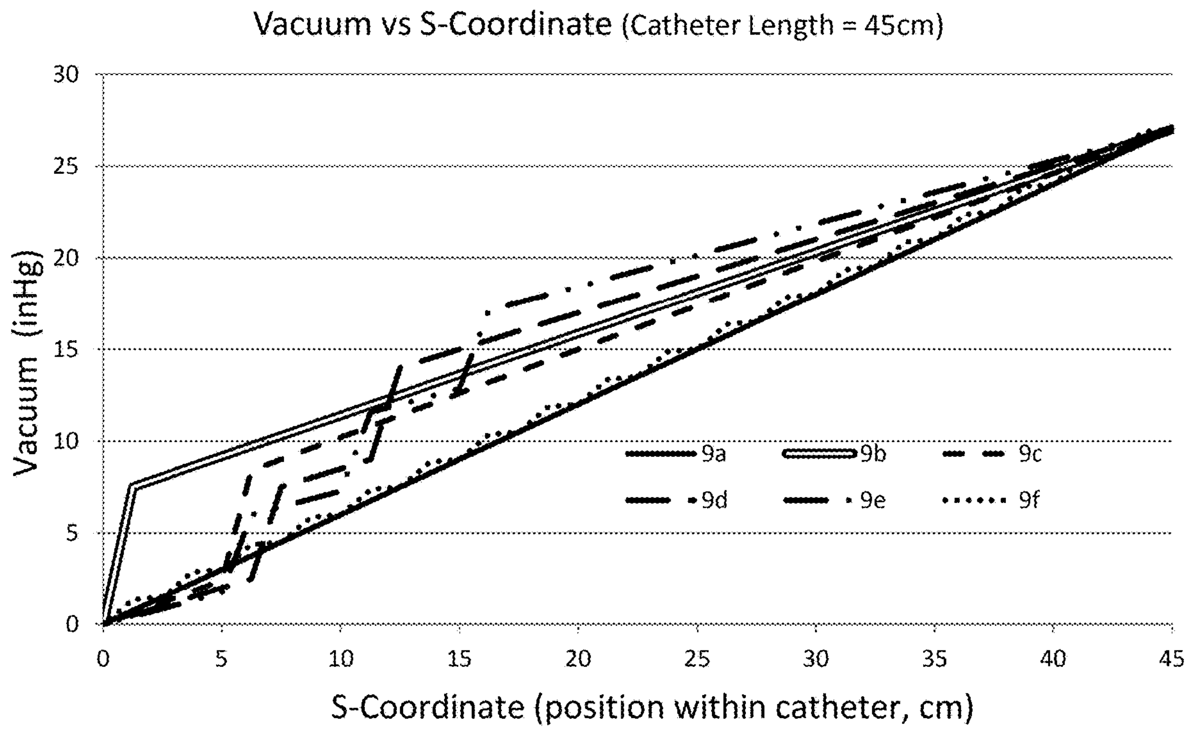
FIGS. 11A and 11B depict illustrative graphs generated in accordance with certain embodiments of the present invention, wherein calculated pressure data within a catheter are graphically depicted.

FIG. 11A graphically depicts machine-computed vacuum levels as a function of position along a catheter. The input data to generate FIG. 11A correspond to the catheter state depictions of FIGS. 9A-9F and their stated values (e.g., bolus viscosity, bolus length, etc.). In this example, Eq. 1 and the summation convention of Eq. 0 were utilized to compute the graphically displayed pressure values along the catheter. The representation of FIG. 11A may be called the pressure distribution within a catheter. FIG. 11A is significant because the vacuum level that is present at each bolus interface is determined by calculation in certain VVA embodiments. To successfully aspirate a high-viscosity thrombotic bolus, a sufficient vacuum level typically is present (at the proximal bolus interface) to overcome the frictional forces holding it stationary. Prior art efforts to improve thrombectomy efficacy include increasing vacuum levels within connecting tubes and at the proximal end of the catheter, primarily by increasing the vacuum level in the reservoir. In contrast, certain VVA embodiments act to generate favorable vacuum levels, at favorable locations within the catheter, at favorable times throughout an aspiration thrombectomy procedure, substantially irrespective of the vacuum level in the reservoir.

Figure 11B:
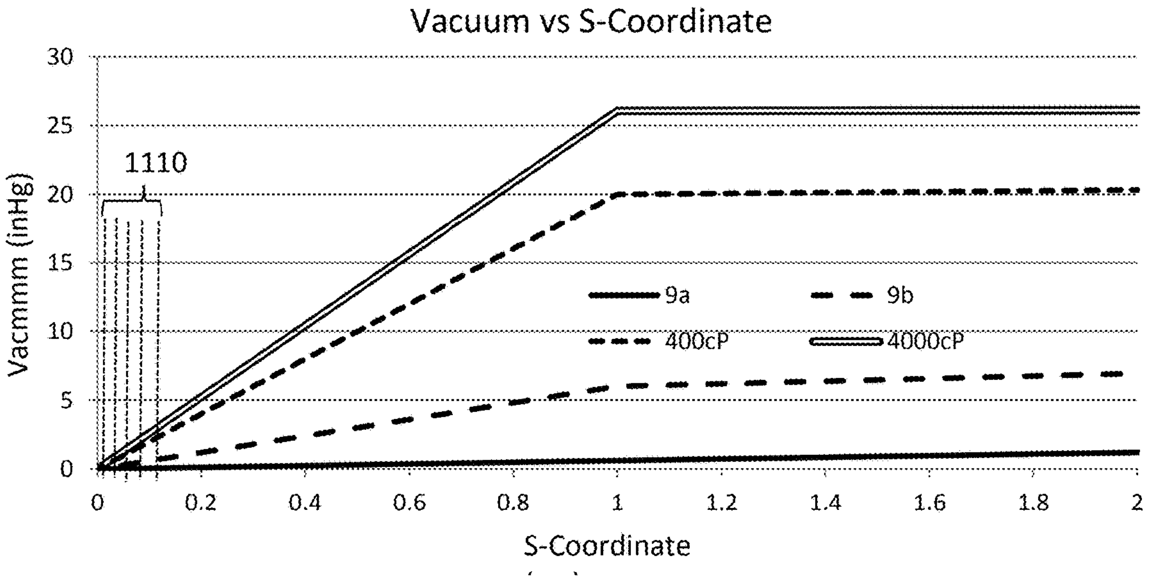

Consider line 9*b* of FIG. 11A, which corresponds to a catheter state wherein a single 40 cP bolus is present at the distal end. The vacuum level at the proximal interface of this entering bolus is approximately 7.5 inHg, significantly greater than all other catheter states examined. FIG. 11B graphically depicts the effects of the viscosity of an entering bolus; the catheter state of FIG. 9B is a single 40 cP bolus, also depicted are the effects of a single 400 cP bolus and a single 4,000 cP bolus. FIG. 11B, as normalized, illustrates that a 4,000 cP bolus, reaching s-coordinate length of approximately 1, experiences substantially system vacuum level, of approximately 27 inHg, at the proximal interface. Pressure distribution calculations, such as depicted in FIG. 11B, are utilized in certain VVA embodiments to model, simulate and/or predict the volume of an incoming bolus (of calculated viscosity) that is expected to cause the catheter to clog. In one VVA example method of calculating this "clogging volume" is comparing the calculated vacuum level at the interface against the system vacuum level. As a general guideline, as the vacuum level at an interface of a distal bolus (e.g., s≤2, s≤4, etc.) approaches the system vacuum level, the expectation value of a clogged catheter (e.g., clog risk) approaches 100%.

Entering boluses of significantly high viscosity (e.g. 400 cP, 1,500 cP, etc.) typically result in measured time constants that are significantly greater than for blood; this condition may be readily detected. FIG. 11B illustrates multiple valve closure instances 1110 which represent opportunities to limit the volume of an entering bolus of significant viscosity (e.g., by closing the vacuum valve). Upon detecting an entering bolus of significant viscosity, certain VVA embodiments invoke responsive actions including, but not limited to: immediately closing the vacuum valve, repositioning and/or reconfiguring catheter 140, 1005, make/break contact methods, dilution, etc. Breaking physical contact with a thrombus may result in the aspiration of substantially pure blood, generating a catheter state similar to that depicted in FIG. 9C. This effectively isolates a portion of a thrombotic mass from any remaining portions thereof. In certain cases, subsequent aspiration of some or all of the remaining portions of thrombus may be aspirated in discrete portions, similar to the illustrative catheter states depicted in FIGS. 9D-9F.

Note a distinction between the analyses presented herein and those of prior art. Disclosed herein is a method to calculate or determine a pressure at an interface of a thrombus within a catheter; this is significantly different from prior art efforts to measure pressure at one or more locations along the catheter and/or connecting tube. An important distinction is that pressure measurement devices (e.g., transducers, gages, etc.) typically remain fixed (with respect to the catheter and/or connecting tube), whereas thrombotic masses and their interfaces are ideally moving. Certain VVA embodiments utilize calculated pressure data to display dynamic visualization of the pressure levels present within the catheter (e.g., FIGS. 11A-11B, etc.) to a clinician and/or store these data. Certain VVA embodiments compare calculated pressure data to one or more threshold values and quantitatively assess a catheter state for derived variables such as clog risk, flow rate, pressure distribution, etc.

FIG. 7A graphically depicts a mathematical model for volume vs pressure that is utilized in certain VVA embodiments; but time and position in space are absent. FIGS. 8A-8B graphically depict a model for vacuum decay that is utilized in certain VVA embodiments; but position in space (e.g., along s-coordinate 158) is absent. FIG. 11A graphically depicts computed vacuum levels at locations along catheter 140, or dilution catheter 1005, along s-coordinate 158; but time is absent. The pressure distributions depicted in FIGS. 11A-11B provide no insight to the flow rate or time constant. For this reason, pure SAE 30 oil (at approximately 100 cP) and pure water (at approximately 1 cP) share the same line (9*a*) of FIG. 11A, despite that the flow rates and time constants differ by substantially two orders of magnitude. In certain VVA embodiments, the graphical depiction of FIGS. 11A and/or 11B is intermittently updated, for example with each AMC. Certain VVA embodiments generate, and optionally display to the clinician, dynamic visualizations of the pressure distribution along the catheter in real time.

Data for FIGS. 11A-11B are computed from the example catheter states depicted in FIGS. 9A-9F. This is an application of Eq. 8A and Eq. 9A upon catheter states comprising: (1) a number of discrete 40 cP bolus 940, and (2) a number of discrete blood bolus 960. Data utilized to generate FIG. 11A retains the (numerical example) convention that each bolus has approximate volume of 1 cc for illustration and calculation purposes. The total pressure drop along catheter 140 and/or dilution catheter 1005 is stated to be approximately 27 inHg, or substantially the difference between the system vacuum level and intravascular, nominal, atmospheric or any reference pressure.

FIG. 11A and FIG. 11B are included, among other reasons, to illustrate that pressure, at any s-coordinate 158 location along catheter 140, may be calculated and graphically displayed; pressure distributions for the catheter states of FIGS. 9A-9F are shown. Note that the configuration of FIG. 9A exhibits a time constant of 1 second whereas the configuration of FIG. 9F exhibits a time constant of 5.5 seconds. While the vacuum vs s-coordinate traces of FIG. 9A and FIG. 9F appear quite similar in FIG. 11A, it is instructive to note that the catheter state depicted in FIG. 9A may be considered to be 5.5 times "faster" and 5.5 times "less likely to clog" than the catheter state depicted in FIG. 9F. However, the rate at which dynamic visualizations of pressure distributions (e.g., FIGS. 11A-11B, etc.) change is an indicator of the time constant, and hence the flow rate. In cases wherein a clinician observes an adverse pressure distribution, or a flow rate level of concern, the clinician may enact manual and/or automated counter-measures, such as through manual catheter manipulation, clinician feedback controls, AMC mode selection, etc.

FIG. 11A and FIG. 11B illustrate a method to expose a distal thrombus to a higher vacuum level by decreasing the viscosity of the fluid within the catheter. A valid inference of this is that substituting saline (at approximately 1 cP viscosity) for pure blood will further increase the vacuum level to which a distal thrombus (i.e., entering bolus 911) is exposed. Some VVA embodiments utilize a "saline flush" to displace blood within catheter 140 in order to decrease the time constant (to as little as approximately/4 the value in blood). An intended consequence of this is that the flow rate is increased, and the time constant is decreased, both by a factor of up to approximately 4. Saline flush AMC modes are prescribed, in certain VVA embodiments and/or methods, to prepare a catheter to more efficaciously aspirate certain thrombotic masses under certain conditions.

A first example case where certain VVA embodiments may select a saline flush AMC mode is ischemic stroke; in many cases a fresh thrombotic mass totally occludes one or more cerebral arteries. In this clinical instance the catheter tip may be more likely to "seal" with a fresh, elastic thrombotic mass. Certain VVA embodiments and/or methods aspirate fresh, elastic thrombotic masses, characteristic of ischemic stroke procedures, by increasing the subsequent flow rate before thrombus is contacted and aspirated. In certain VVA embodiments, derived variables including flow rate are continuously and/or intermittently determined and compared against threshold values (e.g., clog risk, catheter viscosity, bolus viscosity, etc.); certain VVA embodiments and/or methods stop aspiration (e.g., close vacuum valve 130, etc.) upon reaching a threshold value. At this degree of catheter "loading", the catheter tip may be withdrawn to disengage physical contact with the thrombus; subsequently aspirating pure blood until the harvested thrombotic mass has exited the catheter. This process may be repeated indefinitely for remaining thrombotic masses and/or portions thereof.

A second example case where certain VVA embodiments and/or methods may select a saline flush AMC mode is chronic total occlusion of a femoral artery; in many such cases, cohesive, organized, fibrotic thrombus types may be more likely to agglomerate and "filter" at or near the catheter tip. Certain VVA embodiments and/or methods aspirate certain thrombus types by generating substantially increased fluid velocities in proximity to thrombotic masses, either internal or external to catheter 140. To efficaciously aspirate certain thrombus types by high fluid velocity means, we introduce "dynamic pressure"=½ $\rho v^2$, where, in this instance, v us the fluid velocity and p is the fluid density, assumed constant. The kinetic energy per unit volume of fluid may be defined as "dynamic pressure"=½ $\rho v^2$. Certain VVA embodiments store and release potential energy available to generate significant kinetic energy, per unit volume of fluid, in the locality of the catheter tip. Thereby, effects including, but not limited to: entrainment, erosion, high-shear boundary layer, turbulence, fracture, cleavage, etc., may mechanically disintegrate certain thrombus types more efficaciously.

Figure 12A:
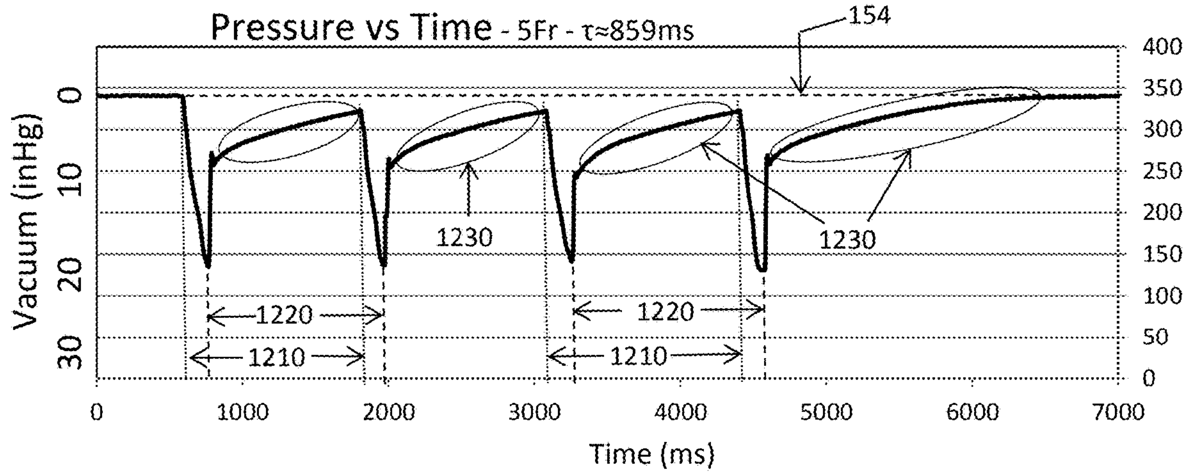
FIG. 12A graphically depicts experimental pressure waveform data collected upon a VVA system embodiment and a 5 Fr×1 m catheter.

FIG. 12A graphically depicts an experimental pressure vs time (pressure waveform) plot. These data were collected upon a VVA apparatus substantially equivalent to VVA system 401, depicted in FIGS. 4A-4D, herein referred to as "the experimental apparatus." The experimental apparatus of FIG. 12A is configured with a 5 Fr (≈1.67 mm≈0.065" diameter)×1 m long catheter 140. The catheter state is containing and aspirating pure water. Data from a sequence of 4 AMCs are depicted; the experimental bolus volume of each AMC is approximately 1 cc per AMC.

At time zero, of FIG. 12A, the machine state is: vacuum valve 130 in the open state and isolation valve 210 in the closed state; the pressure state is substantially at any reference pressure which may be atmospheric, intravascular, or any reference pressure. At approximately 800 ms, 1800 ms, 3100 ms and 4400 ms, the machine state is changed to vacuum valve 130 in the closed state and isolation valve 210 in the open state. These events are annotated vacuum closed-isolation opened 1210. The pressure state (right hand scale) is seen to decrease as the volume of non-isovolumetric component (e.g., bulb 405, elastic tubing 230, etc.) decreases with time in an "evacuation step." At some characteristic time afterward, the machine state is changed to vacuum opened-isolation closed 1220; this is followed by a characteristic increase in pressure toward the reference pressure as "refilling" of any non-isovolumetric components begin.

The embodiment selected for experimentation and data collection is substantially equivalent to VVA system 401, which utilizes pinch valves as depicted in FIG. 4A through FIG. 4F. However, these pinch valves displace a finite volume of fluid as they are cycled between open closed and open states. Rapid actuation of many types of valve (e.g., angle, globe, ball valve, etc.) may cause shocks, oscillations or other disturbances as the valves are opened and/or closed. This effect is visible in the rapid increase in pressure (large positive slope) immediately following the machine state change of vacuum opened-isolation closed 1220. The pinch-type valves of the experimental apparatus are first-generation and displace substantial volume; while this is not ideal, it is illustrative of the robust nature of certain VVA system control algorithms. It is acknowledged that many types of valves displace a characteristic fluid volume upon actuation. This non-isovolumetric characteristic or certain valves is herein considered negligible volumetrically, however the pressure waveform data may be significantly affected. Certain VVA embodiments comprise valves that displace volumes within a range of substantially 0 μl to in excess of 1 cc, depending upon the scale of the apparatus among other considerations.

Following the rapid expansion at vacuum opened-isolation closed 1220, pressure steadily rises in a region annotated as expansion 1230. Data collected within expansion 1230 regions are well-suited of application of techniques including flow measurement, time-domain viscometry, etc. In FIG. 12A, the expansion 1230 regions are slightly less than 1 second in duration.

In the first 3 executions of the AMC, the machine state is changed to vacuum closed-isolation opened 1210; this occurs at a pressure state that is slightly less than reference pressure 154. In the $4^{th}$, and final, AMC the machine state is left unchanged and the pressure state equilibrates to substantially that of reference pressure 154. For the 5 Fr catheter of FIG. 12A, the 4 AMC measurements of the time constant were machine calculated to be: 840 ms, 878 ms, 873 ms and 845 ms for an average of 859 ms.

Figure 12B:
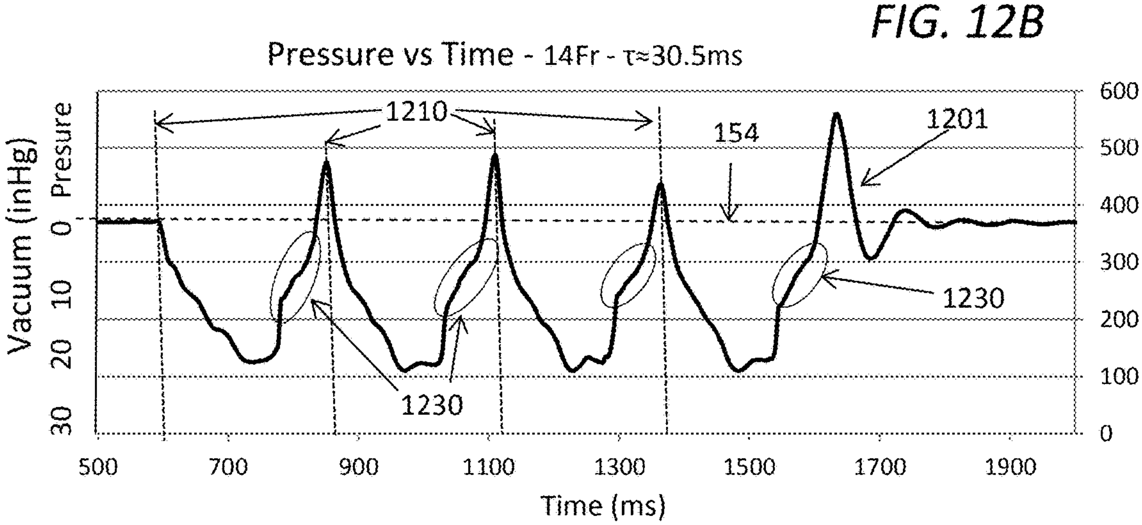
FIG. 12B graphically depicts experimental pressure waveform data collected upon a VVA system embodiment and a 14 Fr×1 m catheter.

FIG. 12B graphically depicts data collected upon the experimental apparatus of FIG. 12A, however the experimental apparatus is configured with a 14 Fr (≈4.67 mm≈0.184" diameter)×1 m long catheter. At times approximately 600 ms, 850 ms, 1125 ms and 1380 ms, the machine state is changed to vacuum closed-isolation opened 1210. In first 3 executions of the AMC, the pressure state is substantially greater than reference pressure 154. In the $4^{th}$, and final, AMC the machine state is left unchanged and the pressure state is oscillatory, characteristic of ringing 1201. The pressure oscillations persist for longer than 1 second and the pressure state equilibrates to substantially that of reference pressure 154. Four measurements of the time constant were machine calculated to be: 28 ms, 33 ms, 28 ms and 33 ms for an average of 30.5 ms. The four expansion 1230 zones are visibly smaller (and of shorter duration) in FIG. 12B, when compared to FIG. 12A; these are followed by a rapid increase in pressure which “spikes” and exceeds reference pressure 154. The pressure peak (at approximately 560 on the right hand, transducer, scale), and the phenomenon of ringing 1201 are distinctly visible. Due to factors including: rapid fluid acceleration, ringing, overpressures, etc., data outside of the four expansion 1230 zones are not typically as meaningful or valuable in performing calculations utilized in many VVA embodiments.

The fluid within catheter 140 is at substantially zero velocity at times when the machine state is vacuum closed-isolation open 1210 (phenomena such as leaky valves, water hammer, ringing, shock, etc. notwithstanding). Some instances of closing vacuum valve 130 cause the fluid in catheter 140 to decelerate to substantially zero velocity in a short period of time (range of approximately Ous to in excess of 50 ms). Some instances of opening vacuum valve 130 cause the fluid in catheter 140 to accelerate toward some characteristic velocity. Thus, the act of opening vacuum valve 130 typically causes any fluid in catheter 140 to accelerate toward some characteristic velocity, and closing vacuum valve 130 typically causes any fluid in catheter 140 to decelerate to substantially zero velocity. Ringing 1201, over-pressure peaks and oscillatory behavior are evident in FIG. 12B (14 Fr), but not in FIG. 12A (5 Fr). Damping is herein identified as a difference between the underdamped response of the 14 Fr case (FIG. 12B) compared to the overdamped (or critically damped) response of the 5 Fr case (FIG. 12A). Certain VVA control algorithms analyze the “vacuum decay” during expansion 1230; this is exacerbated by phenomena including ringing 1201, overpressure (i.e., exceeding intravascular pressure 154) and shock, if present.

Figure 12C:
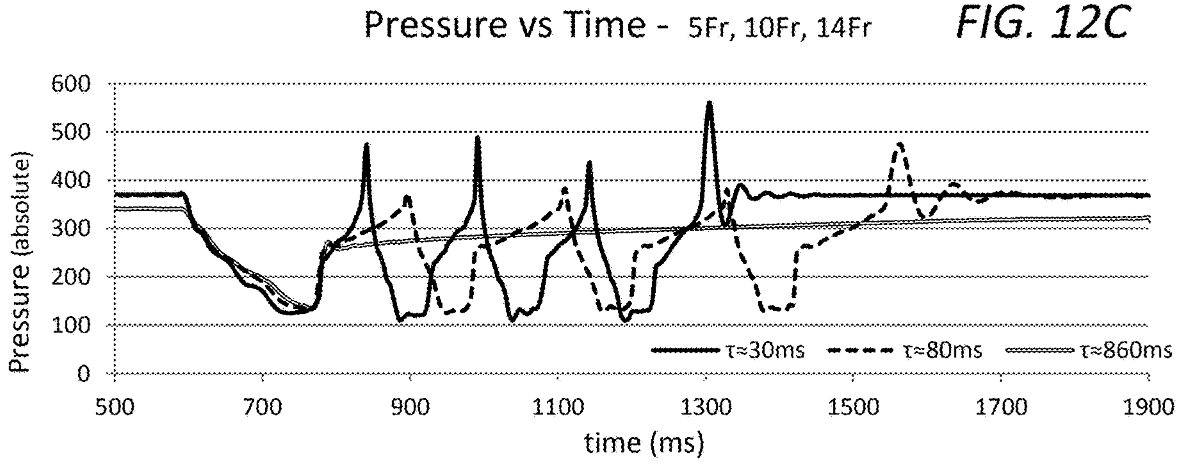
FIG. 12C graphically depicts superposed experimental pressure waveform data for 5 Fr, 10 Fr and 14 Fr catheters.

It is important to note that the data collected in FIG. 12A (with a measured time constant of approximately 859 ms) are collected over a time interval of approximately 6 seconds. The corresponding data of FIG. 12B (with a measured time constant of approximately 31 ms) are similarly collected over a time interval of less than approximately 1.5 seconds. These data are collected using a common algorithm which closes vacuum valve 130 after a time constant is calculated by a method disclosed herein. FIG. 12A-12C illustrate that a single experimental VVA control system algorithm is robust to approximately three-fold changes in diameter and thirty-fold changes in measured time constant.

FIG. 12C graphically depicts data collected upon 5 Fr, 10 Fr and 14 Fr catheters overlaid, or superposed, upon one another. The respective time constants (τ) are measured by the experimental apparatus to be approximately 860 ms, 80 ms and 30 ms. FIG. 12C illustrates that ringing 1201 and overpressure occurs in the 10 Fr and 14 Fr catheters; this is consistent with underdamping or an underdamped system. Comparison of FIG. 12A, FIG. 12B and FIG. 12C also provides insight to a well-established problem of thrombectomy: blood loss. The volume of aspirate transferred for the 10 Fr and 14 Fr catheters is approximately equal (4 cc) in FIG. 12B and FIG. 12C. The volume of aspirate transferred for the 5 Fr catheter is only approximately 1 cc in FIG. 12C; this is because only a single iteration of the AMC was completed in the time-frame of the graph. FIG. 12C illustrates the phenomenon that, as the time constant is increased, the pressure waveform transitions from an oscillatory, underdamped nature to a non-oscillating exponential decay (a solution to Eq. 5).

To a first approximation, the average flow rate through the 14 Fr and 10 Fr catheters is approximately 7.5 and 5.5 times greater than the corresponding average flow rate through the 5 Fr catheter. The algorithm used in FIG. 12A, FIG. 12B and FIG. 12C was developed to measure the time constant (four times, to establish repeatability) and initiate the next AMC after measurement of the time constant is complete. The algorithm was developed to make robust measurements of the time constant in the presence or absence of ringing 1201, overpressure or oscillatory behavior. This algorithm was not developed expressly to measure average flow rate, however a first approximation of flow rate is readily available. Not coincidentally, blood loss is not much of a concern with a 5 Fr catheter, when compared to a 14 Fr (or larger, e.g., 16 Fr, 20 Fr, 26 Fr, etc.) catheter.

Eq. 5, Eq. 6 and Eq. 7 are derived from the Hagen-Poiseuille Equation (Eq. 1). But Eq. 1 is best applied to steady, laminar flow and limitations arise in fluid flow regimes that have significant fluid acceleration. Rapid acceleration of fluids may occur in embodiments exhibiting a small time constant (range of approximately 10 ms to in excess of 500 ms). Any combination of low viscosity, stiff system (i.e., large value of bulk modulus, K) and/or large bore catheter may cause the system pressure state to be oscillatory, rather than smoothly transitioning between one pressure state and another; the effect is shown in comparing FIG. 12A, FIG. 12B and FIG. 12C.

FIGS. 12A-12C are included, among other reasons, to illustrate the motivation to control, rather than attempt to analyze, phenomena such as oscillations and ringing. Comparing the relative size/duration of expansion 1230 zones of FIG. 12A and FIG. 12B provides motivation for VVA embodiments that actively shift, offset, bias or otherwise change the time constant by altering system variables. More specifically, certain VVA embodiments are enabled to change the time constant by changing the bulk modulus (K) and/or the catheter "flowability" (Γ). In some cases, the time constant is increased to improve data quality as evidenced by comparing FIG. 12A and FIG. 12B. In some cases, the time constant is decreased in order provide clinically-relevant flow conditions such as rapid aspiration or high vacuum levels.

The final AMC iteration of FIG. 12B illustrates phenomena similar $t_0$, and herein characterized by, a Damped Harmonic Oscillator (DHO), often represented as consisting of a mass/spring/damper. Disclosed herein is an alternative formulation of the DHO consisting of a mass (of aspirate within a catheter), a spring (the VVA bulk modulus, K) and a damper (the combined, effective viscosity of the aspirate within the catheter). The differential equations of a DHO require boundary and initial conditions to elicit a solution; certain VVA embodiments alter the initial conditions in order to alter the solution. In this case, altering the solution means to change the initial AMC conditions in order that the resulting aspirate flow is correspondingly changed. An example of this is selecting low-vacuum level AMC mode (e.g., 20 inHg, 15 inHg, etc., instead of the system vacuum level); this AMC mode is not as likely to ring or oscillate because the aspirate does not achieve sufficient velocity to overshoot or "overpressure." This enables certain VVA embodiments to control fluid oscillations by reducing the initial pressure of an AMC. Certain VVA embodiments are enabled to reduce or eliminate certain fluid oscillations by selecting AMC modes that prescribe initial vacuum levels that are below (e.g., 25 inHg, 20 inHg, 13 inHg, etc.) the available system vacuum level. The method of selecting AMC modes that operate at reduced vacuum levels represents an example case of VVA system control over phenomena including: underdamping, ringing, pressure spikes, overpressures, etc. Lower-vacuum level AMC modes are typically utilized in clinical situations wherein thrombus is being sought rather than engaged and aspirated. Among the advantages of this are minimized blood loss and improved data quality.

FIGS. 13A-13F diagrammatically depict not-to-scale, generalized or conceptual models of mass-spring-damper systems; these models are, in certain aspects, analogous to certain VVA systems, components and/or embodiments disclosed herein. These models facilitate the derivation and solution of equations of motion using a pressure formulation, as opposed to a spatial or position formulation, as may be found in many textbooks. FIGS. 13A and 13C may be considered diagrammatically analogous to a spring-loaded syringe, a stopcock and a catheter; as such it may be considered prior art. However, the disclosed coordinate systems ($\chi$-coordinate 1335, s-coordinate 158 and x-coordinate 1330 are novel additions to existing art; these improvements enable certain VVA calculations such as position, velocity, acceleration, etc. of fluids including thrombotic masses.

FIG. 13A depicts a conceptual model of a VVA apparatus with (massless, frictionless) piston 1310 sliding in non-isovolumetric housing 1305 and spring 1315. Spring 1315 is substantially in static equilibrium at the free length at $\chi$-coordinate 1335 $\chi$=0. Valve 1320 is in the open state. Aspirate flow through catheter 140 is enabled; pressure equilibrates between catheter 140 and the interior of non-isovolumetric housing 1305, i.e. the pressure at s=0 is substantially equal to the pressure within non-isovolumetric housing 1305. The position of piston 1310 is referenced by $\chi$-coordinate 1335 and is positive to the right. Static pressure of atmosphere, typically acting upon (the left hand face of) piston 1310 (or analogue, e.g., bulb 405, elastic tubing 230, etc.) is considered constant and overlooked in FIGS. 13A and 13C. In FIG. 13A, the spring 1315 is easily identified, however the mass (of interest) is the mass of fluid within catheter 140, and the damper is the viscosity of that fluid.

FIGS. 13A and 13C illustrate that (1) movement of piston 1310 changes the volume contained within the model, (2) spring 1315 illustrates a means to store energy, and (3) valve 1320 illustrates a means to constrain the stored energy. Further illustrated is that motion of piston 1310 is "dynamically coupled" to motion of $i^{th}$ bolus 1350 by an "incompressible" fluid column of aspirate. Motion of piston 1310 changes the volume contained within the model, and exchanges energy with spring 1315. Typically, energy is being stored as piston 1310 moves rightward and released as piston 1310 moves leftward. Motion of piston 1310 imparts motion to $i^{th}$ bolus 1350; during this motion, each $i^{th}$ bolus 1350 experiences at least two forces: pressure and damping forces. By convention used herein, s-coordinate 158 is shown to be approximately s=0 at the distal end of catheter 140; x-coordinate 1330 is shown referencing an interface of $i^{th}$ bolus 1350. In this context, i is typically a non-negative integer that "identifies" any representative $i^{th}$ bolus 1350 of aspirate within catheter 140. N is the typically the total number of boluses in catheter 140.

FIG. 13B depicts representative $i^{th}$ bolus 1350 as a differential fluid volume element of diameter D and differential length, $dx_i$. Two forces act upon $i^{th}$ bolus 1350: pressure force, $F_p$ 1355 (acting in the positive x and s directions), and viscous or damping force $F_d$ 1365 (acting in the negative x and s directions). Damping force $F_d$ 1365 is in the opposite direction to pressure force $F_p$ 1355 and is proportional to the: diameter (D), viscosity ($\mu_i$), length ($dx_i$) and velocity (*) of $i^{th}$ bolus 1350. The velocity of any $i^{th}$ bolus 1350, at any position x (along s-coordinate 1330 or s-coordinate 158) is the time derivative of x, represented herein as dx/dt or $\dot{x}$. At times when $i^{th}$ bolus 1350 is substantially stationary (i.e., $\dot{x}$=0), the magnitude of damping force 1365 is typically also substantially zero, because there is substantially no viscous frictional loss. Under many conditions, a pressure force 1355 applied to $i^{th}$ bolus 1350 typically causes an acceleration (i.e., $\ddot{x}\neq0$).

FIG. 13C depicts the conceptual model of FIG. 13A wherein piston 1310 is shown translated in the ($\chi$-coordinate 1335 direction) to $\chi_0$, compressing spring 1315. Valve 1320 is in the closed state, preventing flow of aspirate through catheter 140. A pressure discontinuity exists across valve 1320, wherein the pressure within non-isovolumetric housing 1305 is substantially less than the reference pressure present at the distal end of catheter 140. From the static equilibrium configuration of FIG. 13C, opening valve 1320 will release the energy stored in spring 1315. This results in low pressure (vacuum) being applied to the proximal end of catheter 140 and consequent flow of aspirate. Acting under spring 1315 force, piston 1310 accelerates (to the left, in the negative $\chi$-coordinate 1335 direction. Concurrently, the aspirate in catheter 140 accelerates in the positive x coordinate 1330 and s coordinate 158 directions.

From the machine state depiction of FIG. 13C, valve 1320 may be changed to the open state, releasing the energy stored in spring 1315. Piston 1310 may or may not "overshoot" $\chi=0$ and attain negative values of x as equilibrium is tended toward. Underdamped systems may exhibit this "overshoot" as ringing 1201, oscillations or pressure peaks or spikes. There may be a threshold value of $\chi_0$ below which underdamped systems do not exhibit oscillations or ringing; this may be because insufficient stored energy available in the system's initial conditions. As with many mechanical systems, the characteristic of spring 1315 is highly deterministic of the system response; spring 1315 could be long or short, stiff or soft. Springs are typically characterized by a spring constant; the VVA analogue of the spring constant is the bulk modulus (K). Thus, in FIG. 13, if spring 1315 is "stiff" (i.e., exhibits a large spring constant) then the analogous VVA system is "stiff" (i.e., exhibits a large bulk modulus, K).

FIGS. 13A and 13C depict a conceptual analogue of certain VVA embodiments to illustrate that: (1) linear translation of piston 1310 changes the volume of the system in a calculable manner ($\Delta V \approx Area_{piston} \times \Delta\chi$), (2) potential energy may be stored in a deformed mechanical component (e.g. spring 1315, bulb 405, elastic tubing 230, etc.), and (3) the position of piston 1310, along the $\chi$-coordinate 1335, is dynamically coupled to the position of $i^{th}$ bolus 1350, along the x-coordinate 1330.

FIGS. 13D-13F depict a textbook example diagram of a Damped Harmonic Oscillator (DHO) model comprising a mass, spring and damper; these figures are identified as prior art. Eq. 12 is a standard equation of motion for a damped harmonic oscillator (DHO).

$$m\ddot{x} + b\dot{x} + kx = 0 \qquad \text{Eq. 12}$$

Where m is the mass, b is a damping coefficient, k is a spring constant, x is position, $\dot{x}$ and $\ddot{x}$ are velocity and acceleration (of the mass). Eq. 12 may be applied to the mass/spring/damper illustrations of FIGS. 13D-13F. Referring to FIG. 13A and FIG. 13B, some VVA embodiments directly measure the position of piston 1310 in the $\chi$-coordinate direction, or analogue, such as measuring the diameter of bulb 405, etc. However, typical VVA embodiments infer the position of piston 1310 (or analogue) by measuring pressure.

Certain embodiments, such as VVA system 201, 401, etc., feature a control algorithm wherein the apparatus is modeled as a DHO. Novel equations of motion are derived herein in a pressure formulation; these equations are utilized to calculate certain derived variables, e.g., viscosity, flow rate, etc. However, certain VVA embodiments utilize a mathematical formulation wherein pressure (P) is the independent variable; this is in contrast to a DHO wherein position (x) is the independent variable. The linear equations of motion of a DHO are "re-cast" from position-based formulation to pressure-based formulations.

In the linear coordinate system formulation of FIGS. 13D-13F, mass 1340 (e.g., the summation of the masses of each N boluses, or alternatively, the mass of a single $i^{th}$ bolus 1350) is connected to piston 1310 which slides in damper body 1325. In FIG. 13D, the spring is shown in the free-length or equilibrium configuration at x=0 in the x-coordinate 1330 direction. FIG. 13E depicts the mass/spring/damper model depicted in FIG. 13D wherein the spring is compressed by some distance $x_0$. Mass 1340 is secured in place by hook 1345, which acts analogously to valve 1320 to "isolate" or constrain the system in a stored-energy static equilibrium state. Upon releasing hook 1345, mass 1340, 1350 accelerates (in the negative x-coordinate 1330 direction) and is resisted by piston 1310 sliding through damper body 1325. The system may be underdamped (and overshoot, and/or exhibit ringing 1201), critically damped or underdamped depending upon the values of the mass 1340, the spring 1315 constant and the damping coefficient.

In the static equilibrium state depicted in FIG. 13C, the pressure state within non-isovolumetric housing 1305 is substantially less than the pressure within catheter 140. Energy stored in compressed spring 1315 acts to reduce the pressure to within housing 1305; a pressure discontinuity exists across valve 1320. Opening valve 1320 releases the stored energy and exposes a proximal end of catheter 140 to a reduced pressure state; this typically initiates flow; in other words the mass (e.g., mass 1340, $i^{th}$ bolus 1350, etc.) accelerates.

Eq. 13 is derived and herein disclosed as an analogous pressure formulation of Eq. 12 wherein the independent variable is pressure (P), not position (x). A significant benefit of Eq. 13 is that calculations are performed directly upon pressure (the measured system variable). Eq. 13 is a coordinate transformation of Eq. 12, from distance-time coordinate space to pressure-time coordinate space. The elegance of calculating certain VVA parameters in pressure-time coordinate space manifests in benefits including, but not limited to: (1) straightforward normalization methods, (2) minimizing computational requirements (number of computations), (3) minimizing latency (interval between pressure measurement and computation of any derived variables), (4) minimizing roundoff and truncation errors (performing fewer computations and that may lead to error propagation).

$$P'' + \alpha\left(\frac{\mu}{\Gamma}\right)P' + \beta KP = 0 \qquad \text{Eq. 13}$$

Where P is pressure, P' and P" are the first and second time derivatives of pressure, u is the viscosity of the aspirate, Γ is the catheter flowability, and K is substantially equivalent to the VVA bulk modulus, K. α and β are dimensioned proportionality constants, however there is no need to solve for these. In Eq. 13, the quantity ($\alpha\mu/\Gamma$) is substituted for the damping coefficient (b) of Eq. 12; this clearly indicates that the ratio of the aspirate viscosity divided by the catheter flowability, along with the VVA bulk modulus (K), are strongly deterministic of the system response. Certain VVA embodiments exert control over otherwise-fixed system parameters (e.g., K, Γ, P, etc.) such that they become system variables under VVA system control.

Eq. 13 is derived and disclosed herein as a generalized governing equation of fluid flow through a conduit, wherein a catheter is a specific case thereof. This formulation is appropriate for application to aspiration thrombectomy systems because thrombus-laden aspirate flow is typically an ongoing sequence of pressure-driven fluid accelerations and decelerations. Eq. 13 is remarkable because it identifies the four VVA parameters and/or variables (P, Γ, K and μ) that dictate the ensuing fluid motions following a disturbance from a static equilibrium state. In prior art, 3 out of 4 of these (P, Γ, and K) are typically fixed system parameters; this leaves only the aspirate viscosity (μ), which is a clinical variable. Because the viscosity of an entering bolus of aspirate is substantially unknown, certain VVA embodiments determine if the system response is underdamped or overdamped. As an example, if a system is underdamped (ringing), a VVA system response may be to decrease the vacuum level of a subsequent AMC mode, thereby storing less energy. Conversely, if the system is significantly overdamped, a VVA system response may be to increase the vacuum level of an AMC mode, thereby storing more energy. VVA system embodiments that vary the system response by means other than initial pressure are disclosed subsequently.

A general solution to Eq. 13 is given in Eq. 14.

$$P(t) = P_0 e^{rt};\ r = \frac{-c \pm \sqrt{c^2 - 4K}}{2};\ r = \frac{-c \pm \sqrt{\Delta}}{2} c = \alpha\left(\frac{\mu}{\Gamma}\right) \quad \text{Eq. 14}$$

where a "damping coefficient"

$$c = \alpha\left(\frac{\mu}{\Gamma}\right)$$

is introduced for compactness, r may be real (overdamped), zero (critically damped) or complex (underdamped); Δ is shorthand notation for the discriminant ($c^2-4K$), which may be positive, zero or negative. Cases where r is a real number are shown herein to be successfully modeled and analyzed by employing Eq. 6 (resulting in exponential vacuum decay). Eq. 14 (derived from the mass/spring/damper equations of motion) and Eq. 6 (derived from the Hagen-Poiseuille Eq. 1) may be made equivalent by the substitution of ($r=-1/\tau$) in cases where r is a real number. In other words, in sufficiently damped systems, solutions to Eq. 6 (Hagan-Poiseuille) are identical to solutions to Eq. 14 (Damped Harmonic Oscillator).

A solution to Eq. 14 for the underdamped case, ($c^2-4K$) <0, is given in Eq. 15; overpressures and "ringing" typically arise in underdamped systems. $A_1$ and $A_2$ are constants that are determined by the initial conditions (initial pressure and initial rate of change of pressure), although calculation of these constants is typically unnecessary.

$$P(t) = e^{-ct/2}(A_1\cos(\beta t) + A_2\sin(\beta t));\ y = \frac{\sqrt{4K - c^2}}{2} \quad \text{Eq. 15}$$

γ is introduced in Eq. 15 for compactness; γ has physical significance as the natural frequency of the damped system. Underdamping occurs in cases where the discriminant of γ ($\Delta=c^2-4K$) is negative; or, when $c^2<4K$. Physically, this means that if the value of the damping coefficient squared, $(\alpha\mu/\Gamma)^2$, is less than some value (typically approximately 4 times the bulk modulus), then the system is expected to undergo oscillations to some degree; but this is also dependent upon the initial conditions. There is typically no reason to calculate the values of system variables/parameters such as Γ, K, α, β, c, etc., Eq. 13 and Eq. 14 "tell us what to do" if the VVA response is outside the desired range. For instance, if the flow rate is too high, this means that any of the following may be true: the viscosity is "too low," and/or the catheter flowability is "too great" and/or the bulk modulus is "too great," and/or the initial differential pressure is "too great." In cases such as these, certain VVA embodiments are enabled to "decrease the catheter flowability" and/or "decrease the bulk modulus, K," and/or "change initial conditions, decrease $P_0$," etc.

Eq. 15 unambiguously identifies two variables that typically affect a VVA system response: the VVA bulk modulus (K) and the damping coefficient (αμ/Γ). The damping coefficient is dependent upon the catheter flowability (Γ) and the viscosity (μ) of the aspirate (α being a generally unknown, arbitrary constant). Note that an objective of an aspiration thrombectomy procedure is to aspirate a maximum quantity of more-viscous thrombus concurrently with a minimum quantity of blood. Certain VVA embodiments are enabled to change certain system variables, e.g., vacuum level, volume of aspirate, flow rate, VVA bulk modulus, catheter flowability, etc. In many cases, this is done to better measure, and adapt to, the clinical variable: the viscosity of the fluid entering a catheter.

Previously herein, both the catheter flowability (Γ) and the VVA bulk modulus (K) were typically considered constant in many VVA embodiments. However, to further control flow of aspirate, certain VVA embodiments are enabled to transform certain fixed process parameters into control variables. Examples include VVA embodiments that feature either variable-K and/or variable Γ capabilities. The motivation for these VVA embodiments is to adjust or control the time constant such that the flow rate of aspirate is optimized for factors such as: blood loss (e.g., select greater values of time constant), maximum aspiration vacuum levels (e.g., select lesser values of time constant), etc.

Figures 14A, 14B, 14C, 14D, 14E:
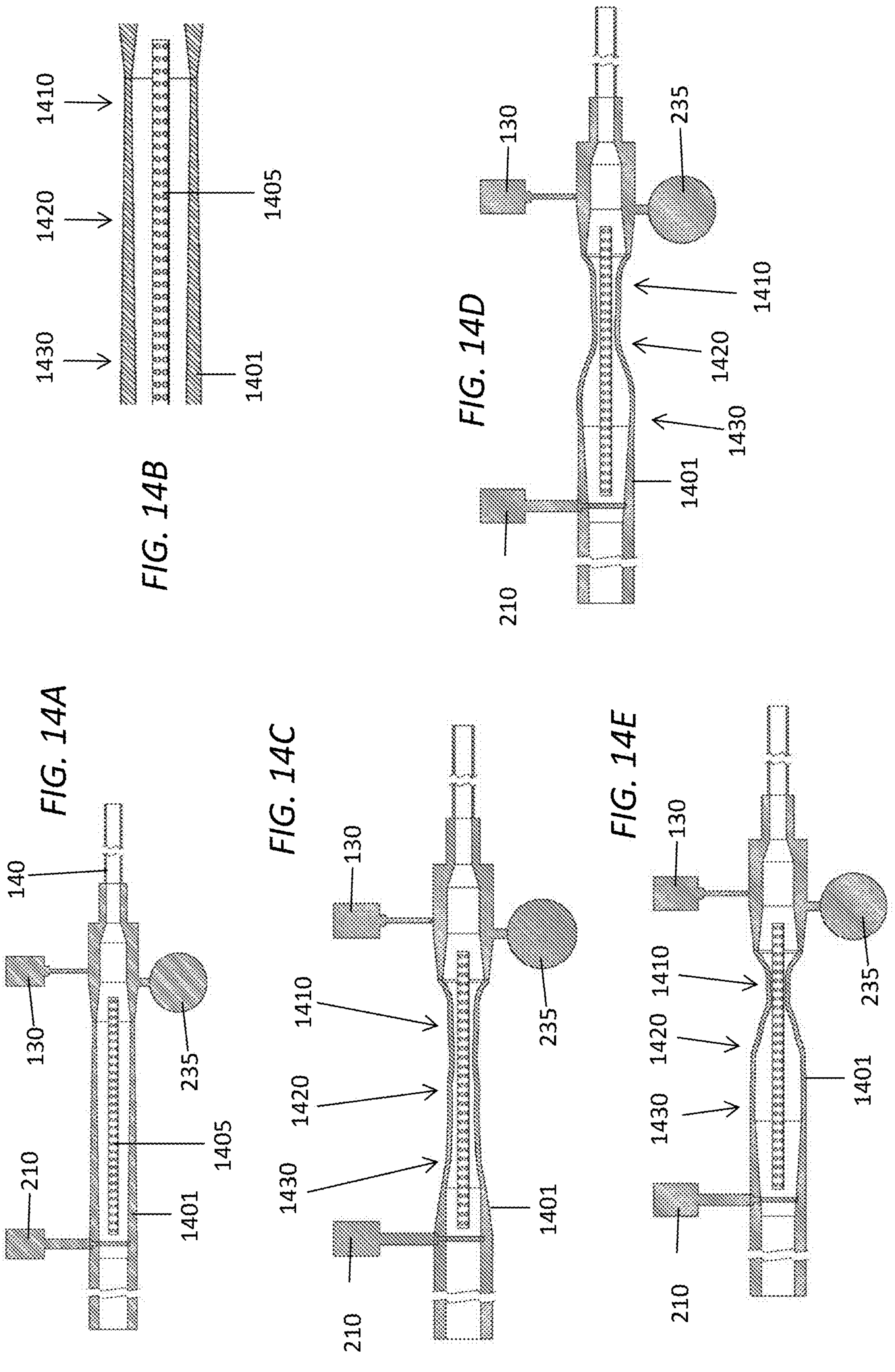
FIG. 14A depicts a VVA system component in accordance with an illustrative embodiment of the present invention, wherein a variable-K tube is installed in the VVA system of FIG. 4A.
FIG. 14B is a section view of variable-K tube of FIG. 14A, illustrating tapered wall thickness.
FIG. 14C depicts variable-K tube of FIG. 14A, wherein variable K-tube is collapsed in all 3 regions.
FIG. 14D depicts variable-K tube of FIG. 14A, wherein variable-K tube is collapsed in 2 of 3 regions.
FIG. 14E depicts variable-K tube of FIG. 14A, wherein variable-K tube is collapsed in 1 of 3 regions.

FIG. 14A depicts variable-K tube 1401, a non-isovolumetric component common to certain VVA embodiments, wherein the value of bulk modulus, K, varies across a pressure range. The value of K at each pressure level may be experimentally determined by differentiating volume vs pressure data to find dV/dP. In certain VVA system embodiments, a lookup table such as variable K dataset may be created, such as presented in FIG. 7C. In certain VVA embodiments, experimental measurements of K vs pressure may be mathematically modelled (e.g., K=1.5+P/7, etc.). In certain VVA system embodiments (e.g., VVA system 401, etc.), variable-K tube 1401 replaces certain non-isovolumetric components (e.g., bulb 405, etc.); thereby the apparatus is operable across a significant range of bulk modulus, K. At certain times, variable-K tube 1401 may be isolated by changing the machine state to one wherein each of vacuum valve 130 and isolation valve 230 is in the closed state. Significant potential energy may be stored in this apparatus state.

FIG. 14B depicts an enlarged view of variable-K tube 1401 illustrating a tapered wall thickness. Low-K region 1410, to the right of FIG. 14B, is depicted as having a comparatively thin wall thickness; therefore this region collapses "first." Mid-K region 1420 is depicted as having a substantially "nominal" wall section thickness, therefore this region collapses "next." High-K region 1430 is depicted as having a comparatively "thick" wall section thickness; therefore, this region collapses "last." Anti-collapser 1405 is present to prevent regions such as low-K region 1410 from collapsing and occluding flow; alternative structures include meshes, cages, internal nubs, flutes, ribs or other protrusions on interior surfaces of variable-K tube 1401.

FIG. 14C depicts variable-K tube 1401 in a first pressure state wherein each of low-K region 1410, mid-K region 1420, high-K region 1430 is in a collapsed configuration. FIG. 14D depicts variable-K tube 1401 in a second pressure state wherein each of low-K region 1410, mid-K region 1420 is in a collapsed configuration, and high-K region 1430 is expanded to a greater volumetric state. FIG. 14E depicts variable-K tube 1401 in a third pressure state wherein each of high-K region 1430, mid-K region 1420 is in an expanded configuration, and low-K region 1410 is in a collapsed configuration. FIG. 14A depicts variable-K tube 1401 in a static equilibrium pressure state wherein each of low-K region 1410, mid-K region 1420, high-K region 1430 is in an expanded configuration. The pressure state within variable-K tube 1410 is substantially equal to the reference pressure (e.g., intravascular, atmospheric, etc.) present at the distal end of catheter 140.

FIGS. 14A-14E illustrate that certain variable-K non-isovolumetric components, e.g., variable-K tube 1401, may be constructed of substantially any elastic reservoir that may comprise features such as: irregular geometries, variable wall thickness, etc. In certain cases, variable-K tube 1401 comprises a section of tubing (e.g., silicone, latex, polyurethane, PVC, etc.) with conical bore and/or exterior. Variable K tube 1401 is shown with generally conical surfaces; other embodiments including stepped, ribbed, striated, fluted, etc. geometric shapes and surfaces are anticipated.

FIGS. 14A-14D also illustrate that the displaced volume (not identified in FIGS. 14A-14E) of variable-K tube 1401 may be significantly larger than other VVA embodiments, ranging up to 100 cc or greater. For example, a 30 cc variable-K tube 1401 may have a "first" 10 cc of displaced volume that exhibits a value of K that is approximately 20% of maximum. The "second" 10 cc of displaced volume may exhibit a value of K that is approximately 60% of maximum. And the "last" 10 cc of displaced volume may exhibit a value of K that is approximately 100% of maximum. The benefits of variable-K VVA embodiments include an ability to actively control the time constant in response to clinical variables. In certain variable-K tube 1401 embodiments, changing the pressure state of variable-K tube 1401 causes a change in the VVA system response, e.g., time constant, flow rate, etc.

Theoretical basis: From Eq. 15, if the value of ($c^2-4K$) is less than zero, the system will typically be underdamped. In this case, the bulk modulus (K) is "too large" for the available damping. The damping coefficient (c) is typically dependent upon factors including: the viscosity of the aspirate ($\mu$), catheter flowability ($\Gamma$). Certain VVA control algorithms may select high-K AMC modes to decrease the time constant; this may provide increased vacuum levels for efficacious thrombus aspiration. Certain VVA control algorithms may select AMC modes that operate in low-K modes to increase the time constant; this may result in the cessation of oscillations and ringing. Certain VVA control algorithms may, at times during a procedure, select from low-K AMC modes, for instance for purposes such as: low-flow-rate data acquisition and minimal blood loss etc.; at other times during the procedure, the VVA control algorithm may select from high-K AMC modes, for instance for purposes such as: greater vacuum levels and flow rates, etc.

Figure 15A:
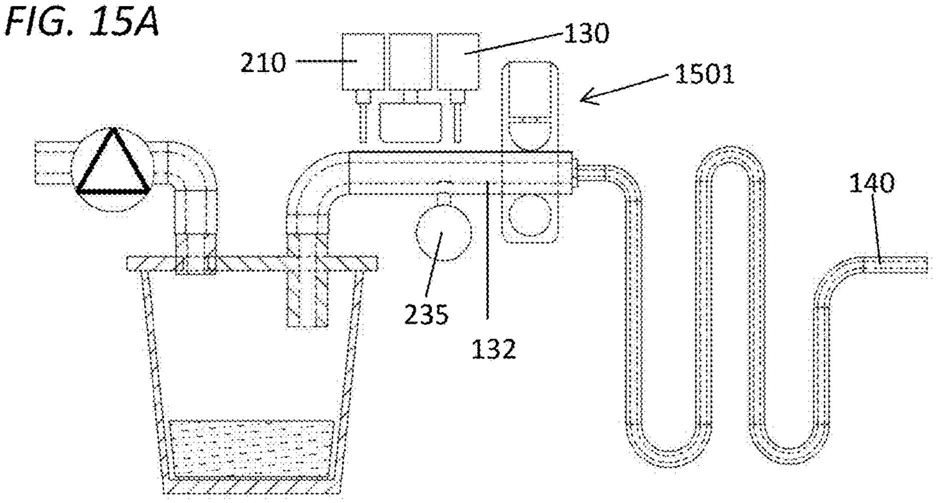
FIG. 15A depicts the VVA system of FIG. 2A, that additionally comprises a damping mechanism.

FIG. 15A depicts VVA system 201 of FIG. 2A that additionally comprises a subassembly, damping mechanism 1501, in accordance with an illustrative embodiment of the present invention. Damping mechanism 1501 acts to, at certain times and machine states, restrict fluid flow through catheter 140, thereby reducing the flow rate and increasing the time constant. FIG. 15A depicts damping mechanism 1501 in a first machine state having substantially no effect upon the flow rate through catheter 140.

Figure 15B:
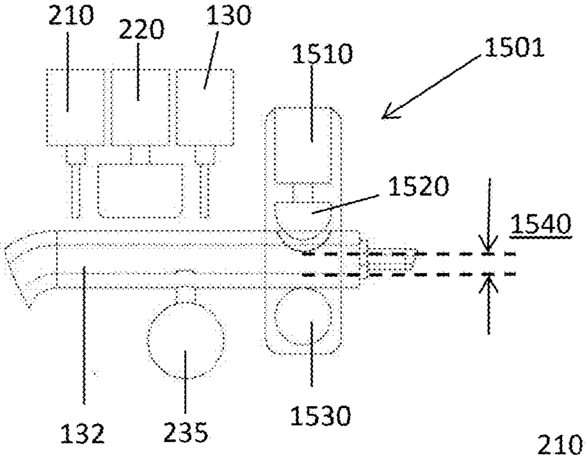
FIG. 15B depicts the damping mechanism of FIG. 15A in a first restrictive state.

FIG. 15B depicts damping mechanism 1501 of FIG. 15A in a second machine state, wherein flow through catheter 140 is partially restricted. VVA system 201 system components including elastic tubing 132, isolation valve 210, displacement mechanism 220, and pressure gage 235 are identified. Damping actuator 1510 is depicted in a second actuator state wherein damping jaw 1520 is displaced downward toward damping anvil 1530. Damping clearance 1540 is depicted; in certain VVA embodiments, damping clearance 1540 is a system variable under VVA system control.

Figure 15C:
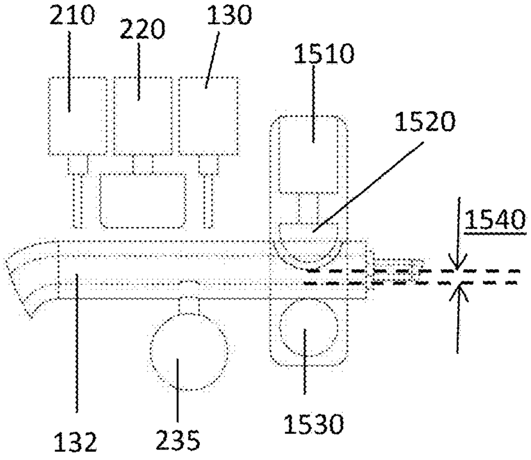
FIG. 15C depicts the damping mechanism of FIG. 15A in a second restrictive state.
Figure 15D:
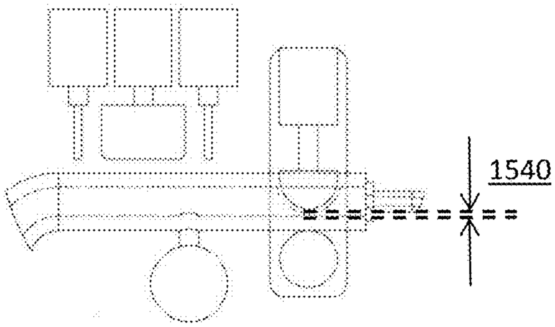
FIG. 15D depicts the damping mechanism of FIG. 15A in a third restrictive state.

FIGS. 15C-15D depict damping mechanism 1501 of FIG. 13A in $3^{rd}$ and $4^{th}$ actuator states of damping actuator 1510. Damping clearance 1540 is depicted to assume 4 values in the 4 actuator states of damping actuator 1510 in FIGS. 15A-15C. Damping is increased by "closing down" or "squeezing down" a portion of connecting tube 132, thereby creating a flow restriction. This flow restriction effectively increases the damping coefficient (c) and consequently, the time constant.

Damping mechanism 1501 is significant because it enables certain VVA embodiments to reduce the flow rate at certain times during a procedure, such as while seeking thrombus and/or controlling blood loss. Upon detection of thrombus within catheter 140, certain VVA embodiments change damping actuator 1510 to the $1^{st}$ actuator state to allow unrestricted flow though catheter 140. Thereby, certain VVA embodiments limit blood loss at times wherein the apparatus is in a second machine state (FIG. 15B); at other times, the apparatus may be reconfigured to a first machine state (FIG. 15A) that does not limit aspirate flow rate. In certain VVA embodiments, a measured value of time constant ($\tau$) is compared against a threshold value to make the machine state determination. Damping mechanism 1501 is typically utilized during periods of an aspiration thrombectomy procedure wherein the contents of catheter 140 are substantially pure blood; this may be done to limit blood loss, and/or improve data quality while seeking thrombus.

Figure 15E:
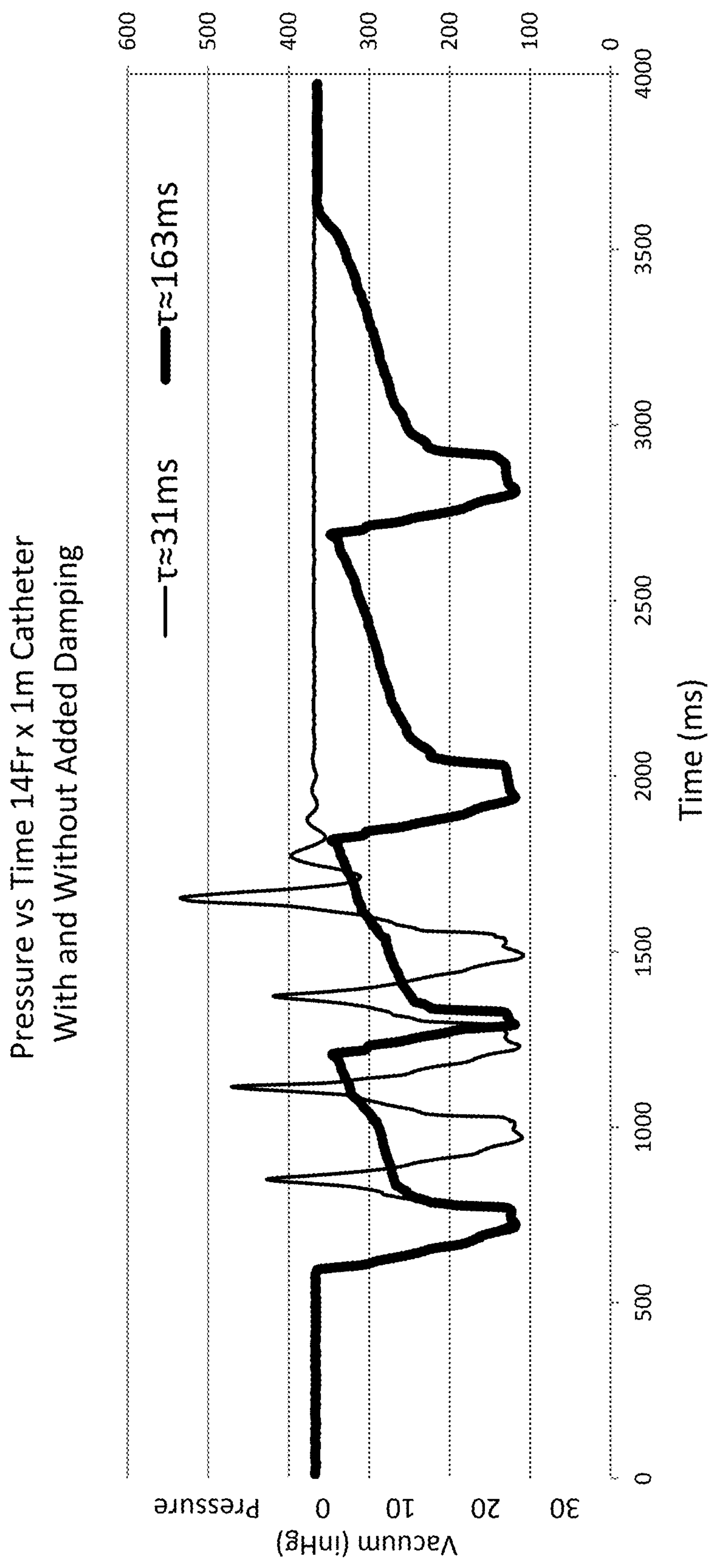
FIG. 15E graphically depicts experimental data wherein changing the state of damping mechanism changes the time constant.

FIG. 15E graphically depicts 2 experimental VVA pressure waveform data sets that are overlaid, or superposed, upon one another. All data are collected upon the experimental apparatus of FIG. 12B; however the two distinct pressure waveforms result from two different actuator states of damping actuator 1510. The underdamped, oscillatory pressure waveform ($\tau \approx 31$ ms) is effectively changed to the damped pressure waveform ($\tau \approx 163$ ms) by changing the machine state of the apparatus. In certain variable-damping VVA embodiments, changing the machine state of damping mechanism 1501 and/or damping actuator 1510 causes a change in the VVA system response, e.g., damping, flow rate, etc.

The visible difference in pressure waveforms in FIG. 15E also illustrates a significant change in time constant. The time constant is seen to increase from approximately 31 ms to approximately 163 ms caused by additional damping. In the undamped case ($t \approx 31$ ms), ringing and oscillations (though abated by early AMCs) are indicative of high-velocity aspirate flow, and a valid clinical inference is that the aspirate is predominantly blood. In the undamped case of FIG. 15E, ($\tau \approx 31$ ms), approximately 4 cc of blood is aspirated in approximately 1 second. In the damped case ($\tau \approx 163$ ms), wherein damping mechanism 1501 is changed to the $4^{th}$ state (FIG. 15D), that same 4 cc of blood is aspirated in approximately 3 second. In certain embodiments, a VVA system control algorithm analyzes each AMC for underdamping, as may be characterized by pressure spikes and ringing, by measuring the time constant. Certain VVA embodiments thereby control certain system variables including time constant ($\tau$) and/or flow rate (Q) by means of flow restriction. In certain VVA embodiments, such as those comprising damping mechanism 1501, certain system variables (e.g., flow rate, time constant, etc.) are system variables that are changed by VVA system controller 2401.

The previous example utilized a 14 Fr×1 m long catheter, having a specific catheter flowability ($\Gamma=\pi R^4/8L$), in water at 1 cP. Because certain VVA embodiments utilize aspects of similarity, it is straightforward to calculate that the pressure waveform data are similar to that of blood (at 4 cP) in a catheter with a diameter of approximately 19.8 Fr, or a 20 Fr catheter. Conducting experiments upon a 14 Fr catheter in water thereby simulates flow of blood through a 20 Fr catheter. Thus, FIG. 15E is simultaneously representative of water in a 14 Fr catheter, blood in a 20 Fr catheter and also SAE 10 motor oil in a 25 Fr catheter; these flows are considered similar by certain VVA embodiments, in accordance with the teachings disclosed herein. The data presented in FIG. 12A included 5 Fr, 10 Fr and 14 Fr catheters. By similar calculations, flow of water through a 5 Fr catheter is similar to flow of blood through a 7 Fr catheter, and flow of water through a 10 Fr catheter is similar to flow of blood through a 14 Fr catheter. The benefits of designing certain VVA embodiments that utilize similarity and scalability are evident in the value of experimental data collected thereupon. These data may be collected upon household or laboratory liquids and combinations thereof, to simulate clinical scenarios and with unparalleled accuracy and informative data collection.

Eq. 13, a generalized equation of fluid motion in pressure coordinates, identifies 3 variables that affect pressure and flow rate: aspirate viscosity ($\mu$), catheter flowability ($\Gamma$), and bulk modulus (K). Of these 3 variables, aspirate viscosity is an uncontrolled clinical variable that is expected to range from approximately 4 cP to perhaps in excess of 10,000 cP. The remaining two variables, catheter flowability ($\Gamma$) and bulk modulus (K) are VVA system variables in certain VVA embodiments. Catheter flowability ($\Gamma$) is changed in certain VVA embodiments by damping mechanism 1501. Bulk modulus (K) is changed in certain VVA embodiments by variable-K tube 1401.

Figures 16A, 16B, 16C, 16D, 16E:
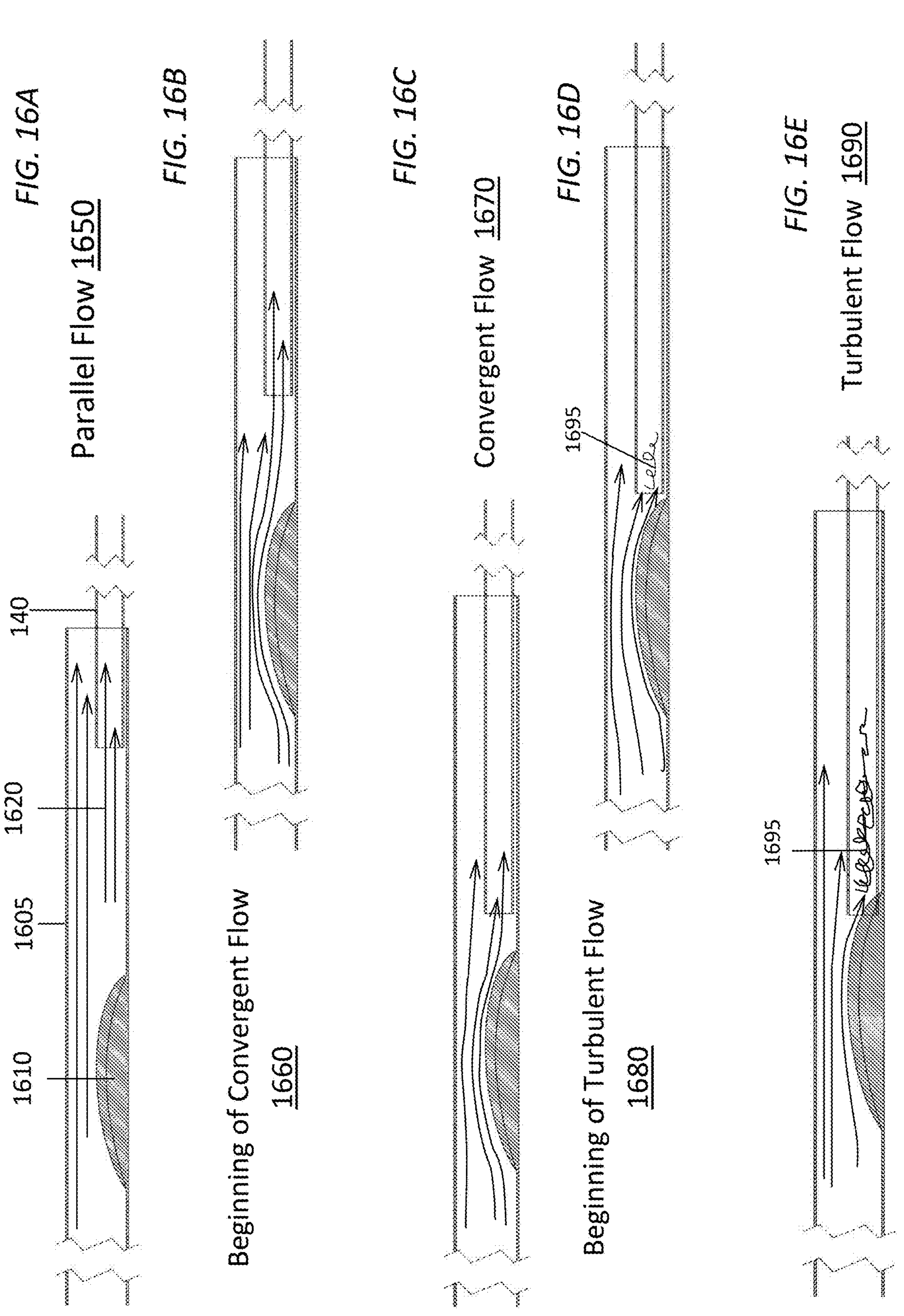
FIG. 16A depicts a representative catheter, vessel wall and thrombus wherein blood is in depicted in a parallel flow regime.
FIG. 16B depicts the beginning of a convergent flow regime.
FIG. 16C depicts a convergent flow regime.
FIG. 16D depicts a transition to a turbulent flow regime.
FIG. 16E depicts a turbulent flow regime.

FIG. 16A depicts vessel wall 1605, thrombus 1610 and catheter 140, wherein the tip of catheter 140 is located some distance from thrombus 1610. Thrombus 1610 is said to be in the "far-field" of the tip of catheter 140. In this context, far-field means that thrombus 1610 is "too far" away to affect (i.e., impart curvature to) streamlines 1620 entering catheter 140. FIG. 16A illustrates a flow regime known as parallel flow 1650, which typically maximizes flow rate and minimizes viscous losses. The measured viscosity of the aspirate is not significantly affected by thrombus 1610 in the configuration of FIG. 16A.

FIG. 16B depicts beginning of convergent flow 1660 wherein catheter 140 is in closer proximity (than FIG. 16A) to thrombus 1610. The flow regime is transitioning from a parallel flow regime to a convergent flow regime. Streamlines are beginning to take on a curved shape; this may be accompanied by viscous losses and a decrease in the total or stagnation pressure. The inlet pressure near the tip of catheter 140 is slightly lower than in FIG. 16A; this decrease in inlet pressure may be detectable as a decrease in flow rate. Because the inlet pressure is decreased, so too is the differential pressure across catheter 140; therefore the flow rate may be measurably diminished as the tip of catheter 140 approaches thrombus 1610.

FIG. 16C depicts catheter 140 in closer proximity to thrombus 1610, resulting in a convergent flow 1670 regime. The stagnation and total pressures may be further reduced at the tip of catheter 140. FIG. 16D depicts catheter 140 advanced closer to thrombus 1610, resulting in a beginning of turbulent flow 1680 regime; turbulence 1695 is depicted in FIGS. 16D and 16E. The stagnation and total pressures are further reduced at the tip of catheter 140. At the proximity depicted in FIGS. 16D and 16E, thrombotic material may "slough off" of thrombus 1610; this will tend to further reduce the flow rate. FIG. 16E depicts tip of catheter 140 in close proximity to thrombus 1610 such that a turbulent flow 1690 regime develops. While catheter 140 and thrombus 1610 are shown in contact with each other, a "seal" between the two is not shown to be present. Thrombus 1610 partially occludes the tip of catheter 140. This reduces the flow area for blood to enter the tip of catheter 140; flow velocities are increased and viscous losses are incurred. For a given differential pressure, the flow rate is typically significantly diminished in a turbulent flow 1690 regime, such as depicted in FIG. 16E.

The sequence of events depicted in FIGS. 16A-16E illustrates advancing catheter 140 toward thrombus 1610 while continuously or intermittently measuring VVA variables such as viscosity, time constant and/or flow rate. Any gradual, incremental or significant decrease in measured flow rate, occurring concomitantly with repositioning of catheter 140 may allow inference to the distance to thrombus 1610, in particular when that distance is "closing," or becoming smaller. Certain VVA embodiments feature non-contact detection of thrombus and may include approximate distance measurements. Non-contact detection may be enhanced by incorporation into certain embodiments, such as VVA system 1001 (see FIGS. 10A-10D). In such embodiments, components such as sleeve 1010 may be reconfigured to increase/decrease the distance (e.g., extension distance 1015, FIG. 10C) between thrombus 1610 and the effective tip of dilution catheter 1005.

Continuously or intermittently changing the distance between the effective tip of catheter 140 (or dilution catheter 1005) and thrombus 1610 may enhance the non-contact detection and measurement capabilities of certain VVA embodiments. To approximate the position of the catheter tip, certain VVA embodiments feature position sensors and/or accelerometers at or near a proximal end of catheter 140 (or dilution catheter 1005). As an example referencing FIG. 2D, position sensors and/or accelerometers may be integrated within, or placed in proximity to, VVA components such as: distal pressure gage 226, connecting tube 232*b*, or a proximal end of catheter 140 (or dilution catheter 1005), etc. Measuring the position and/or rotation at or near a proximal end of catheter 140 (or dilution catheter 1005) enables certain VVA embodiments to make inferences regarding the position of the distal tip of catheter 140 (or dilution catheter 1005). Correlation of the axial position (of catheter 140 or dilution catheter 1005) to a change in flow rate enables certain VVA embodiments to effectively "measure" the distance between the tip of catheter 140 (or dilution catheter 1005) and thrombus 1610.

Figure 17:
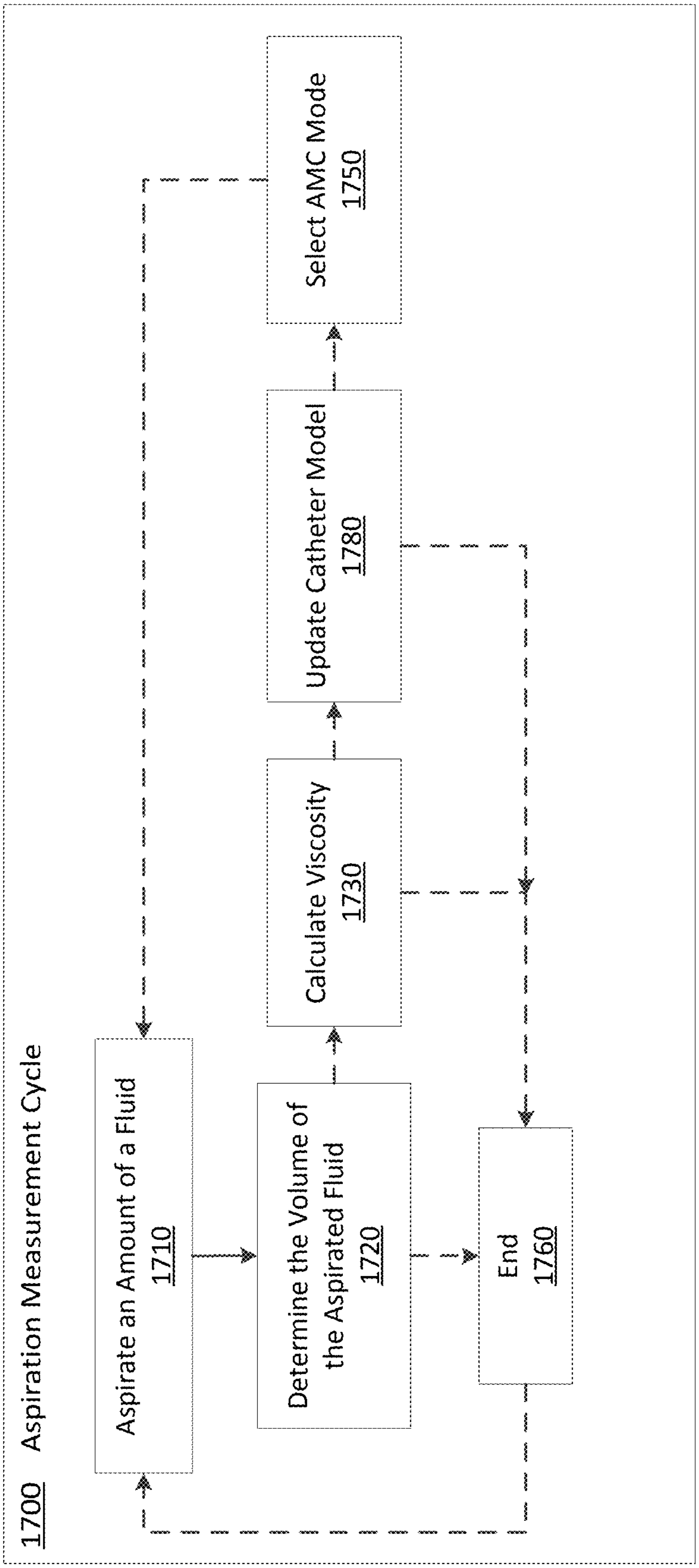
FIG. 17 depicts a block flow diagram of a method for an Aspiration Measurement Cycle.

FIG. 17 depicts a block flow diagram of method 1700 Aspiration Measurement Cycle. In accordance with operation 1710 aspirate an amount of a fluid, a bolus of fluid is aspirated into catheter 140, e.g., by cycling vacuum valve 130, or other changes to the machine state. In accordance with operation 1720 determine the volume of the aspirated fluid, the volume of fluid, aspirated in operation 1710, is determined, e.g., utilizing Eq. 2, FIG. 7C, etc. In certain VVA embodiments, operation 1720 diverts control process End 1760, without further steps.

Operation 1730 calculate viscosity is an optional, albeit desirable, calculation of certain derived variables. In accordance with operation 1730, the time constant ($\tau_{current}$) and/or catheter viscosity ($\mu_{current}$) are calculated by Eq. 5, Eq. 8 or similar derivation. The viscosity of entering bolus 911 ($\hat{\mu}_0$)

may be calculated by Eq. 9 or similar derivation. Method 1700 may terminate after operation 1730 by diverting to operation End 1760 in certain VVA embodiments. Operation 1780 update catheter model is an optional, albeit desirable, step that updates data within catheter model/data array 1901. In certain cases, data collected in operations 1720 and 1730 are written to one or more instances of catheter model/data array 1901. Subsequent to operation 1780, method 1700 may terminate at process End 1760, in certain VVA embodiments. Operation 1750 select AMC mode is an optional, albeit desirable, step of selecting an AMC mode, e.g., initial vacuum level, damping, dilution, etc. Operation 1750 select AMC mode configures the apparatus for the next AMC; subsequent to operation 1750, method 1700 returns control to operation 1710, Aspirate an Amount of Fluid. In VVA embodiments wherein method 1700 terminates at operation 1780 or before, default AMC mode settings (e.g. system vacuum level, no damping, no dilution, etc.) may be utilized in certain VVA embodiments. Method 1700 may terminate at operation End 1760; alternatively, method 1700 may be repeated indefinitely, as shown by the dotted arrow connecting operations 1760 and 1710.

Figure 18A:
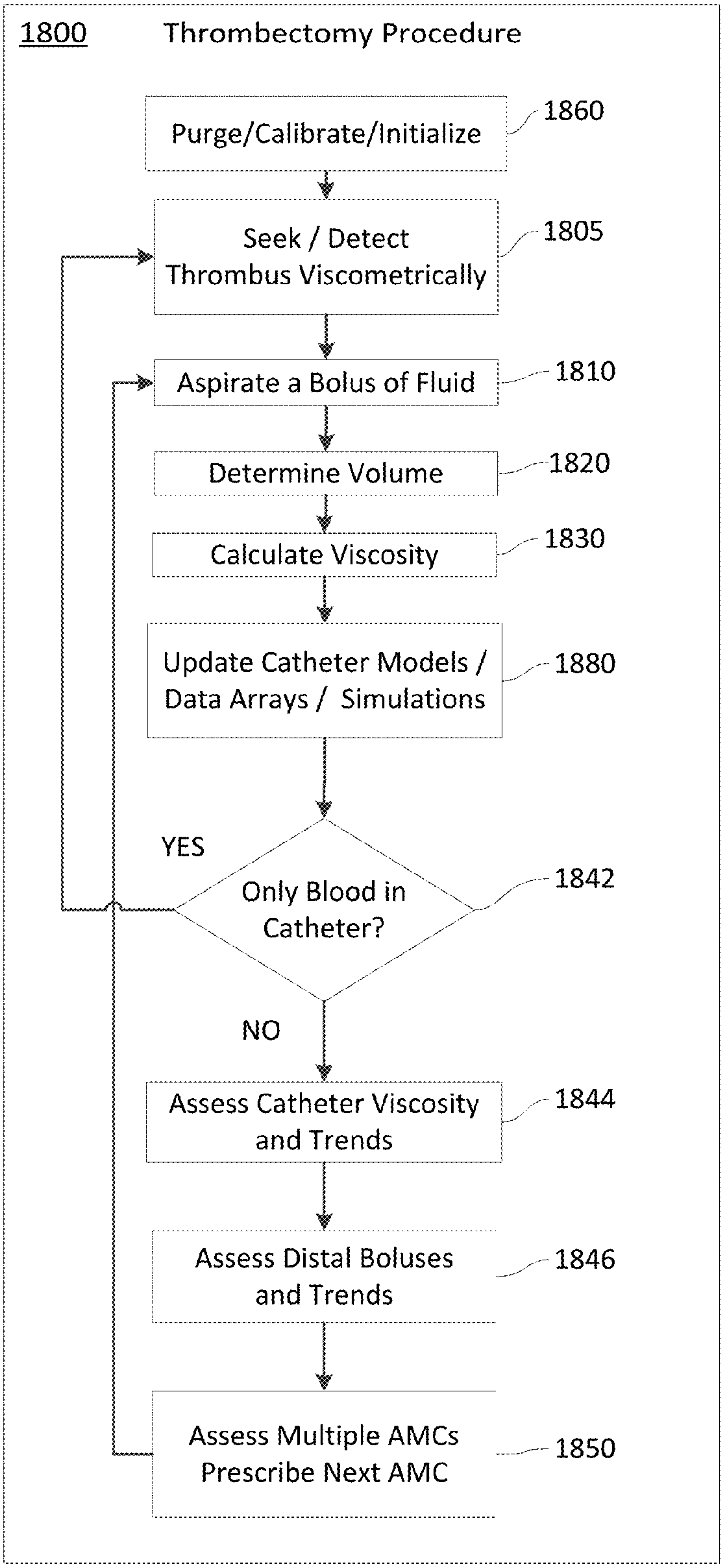
FIG. 18A depicts a block flow diagram of a method to perform a VVA thrombectomy procedure.

FIG. 18A depicts a block flow diagram of method 1800 Thrombectomy Procedure, an example of a VVA control algorithm for conducting an aspiration thrombectomy procedure. Method 1800 thrombectomy procedure "embeds" many operations of method 1700 Aspiration Measurement Cycle, for instance, operation 1830 calculate viscosity is substantially similar to operation 1730 of method 1700. Similarly, operations 1810, 1820, 1880 and 1850 are substantially similar to corresponding operations of method 1700.

Method 1800 thrombectomy procedure additionally includes purge/calibrate/initialize functions (e.g., operation 1860), an example conditional "IF" statement (e.g., operation 1842), and evaluates projections, trends and/or simulations (e.g., operation 1850). Conditional statements are utilized in certain VVA control algorithms to divert control, for instance in response to clinical variables and/or conditions including those requiring: limited computational resources, immediate action, clinician input, etc.

Figure 18B:
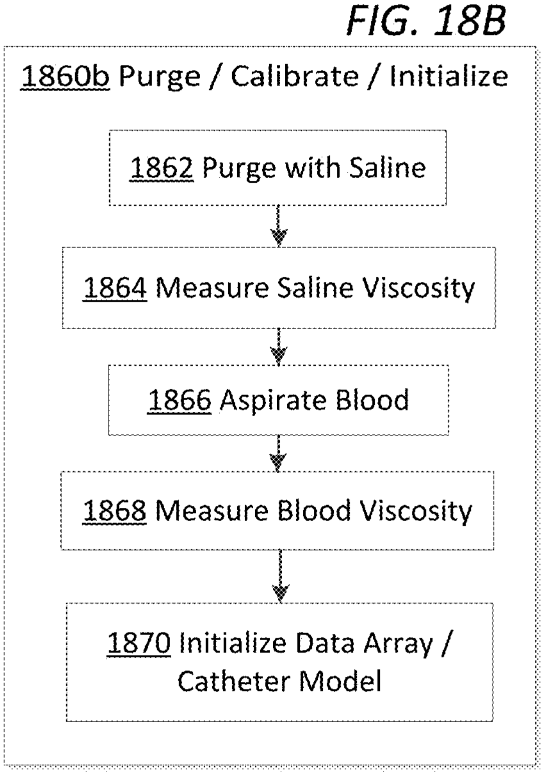
FIG. 18B depicts a block flow diagram of a method to perform purge/calibrate/initialize functions.
Figure 18C:
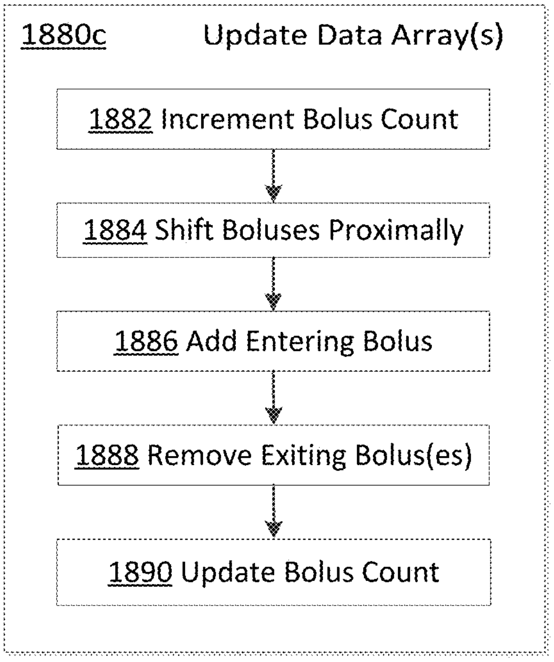
FIG. 18C depicts a block flow diagram of a method to update data arrays.

FIG. 18B depicts a block flow diagram of method **1860*b* to prepare a VVA apparatus for a thrombectomy procedure. FIG. 18C depicts a block flow diagram of method 1880*c* wherein catheter model/data array 1901 is updated with "new" data; these data may be as-measured (current) or synthetic (simulation). FIGS. 18A-18C are discussed in detail subsequent to FIG. 19**, wherein the data structure for computations is disclosed.

Figure 19:
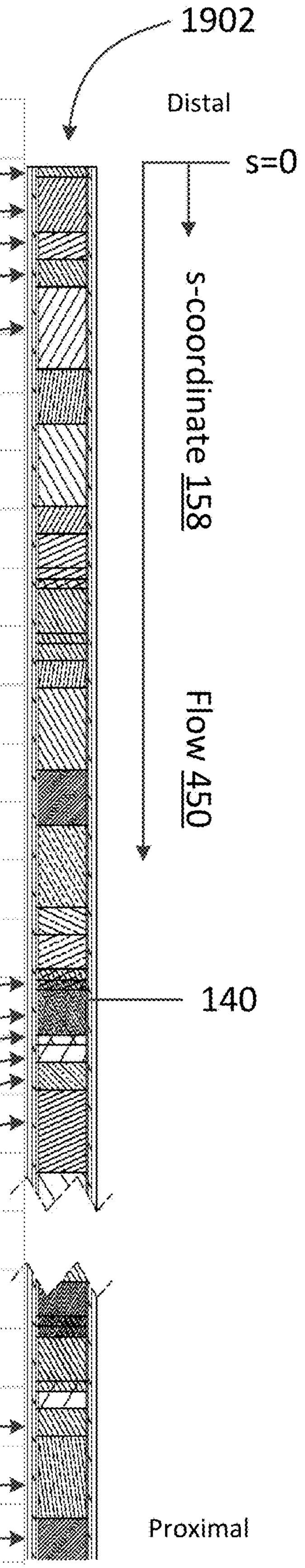
FIG. 19 depicts a catheter model adjacent to a corresponding catheter model/data array.

FIG. 19 depicts catheter model 1902 in cross-section view and corresponding catheter model/data array 1901 in tabular form. Catheter model 1902 is a mathematical model of the physical contents of catheter 140, i.e., the catheter state. Catheter 140 is oriented vertically to align visually with corresponding catheter model/data array 1901. In this instance, corresponding means that measurement data written to catheter model/data array 1901 share one-to-one correspondence with discrete boluses of aspirate present within catheter model 1902. In other words, catheter model/data array 1901 contains a sequence of measurement values of entering bolus 911. These measurement values are, in certain cases, "summed" to generate a real-time mathematical model of the physical contents of catheter 140. FIG. 19 depicts a catheter state wherein catheter model 1902 comprises a linear array of N boluses. Each of the N boluses has corresponding measurement data written to catheter model/data array 1901. Thus, catheter model/data array 1901 is highly-correlated to catheter model 1902 and a current catheter state. Unlike pressure waveform parameterization methods of prior art, certain VVA embodiments transform raw pressure waveform data into a compact, physically-meaningful representation. Thereby, certain VVA embodiments efficiently compute and/or update certain system variables with significantly reduced computational demands.

Catheter model 1902, as depicted in FIG. 19, is comprised of catheter 140 and N individual boluses of aspirate; the direction of aspirate flow 450 and s-coordinate 158 are shown. It is important to note that catheter model 1902 is a quantitative determination of the catheter state of catheter 140, or the physical contents thereof. Catheter model 1902 is generated and depicted for illustrative purposes, including illustration of: one-to-one correspondence to catheter model/data array 1901, a plurality of boluses of aspirate, e.g., B1 through Bn, each of known volume and viscosity, etc.

At the distal end (i.e., upper) of catheter 140, the uppermost bolus is annotated as B1, indicating that this bolus is currently in the 1$^{st}$ position within catheter 140. Herein, uppermost bolus B1 is also called entering bolus 911, corresponding to FIG. 9B, although the figures are oriented differently. Moving proximally (i.e., downward) along catheter 140, bolus B2 is adjacent to, and shares a boundary with, bolus B1 at an interface. Because adjacent boluses (e.g., B1 and B2, B7 and B6, Bi and Bi+1, etc.) share a boundary at an interface, a no-pressure jump boundary condition may be computationally enforced. The no-pressure jump boundary condition enables calculation of pressure at any interface between adjacent boluses. This discretization method, in the s-coordinate 158 direction, enables calculation of the lengthwise pressure distribution along a catheter as depicted in FIG. 11A and FIG. 11B. On a larger scale, application of Eq. 1 (Hagen-Poiseuille) across the overall length of the catheter enables measurement of the current catheter viscosity. On a smaller scale, application of Eq. 1 across the length of any or all boluses enables calculation of the pressure drop across each bolus. Calculation of the pressure drop across each bolus enables calculation of the pressure at each bolus interface. FIG. 19 depicts approximately N−1 interfaces between contiguous boluses (e.g., Bi−1, Bi, Bi+1, etc.); certain VVA embodiments compute the local pressure at any, some or all of these interfaces. Thereby, dynamic visualizations of pressure distributions, along the catheter length (e.g., FIGS. 11A and 11B), may be available for display in real time to clinicians, remote observers, etc.

FIG. 19 illustrates a representative bolus numbering scheme that is convenient for programming computer routines such as method **1880*c*, which updates catheter model/data array 1901. FIG. 19 depicts 6 contiguous boluses annotated Bi−2, Bi−1, Bi, Bi+1, Bi+2, and Bi+3. A dummy or loop index, i, is shown "currently" set to i=17, such that i−2=15, i−1=16, i=17, i+1=18, i+2=19, i+3=20, and so forth. At the proximal (i.e., lower) end of catheter 140, the lowermost bolus is annotated Bn, with distally adjacent boluses Bn−1 and Bn−2. All boluses within catheter 140 are typically numbered similarly. Herein, N is typically used to represent the current number of boluses contained within catheter 140. Operationally, N is typically changing as boluses of arbitrary length enter catheter 140 enter from the distal end and exit from the proximal end. FIG. 19 illustrates that certain VVA embodiments "know the position of" and "track" each bolus of aspirate as it traverses catheter 140** from the distal tip (where "all clogs start") to the proximal end (whereupon the aspirate is transported to waste).

FIG. 19 depicts a current instance of catheter model/data array 1901 and a corresponding catheter model 1902. Representative catheter model/data array 1901 is an [N rows×M columns] matrix dimensioned to N (the number of boluses) by M (set equal to four, in this instance). The four columns of data are selected, in this example case, to be: μ, I, μ×I, % PD; these data are adjacent to the bolus # column, included to enumerate and illustrate the one-to-one correspondence of each row of data with each bolus within catheter model 1902. The left two data columns of catheter model/data array 1901 contain the product of μ and I (bolus viscosity×bolus length) and % PD (% pressure drop across the $i^{th}$ bolus). These values (μ×I and % PD) are readily calculable from measurement values of μ and I; they are included as physically relevant examples of data populating catheter model/data array 1901. The dimension of the matrix catheter model/data array 1901, depicted in FIG. 19 is [N×4]; in this case, the number of rows is equal to the number of boluses, N; in other words, the matrix of FIG. 19 is not over-dimensioned. Certain VVA embodiments over-dimension certain data arrays, including instances of catheter model/data array 1901. Certain VVA data arrays, e.g., catheter model/data array 1901, are typically dimensioned between [2×1,000] and [20×100,000]. It is important to note that over-dimensioning arrays does not substantially affect processing speeds; hardware features such as dynamic memory allocation (DMA) are utilized in certain VVA embodiments.

FIG. 19 depicts catheter model/data array 1901 wherein the number of columns, C=4 (e.g., μ, I, μ×I, % PD), and N is an arbitrary number of boluses present in catheter 140 of catheter model 1902. VVA matrices are typically dimensioned between 2≤C≤20 number of columns. In other words, as many as 20 data entries (e.g., viscosity, volume, time constant, pressure, machine states, etc.) may be stored; each row of data entries corresponding to each bolus of fluid. Memory optimization techniques such as sparse storage and dynamic allocation may be utilized in certain VVA embodiments to speed data handling of large arrays. For subsequent calculation purposes, example instances of catheter model/data array 1901 are stated to be dimensioned to [1,000×2], corresponding to 1,000 boluses of aspirate with measured bolus viscosity ($\hat{\mu}_i$) and bolus volume ($\hat{v}_i$). The example (1,000×2) floating point data array requires approximately 8 kB of memory; this is used herein as an example array for computational performance benchmarks, subsequently discussed.

FIG. 19 illustrates several important aspects of certain VVA embodiments, such as the matrix structure of catheter model/data array 1901 and the one-to-one correspondence with catheter model 1902, which quantitatively characterizes the catheter state of catheter 140. Aspects of disclosed methods including 1700 Aspiration Measurement Cycle, 1800 Thrombectomy Procedure, **1860*b* Purge/Calibrate Initialize and 1880*c* Update Data Array(s) computationally operate upon catheter model/data array 1901** to perform their respective functions. Certain VVA embodiments and/or methods also control the machine state, e.g., valve states, actuator states, initial/final pressures, etc. Integration of data handling and machine state control is now discussed.

Returning to method 1800 thrombectomy procedure, depicted in FIG. 18A, which is a representative example VVA control algorithm for conducting an aspiration thrombectomy procedure. Operation 1860, Purge/Calibrate/Initialize, acts to fill and purge catheter 140, calibrate the apparatus and initialize one or more data arrays; this is further disclosed in conjunction with method **1860*b* and FIG. 18B. Operation 1805 is Seek/Detect Thrombus Viscometrically; clinically this may include actions such as repositioning and/or reconfiguring of the catheter. Certain VVA embodiments are operable in one or more "low vacuum/low flow rate" AMC modes to viscometrically detect thrombus while simultaneously minimizing blood loss. In certain VVA embodiments, measurement data from non-contact thrombus detection may provide catheter-position feedback to the clinician by means such as audible instruction and/or video display(s). In certain VVA embodiments, measurement data from non-contact thrombus detection may be utilized to change a machine state, e.g., reconfigure dilution catheter 1001, adjust AMC pressure levels, etc. Perhaps after repositioning or reconfiguring the catheter, operation 1810 Aspirate a Bolus of Fluid is executed. In many VVA embodiments, operation 1810 is executed by changing the machine states of components such as: vacuum valve 130, chamber valve 455, exogenous-fluid valve 520, displacement mechanism 220**, etc.

Operation 1820 Measure Volume, measures the volume of entering bolus 911, and is similar to operation 1720 of method 1700. Operation 1830 Calculate Viscosity calculates catheter viscosity ($\mu_{current}$) and/or the viscosity of entering bolus 911 ($\hat{\mu}_0$) and is similar to 1730 of method 1700. Operation 1880 update catheter models updates one or more instances of catheter model/data array 1901, in some cases with data acquired in operations 1820 and 1830. Details are disclosed in conjunction with method **1880*c* and FIG. 18C. Operation 1842 Only Blood in Catheter? is a first example of a VVA control algorithm utilizing conditional statements such as: IF, ELSE, AND, etc., acting upon derived variables (e.g., catheter viscosity, bolus viscosity) as arguments. Operation 1842 assesses if catheter model 1902 is substantially comprised of blood; if so, control is diverted to operation 1805 whereupon thrombus is "sought." As an example, a representative line of computer code for operation 1842 may be: IF($f_1 \cdot \mu_{blood} < \mu_{current}$ AND $\mu_{current} < f_2 \cdot \mu_{blood}$) THEN GOTO operation 1805**. In this instance, $f_1$ may be in the range of 0.95 to 0.98 and $f_2$ may be in the range of approximately 1.01 to 1.05. User-defined parameters such as $f_1$ and $f_2$ may be rationally proposed and experimentally confirmed, or otherwise derived or determined.

Operation 1842 is significant because it is representative of machine-executed conditional statements based upon data other than pressure and/or pressure parameterizations as input data, or arguments. Certain VVA embodiments utilize conditional logic (e.g., IF/THEN/ELSE, AND, OR, TRUE, FALSE, etc.) upon derived variables (e.g., viscosity, volume, flow rate, clog risk, etc.). This is in contrast to certain prior art embodiments wherein conditional logic is limited to (1) pressure parameterizations (e.g., differential, peak, deviation, variance, median, max, min, etc.), and/or (2) discrete state indicators (e.g., open score, occlusion score, escalate count, etc.). Certain VVA embodiments utilize conditional logic operators upon VVA derived variables to, in certain instances, re-direct, interrupt and/or divert the process flow of method 1800. In certain VVA embodiments, conditional logic statements are evaluated with derived variable data as arguments; examples include operations 1844 Assess Catheter Viscosity and Trends, 1846 Assess Distal Boluses and Trends, and 1850 Assess Multiple AMCs.

Operation 1844 Assess Catheter Viscosity and Trends is a quantitative determination and evaluation of the magnitude and trend of the catheter viscosity ($\mu_{current}$). For instance, if the catheter viscosity is 40 cP and has been rising steadily at approximately 1 cP/AMC, linear projection "predicts" a threshold value of 50 cP may be reached after approximately 10 additional, similar AMCs. From an equivalent time constant perspective, an example time constant may be 4 seconds and rising steadily at 0.1 second/AMC; linear extrapolation or projection "predicts" that the time constant may reach 5 seconds after approximately 10 additional, similar AMCs. Typically, with each AMC, these "predictions" are updated and "corrected." For instance, a subsequent AMC may "predict" that the catheter viscosity may reach the value of 50 cP after only 3 additional, similar AMCs. The first "prediction" of 10 similar AMCs was "corrected" to 3 similar AMCs. This is an example of Model Predictive Control (MPC) that is utilized in certain VVA embodiments, in this instance to assess the trend in catheter viscosity.

Operation 1846 Assess Distal Boluses and Trends is a quantitative determination and evaluation of the magnitude and trend of the viscosities of entering boluses 911 ($\hat{\mu}_0$). If "all clogs start at the catheter tip," then operation 1846 is a "detector" of potential clogs at the source. Operation 1846 is significant because it provides certain VVA embodiments with insight to the thrombus morphology (e.g., fresh, well-developed, collagenaceous, fibrotic, etc.). For instance, fresh thrombus may exhibit a more gradual rise and decline in measured bolus viscosity because the tissue may not be well cohered or adhered to vessel walls. Conversely, well-developed thrombus may exhibit a more erratic, "peaky" or "spiky" measured bolus viscosity as discrete portions of well-developed thrombus are "cleaved" from the cohesive and/or adhesive forces holding them stationary.

As in operation 1844, techniques such as predictor-corrector methods (MPC) may be utilized operation 1846, however such "predictions" are typically made upon the viscosity of the next entering bolus 911 ($\hat{\mu}_0$), rather than predictions made upon catheter viscosity ($\mu_{current}$), as in operation 1844. As an example, the viscosity of entering bolus 911 (*o*) is currently 60 cP and has been rising steadily at 5 cP/AMC. Operation 1846 may "predict" a viscosity of entering bolus 911 ($\hat{\mu}_0$) to exceed an arbitrary threshold viscosity of 100 cP to occur in 8 additional, similar AMCs. In this instance, similar means that the viscosity of aspirate follows predictive models such as linear and/or curvilinear extrapolation, trend line analysis, etc. Of course, there is no reason to suspect that the measured results of upcoming AMCs will be "similar," i.e., adhere to any predictive model. However, as additional data are input to one or more predictive models with each AMC, standard statistical techniques such as correlation coefficients may be computed. Thereby, each predictive model (e.g., linear, exponential, curvilinear, polynomial, etc.) may be assessed for predictive capabilities in response to changing clinical variables, e.g., entering bolus viscosity, thrombus morphology, physical properties, etc.).

Both operations 1844 (catheter viscosity) and 1846 (distal bolus viscosity) enable certain VVA embodiments to make "predictions" regarding the results of upcoming AMCs. In their respective descriptions, linear and/or non-linear extrapolations or projections were cited as examples wherein data are extrapolated based upon recent trends. This is one example of "simulations" that are conducted in certain VVA embodiments. Also significant are VVA "competing simulations" of events that do not exclusively involve extrapolation, but inject "synthetic data" and advance these catheter models/data arrays in time. In certain VVA embodiments, computation of simulations may be executed concurrently (i.e., in real time) with method 1800, such that simulation data are available for assessment in operation 1850 prescribe next AMC. Operation 1850 assesses data (e.g., from operations 1880, 1844, and/or 1846, etc.) and prescribes an AMC mode. Note that operation 1750 of method 1700 selects an AMC mode, perhaps from a set of a plurality of available AMC modes. However, operation 1850 of method 1800 "prescribes" a next AMC; this selection of an AMC mode and also adjust certain parameters, e.g., initial vacuum level, target bolus volume, damping actuator 1510 state, dilution actuator 1040 state, etc. In certain cases, VVA embodiments prescribe an AMC mode based, at least in part upon certain computed simulations exhibiting favorable parameters such as: outcome score, catheter state, thrombectomy efficacy, etc. Simulations are disclosed in further detail in conjunction with FIG. 25.

Method 1860*b* purge/calibrate/initialize is depicted in block flow diagram form in FIG. 18B and is a representative example VVA control algorithm to purge, calibrate, and initialize data arrays of a VVA apparatus. Operation 1862 Purge with Saline is typically comprised of steps such as immersing the catheter tip in saline and changing the states of components such as vacuum valve 130, isolation valve 210, displacement mechanism 220, exogenous-fluid valve 520, etc. Once primed and purged with saline, operation 1864 Measure Saline Viscosity is executed to determine calibration data such as $\tau_{saline}$, $\mu_{saline}$, $Q_{saline}$, etc. Operation 1866 Aspirate Blood typically commences upon vascular access to the patient, whereupon blood aspirated into the catheter. Operation 1868 Measure Blood Viscosity is executed to determine calibration data such as $\tau_{blood}$, $\mu_{blood}$, $Q_{blood}$, etc. Operations 1864 and 1868 thereby generate a two-point calibration curve (saline and blood) from which ongoing viscosity measurements may be referenced throughout the procedure. In certain instances, a VVA apparatus may be recalibrated to blood or any other fluid, e.g., saline, subsequently during, or throughout a procedure. Thus, any or all of operations, (e.g., 1868, 1864, etc.) of method 1860*b* at least once during a method 1800 thrombectomy procedure.

The two-point calibration curve of method 1860*b* is significant because viscosity calibrations and measurements are taken upon saline and patient blood; any subsequent process data are substantially compared to these calibration data, and not external sources. The viscosities of both saline and patient blood are measured as they are aspirated through the catheter and apparatus, typically at the start of a procedure in method 1860*b*. Subsequently within a typical procedure, measurement data are compared (e.g., ratiometrically, algebraically, etc.) to calibration data and/or previously-acquired data from the same catheter and apparatus. There is reduced reliance upon outside/reference/database/library data (for comparison) because the relevant VVA measurements (e.g., pressure, viscosity, volume, time, etc.) are substantially compared against one another. A result of this is that certain VVA embodiments are substantially unaffected by certain sources of experimental error such as: pressure transducer bias or non-linearity, on-board clock errors, DC bus voltage, manufacturing defects in a catheter such as a burr, bulge, kink, constriction, etc.

In certain VVA embodiments, measurement data are typically compared ratiometrically to one another (e.g., $\tau_1/\tau_2$, $\mu_{current}/\mu_{previous}$, etc.), thereby minimizing certain sources of systematic experimental error such as: offset, bias or non-linearities, etc., inherent in the measurement system. This highlights a distinction between VVA and prior-art aspiration thrombectomy systems. Certain prior-art methods "find" and measure "features" (e.g., peaks, valleys, deviations, etc.) and then parameterize those features (e.g., maximum absolute rebound pressure, median ending distal pressure, etc.). This parameterization quantifies identifiable features in the signal and expresses them as a structured pattern, which can then be compared against other patterns for classification or recognition. Pattern matching methods compare these parameterized waveforms against a static set of stored reference patterns, which likely represent observable clinical states or outcomes (e.g., successful aspiration, clog formation, free-flowing fluid, partial occlusion, etc.). Such prior-art systems compare internal data (e.g., pressure waveforms, parameterization values, etc.) against external data (e.g., stored reference patterns, peak pressure thresholds, pressure amplitude thresholds, etc.). Prior-art systems compare internally-generated data against an externally-generated static dataset compiled from case studies and training data derived from a population of similar—but not identical—apparatuses. Such prior-art aspiration thrombectomy systems are therefore dependent upon experiment reproducibility, because data must be transportable from system to system, catheter to catheter and patient to patient. Conversely, certain VVA embodiments are enabled to operate "autonomously" with reduced reliance upon reference patterns, case studies, training data sets, pressure threshold values, etc. Thereby, VVA embodiments are typically less affected by systematic error, in part because many or all VVA control algorithm decisions (e.g., conditional statements, inferences, model predictive control, etc.), predominantly utilize data collected upon one apparatus, one catheter and one patient during one procedure.

Operation 1870 dimensions and initializes any, some or all instances (e.g., current, simulation, storage, etc.) of catheter model/data array 1901 and storage data array 2651 (FIG. 26), if utilized. As an example for subsequent calculations, a representative VVA embodiment is initialized to 1,000 regularly-spaced boluses of aspirate in a 1 meter long catheter. The initialization value for bolus length is therefore 1 mm. This example uses the bolus length convention for visual clarity referencing catheter 140 of arbitrary diameter. The volume of any $i^{th}$ bolus ($\hat{v}_i$) may be found by multiplying bolus length by the cross sectional area of catheter 140, if desired.

As an example of initialization, the viscosity of blood is measured to be $\mu_{blood}$=4.0 cP (e.g., in operation 1868); all array elements are assigned the viscosity of 4.0 cP, because the catheter was filled with blood in operation 1866. Likewise, all 1,000 array elements are assigned a length of 1 mm. The computational grid is initialized with 1,000 boluses, each of 1 mm length and viscosity $\mu_{blood}$=4.0 cP. For successive computations, the value of $\mu_{blood}$=4.0 is typically stored as a reference viscosity; however, this value may be updated at any time thereafter. After initialization, catheter model/data array 1901 corresponds to physical catheter model 1902 comprising approximately 1,000 discrete boluses of aspirate (e.g., Bi−1, Bi, Bi+1, etc.); each discrete bolus of aspirate comprising pure blood at the reference viscosity of 4.0 cP.

Method 1880*c*, depicted in FIG. 18C, is a representative algorithm for updating catheter model/data array 1901. Operation 1882 increments the bolus count by one (e.g., N=N+1). Operation 1884 shifts boluses proximally, or downward in catheter model 1902 depiction of FIG. 19. Operation 1886 adds entering bolus B1 to catheter model/data array 1901; this corresponds to the ingestion of entering bolus 911 into the distal end of catheter 140 and/or catheter model 1902. By convention, entering bolus 911 is assigned an arbitrary index value, typically i=1 or i=0. In FIG. 19, entering bolus 911 is annotated as B1, identifying this bolus to be in position 1 of catheter model/data array 1901 and corresponding catheter model 1902.

Operation 1886, add entering bolus, writes new data entries (e.g., viscosity, length/volume, etc.) into catheter model/data array 1901 at the distal end, "where all clogs start". Operation 1888, remove exiting bolus(es), and operation 1890, update bolus count, calculate and remove a number of boluses (including portions thereof) from catheter model/data array 1901. This corresponds to a volume of aspirate exiting catheter model 1902 from the proximal (i.e., lower) end, i.e., exiting bolus 912 of FIG. 9B. FIG. 19 annotates the $N^{th}$ (i.e., the "last") bolus as Bn; some or all of boluses Bn, Bn−1, Bn−2, . . . , etc., or portions thereof, may be "removed" from the catheter model/data array 1901 in operation 1888. Operation 1890 recalculates and updates the bolus count, N, such that the additive lengths of all boluses is substantially equal to the length of catheter 140.

Method 1880*c* is a detailed example of operation 1880 update catheter model of method 1800. In many VVA embodiments, method 1880*c* is executed multiple times per AMC. In some cases, one instance of model/data array 1901 stores current measurement data and reflects the physical contents of catheter 140, or the catheter state. Other instances of catheter model/data array 1901 may be used for tasks including simulation and/or data storage. Method 1880*c* is executed in a substantially identical manner upon either current or simulation instances of catheter model/data array 1901.

Operation 1886 add entering bolus, acting upon current catheter model/data array 1901, writes as-measured data to current catheter model/data array 1901. With each AMC, as-measured data are typically written to current catheter model/data array 1901; previous data are typically overwritten, thereby keeping the catheter model/data array "current." However, many VVA embodiments store any or all data in one or more stored data arrays, as is subsequently disclosed in conjunction with procedure log files in FIG. 26. Operation 1886 Add Entering Bolus, acting upon simulation instances of catheter model/data array 1901, writes synthetic data to simulation catheter model/data array 1901. Synthetic data are subsequently discussed in conjunction with FIG. 25.

Figure 20A:
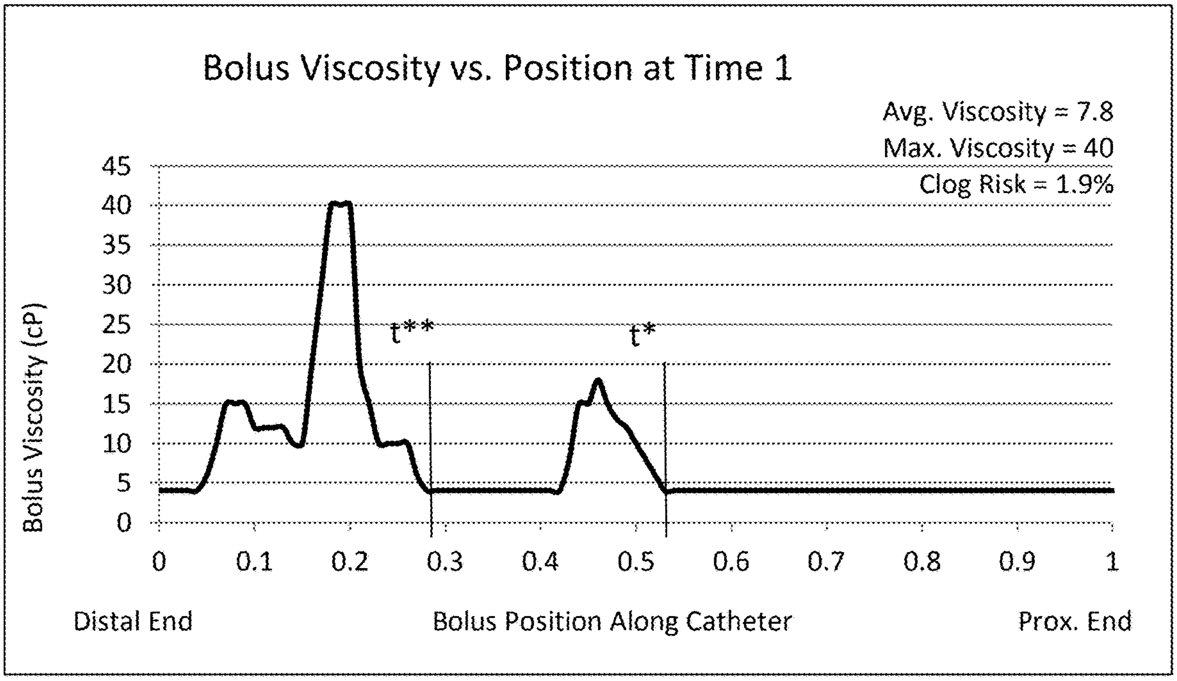
FIGS. 20A-20B depict illustrative graphs generated in accordance with certain embodiments of the present invention, wherein bolus viscosity vs. position at a first time and at a second time are depicted.

FIG. 20A is a graphical depiction, or display, of "instantaneous" bolus viscosity vs position at Time 1 corresponding to physical catheter model 1902 at a first time. The x-axis of FIG. 20A is position along the catheter axis, or the s-coordinate 158; this axis is normalized to 1. Bolus viscosity (in units of cP) is the ordinate or y-axis. FIG. 20A illustrates that, for an example 1 meter long catheter, approximately the proximal 45 cm of the catheter contains substantially pure blood at approximately 4 cP. At some time t*, a thrombotic mass of maximum viscosity 18 cP entered catheter model 1902 (e.g., as B1); subsequently, at time t, a second thrombotic mass entered catheter model 1902. Two distinct thrombotic masses are depicted in FIG. 20A at time 1**.

Figure 20B:
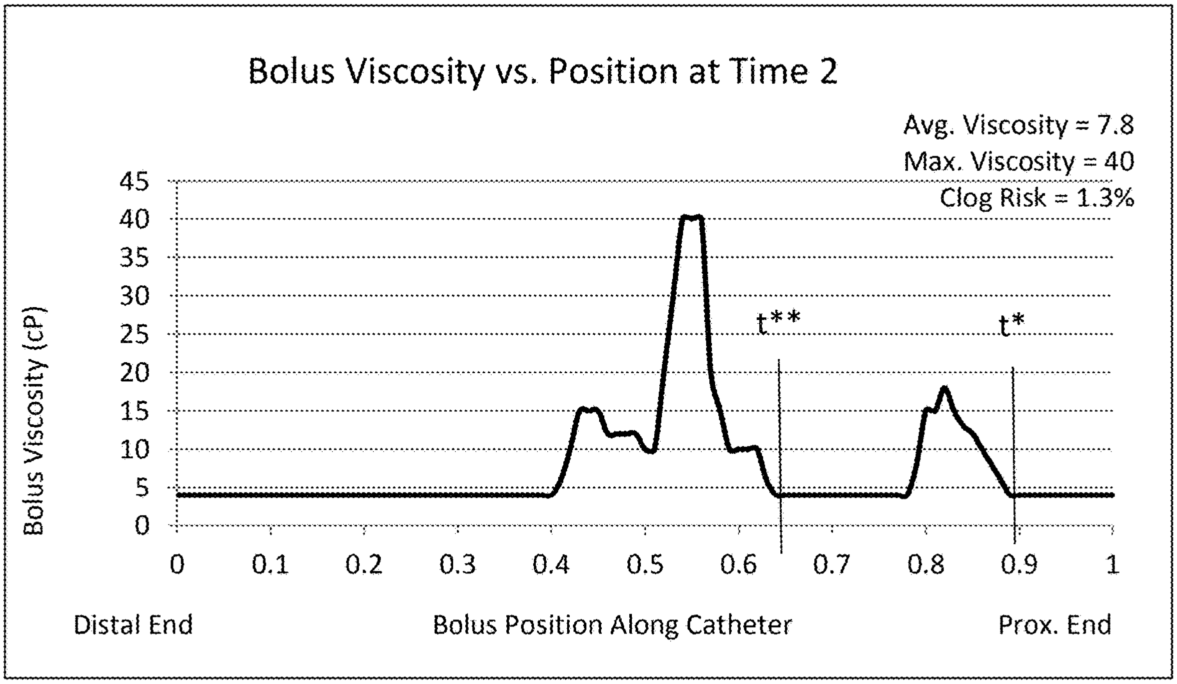

FIG. 20B is the graphical depiction of FIG. 20A at a second time. The thrombotic masses of FIG. 20A have translated proximally toward the VVA apparatus. From FIGS. 20A-20B, it may be observed that (1) substantially pure blood was aspirated prior to time t*; (2) between time 1 and time 2, only substantially pure blood was aspirated, (3) between t* and time 1, two thrombotic masses entered the catheter tip. Also shown in FIG. 20A and FIG. 20B are relevant statistics such as the average viscosity, maximum viscosity and clog risk. FIGS. 20A-20B are representative of graphical displays and dynamic visualization that are featured in certain VVA embodiments. This enables clinicians, staff and/or remote observers to visually and quantitatively assess the progress of the thrombectomy procedure. This affords the clinician insight to adjust, change or abort any operations planned and/or underway by VVA control algorithms.

Figure 21:
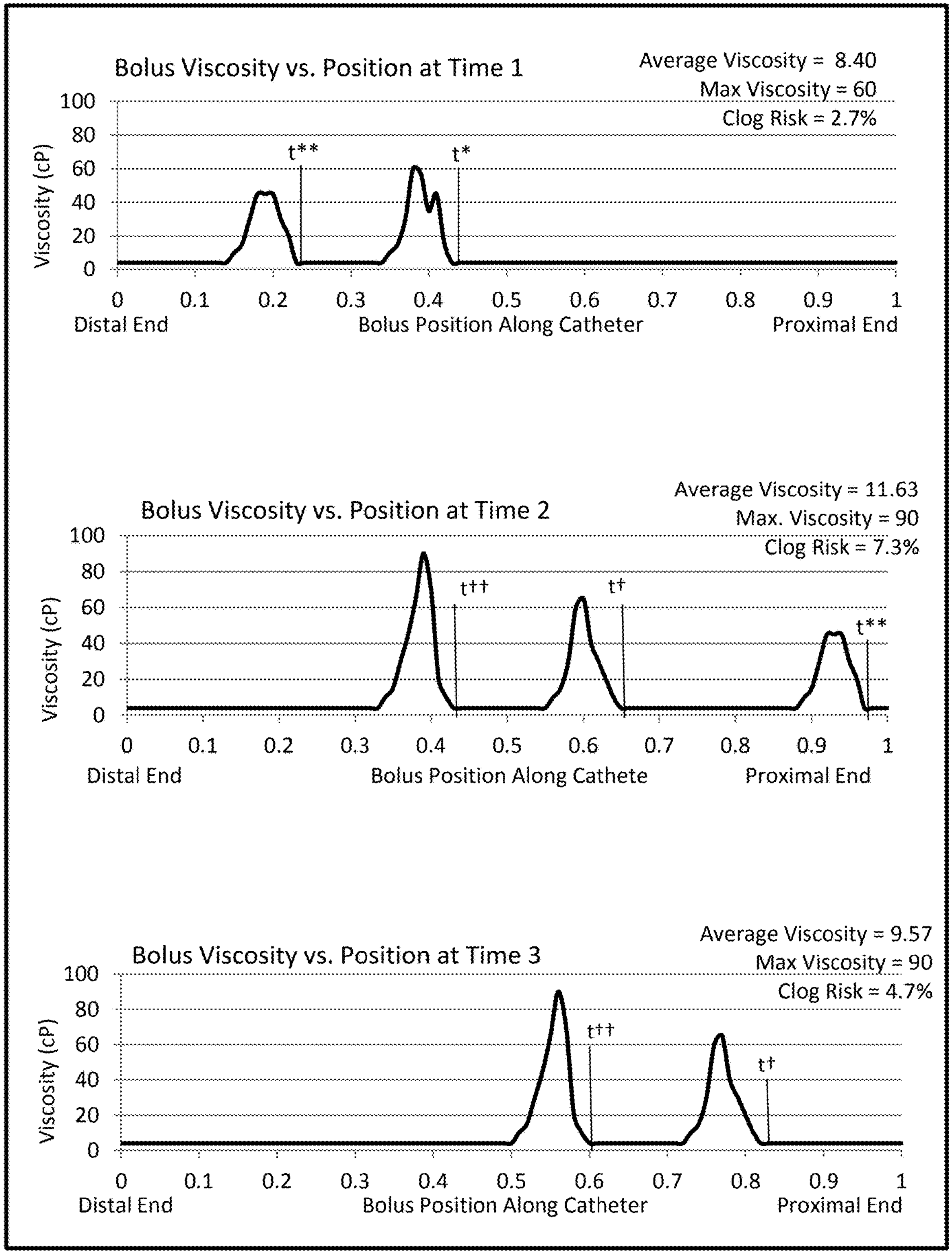
FIG. 21 depicts illustrative graphs generated in accordance with certain embodiments of the present invention, wherein a sequence of bolus viscosity vs. position is depicted at first, second and third times.

FIG. 21 depicts 3 graphical displays of bolus viscosity vs position at Time 1, Time 2, and Time 3 as examples of dynamic visualization, whereby a clinician, staff and/or remote observers may view real-time graphical depictions of thrombotic masses as they traverse catheter 140. The upper graph of FIG. 21, at time 1, illustrates: (1) prior to time t*, approximately 55 cm of blood was aspirated, (2) at time t* a thrombotic mass of approximately 1 cm length and 60 cP maximum viscosity entered catheter 140, (3) at time t a second thrombotic mass of approximately 1 cm length and 45 cP maximum viscosity was aspirated, and (4) substantially pure blood comprises approximately the distal 15 cm of catheter 140**.

The center graphical display of FIG. 21, at time 2, illustrates: (1) at time $t^+$ a thrombotic mass of approximately 1 cm length and 60 cP maximum viscosity entered catheter 140, (2) at time $t^{++}$ a thrombotic mass of approximately 1 cm length and 90 cP maximum viscosity entered catheter 140, (3) between time 1 and time 2, the first thrombotic mass (time-stamped t*) has exited the proximal end of catheter 140, (4) substantially pure blood comprises approximately the distal 33 cm of catheter 140.

The bottom graphical display of FIG. 21, at time 3, illustrates: (1) between time 2 and time 3, the second thrombotic mass (time-stamped t) has exited the proximal end of catheter 140, (2) substantially pure blood comprises approximately the distal 50 cm of catheter 140. FIG. 21** also illustrates that real-time data may be displayed; by way of example and not limitation, average viscosity, maximum viscosity and clog risk are selected for display.

Figure 22:
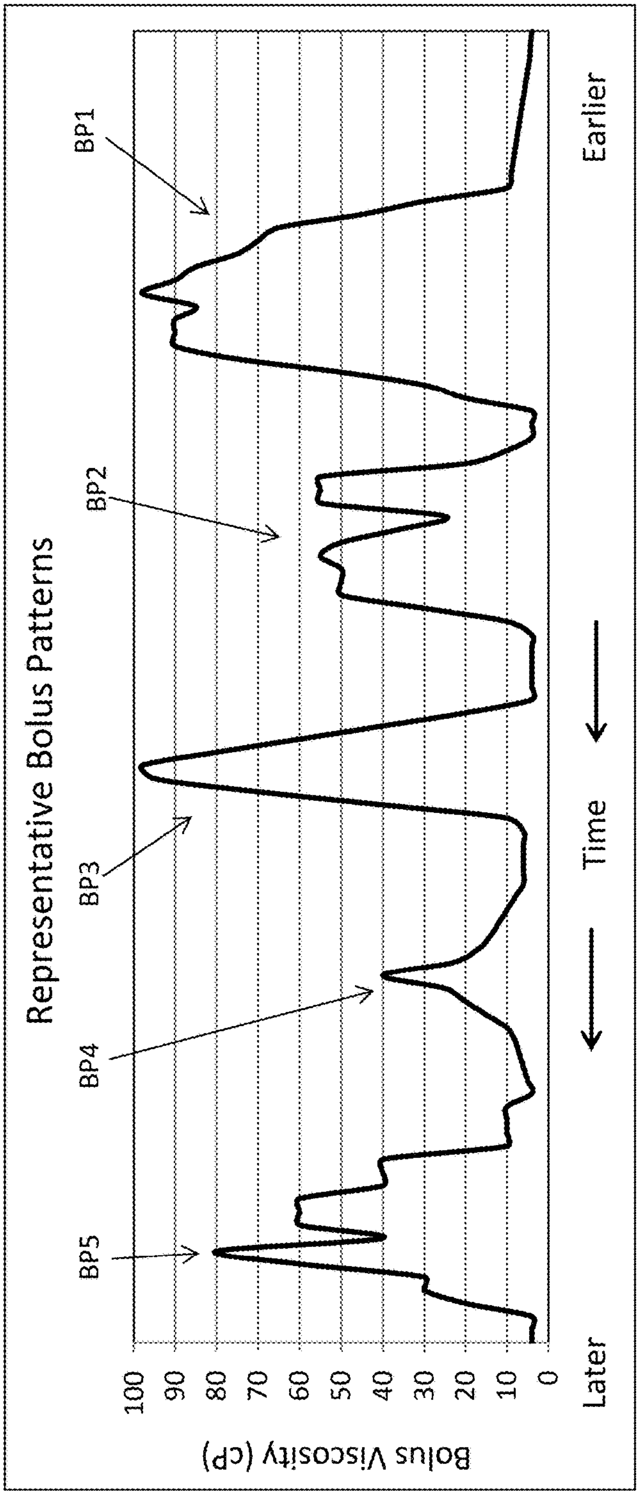
FIG. 22 depicts an illustrative graph generated in accordance with certain embodiments of the present invention wherein 5 representative bolus patterns are depicted.

FIG. 22 graphically depicts five representative "bolus patterns" identified as BP1, BP2, BP3, BP4 and BP5. Graphical displays, such as depicted in FIGS. 20A-21, typically have as-measured data injected from the left hand side of the graph; the direction of time flow is shown. For these reasons, the right hand side of FIG. 22 is labeled "Earlier" and the left hand side labeled "Later." FIG. 22 also illustrates that detected thrombotic masses exhibit distinct profiles; these profiles may be characteristic of thrombus type, morphology, physical properties, etc.

Representative bolus pattern BP1 entered catheter 140 "first" or "earliest." Starting from the right hand side of BP1 of FIG. 22, a gradual increase in viscosity is observed; this may be characteristic of non-contact thrombus detection. As catheter 140 tip is advanced toward a thrombus, detectable flow anomalies such as convergent/or turbulent flow enable certain VVA embodiments to estimate the distance to the thrombus until contact is made. BP1 exhibits a steep increase in viscosity once contact with the thrombus is established; this may be characteristic of more developed thrombus which may be better cohered and/or adhered to the patient vasculature. The sharp peak may be characteristic of cohesive and/or adhesive forces being overcome.

Bolus pattern BP2 also exhibits an initial steep increase in viscosity, a plateau is observed and a dip or valley is observed. BP2 may be characteristic of actively making/breaking contact with thrombus, or an intermittent seal phenomenon. For instance, a seal could be breached between the tip of catheter 140 and a thrombus, admitting blood into the catheter through the seal breach; that seal is subsequently re-established. Softer thrombus morphologies may tend to seal more effectively, whereas firmer, better developed thrombus morphologies may tend to obstruct and partially occlude the tip of catheter 140, rather than create a seal.

Bolus pattern BP3 exhibits symmetrical properties and is generally devoid of irregularities; this may be characteristic of softer, fresher thrombus morphologies. Representative bolus pattern BP4 exhibits a gradual increase in viscosity, this may be from non-contact thrombus detection. A generally gradual and symmetric bolus pattern subsequently emerges in BP4. Bolus pattern BP5 exhibits many of the characteristics previously described: irregularities such as shoulders, peaks and valleys may be characteristic of mixed thrombus morphology where seals are created and breached, softer interior thrombus is exposed and aspirated, etc.

The graphical displays of FIGS. 20A-22 represent viscosity on the y-axis and time or position on the x-axis. A fundamental objective of aspiration thrombectomy is to transport a maximum amount of thrombus to waste with a minimum amount of blood loss. If only blood is aspirated, the graphs would be a "flat line" at approximately 4 cP. Therefore every "elevation" above 4 cP (in the representative graphs depicted herein represent) is a quantitative indicator that a fundamental objective of thrombectomy is being accomplished (and to what degree). Measuring the area under curves, such as depicted in FIGS. 20A-22, is a measurement of thrombus concentration of the aspirate currently within catheter 140. However, the area under the viscosity vs position curves is also a measure of the likelihood of clogging a catheter. Certain VVA embodiments perform numerical integration (e.g., trapezoid rule, Simpson's Rule, Gauss Quadrature, etc.) upon viscosity vs position data to measure the cumulative amount of thrombus (1) currently in catheter 140 and/or (2) harvested during and throughout a procedure.

VVA bolus patterns (e.g., BP1, BP2, BP3, etc.) reveal characteristics of thrombus morphologies; changes in viscosity may be gradual or immediate, irregularities such as peaks and valleys may or may not develop. The shape, height and area under the curve of each bolus pattern may be utilized to characterize thrombus. As an example, bolus pattern BP3 may be described as a generally normal distribution with small standard deviation. Bolus pattern BP4 may be described as a generally normal distribution with larger standard deviation. BP3 and/or BP4 may be characteristic of soft, fresh thrombus which is highly viscous and not hard or brittle.

Bolus patterns such as BP2 and BP5 may be described as bi-modal or tri-modal; this may be characteristic of hard, brittle or fibrotic thrombus. Bolus pattern BP1 may be described as substantially normal with central peaks and valleys; though the standard deviation of BP1 is significantly greater that BP3, another quantitative distinguishing characteristic. BP1 may be characteristic of fresh, soft thrombus that was adhered to a vessel wall until the adhesive forces were overcome. Each thrombotic mass that is aspirated by certain VVA embodiments leaves behind a "signature." Certain VVA embodiments store this "thrombus signature" data and compile these data for further utilization including, but not limited to: statistical parameterization (e.g., bi-modal, normal, skewed, variance, etc.), thrombus model matrix, pattern matching, training data, etc.

A trend in aspiration thrombectomy systems has been to rapidly change machine state (e.g., change the state of vacuum valve 130); herein referred to as a "pulse train." Pulse trains are likely beneficial because a rapid succession of impulses may act to dislodge thrombus for aspiration.

Figure 23:
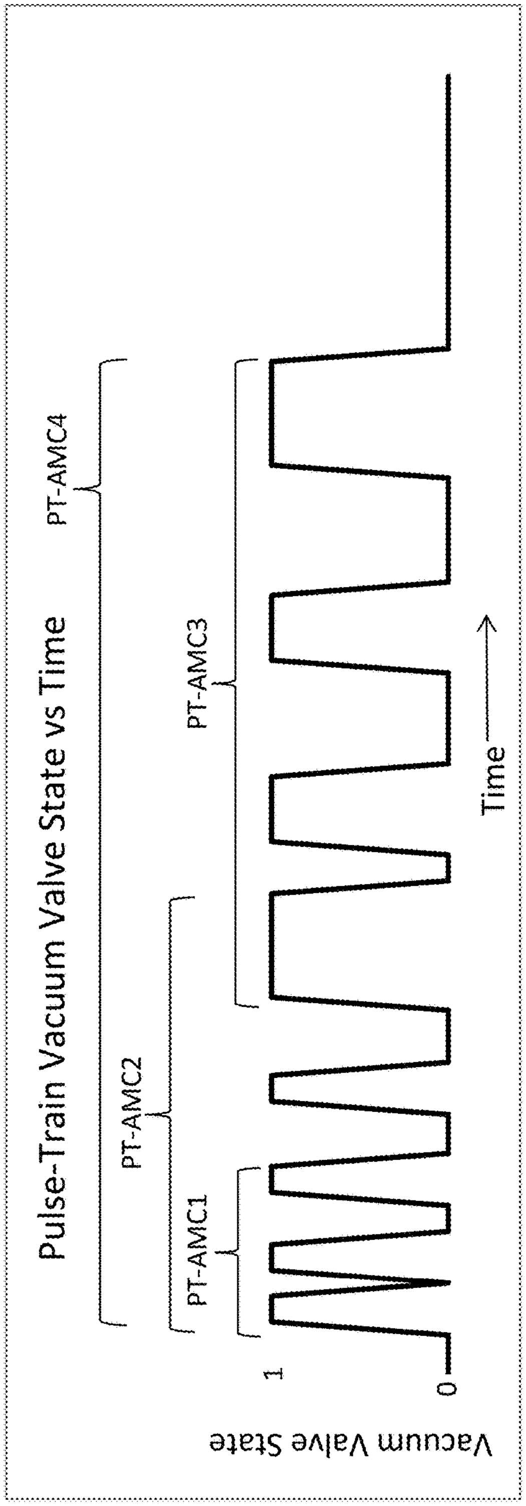
FIG. 23 graphically depicts representative valve state sequences for 4 pulse-train Aspiration Measurement Cycles (PT-AMC).

FIG. 23 graphically depicts representative VVA pulse train protocols wherein the state of vacuum valve 130 is cycled in arbitrary patterns. The rate at which VVA pulse trains occur is limited by the response time of components, solenoids, typically valves, actuators, and other system components, therefore the time axis is not labeled in units.

FIG. 23 illustrates four such representative pulse train AMC modes identified as PT-AMC1, PT-AMC 2, PT-AMC 3, and PT-AMC 4. Representative pulse train 1 PT-AMC 1 comprises three cycles of vacuum valve 130 state; two in rapid succession and a third after a short pause. PT-AMC2 comprises PT-AMC1 plus two additional cycles of vacuum valve 130 state. PT-AMC3 comprises four cycles of vacuum valve 130 state and illustrates that the duration and times may be arbitrarily varied. PT-AMC4 is comprised of the eight cycles of vacuum valve 130 state depicted in FIG. 23.

Certain VVA embodiments, executing PT-AMC 1, may complete the 3 cycles of vacuum valve 130 in approximately 0.1 second. Rapid valve actuation, such as PT-AMC 1, may generate a noisy data stream; typical VVA measurements attempted upon such a noisy data stream may be error prone. However, by combining two or more cycles of vacuum valve 130 into a single pulse-train AMC, the thrombectomy efficacy of pulse train valve actuation (or pulse-train AMC modes) may be quantitatively assessed against any other AMC modes (pulsed or un-pulsed) disclosed herein. Certain Pulse-Train AMC modes cycle machine state rapidly and temporarily suspend certain VVA analysis and/or measurements (e.g., pressure, time constant, viscosity, etc.) until, say, the final valve closure, whereupon the volume and viscosity of entering bolus 911 may be measured.

As an example utilizing pulse train AMC modes, refer to operation 1850 of method 1800, wherein a next AMC is prescribed. A pulse train AMC mode (e.g., PT-AMC1 at 28 inHg, 3 pulses, etc.) may be prescribed. Subsequently, in operation 1810, Aspirate a Bolus of Fluid, vacuum valve 130 is cycled three times, instead of one. As with many AMC modes, initial and final pressures are typically utilized to calculate the volume of entering bolus 911. The time constant of entering bolus 911 may be calculated or estimated by pulse train vacuum valve state vs time data of FIG. 23. Example methods to calculate or estimate the time constant for pulse train AMC modes include: summing the valve-open times, integrating the area under the curves, duty-cycle calculations, etc.

Pulse-train AMC modes may provide diagnostic insight, in addition to therapeutic functionality in certain VVA embodiments. In certain VVA embodiments, pulse-train AMC modes are utilized for identification of and discrimination between thrombus types. As an example, certain thrombus morphologies (e.g., soft, fresh, etc.) may respond poorly to certain pulse train AMC modes for reasons including, but not limited to: elasticity, cohesion, etc. of the thrombus. Conversely, other thrombus morphologies (e.g., organized, brittle, fibrotic, etc.) may respond well to those pulse train AMC modes for reasons including fracture, dislodgement, entrainment, etc.

The representative pulse trains depicted in FIG. 23 are arbitrary and of no particular significance; therefore one may only speculate, for instance that PT-AMC4 will outperform PT-AMC1. However, each executed AMC mode (pulsed or non-pulsed) is typically assessed quantitatively for thrombectomy efficacy (e.g., bolus volume and viscosity, etc.); in this manner, executed pulse-train AMC mode settings may be correlated to thrombectomy efficacy and/or outcome scores. Certain VVA embodiments utilize one or more data arrays to store AMC mode parameters and/or settings; these data may be correlated to success metrics including, but not limited to catheter viscosity, bolus viscosity, clog risk, etc. Example data arrays include storage, simulation, and/or current instances of catheter model/data array 1901, procedure log file 2601, etc. In certain VVA embodiments, these data are analyzed intra-procedurally to assess which, if any, pulse trains are efficacious. In certain embodiments, pulse-train correlation data are included procedure log file 2601. Data from a plurality of procedure log file 2601 may be compiled to include data from a plurality of patients, procedures, catheters, etc. These compiled procedure log file 2601 data are, in certain cases, utilized to update VVA algorithms, software, firmware, etc.

Figure 24:
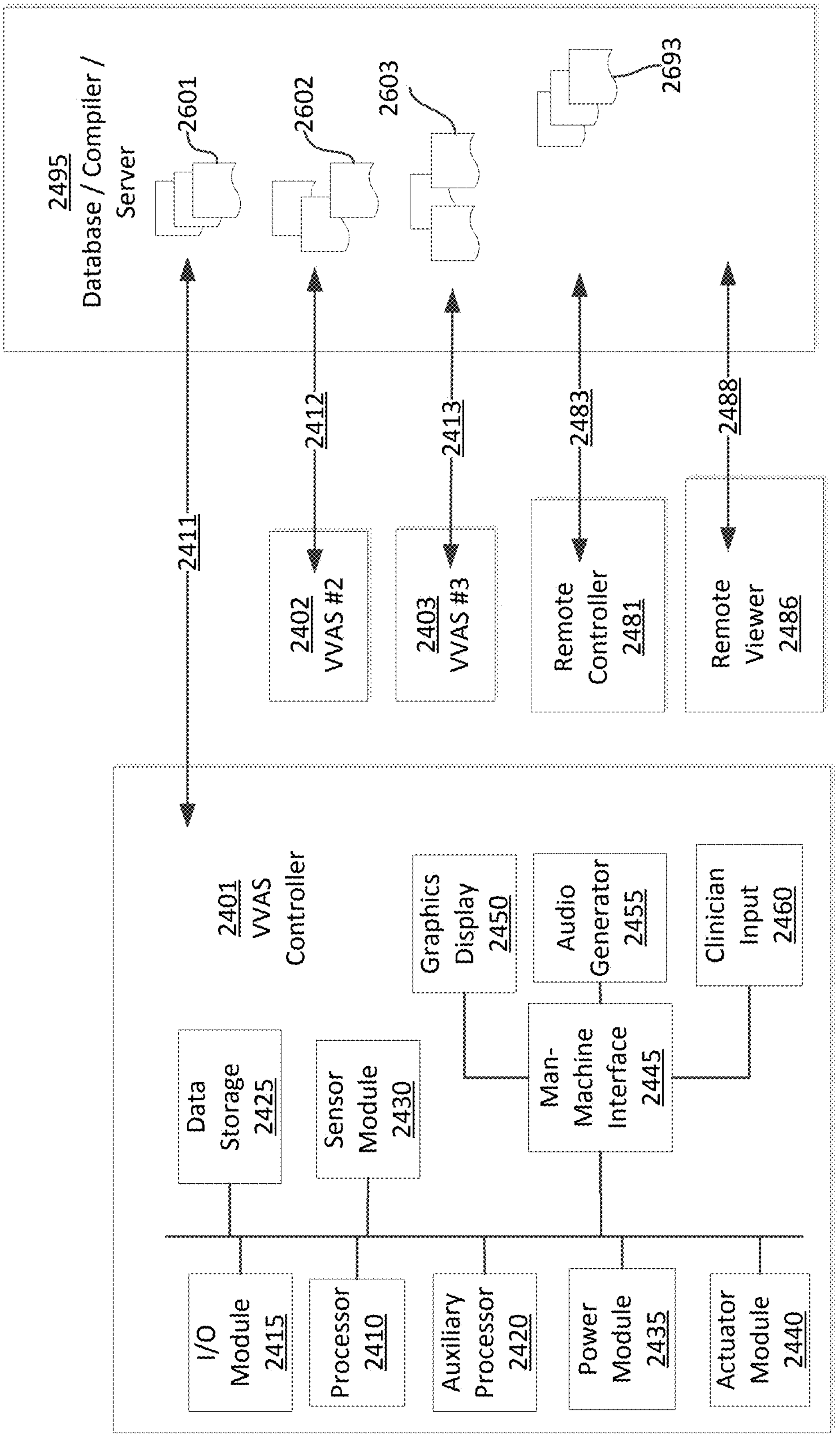
FIG. 24 is a block diagram depiction of multiple instances of VVA system embodiments of the present invention, wherein data communication with a database/compiler/server is depicted.

FIG. 24 depicts, in block diagram form, VVAS controller 2401, VVAS controller #2 2402, VVAS controller #3 2403, remote controller 2481, and remote viewer 2486 in data communication with database/compiler/server 2495. To illustrate multiple instances of VVA system controller 2401 in FIG. 24, the naming convention "VVAS #X" is utilized. VVAS #2 and VVAS #3 are similar instances of VVAS controller 2401, each comprising a substantially equivalent configuration of hardware and software components; these multiple instances of VVAS controllers 2401, 2402, 2403, etc. may be geographically remote. VVAS controller 2401 exchanges data with database/compiler/server 2495 through a first data communication channel 2411. Similarly, VVAS #2 communicates with database/compiler/server 2495 through a second data communication channel 2412, and VVAS #3 communicates database/compiler/server 2495 through a third data communication channel 2413. Remote controller 2483 exchanges data with database/compiler/server 2495 through a fourth data communication channel 2483. This enables certain VVA embodiments to utilize remote computing; this may be for reasons including, but not limited to: superior computational resources, manufacturing costs, advanced VVA algorithms, fail-safe redundancy, etc.

Remote viewer 2486 exchanges data with database/compiler/server 2495 through a fifth data communication channel 2488. Remote viewer 2486 typically comprises combinations of hardware and software that enable remote viewers to view any, all, or user-selected portions of an aspiration thrombectomy procedure. Furthermore, remote viewers are enabled to pause, rewind, slow-motion, time-lapse, etc. select portions of a procedure; these functions are similar to those featured in typical digital video recorders. Remote viewers are typically enabled to view procedures from any geographically distributed VVA apparatus. Remote viewers are typically enabled to view procedures in real-time, or substantially any time thereafter. A benefit of these video-playback functions is "slow motion replay" of significant portions of a procedure to ascertain cause-effect relationships; examples include: "immediate clog," significant deviation from expectation values, assessment and/or development of AMC modes and selection algorithms, assessment of threshold values, bolus pattern analysis, etc. Remote viewing capabilities of certain VVA embodiments and/or methods better enable engineers, software/algorithm developers, clinicians, educators, etc. to propose, discuss, experiment, evaluate and/or change certain VVA parameterizations, threshold values, thrombus model matrix, bolus pattern identification/parameterization, flowcharts, algorithms, etc.

FIG. 24 depicts certain functional modules of VVAS controller 2401 in block diagram form. I/O module 2415 provides communication and data exchange with systems external to VVA apparatuses (e.g., database/compiler/server 2495, etc.). Updates to VVA VVAS controller 2401, such as software and/or firmware upgrades, databases, libraries, historical data, etc. may be transmitted and/or received through I/O module 2415. In many VVA embodiments, I/O module 2415 exchanges data with database/compiler/server 2495 through data communication channel 2411. In many VVA embodiments, a data communication channel typically comprises a data communication pathway comprising a wireless or wired link to a local router, the router being operatively coupled to a wide area network (WAN), such as the Internet, thereby enabling bi-directional data exchange between geographically distributed devices through a networked infrastructure comprising local access links, routing nodes, and internet backbone services. I/O module 2415 may comprise communication through means such as Wifi, Bluetooth®, Ethernet, cel phones, Micro SD cards, USB flash drives, etc. In certain VVA embodiments, clinician input 2460 is transmitted to I/O module 2415 via Wifi, Bluetooth®, cel phones, tablets, etc.

Auxiliary processor 2420 is an optional processor that may be utilized for machine tasks including, but not limited to: computing simulations, data collection, data analysis, data integration, computations, actuator controllers, motor controllers, etc. When present, auxiliary processor 2420 may be of similar or different processor capabilities and speeds from processor 2410. Data storage 2425 may store data comprising computer source code, catheter model/data array 1901, procedure log file 2601, thrombus model matrix 2501, outcome scores, stored data array 2651, PT-AMC parameter(s), lookup tables (e.g., FIG. 7C), etc. Data storage 2425 may comprise any or all of the following examples: Solid State Drives (SSD), Hard Disk Drives (HDD), Random Access Memory (RAM), Micro SD cards, USB flash drives, etc.

Sensor module 2430 is typically comprised of pressure transducers, amplifiers, rotary and/or linear encoders, strain gauges, etc. Power module 2435 provides electric power to VVA system controller 2401 modules and may be comprised of transformers, voltage regulators, frequency generators, capacitors, DC busses, etc. Actuator module 2440 may comprise relays, solenoids, positioners, linear actuators, motors, motor controllers, etc. including any requisite peripherals and accessories. Man-machine interface 2445 module bi-directionally distributes relevant data including, but not limited to: data for graphical display, video and/or audio feedback to the clinician, settings, inputs, controls, etc. Graphics display 2450 may comprise one or more video displays configured to display static and/or dynamic images such as: bolus patterns such as depicted in FIGS. 20A-22, pressure distribution patterns as depicted in FIG. 11A-11B, outcome scores, etc. Relevant derived variables including current catheter viscosity, entering bolus 911 viscosity, clog risk, total thrombus harvested, total blood lost, etc. may also be displayed as depicted in FIGS. 20A-22. Audio generator 2455 may comprise tone generators, text-to-speech generators, speakers, etc. Derived variable data such as current catheter viscosity, entering bolus 911 viscosity, clog risk, etc. may be conveyed to a clinician through means including text-to-speech audio, varying pitches, cadences, volumes, etc.; in some embodiments, audio is conveyed to a clinician by Bluetooth® and/or cellular telephones. Clinician input module 2460 may comprise knobs, switches, keypads, touchscreens, mouse, joystick, footpedal, voice command, Bluetooth®, cel phones, etc.

Typical VVA computational and data storage resources are minimalistic, in part due to embedded mathematical models, such as governing and constitutive equations of fluid and solid mechanics. VVA data sets are not only small, but highly correlated; for instance, each row of catheter model/data array 1901 of FIG. 19 contains data corresponding to a specific bolus of catheter model 1902. Thereby, many VVA embodiments perform machine calculations upon small, correlated data sets.

FIG. 24 depicts processor 2410, data storage 2425 module, and auxiliary processor 2420. In some VVA embodiments, auxiliary processor 2420 is optional. However, in certain VVA embodiments, such as those performing bulk updates, computing multiple competing simulations, performing real-time data analysis, writing/rewriting stored data, etc., one or more instances of auxiliary processor 2420 may be present. Calculation of multiple competing simulations will typically require more computational resources than a single Arduino® single-board computer.

Operation 1880 is among the more computationally-intensive machine-executed methods typically arising in VVA embodiments and control algorithms. Operation 1880, acting upon representative 1,000×2 catheter model/data array 1901, may be executed up to approximately 1,000 times/second on an Arduino®@16 Mhz; 750,000 times/second on a Raspberry Pi® 4@1.5 GHz; and 1,550,000 times/second on an UP Board® utilizing Intel® i5-6500 Quad-core at 3 GHz.

A typical VVA Aspiration Measurement Cycle may be completed in as little as approximately 250 ms (range of approximately 250 ms to in excess of 1 minute); this may be used herein as a minimum estimate of the length of time for the competing simulations to have been computed for assessment in operation 1850. For conservative example purposes, consider a 1,000×2 catheter model/data array 1901 being projected out 10 AMCs (e.g., iterations of method 1880) into the future. An Arduino® is capable of running approximately 25 such simulations in 250 ms, a Raspberry Pi® 4 is capable of running approximately 25,000 simulations, and an Intel® i5 is capable of running approximately 250,000 simulations in the 250 ms allotted as a "minimum." These estimates are conservative because: (1) not all simulations require 10 iterations, undesirable outcomes, such as clog, may be immediately terminated, and (2) many AMC's allow far more computation time than 250 ms.

It is important to note that certain computational methods, e.g., method 1880*c* are presented as a time-sequence that logically coincides with advancing catheter model 1902 and/or catheter model/data array 1901 in time. Significantly more efficient computational methods and data structures are omitted herein for clarity and context. The computational examples presented herein combine a very slow processor, an unoptimized data structure and a very slow algorithm; despite these worst-case estimates, approximately 1 million simulations may be computed per second upon modest computational resources. It is also important to note that computing literally trillions of simulations and evaluating the results may be performed in less time than commercially-available CFD software require to grid and model steady-state flow of a homogeneous fluid. Of course, the CFD software has orders-of-magnitude superior results by all metrics; nevertheless the present invention offers significant utility in certain applications.

To compute, or project, simulations (e.g., of catheter model/data array 1901) into the future, many VVA embodiments "inject" (i.e., write) synthetic data to a simulation instance of catheter model/data array 1901, such as in operation 1886 of method 1880*c*. One or more data sources may be utilized to generate synthetic data for simulations, as subsequently discussed. Synthetic data are typically written to simulation instances of catheter model/data array 1901. As examples, simulations may be run based upon scenarios such as: "what if 10 cc of blood is aspirated before the remainder of the current thrombus is aspirated," "what if the catheter tip is retracted 2 mm and pulse-train AMC modes are selected," etc.). Because of computational efficiency of certain VVA algorithms, simulations, based upon synthetic data, may be run as "background processes" concurrently with other VVA functions and operations.

Any AMC, whether it is executed or a computed simulation, may be assigned one or more outcome scores. As an example, on outcome score may be defined as an algebraic combination of gain functions (volume/viscosity of thrombus harvested, high flow rate, etc.) and loss function (blood loss, flow rate, procedure duration, clog, etc.). In certain VVA embodiments, an algebraic expression such as: Outcome Score=[100−$c_1$(thrombus volume)−$c_2$(blood volume)−$c_3$(flow rate)], etc. may be developed, where $c_1$, $c_2$, and $c_3$ are proposed and/or experimentally determined. Another example of determining an outcome score is based upon the measured values of measured and/or derived variables such as; catheter viscosity ($\mu_{current}$), bolus viscosity ($\ddot{\mu}_0$), bolus volume ($\hat{v}_0$), time constant ($\tau_{current}$), etc.

An objective of certain AMC modes, at certain times during a procedure, is to aspirate pure blood, rather than thrombus; this objective may be accomplished by certain VVA embodiments and/or methods such as make/break contact, dilution, etc. In such instances, aspiration of pure blood ($\hat{\mu}_0 \approx \mu_{blood}$) may be assigned an outcome score of 100 (on a scale of 100). Outcome scores may be any combination integers and/or real numbers, with negative numbers being allowed. Typical VVA outcome scores are normalized to ranges such as (−100.0 to 100.0), (0.0 to 100.0), (0 to 100), etc.

It is important to note that outcome scores, disclosed herein, differ fundamentally from system state scores of prior art. The prior-art system state parameterization includes occlusion scores, open scores, escalate counts, etc., taking values from the set of {0, 1, 2, 3, . . . , n}. This method comprises a "running count" of repetitions of certain pressure waveform occurrences (or parameterizations thereof) matching certain patterns (or parameterization windows). In these prior art embodiments, pressure waveform data are parameterized (e.g., MAD/med, starting distal pressure, variance, etc.) and the system state scores are incremented/decremented after parameterization of as-measured data. By contrast, VVA outcome scores are quantitative assessments of the thrombectomy efficacy (e.g., catheter viscosity, bolus viscosity, bolus volume, flow rate, etc.) of an AMC. In some cases, this assessment includes AMC mode settings (e.g., initial and final pressure, damping, dilution, etc.), and may further include considerations such as current catheter state and/or trends.

Certain VVA simulations are computed, among other reasons, to project and/or predict the results of certain AMC modes that may be prescribed, as in operation 1850 of method 1800. In certain VVA simulations, synthetic data (e.g., operations 1820, 1830, etc.) are written to one or more simulation instances of catheter model/data array 1901. Synthetic data may be generated by multiple methods.

A first method of generating synthetic data utilizes extrapolation and/or trend-line analysis of recently-acquired data for simulations. Synthetic data may be generated based upon trends in current catheter viscosity (e.g., operation 1844 of method 1800), entering bolus viscosity (e.g., operation 1846), etc. As an example case wherein the most-recent 4 current viscosity measurements ($\mu_{current}$) are: $\mu_1$=4, $\mu_2$=6, $\mu_3$=8, $\mu_4$=10 cP, linear extrapolation provides expectation values: <$\mu_5$>=12, <$\mu_6$>=14, <$\mu_S$>=16, <$\mu_9$>=18 cP. However, if the measured value of $\mu_S$ (with expectation value <$\mu_5$>=12) is measured to be $\mu_5$=30, the updated expectation value for viscosity becomes approximately <$\mu_6$>=26 (an 85% correction) in a single measurement and recalculation. This example utilized 4 newly-acquired data points that are linearly extrapolated out to predict 4 future data points. An appropriate number of newly-acquired data points, as well as an accurate or appropriate number of projected data points may be determined by experimentation and verified by methods such as comparing projected outcome scores to measured outcome scores. Selecting extrapolation data as synthetic data is rational because it provides a computationally efficient estimate of future events.

A second method of generating synthetic data utilizes "cherry-picked" instances of recently-acquired data for simulations. As an example utilizing cherry picked data, if a specific AMC mode is prescribed in operation 1850 of method 1800, and if that specific AMC mode was executed previously in the procedure (range of less than 1 second to in excess of 1 hour), then certain recently-acquired data (e.g., viscosity, bolus volume/length, time constant, etc.) may be written to instances of simulation catheter model/data array 1901 as synthetic data. Selecting recently-acquired measurement data as synthetic data is rational based upon the fact that similar data were acquired from the same patient, apparatus and similar thrombus morphology.

A third method of generating synthetic data utilizes mathematical models, historical data, and/or compilations thereof (i.e., data other than collected during the current procedure) for simulations. Historical data for simulations may be selected that are consistent with clinical variables including, but not limited to: procedure type (e.g., PE, DVT, CTO, IS, etc.), thrombus morphology (fresh, organized, fibrotic, calcified, etc.), physical properties (e.g., elastic, firm, hard, brittle, cohesive, adhesive, etc.). In other words, a matrix, data base or knowledge base may provide simulation data consistent with anticipated clinical data. As an example, compilations of clinical data comprise a knowledge base wherein an expected result (i.e., expectation value) of a moderate pulmonary embolism thrombectomy procedure is substantially between approximately 30 cc and 100 cc comprised of substantially fresh, cohesive, elastic thrombus.

Because many VVA embodiments utilize data sets that are small and highly correlated, compilations of historical data from a large number of procedures are also small and highly correlated. For instance, a 64 GB storage device (e.g., USB flash drive, SD card, etc.) may be adequate to store as many as 64,000 procedure log files 2601, 2602, 2630, etc. at approximately 1 MB storage per procedure log file 2601.

Herein, certain speculative correlations between thrombus type and/or morphology (e.g., fresh, elastic, organized, brittle, etc.) to AMC mode (e.g., pulse-train, maximum-attainable vacuum, pressure pulse, etc.) are disclosed. The example correlations consider certain clinical variables (e.g., procedure type, thrombus morphology, physical properties, etc.) and how these may affect outcomes of different AMC modes. This highlights an important distinction between VVA paradigms and those of prior art. Because pressure data are transformed into physically-relevant derived variables (e.g., volume, viscosity, flow rate, clog risk, etc.), these data may be readily correlated to physically-relevant clinical variables (e.g., procedure type, thrombus morphology, physical properties, thrombus volumes, etc.). Data collected upon certain VVA embodiments may be correlated to similar data by procedure (e.g. DVT, PE, etc.), thrombus morphology (e.g. fresh, organized, fibrotic, etc.), physical properties (e.g. soft, cohesive, brittle, etc.), volume of thrombus harvested, etc. Certain VVA embodiments utilize initial correlations between AMC mode, bolus pattern, and clinical variables. In some cases, these initial correlations may be intuitive and/or speculative in nature. Certain VVA embodiments utilize an optimization method wherein speculative correlations are followed by empirical refinement. In other words, a VVA apparatus may be initialized with speculative correlations between VVA system variables, clinical variables and thrombectomy efficacy, but collected data and empirical refinement, i.e., feedback learning, are utilized to make knowledge-based adjustment to system parameters.

Database/compiler/server 2495 comprises data storage for multiple instances of procedure log file 2601, generated by VVA system controller 2401. Similarly, data are stored for multiple instances of procedure log files 2602, 2603, generated by multiple instances of VVA system controllers 2402, 2403. Certain VVA system files 2693 are stored in database/compiler/server 2495; examples include source code, thrombus model matrix, threshold values, mathematical models, lookup tables, historical data, etc.

In certain embodiments, data from multiple procedure log files 2601, 2602, 2603, etc. are compiled, correlated and cross-correlated. Each instance of clinical data from procedure log file 2501 may be compiled with similar clinical data and added to a VVA knowledge base. As multiple instances of VVA system controller 2401, 2402, 2403, etc. collect data from multiple instances of a certain AMC mode 1 (e.g., 27 inHg, 1 cc), these data may be broken into sub-groups by clinical variables (e.g., procedure type, thrombus morphology, etc.). Thereby the efficacy and/or outcome score of AMC mode 1 may be statistically determined from a compilation of historical data; furthermore, these data may be grouped by certain clinical variables. For instance, an average efficacy of AMC mode 1 may be 30% in fresh, elastic thrombus; the average efficacy of that same AMC mode 1 may be 60% in organized, cohesive thrombus. Thereby, the efficacy of specific AMC modes may be correlated to specific clinical variables. These data may be cross-correlated such that specific clinical variables (e.g., procedure type, thrombus morphology, etc.) are correlated to the efficacy of multiple AMC modes, e.g., AMC mode 1, mode 2, mode 3, etc. Thereby, cross-correlation of VVA system variables to clinical variables (e.g., procedure type, thrombus morphology, physical properties, etc.) may be utilized to select from efficacious AMC modes specific to clinical variables.

FIG. 25 depicts thrombus model matrix 2501, which correlates procedures, thrombus morphologies, physical properties, anticipated thrombus volume, AMC modes/simulations and coefficients a-h. The four example procedures are grouped in rows, and further sub-grouped as follows: (1) Ischemic Stroke (IS), sub-grouped to of the Middle Carotid Artery MCA* and Internal Carotid Artery ICA, (2) Pulmonary Embolism (PE), sub-grouped to Moderate, Sub-Massive and Massive, (3) Deep Vein Thrombosis (DVT), sub-grouped to Popliteal, Femoral and Iliac veins, and (4) Chronic Total Occlusion (CTO), sub-grouped to Popliteal, Femoral and Coronary arteries. Ischemic stroke of the middle carotid artery is selected for examples herein and is annotated MCA*.

Thrombus Morphology (Morph) column lists anticipated and/or historically determined thrombus morphologies by procedure sub-group. Physical Properties column lists anticipated and/or historically determined physical properties of anticipated thrombus morphology by procedure sub-group. Volume (cc) column lists anticipated and/or historically determined volumes of thrombotic aspirate per procedure sub-group; these volumetric data may comprise any combination of thrombus volume, thrombus+blood volume, saline, etc. The remaining columns (modes/simulations, a through h) contain variable data that may be, in some cases, static (i.e., remain constant throughout a procedure) or dynamic (i.e., updated one or more times during a procedure).

Thrombus model matrix 2501 is sub-grouped to clinical variables 2510, to the left of FIG. 25, and VVA system variables 2520, to the right. Certain VVA embodiments are re-configurable to select, change, or otherwise determine certain VVA system variables 2520 based, at least in part upon clinical variables 2510. For instance, in the example procedure MCA* a VVA embodiment may be configured to select from AMC modes a, b, c, d, f, and g to the exclusion of the remaining modes (i.e., e and h). In certain VVA embodiments, multiple instances of thrombus model matrix 2501 are generated, utilized and/or stored.

AMC modes/simulations legend, at the bottom of FIG. 25, lists 8 example AMC modes, a-h: AMC mode a is system vacuum, AMC mode b is reduced vacuum, AMC mode c is pressure pulse, AMC mode d is pulse train, AMC mode e is dilution, AMC mode f is saline flush, AMC mode g is make/break contact, and AMC mode h is full aspiration. The example VVA system embodiment is configured to select from 1 these 8 available AMC modes, a-h, in operation 1850 (prescribe next AMC) of method 1800. The 8 example AMC modes, a-h, along with certain methods, settings, setpoints, etc., are presented by way of example and not limitation. Regardless of any organizational structure or level of detail, instances of thrombus model matrix 2501 typically contain an array of clinical variables 2510 having correspondence with, and/or correlation to, an array of VVA system variables 2520.

Multiple instances of thrombus model matrix 2501 are utilized in certain VVA embodiments for different functions. In a first example function, instances of thrombus model matrix 2501 comprise "recipes" for upcoming AMC mode selection. The origin of these recipes may be any combination of speculation, in-vitro experimentation, catheter features, etc. Referencing example procedure MCA* of FIG. 25, wherein a clinical variable is ischemic stroke of the middle cerebral artery, AMC modes: a, b, c, d, f, and g may be selected in proportions substantially that of: 22%, 17%, 18%, 15%, 10% and 18%. In certain VVA embodiments and cases, these recipe data are utilized as synthetic data for simulations. In certain VVA embodiments and cases, these recipe data at least in part comprise input data for upcoming AMC mode selection (i.e., operation 1850 of method 1800) by VVA system controller.

In a second example function, instances of thrombus model matrix 2501 comprise compilations of historical data collected from multiple procedures. In this example, numerical values populating certain array elements are statistically-obtained "correlation levels;" in FIG. 25, correlation levels are normalized to 1 or 100%. In this context, AMC mode a: maximum vacuum is correlated to clinical variable MCA* at a 22% level. Likewise, AMC mode d: pulse train is correlated to clinical variable MCA* at a 15% level, and so forth. Correlation levels may be defined in different ways in different contexts. A first example definition of correlation level is the average outcome score of historical data collected one or more procedures. A second example definition of correlation level may be computed from one or more success metrics, such as viscosity, flow rate, blood loss, clog risk, etc. In this second case, correlation data may be compiled from historical data collected over multiple procedures.

This second example function, wherein instances of thrombus model matrix 2501 comprise a compilation of historical data, is significant because these historical data are sub-grouped based upon coefficients a-h of FIG. 25. FIG. 25 illustrates that AMC mode a is correlated at 22% level for procedure MCA*, 15% level for ischemic stroke of internal carotid artery (IS ICA), 21% for moderate pulmonary embolism (PE Moderate), 17% for sub-massive PE, etc. Thereby, certain VVA embodiments utilize historically and/or statistically-determined AMC mode selection criteria data that are correlated to statistically-significant clinical data that are grouped by procedure type. While AMC mode a is correlated, in FIG. 25A, at a 22% level for procedure MCA*, historical data likely reveals that an exclusive protocol of mode a is likely to reach a point of diminishing returns. Certain VVA embodiments select AMC modes from a statistically-determined distribution, or hierarchy, such as depicted in columns a-h of FIG. 25.

In a third example function, instances of thrombus model matrix 2501 comprise synthetic data that are utilized in simulation instances of catheter model/data array 1901. In this case, numerical values certain array elements may comprise any combination of: changes, disturbances, perturbations, variations, redistributions, etc. to coefficients a-h of FIG. 25. As an example referencing procedure MCA*, mode a is assigned a 22% correlation level, while mode b is assigned 17% correlation level. In such cases, numerical entries, such as coefficient a=22%, coefficient b=17%, etc., are changed, for instance to (coefficient a=12%, coefficient b=27%, etc.). While the coefficient of AMC mode b is depicted at a 17% level in FIG. 25, certain VVA embodiments compute simulations that explore the efficacy of AMC mode b at the greater level, e.g., 27%. This third example function is significant because certain VVA embodiments thereby introduce stochastic (i.e., randomly determined) processes in computed simulations.

In a fourth example function, instances of thrombus model matrix 2501 comprise a dynamic array of expectation values of outcomes of AMC modes a-h. The expectation values may be success metrics such as outcome score, viscosity, clog risk, time constant, thrombus harvested, etc. In this instance, thrombus model matrix 2501 is dynamic; meaning that certain array elements may be updated a plurality of times within a procedure. Thereby, any or all coefficients a-h may be changed within a procedure. As an example, in representative case MCA*, coefficient a may be reduced, for instance from 22% to 15%. For instance, because AMC mode a is determined to underperform in the current procedure; for reasons such as measurement of excessive blood loss without significant thrombus harvested.

Coefficients a-h are normalized to 100% in FIG. 25, therefore decreasing the value of coefficient a results in an increase in the value of any or all of the remaining coefficients b-h. In certain cases wherein success metrics for AMC mode a are computed to deviate beyond certain threshold values, then alternate AMC modes b-h may be preferentially prescribed, e.g., operation 1850 of method 1800.

Referencing example MCA* procedure, AMC mode a is correlated at the highest level, 22%, and may be preferentially selected over the alternate AMC modes. In certain VVA embodiments, an executed instance of AMC mode a is expected to exhibit success metrics that fall within the statistically-derived range of success metrics for AMC mode a in a MCA* procedure. In cases wherein one or more computed success metrics for a certain AMC mode lie outside of threshold values, certain VVA embodiments may dynamically change the correlation levels of thrombus model matrix 2501. In certain cases, this may be in response to clinical variables 2510 lying outside of expected, threshold and/or predetermined values. Referring to example procedure MCA* wherein thrombus morphology is expected to be fresh and the physical properties are expected to be cohesive and elastic. However, in certain atypical MCA* thrombectomy procedures, the clinical variables 2510 thrombus morphology and physical properties may be, for instance, organized and firm. In this fourth function, instances of thrombus model matrix 2501 comprises a dynamic array of expectation values for success metrics. Thereby, certain VVA embodiments are enabled to dynamically adjust in response to atypical clinical variables including, but not limited to: thrombus morphology, physical properties, etc. Dynamic adjustment of coefficients a-h enables certain VVA embodiments to respond to clinical variables, in this case due to an underperforming AMC mode given the clinical variables.

In certain VVA embodiments, threshold values for success metrics are statistically determined from compiled data collected over multiple procedures. Certain VVA embodiments compute expectation values for success metrics (e.g., clog risk, bolus viscosity, etc.) based upon input data including, but not limited to: catheter state, AMC mode, initial and final pressures, target bolus volume, time constant, etc. Expectation values may be computed utilizing one or more mathematical models including, but not limited to: regression/trend line analysis, simulations, machine state, e.g., vacuum levels, dilution, make/break contact, etc.

As an example of threshold values and outcomes scores, the current clog risk is 40%, and after the next AMC, the expectation value for clog risk is 50%. The mathematical models and/or simulations predict the viscosity of entering bolus 911 ($\hat{\mu}_0$) to be great enough to increase the clog risk to 50%. In certain VVA embodiments, a predetermined threshold value for clog risk, e.g., 120%, is imposed to trigger responsive action. In this case, 120% of the expectation value for clog risk (50%) is 60%; therefore any computed clog risk below 60% does not trigger responsive action. In a first example case, wherein the computed clog risk is 50%, an outcome score of 100% may be assigned, because the computed value for clog risk is equal to the expectation value. In a second example case, wherein the computed clog risk is 40% (i.e., unchanged) an outcome score of 80% may be assigned, because the computed clog risk is 80% of the expectation value. In a third example case, wherein the computed clog risk is 70%, an outcome score of 20% may be assigned, because the computed clog risk is 40% greater than the expectation value and a threshold value for clog risk is exceeded In the four functions of thrombus model matrix 2501 listed above, data generation and utilization of coefficients a-h are disclosed. In certain instances detailed above, coefficients a-h are utilized to compute simulations, rather than executed AMCs. In certain cases, computed simulations have no effect on AMC mode selection. While a number of simulations may be computed in real time, e.g., operation 1880 of method 1800, a substantially unlimited number of simulations may be computed "offline," i.e., deferred or batch processing. These offline-computed simulations may be correlated to one or more instances of stored data array 2651 and/or procedure log file 2501, at substantially any time after generation thereof.

Offline computing of simulations highlights one of many benefits of the data structures disclosed herein; certain instances of stored data array 2651 and/or procedure log file 2601 contain sufficient data that offline simulations may be computed therefrom. As an example, data from an instance of procedure log file 2501 indicate a computed clog risk below a threshold value (e.g., 60%, 75%, etc.) at time 1; subsequently, at time 2, the catheter becomes clogged. Multiple offline simulations may be computed for the period between time 1 and time 2, wherein alternative AMC modes are selected and/or pressures, bolus volumes, etc. are varied. In other words, the apparatus state at time 1 is utilized as an initial condition for a simulation that is computed to a simulated apparatus state as a final condition. In many cases, measurement data are utilized as synthetic data in this offline simulation. In the example case wherein a clog is to be averted, certain AMC modes, e.g., pressure pulse, pulse train, dilution, make/break contact, etc., may be preferentially selected in certain simulation instances. Furthermore, dynamic visualization of bolus patterns (FIGS. 20A-21) and/or pressure distributions (FIGS. 11A, 11B), and computed simulations may be compared against and/or superposed over data from procedure log file 2501. Thus, dynamic visualization enables parties including engineers, clinicians and/or VVA control system algorithm developers to propose, assess, and in certain cases, implement changes that are based upon logic- and/or data-driven inputs.

Many VVA embodiments store data including, but not limited to: measurement data (e.g., time constant, viscosity, volume, etc.), VVA system variables (e.g., pressure, damping, dilution, pressure pulse, pulse train, etc.), procedure type, clinician, facility, patient, catheter, procedure notes, etc. Stored data may be analyzed intra-procedurally, in some cases by processor auxiliary 2410, processor 2420, remote controller 2481, and/or database/compiler/server 2495. Stored data sets typically comprise VVA system variable data including, but not limited to: viscosity, volume, time constant, pressure, flow rate, valve duration, pressure, time, damping, bulk modulus, pulse train, pressure pulse, make/break contact, dilution, etc.

An example, a one-hour long procedure, executing one AMC per second requires approximately 3,600 AMC data entries to be stored; a corresponding stored data array 2651 has less than approximately 5,000×20 elements. Instances of stored data array 2651 do not typically exceed 10,000×20 elements (approximately 782 kB) for a typical aspiration thrombectomy procedure; this requires approximately 782 kB of memory and may be updated on an Arduino® in under approximately 100 ms. Many VVA embodiments perform data analysis, including statistical analysis upon stored data. Analysis of stored data may be conducted concurrently with method 1800. Instances of stored data array 2651 may comprise data including, but not limited to: machine state, pressure state, volumetric state, raw and/or analyzed stored data, procedure, patient, facility, clinician, device and catheter, procedure notes, etc.

FIGS. 26A-26C depict 1$^{st}$, 2$^{nd}$ and last pages of representative VVA procedure log file 2601 and stored data array 2651. VVA procedure log file 2601 typically comprises raw and/or analyzed data including, but not limited to: one or more portions and/or instances of catheter model/data array(s) 1901, stored data array 2651, AMC mode, as-measured data, derived variables, outcome scores, etc. In FIG. 26A, the upper block of data (i.e., from 15:45:00:0 to 15:45:17.795) illustrates data collected while AMC mode seek was executed. AMC mode seek is repeated until thrombus is detected (e.g., by increase in time constant, bolus and/or catheter viscosity, etc.). The lower block of data (i.e., from 15:45:20:545 to 15:45:43.150) illustrates data collected during a representative AMC mode normal. Approximately 10 instances of AMC mode normal were executed, at which time the bolus viscosity returned to that of blood. In many cases, data for VVA procedure log file 2601 comprises any or all portions of one or more instances of stored data array 2651. The 22 second-duration stored data array 2651 is shown in FIG. 26A as an array of approximately 11 rows by 12 data columns. Instances of stored data array 2651 are typically dimensioned to less than 10,000×20 requiring approximately 782 kB storage. FIG. 26B depicts a portion of representative VVA procedure log file 2601, where a plurality AMC modes (e.g., AMC modes a-h of thrombus model matrix 2501, etc.) are executed. FIG. 26C depicts a final portion of representative VVA procedure log file 2601, where procedure totals ae displayed, along with procedure-specific data such as: date, clinic, procedure, catheter, patient, physician, procedure notes, case ID, VVA software revision, etc.

This disclosure of VVA technology is presented in the framework that an evacuated reservoir serves as a representative source of differential pressure for operation of the apparatus. Evacuated-reservoirs were selected for discussion because they typically maintain a substantially constant pressure, which may be utilized as a reference pressure. Alternative sources of differential pressure, featured in certain VVA embodiments, may increase the algorithm complexity; these are omitted for brevity. As examples, in the embodiment of FIGS. 2A-2C, displacement mechanism 220 serves as a source of differential pressure, perhaps rendering evacuated reservoir 102 and air pump 110 unnecessary. In the embodiment of FIGS. 4E-4G, compressed air/vacuum source 475 may serve as a source of differential pressure. In the embodiment of FIGS. 6A-6D, external forces acting upon piston 610 may serve as a source of differential pressure. In certain VVA embodiments, a peristaltic pump may be substituted for example VVA components such as evacuated reservoir 102 and air pump 110. The sources of differential pressure are typically utilized to reduce the pressure at the proximal end of the catheter to a pressure that is less than the pressure at the distal end of the catheter; this typically creates or changes the flow of fluid through the catheter.

This disclosure of VVA technology is presented in the framework that raw pressure data, such as from a pressure transducer, are typically converted into engineering units (e.g., psi, mmHg, atm, Pa, etc.) for pedagogical and explanatory reasons. Unit conversion to engineering units is optional in certain VVA embodiments; raw pressure data may be equivalently analyzed in such embodiments. Though raw-data VVA embodiments may result in increased computational efficiency, they are omitted from discussion herein. It is important to note that many VVA embodiments employ ratiometric analysis, or scaling by a dimensionless ratio. The equations presented and derived herein are presented in engineering units, where dimensional analysis is observed, and dimensionless ratios emerge. VVA embodiments that analyze raw pressure data are therefore equivalent to VVA embodiments that analyze data that has been converted to engineering units.

Herein, viscosity is presented in terms of dynamic viscosity, which some references associate with shear stress rates. Alternatively, viscosity can be expressed as kinematic viscosity, with some sources linking it to flow rates. However, the difference between the dynamic and kinematic forms lies solely in the physical property of density. For the purposes of this disclosure, variations in aspirate density (specific gravity) are considered negligible, thus allowing the dynamic and kinematic formulations to be regarded as functionally equivalent.

In order to provide a clear and consistent understanding of the disclosure and the appended claims, including the scope to be given such terms, the following glossary of terms and definitions is provided.

Fluid—Any homogeneous or heterogeneous matter comprised of vapors, gasses, liquids, suspended solids or slurries thereof that may be transferred through a tube, pipe or catheter by means of a differential pressure existent within the tube, pipe or catheter. The terms Fluid and Liquid may be used interchangeably herein. Fluids continuously deform under finite shear stress.

Solid—A state of matter that resists continuous deformation under finite shear stress.

Viscosity—the resistance of a fluid to flow; herein including the resistance of a homogeneous fluid or inhomogeneous mixture of fluids and/or solids in any proportion to flow through a catheter or conduit. Herein, catheter viscosity may typically be construed to mean the measured, average or effective viscosity of fluid contained within a conduit or catheter. Eq. 0 provides both an integral (approximate) equation and a summation (approximate) equation for the measured, average or effective viscosity.

$$\mu \approx \frac{1}{L}\int_0^L \hat{\mu}\,dx \approx \frac{1}{v}\sum_1^N \hat{v}_i \hat{\mu}_i \qquad \text{Eq. 0}$$

Where L is the length of the catheter, $\hat{\mu}$ is the viscosity of a differential length element (of fluid), N is the number of boluses, v is the volume of the catheter, $\hat{v}_i$ is the volume of the $i^{th}$ bolus and $\hat{\mu}_i$ is the viscosity of the $i^{th}$ bolus. The integral notation convention is integrated over the length of the catheter; the summation notation convention is a summation of volumes of individual boluses of aspirate. The measured, average or effective viscosity may be considered to be an integral over the length of a catheter. The measured, average or effective viscosity may be considered to be a summation of discrete boluses of fluid of known viscosity and volume. The summation notation convention is useful in discretizing the contents of a catheter into discrete boluses. Eq. 0 illustrates that the viscosity of the contents of a catheter may be equivalently formulated in either a length or volume basis.

Bolus—A generally discrete volume of aspirate within a conduit or catheter. The contents of a catheter can be considered a linear array of discrete boluses of aspirate, with the volume and viscosity of each bolus measurable as outlined herein.

Cork or Corking (of a Catheter)—A case of clogging a catheter wherein an excess of thrombus is ingested such that ordinary differential pressure (e.g., steady, interrupted, non-oscillatory, etc. suction/vacuum from a syringe, evacuated reservoir, etc.) forces are ineffective in establishing or restoring flow. A corked catheter represents a case of approximately zero flow and a very large time constant.

Aspirate (noun)—any fluid, liquid, solid, slurry, homogeneous or heterogeneous matter that may be transferred through a conduit or catheter; also the contents of the conduit or catheter.

Aspirate or aspirating (verb)—employ(ing) differential pressure to transfer any fluid, liquid, solid, gas, vapor, slurry or heterogeneous matter through a conduit or catheter. Sources of differential pressure include: non-isovolumetric components, evacuated reservoirs, syringes, compliance chambers, springs, atmospheric pressure, intravascular pressure, phase change, gravity, turbomachinery, fluid jets, pumps, etc.

Attribute Data: Attribute data, also known as categorical data, consists of discrete categories or labels that represent different qualities or characteristics. These categories are typically integer-based and/or non-numeric and qualitative in nature. Attribute data is typically used to describe characteristics that can be counted or categorized. Attribute data are typically graphically depicted as frequency distributions, histograms, bar charts, pie charts, etc.

Variable Data: Variable data, also known as numerical data or continuous data, consists of numeric values that can take any value within a certain range. These values can be measurements of physical properties and are quantitative in nature. Variable data may be expressed in engineering units including: inches, gallons, cP, Pa, ° C., etc.; variable data may be ratiometric and/or expressed as percentages. Variable data may be acted upon using mathematical methods of algebra, linear algebra, calculus, differential equations, etc.

Characteristic of Flow: A language-based descriptor of flow of aspirate within a catheter which is expressed in attribute data terms including: "free flow," "open flow," "restricted flow," "clot," "clog," etc. Also termed "Flow State." Characteristic of flow is not a measurement and may only be monitored for change.

Flow Rate (Q): Typically the volumetric flow rate of a fluid, often expressed in engineering units (e.g., L/min, $m^3/s$, etc.).

Success Metric—A predefined criterion, rule, function, or set of conditions used to evaluate whether a process, system, or outcome satisfies a desired objective or acceptable standard.

Outcome Score—A value, rating, or result derived from evaluating a process, system, or outcome, typically used to characterize the degree to which a desired objective has been achieved.

Clog Risk—An intuitive success metric computed from as-measured data including: measured viscosity, volume and location of thrombus within a catheter, etc.; this metric quantifies the likelihood of clogging a catheter. Experimental data may be used as calibration standards for accuracy.

Immediate or Immediately—Herein, data are considered "immediately" available upon completion of analysis, which typically involves algebraic operations and conditional statements, as utilized in many computer programming languages. It is understood that such computations require a finite, though small, amount of time to complete. The timeframe for "immediately" generally ranges from less than approximately 1 μs to over 1 second, depending on apparatus states and algorithm complexity.

Instantaneous or instantaneously—(1) Herein, an instantaneous measurement refers to the value of any parameter (e.g., pressure, volume, position, etc.), its time derivatives (e.g., dP/dt, dV/dt, dx/dt, etc.) at a specific point in time. In this context, "instantaneous" means the measurement or calculation of a parameter or its rate of change at a specific moment in time. (2) Terms such as "instantaneous contents of a catheter" refer to one or more measurements, metrics or descriptors of the catheter's contents at a specific instant. Instantaneous data are immediately available after any necessary computations.

Equilibrium—a state of balance between opposing forces or actions. Herein, a static equilibrium state typically means: a state of approximately zero flow rate through an apparatus or catheter. A closed vacuum valve and a clogged catheter are prior art examples of static equilibrium states. VVA embodiments tend toward static equilibrium states at a characteristic rate, herein parameterized as a time constant.

Static Equilibrium State: A condition in which all forces and moments acting on a system are balanced, resulting in no linear or rotational motion, and the system remains at rest.

Machine State: A defined condition of a machine at a given time, characterized by the state or position of its components, such as valves, actuators, regulators, sensors, and control settings.

Thermodynamic State: A defined condition of a system at a given moment defined by a specific set of properties such as pressure, temperature and volume.

Catheter State: A defined condition of a catheter at a given time, characterized by the position and viscosity of fluid within the catheter.

Apparatus State: any of all of machine state, volumetric state, pressure state, equilibrium state, catheter state, etc.

Time Constant—The term time constant is used as an intuitive example of the more general term: Equilibrium Rate Characteristic. Instances of the term time constant may typically be construed to mean equilibrium rate characteristic.

Equilibrium Rate Characteristic-Any measure, parameter, or metric that quantifies the rate at which a process, system, or component approaches or reaches a state of equilibrium, stability, or steady-state following a change in conditions. This includes, but is not limited to, time constants, time-variable parameters, non-linear response times, adaptive or state-dependent time measures, or any other temporal metric that describes the dynamic behavior of a system as it moves toward equilibrium. The equilibrium rate characteristic applies to both linear and non-linear systems and is intended to encompass any method or model used to quantify or control the time-dependent progression of a process toward equilibrium, regardless of the specific terminology or mathematical framework employed.

Coordinate Transformation or Transformation—The process of converting data from one coordinate system or state space (e.g., pressure-time space) to another (e.g., volume-time space) using a predefined mapping function that defines a mathematical relationship between corresponding variables in the two spaces. Transforming data from pressure-time space into volume-time space is herein noteworthy because a measurement of an intensive physical property (pressure) is transformed into a measurement of an extensive physical property (volume).

Mathematical Model—a representation of a real-world system using equations, variables, and parameters to describe the relationships between key quantities. Example mathematical models include, but are not limited to, governing equations of fluid mechanics (e.g., Navier-Stokes, Bernoulli, etc.), equations of state (e.g., ideal gas law, Hooke's law, etc.), rate equations, constitutive or empirical equations (e.g., Hagen-Poiseuille, Newton's law of viscosity, etc.). As an example, a catheter model/data array may be a mathematical model of the contents of the catheter, i.e., the catheter state.

Catheter Model/data array—An array of quantitative metrics correlated and/or corresponding to individual discrete boluses of aspirate, wherein parameters and/or variables such as the position, volume and viscosity of each bolus have been measured.

As-measured data—measurement data (e.g., viscosity, length, volume, etc.) that are computed and/or determined; certain of these as-measured data are written to catheter model/data array. The current instance of catheter model/data array is typically comprised of as-measured data.

Synthetic data—data (e.g., viscosity, length, volume, etc.) that may be written to simulation instances of catheter model/data array.

Expectation Value or Expected Value—The expectation value represents the best available estimate of an outcome based on known, measured and/or modeled parameters, variables and/or underlying probabilistic behavior.

Damping—Herein, loss of energy of an oscillating system by viscous dissipation. Damping is important in VVA because increasing damping can: (1) reduce blood loss and/or (2) improve data quality, such as by eliminating oscillations and ringing.

Waste—Any extracorporeal repository for any aspirate (e.g., blood, thrombus, clot, saline, generalized fluids, etc.). The importance of the term waste herein is that VVA embodiments extract tissue from patients, and transport that tissue to waste for therapeutic effect.

Reservoir—any repository for fluids. Example reservoirs include: mammalian vascular systems, evacuated reservoir, collection bag, a sink, the atmosphere, the ocean, etc.

Valve—herein any device for controlling the passage of fluid through a catheter, pipe, conduit, duct, etc. Examples include: pinch valves, angle valves, solenoid valves, ball valves, etc.

Source of differential pressure—herein, "prime movers" of aspirate flow through a catheter. Evacuated reservoirs are selected as a representative source of differential pressure utilized to "pull" aspirate through the catheter. Alternative VVA sources of differential pressure include peristatic pumps, syringe pumps or syringes, "house" vacuum, piston pumps, etc. In certain VVA embodiments, the apparatus itself is a source of differential pressure (e.g., VVA 201)

Incompressible fluid—a fluid with substantially constant density and volume, irrespective of pressure; liquids are typically considered incompressible. Examples: water, saline, blood, thrombus, clot, SAE 30 motor oil, ketchup, etc.

Compressible fluid—a fluid that experiences a significant change in density as the pressure changes; air, gasses and vapors are typically considered compressible. Examples: air, nitrogen, oxygen, steam, water vapor, $CO_2$, etc.

Non-isovolumetric (adj.)—VVA components or elements that deform and change volume during operation of the apparatus.

Fundamental Units—The irreducible, basic physical quantities used to define all other derived units in a measurement system. Examples include mass (M), length (L), and time (T), which serve as the building blocks for expressing physical laws and relationships.

Engineering Units—A practical set of units used to quantify physical properties. Examples include: Pa, mmHg, psi, ml, cc, cm/sec, Pa·s, lpm, etc. These units are often derived from fundamental units but tailored for convenience in specific applications.

The s-coordinate system—a one dimensional coordinate system for identifying spatial locations within a component (e.g., catheter, connecting tube, valve, etc.) that uniquely identifies the position of a point or object within the component. The s-coordinate is independent of the component's position or orientation in space. The coordinate system is based on an intrinsic, arc-length parameterization of the centerline of the catheter, denoted by s, which measures the distance along the catheter from a defined reference point, herein typically the distal end of the catheter.

Control Volume and Control Surfaces-A control volume is a defined region in space through which fluid, energy, or mass may flow, serving as the focus for applying conservation laws such as those of mass, momentum, and energy. The control surfaces are the boundaries of this control volume, which may be physical or imaginary, and through which these quantities can enter or exit.

Atmospheric pressure—Approximately 101 kPa, 14.7 psi, 1.01 bar, etc. at sea level, e.g., Miami, FL. In Mexico City, elevation 2,240 m (7,350') atmospheric pressure is approximately 80 kPa, 11.6 psi, 0.8 bar.

Vacuum-pressure less than a reference pressure, typically atmospheric pressure. Vacuum is typically expressed in units such as inHg, mmHg, etc. relative to atmospheric pressure. Maximum vacuum in Miami, FL is approximately 29.92 inHg (760 mmHg); maximum vacuum in Mexico City is approximately 23.6 inHg (600 mmHg).

Gage pressure-pressure measured relative to a reference pressure, typically atmospheric pressure. "Vacuum" gage units include inHg, mmHg, etc. are gage pressures because they are referenced to atmospheric pressure. "Pressure" gage units include psig, barg, kpag, etc.

Pressure or absolute pressure-Absolute pressure is the total pressure measured relative to a perfect vacuum (zero reference point). It accounts for atmospheric pressure in addition to any pressure exerted by a fluid or gas. Typical units include kPaa, psia, bara, etc. Absolute pressure=gage pressure+atmospheric pressure.

Normalized volume—As used herein, the term "normalized volume" refers to a dimensionless parameter that represents the relative proportion of a system's operational volume range. The normalized volume is not indicative of the physical dimensions or the internal volume of the apparatus itself, but rather a proportional measure of the volume of fluid contained within the apparatus.

Dead volume—As used herein, the term "dead volume" refers to the fixed internal volume of the apparatus that remains unaffected by typical non-isovolumetric operation. The "normalized volume," by contrast, is a dimensionless parameter representing the adjustable portion of the fluid volume within the apparatus relative to an operational range. The total fluid volume of the apparatus is typically the sum of the dead volume and the normalized volume.

Paradigm—a framework of assumptions, models, and preferred methods that shapes how a problem is approached, analyzed, and solved.

The invention claimed is:

1. An apparatus comprising:

a conduit containing a first aspirate fluid;

a non-isovolumetric component fluidically coupled to the conduit and containing a waste aspirate fluid, the non-isovolumetric component operable to change the volume of the waste aspirate fluid contained within the apparatus, the non-isovolumetric component containing a static equilibrium volume of the waste aspirate fluid when the apparatus is in a static equilibrium state;

a transducer operable to measure pressure within the non-isovolumetric component;

a first valve operable to block flow of the first aspirate fluid from the conduit to the non-isovolumetric component;

a second valve operable to block flow of the waste aspirate fluid from the non-isovolumetric component to waste; and a controller that:

a) receives pressure data from the transducer, b) controls the state of the first valve and the state of the second valve, and c) generates a data set, wherein the data set includes a first pressure measured at a first time and a second pressure measured at a second time, the controller thereby determining a characteristic rate at which the apparatus tends toward the static equilibrium state.

2. The apparatus of claim 1 wherein the controller determines a viscosity of the first aspirate fluid.

3. The apparatus of claim 2 wherein the apparatus:

aspirates a second aspirate fluid, and the controller determines a viscosity of the second aspirate fluid.

4. The apparatus of claim 3 wherein the controller determines a volume of the second aspirate fluid.

5. The apparatus of claim 4 wherein the controller generates a data array including:

a) the volume and the viscosity of the second aspirate fluid; and b) the volume and the viscosity of a third aspirate fluid;

the apparatus thereby generating a mathematical model of the aspirate fluids within the conduit.

6. The apparatus of claim 5 wherein the controller updates the data array, thereby generating a simulation of the motion of the aspirate fluids within the conduit.

7. The apparatus of claim 6 wherein as-measured data are utilized to update the data array.

8. The apparatus of claim 6 wherein synthetic data are utilized to update the data array.

9. An apparatus comprising:

a conduit having a proximal end and a distal end, the conduit containing an aspirate fluid;

a non-isovolumetric component containing a waste fluid, the non-isovolumetric component being:

a) fluidically coupled to the proximal end of the conduit, and b) operable to change the volume of the waste fluid contained within the apparatus;

a transducer operable to measure pressure within the non-isovolumetric component;

a source of a differential pressure operable to reduce the pressure at the proximal end of the conduit to a pressure lower than the pressure at the distal end of the conduit;

controller-accessible storage, the controller-accessible storage containing a coordinate transformation that maps the pressure within the non-isovolumetric component to the volume of the waste fluid contained within the apparatus;

a controller that:

a) receives pressure data from the transducer, b) controls the source of differential pressure, c) generates a data set wherein the data set includes a first pressure measured at a first time and a second pressure measured at a second time, d) calculates a time rate of change of pressure, and e) transforms the time rate of change of pressure to a time rate of change of the volume of the waste fluid contained within the apparatus;

the time rate of change of the volume of the waste fluid contained within the apparatus being the flow rate of the aspirate fluid within the conduit;

the apparatus thereby measuring the flow rate of the aspirate fluid within the conduit.

10. An apparatus comprising:

a conduit having a proximal end and a distal end, the conduit containing an aspirate fluid;

a non-isovolumetric component containing a waste fluid, the non-isovolumetric component operable to change the volume of the waste fluid contained within the apparatus, wherein the non-isovolumetric component:

a) has an internal surface fluidically coupled to the proximal end of the conduit such that the pressure within the non-isovolumetric component is substantially equal to the pressure at the proximal end of the conduit, b) has an external surface exposed to an external fluid, c) experiences a differential pressure between the internal surface of the non-isovolumetric component and the external surface of the non-isovolumetric component, and d) contains a first volume of the waste fluid at a first differential pressure, and a second volume of the waste fluid at a second differential pressure;

an external fluid reservoir containing the external fluid; and means to change the amount of the external fluid contained within the external fluid reservoir, wherein the apparatus is operable to change the pressure at the proximal end of the conduit by changing the amount of the external fluid contained within the external fluid reservoir;

the apparatus thereby creating a flow of the aspirate fluid within the conduit.

* * * * *